US010548864B2

(12) United States Patent
Lu et al.

(10) Patent No.: US 10,548,864 B2
(45) Date of Patent: Feb. 4, 2020

(54) ENHANCED ATRA-RELATED COMPOUNDS FOR THE TREATMENT OF PROLIFERATIVE DISEASES, AUTOIMMUNE DISEASES, AND ADDICTION CONDITIONS

(71) Applicants: Beth Israel Deaconess Medical Center, Inc., Boston, MA (US); Pinteon Therapeutics, Inc., Concord, MA (US)

(72) Inventors: Kun Ping Lu, Newton, MA (US); Xiao Zhen Zhou, Newton, MA (US); Shuo Wei, Chestnut Hill, MA (US); Lijun Sun, Harvard, MA (US); Michelle Lynn Hall, Somerville, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 15/557,731

(22) PCT Filed: Mar. 10, 2016

(86) PCT No.: PCT/US2016/021759
§ 371 (c)(1),
(2) Date: Sep. 12, 2017

(87) PCT Pub. No.: WO2016/145186
PCT Pub. Date: Sep. 15, 2016

(65) Prior Publication Data
US 2018/0064666 A1 Mar. 8, 2018

Related U.S. Application Data

(60) Provisional application No. 62/177,395, filed on Mar. 12, 2015.

(51) Int. Cl.
A61K 31/196 (2006.01)
A61K 45/06 (2006.01)
A61K 31/122 (2006.01)
A61K 31/4152 (2006.01)
A61K 31/4166 (2006.01)
A61K 31/4192 (2006.01)
A61K 31/4245 (2006.01)
A61K 31/452 (2006.01)
A61K 31/5375 (2006.01)
A61K 31/203 (2006.01)
A61K 31/4196 (2006.01)

(52) U.S. Cl.
CPC .......... A61K 31/196 (2013.01); A61K 31/122 (2013.01); A61K 31/203 (2013.01); A61K 31/4152 (2013.01); A61K 31/4166 (2013.01); A61K 31/4192 (2013.01); A61K 31/4196 (2013.01); A61K 31/4245 (2013.01); A61K 31/452 (2013.01); A61K 31/5375 (2013.01); A61K 45/06 (2013.01)

(58) Field of Classification Search
None
See application file for complete search history.

(56) References Cited

U.S. PATENT DOCUMENTS

| 4,683,195 | A | 7/1987 | Mullis et al. |
| 4,683,202 | A | 7/1987 | Mullis |
| 5,223,409 | A | 6/1993 | Ladner et al. |
| 5,283,317 | A | 2/1994 | Saifer et al. |
| 5,459,039 | A | 10/1995 | Modrich et al. |
| 5,498,531 | A | 3/1996 | Jarrell |
| 5,952,467 | A | 9/1999 | Hunter et al. |
| 5,972,697 | A | 10/1999 | Hunter et al. |
| 6,462,173 | B1 | 10/2002 | Lu et al. |
| 6,495,376 | B1 | 12/2002 | Lu et al. |
| 6,596,848 | B1 | 7/2003 | Hunter et al. |
| 6,649,611 | B2 | 11/2003 | Blumberg et al. |
| 6,764,698 | B1 | 7/2004 | Byun et al. |
| 7,125,677 | B2 | 10/2006 | Hunter et al. |
| 7,125,955 | B2 | 10/2006 | Hunter et al. |
| 7,148,003 | B2 | 12/2006 | Hunter et al. |
| 7,161,060 | B1 | 1/2007 | Duff et al. |
| 7,164,012 | B2 | 1/2007 | Hunter et al. |

(Continued)

FOREIGN PATENT DOCUMENTS

| JP | 2004-532390 A | 10/2004 |
| WO | WO-94/10300 A1 | 5/1994 |

(Continued)

OTHER PUBLICATIONS

Jaeger et al. (European Journal of Medicinal Chemistry, 28(4), 275-290, 1993).*
U.S. Appl. No. 61/490,338, Lu et al.
U.S. Appl. No. 61/968,862, Lu et al.
Curtis et al., "The genomic and transcriptomic architecture of 2,000 breast tumours reveals novel subgroups," available in PMC Dec. 21, 2012, published in final edited form as: Nature 486(7403):346-52 (2012) (15 pages).
Al-Hajj et al., "Prospective identification of tumorigenic breast cancer cells," Proc Natl Acad Sci U.S.A. 100(7):3983-8 (2003).
Bild et al., "Oncogenic pathway signatures in human cancers as a guide to targeted therapies," Nature. 439(7074):353-7 (2006).
Carell et al., "A novel procedure for the synthesis of libraries containing small organic molecules," Angew Chem Int Ed Engl. 33(20):2059-2061 (1994).

(Continued)

Primary Examiner — Bong-Sook Baek
(74) Attorney, Agent, or Firm — Clark & Elbing LLP

(57) ABSTRACT

The invention features all-trans retinoic acid (ATRA)-related compounds capable of associating with Pin1 and methods of treating a proliferative disorder characterized by elevated Pin1 marker levels, Pin1 degradation, and/or reduced Pin1 Ser71 phosphorylation in a subject by administering an ATRA-related compound. The invention also features methods of treating proliferative disorders, autoimmune diseases, and addiction conditions (e.g., diseases, disorders, and conditions characterized by elevated Pin1 marker levels) by administering an ATRA-related compound in combination with another therapeutic compound.

17 Claims, 83 Drawing Sheets
Specification includes a Sequence Listing.

(56) References Cited

U.S. PATENT DOCUMENTS

| | | | |
|---|---|---|---|
| 7,175,830 | B2 | 2/2007 | Collins et al. |
| 7,592,145 | B2 | 9/2009 | Bao et al. |
| 8,129,131 | B2 | 3/2012 | Lu et al. |
| 8,258,099 | B2 | 9/2012 | Lu et al. |
| 8,771,693 | B2 | 7/2014 | Lu et al. |
| 2002/0002552 | A1 | 1/2002 | Schultz et al. |
| 2002/0025521 | A1 | 2/2002 | Lu et al. |
| 2002/0106348 | A1 | 8/2002 | Huang et al. |
| 2004/0176912 | A1 | 9/2004 | Sowadski et al. |
| 2005/0159485 | A1 | 7/2005 | Jost-Price et al. |
| 2005/0239095 | A1 | 10/2005 | Lu et al. |
| 2005/0250742 | A1 | 11/2005 | Dagostino et al. |
| 2006/0018899 | A1 | 1/2006 | Kao et al. |
| 2006/0074222 | A1 | 4/2006 | Lu et al. |
| 2007/0072875 | A1 | 3/2007 | McMaster |
| 2007/0203236 | A1 | 8/2007 | Smith et al. |
| 2008/0118505 | A1 | 5/2008 | Tedder |
| 2008/0214470 | A1 | 9/2008 | Lu et al. |
| 2008/0248043 | A1 | 10/2008 | Babcook et al. |
| 2009/0053209 | A1 | 2/2009 | Malter et al. |
| 2009/0105249 | A1 | 4/2009 | Benjamin et al. |
| 2009/0258352 | A1 | 10/2009 | Lu et al. |
| 2010/0010084 | A1 | 1/2010 | Yu |
| 2010/0278832 | A1 | 11/2010 | Kamogawa et al. |
| 2011/0034554 | A1 | 2/2011 | Washington |
| 2011/0065704 | A1 | 3/2011 | Ryder |
| 2011/0077250 | A1 | 3/2011 | Ryder |
| 2011/0077298 | A1* | 3/2011 | Chen ............ C07C 69/734 514/529 |
| 2011/0104756 | A1 | 5/2011 | Rodriguez et al. |
| 2012/0183560 | A1 | 7/2012 | Akassoglou |
| 2013/0028900 | A1 | 1/2013 | Lu et al. |
| 2014/0086909 | A1 | 3/2014 | Lu et al. |
| 2014/0219957 | A1 | 8/2014 | Lu et al. |
| 2014/0242100 | A1 | 8/2014 | Lu et al. |
| 2015/0044278 | A1 | 2/2015 | Lu et al. |
| 2015/0133442 | A1 | 5/2015 | Lu et al. |

FOREIGN PATENT DOCUMENTS

| | | |
|---|---|---|
| WO | WO-94/16101 A2 | 7/1994 |
| WO | WO-97/17986 A1 | 5/1997 |
| WO | WO-99/09969 A1 | 3/1999 |
| WO | WO-02/064015 A2 | 8/2002 |
| WO | WO-02/065091 A2 | 8/2002 |
| WO | WO-02/092765 A2 | 11/2002 |
| WO | WO-03/073999 A2 | 9/2003 |
| WO | WO-2004/016751 A2 | 2/2004 |
| WO | WO-2004/101745 A2 | 11/2004 |
| WO | WO-2005/027727 A2 | 3/2005 |
| WO | WO-2006/002097 A2 | 1/2006 |
| WO | WO-2006/028576 A2 | 3/2006 |
| WO | WO-2007/133702 A2 | 11/2007 |
| WO | WO-2008/137488 A1 | 11/2008 |
| WO | WO-2009/146218 A2 | 12/2009 |
| WO | WO-2010/081488 A1 | 7/2010 |
| WO | WO-2010/141738 A2 | 12/2010 |
| WO | WO-2011/056561 A1 | 5/2011 |
| WO | WO-2011/104671 A1 | 9/2011 |
| WO | WO-2012/125724 A1 | 9/2012 |
| WO | WO-2012/149334 A2 | 11/2012 |
| WO | WO-2012/162698 A1 | 11/2012 |
| WO | WO-2013/185055 A1 | 12/2013 |
| WO | WO-2014/152157 A2 | 9/2014 |
| WO | WO-2015/143190 A1 | 9/2015 |
| WO | WO-2016/011265 A1 | 1/2016 |
| WO | WO-2016/145186 A1 | 9/2016 |

OTHER PUBLICATIONS

Cerami et al., "The cBio cancer genomics portal: an open platform for exploring multidimensional cancer genomics data," Cancer Discov. 2(5):401-4 (2012).
Cho et al., "An unnatural biopolymer," Science. 261(5126):1303-1305 (1993).
Davis et al., "RAC1P29S is a spontaneously activating cancer-associated GTPase," Proc Natl Acad Sci U.S.A. 110(3):912-7 (2013).
Dontu et al., "In vitro propagation and transcriptional profiling of human mammary stem/progenitor cells," Genes Dev. 17(10):1253-70 (2003).
Elenbaas et al., "Human breast cancer cells generated by oncogenic transformation of primary mammary epithelial cells," Genes Dev. 15(1):50-65 (2001).
Erb et al., "Recursive deconvolution of combinatorial chemical libraries," Proc Natl Acad Sci U S A. 91(24):11422-11426 (1994).
Esnault et al., "Pin1 modulates the type 1 immune response," PLoS One. 2(2):e226 (2007) (9 pages).
Extended European Search Report for European Patent Application No. 13800857.8, dated Dec. 1, 2015 (7 pages).
Forbes et al., "COSMIC: mining complete cancer genomes in the Catalogue of Somatic Mutations in Cancer," Nucleic Acids Res. 39:D945-50 (2011).
Gianni et al., "Inhibition of the peptidyl-prolyl-isomerase Pin1 enhances the responses of acute myeloid leukemia cells to retinoic acid via stabilization of RARalpha and PML-RARalpha," Cancer Res. 69(3):1016-26 (2009).
Ginestier et al., "Distinct and complementary information provided by use of tissue and DNA microarrays in the study of breast tumor markers," Am J Pathol. 161(4):1223-33 (2002).
International Preliminary Report on Patentability for International Application No. PCT/US2015/040771, dated Jan. 17, 2017 (9 pages).
International Preliminary Report on Patentability for International Patent Application No. PCT/US2015/021522, dated Sep. 21, 2016 (8 pages).
International Search Report and Written Opinion for International Application No. PCT/US13/44747, dated Nov. 12, 2013 (18 pages).
International Search Report and Written Opinion for International Application No. PCT/US14/27017, dated Oct. 28, 2014 (19 pages).
International Search Report and Written Opinion for International Application No. PCT/US15/21522, dated Aug. 10, 2015 (19 pages).
International Search Report and Written Opinion for International Application No. PCT/US15/40771, dated Jun. 30, 2016 (13 pages).
International Search Report and Written Opinion for International Application No. PCT/US16/21759, dated Aug. 12, 2016 (18 pages).
International Search Report and Written Opinion for International Application No. PCT/US2012/029077, dated Jul. 18, 2012 (8 pages).
International Search Report for International Application No. PCT/US2012/039850, dated Oct. 3, 2012 (3 pages).
Jeong et al., "Novel role of Pin1 induction in type II collagen-mediated rheumatoid arthritis," J Immunol. 183(10):6689-97 (2009).
Kao et al., "Correlation of microarray-based breast cancer molecular subtypes and clinical outcomes: implications for treatment optimization," BMC Cancer. 11:143 (2011) (15 pages).
Keller et al., "Defining the cellular precursors to human breast cancer," Proc Natl Acad Sci U.S.A. 109(8):2772-7 (2012).
Kunju et al., "EZH2 and ALDH-1 mark breast epithelium at risk for breast cancer development," Mod Pathol. 24(6):786-93 (2011).
Lam et al., "Prolyl isomerase Pin1 is highly expressed in Her2-positive breast cancer and regulates erbB2 protein stability," Mol Cancer 7(91):1-12 (2008).
Lee et al., "Death-associated protein kinase 1 phosphorylates Pin1 and inhibits its prolyl isomerase activity and cellular function," Mol Cell. 42(2):147-59 (2011).
Liou et al., "Loss of Pin1 function in the mouse causes phenotypes resembling cyclin D1-null phenotypes," Proc Natl Acad Sci U.S.A. 99(3):1335-40 (2002).
Luo et al., "Prolyl isomerase Pin1 acts downstream of miR200c to promote cancer stem-like cell traits in breast cancer," Cancer Res. 74(13):3603-16 (2014).
Ma et al., "A functional polymorphism in PIN1 that prevents its suppression by AP4 is associated with delayed onset of Alzheimer's disease," available in PMC Apr. 1, 2013, published in final edited form as: Neurobiol Aging. 33(4):804-13 (2012) (18 pages).
Mani et al., "The epithelial-mesenchymal transition generates cells with properties of stem cells," Cell 133: 704-715 (2008).

(56) References Cited

OTHER PUBLICATIONS

Mori et al., "A dual inhibitor against prolyl isomerase Pin1 and cyclophilin discovered by a novel real-time fluorescence detection method," Biochem Biophys Res Commun. 406(3):439-43 (2011).

Nagaoka et al., "Possible involvement of peptidylprolyl isomerase Pin1 in rheumatoid arthritis," Pathol Int. 61(2):59-66 (2011).

Office Action for U.S. Appl. No. 14/334,052, dated Nov. 20, 2014 (21 pages).

Parker et al., "Supervised risk predictor of breast cancer based on intrinsic subtypes," J. Clin. Oncol. 27(8):1160-7 (2009).

Ranganathan et al., "Structural and functional analysis of the mitotic rotamase Pin1 suggests substrate recognition is phosphorylation dependent," Cell. 89(6):875-86 (1997).

Ryo et al., "Pin1 regulates turnover and subcellular localization of beta-catenin by inhibiting its interaction with APC," Nat Cell Biol. 3(9):793-801 (2001).

Schmidt et al., "The humoral immune system has a key prognostic impact in node-negative breast cancer," Cancer Res. 68(13):5405-13 (2008).

Tun-Kyi et al., "Essential role for the prolyl isomerase Pin1 in Toll-like receptor signaling and type I interferon-mediated immunity," Nat Immunol. 12(8):733-41 (2011) (27 pages).

Written Opinion of the International Searching Authority for International Application No. PCT/US2012/039850, dated Oct. 3, 2012 (5 pages).

Wulf et al., "Pin1 is overexpressed in breast cancer and cooperates with Ras signaling in increasing the transcriptional activity of c-Jun towards cyclin D1," EMBO J. 20(13):3459-72 (2001).

International Preliminary Report on Patentability for International Patent Application No. PCT/US2013/044747, dated Dec. 9, 2014 (8 pages).

Notice of Reasons for Rejection and English Translation for Japanese Patent Application No. 2015-516246, dated Mar. 28, 2017 (12 pages).

* cited by examiner

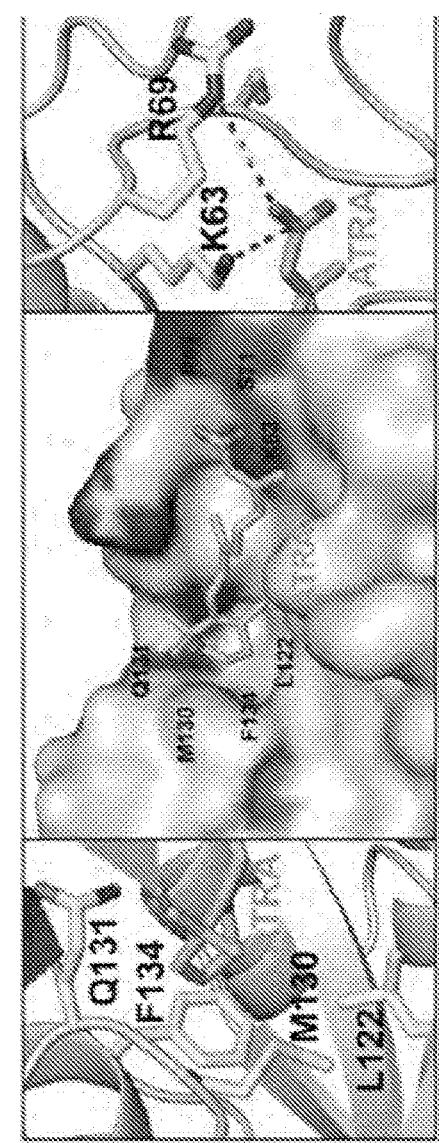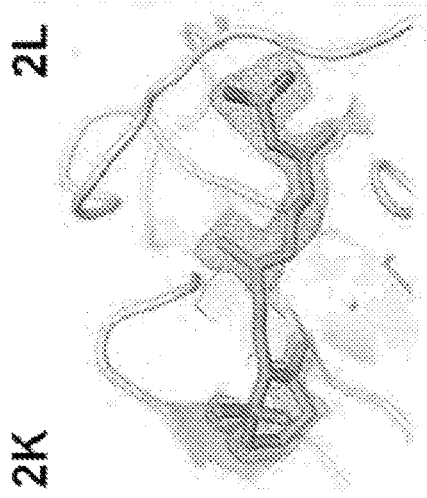
Figure 2

Residues close to cyclohexenyl moiety
5A within 4 Angstroms
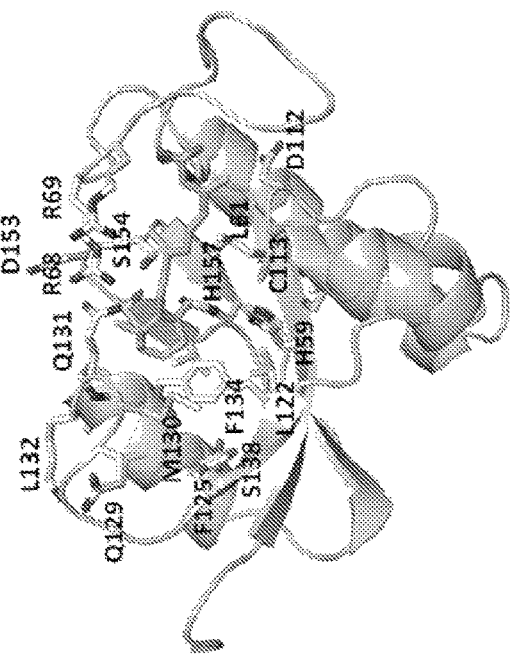
H59
R68
L122
M130
Q131
F134
S154
H157
5B within 8 Angstroms
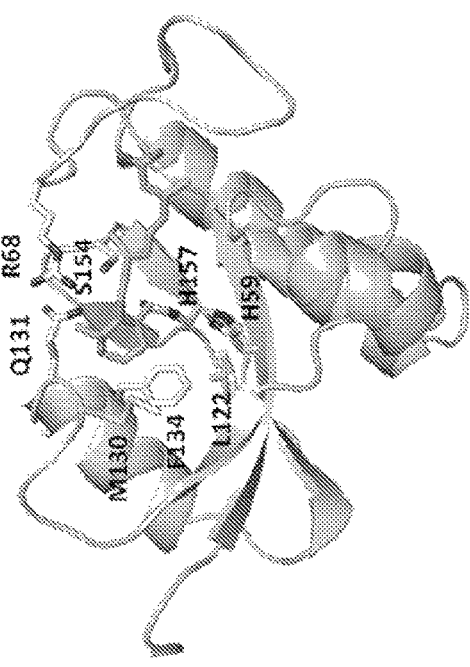
| | | |
|---|---|---|
| H59 | S115 | F134 | I156 |
| L60 | L122 | E135 | H157 |
| L61 | F125 | S138 | I159 |
| K63 | Q129 | V150 | |
| R68 | M130 | T152 | |
| R69 | Q131 | D153 | |
| D112 | K132 | S154 | |
| C113 | P133 | G155 | |
Figure 5

Residues close to double bonds
6A within 4 Angstroms
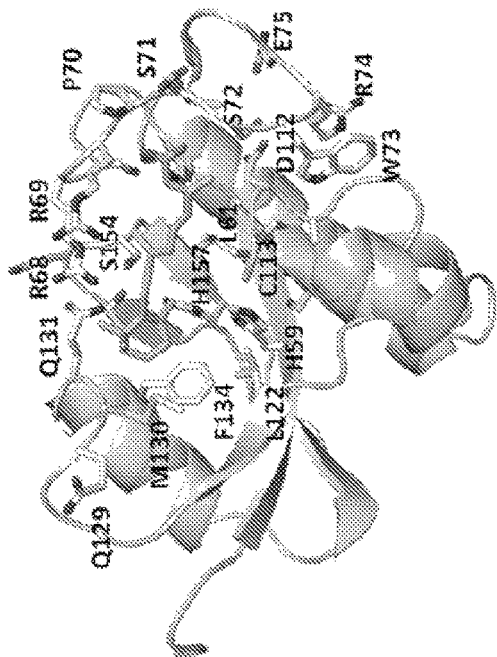
K63
R68
R69
S71
S72
D112
S154
6B within 8 Angstroms
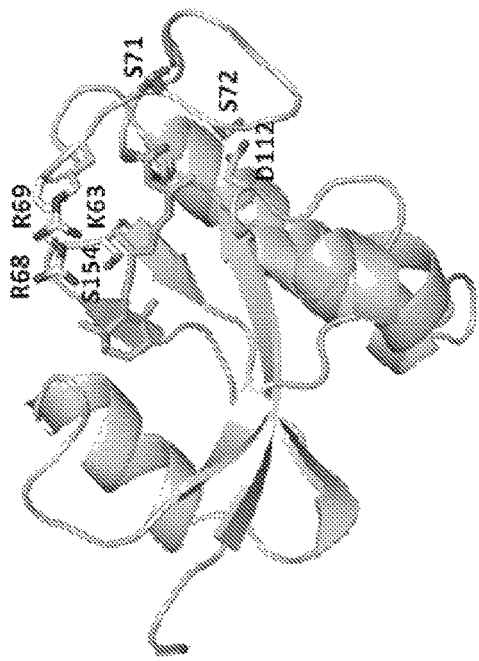
| | | |
|---|---|---|
| H59 | S72 | S114 | T152 |
| L61 | W73 | S115 | D153 |
| K63 | R74 | L122 | S154 |
| S67 | Q75 | F125 | G155 |
| R68 | I78 | Q129 | H157 |
| R69 | S111 | M130 | |
| P70 | D112 | Q131 | |
| S71 | C113 | F134 | |
Figure 6

Residues close to carboxylic group
7A within 4 Angstroms
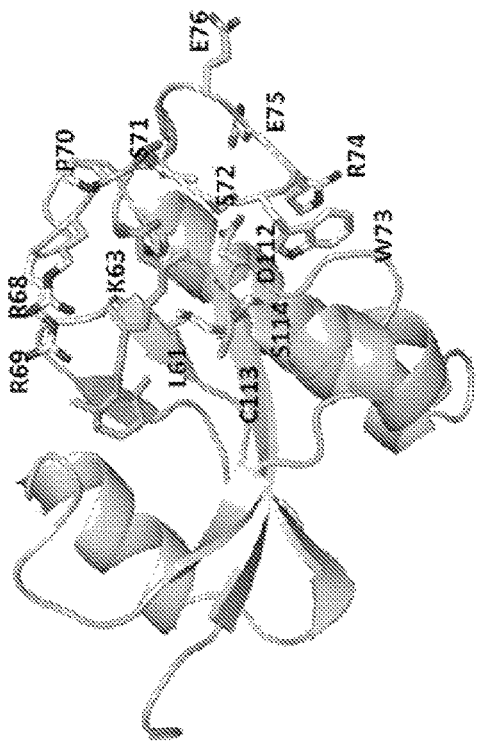
7B within 8 Angstroms
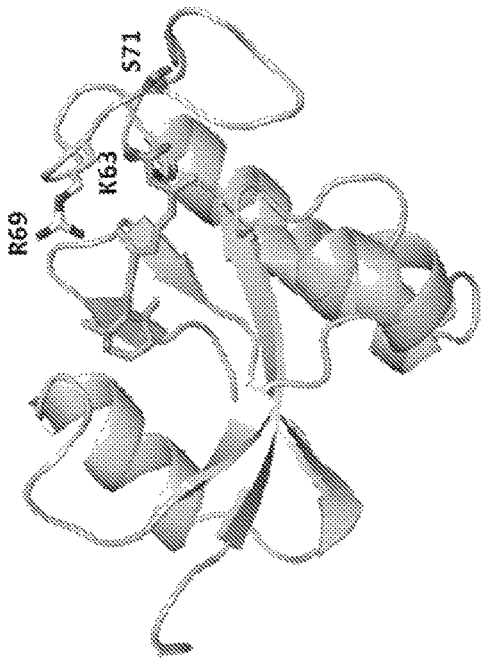
K63
R69
S71
| | | | |
|---|---|---|---|
| H59 | S71 | D112 | Q131 | D153 |
| L60 | S72 | C113 | K132 | S154 |
| L61 | W73 | S114 | P133 | G155 |
| K63 | R74 | S115 | F134 | I156 |
| S67 | Q75 | L122 | E135 | H157 |
| R68 | E76 | F125 | S138 | I159 |
| R69 | I78 | Q129 | V150 | |
| P70 | S111 | M130 | T152 | |
Figure 7

Potential pocket P1 – within 8 Angstroms
(extended from L122)
Important residues:
| | | |
|---|---|---|
| C57 | S114 | R119 | A124 |
| H59 | S115 | G120 | F125 |
| L61 | A116 | D121 | Q129 |
| D112 | K117 | L122 | M130 |
| C113 | A118 | G123 | F134 |
10A
10B
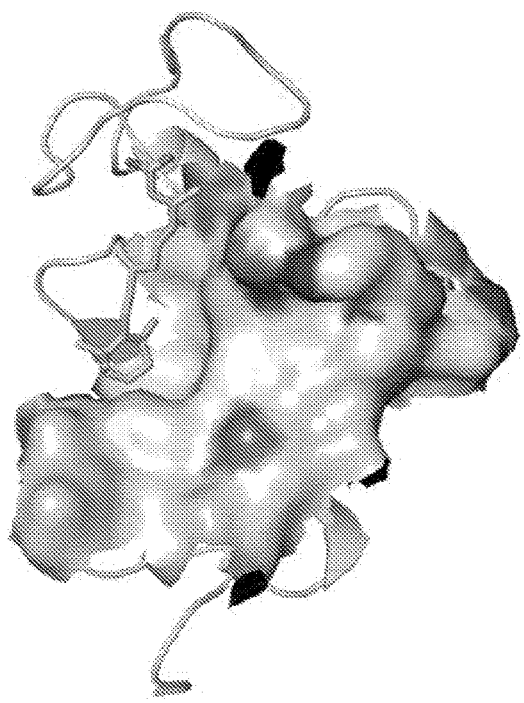
Interface surface
10C
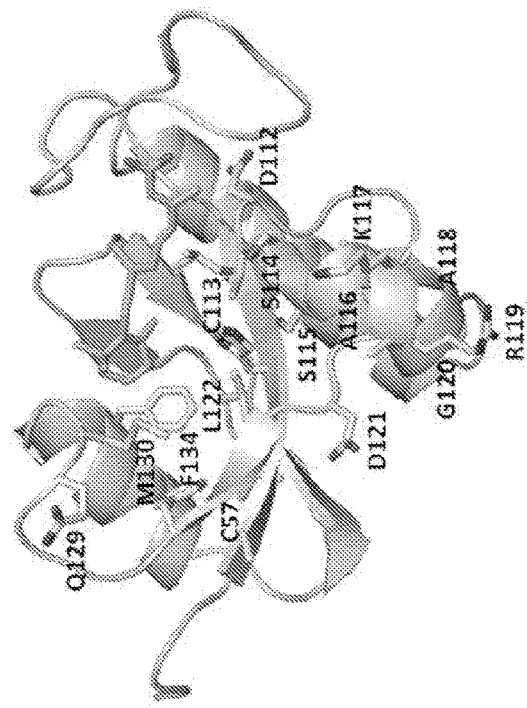
Residue sidechain distribution
Figure 10

11A
Potential pocket P2 - within 4 Angstroms
(extended from hexa-carbon moiety of ATRA)
Important residues:
H59   Q131
R68   F134
L122  S154
M130  H157
11B
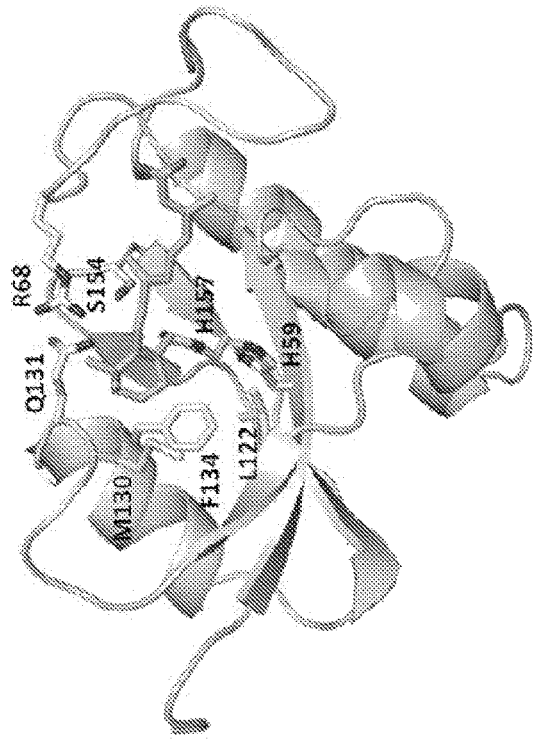
Interface surface
11C
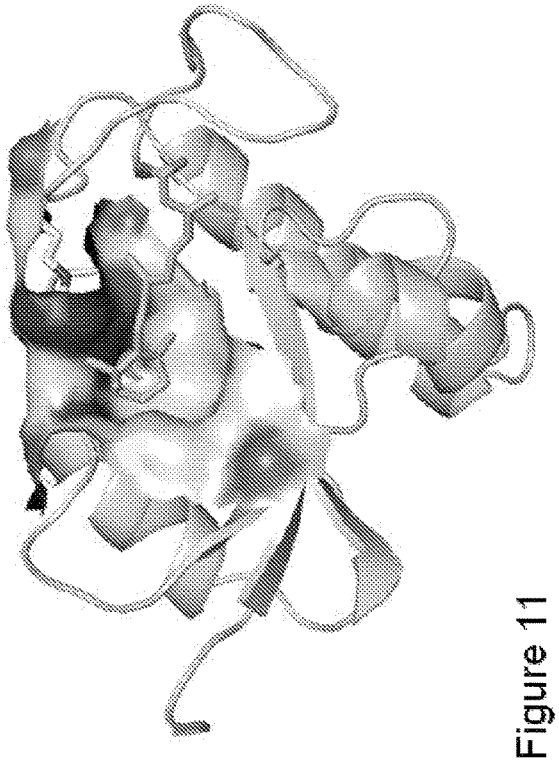
Residue sidechain distribution
Figure 11

12A
Potential pocket P2 – within 8 Angstroms
(extended from hexa-carbon moiety of ATRA)
Important residues:
| | | | | | |
|---|---|---|---|---|---|
| H59 | K63 | C113 | Q129 | P133 | V150 | G155 |
| L60 | R68 | S115 | M130 | F134 | T152 | I156 |
| L61 | R69 | L122 | Q131 | E135 | D153 | H157 |
| V62 | D112 | F125 | K132 | S138 | S154 | I159 |
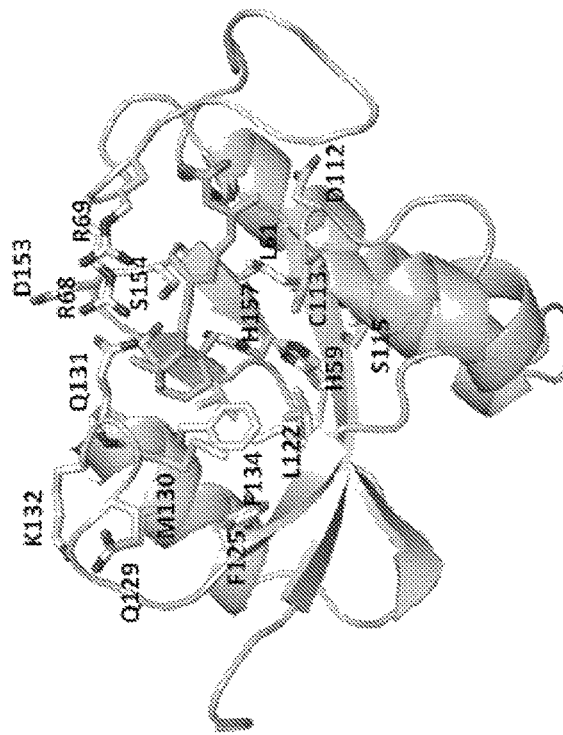
12C
Residue sidechain distribution
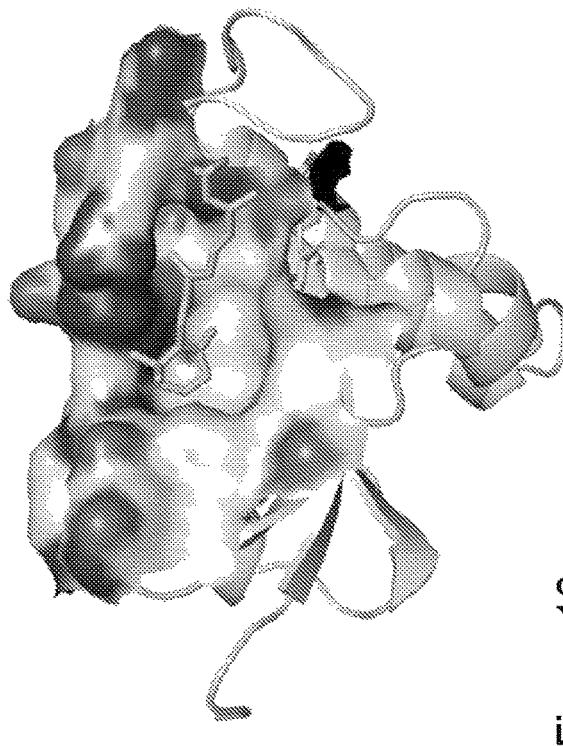
12B
Interface surface
Figure 12

Potential pocket P3 - within 4 Angstroms
(extended from R68, M130 and Q131)
important residues:
R68  Q131
Q129 K132
M130 D153
13A
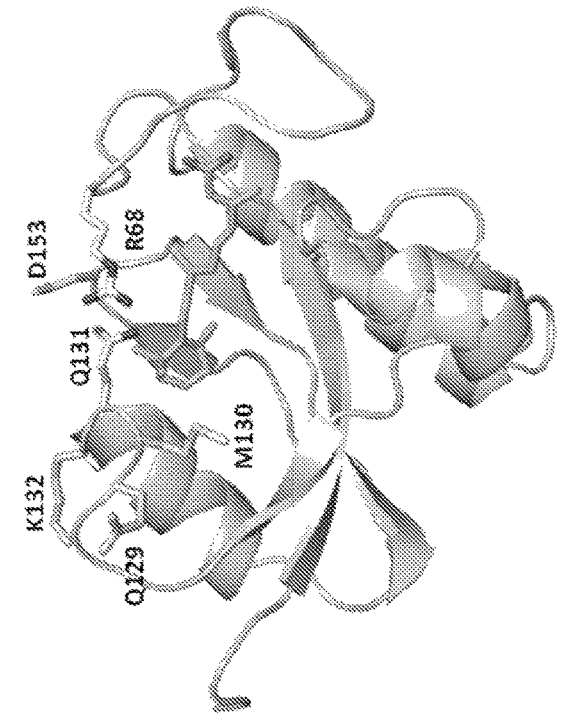
13C  Residue sidechain distribution
13B  Interface surface
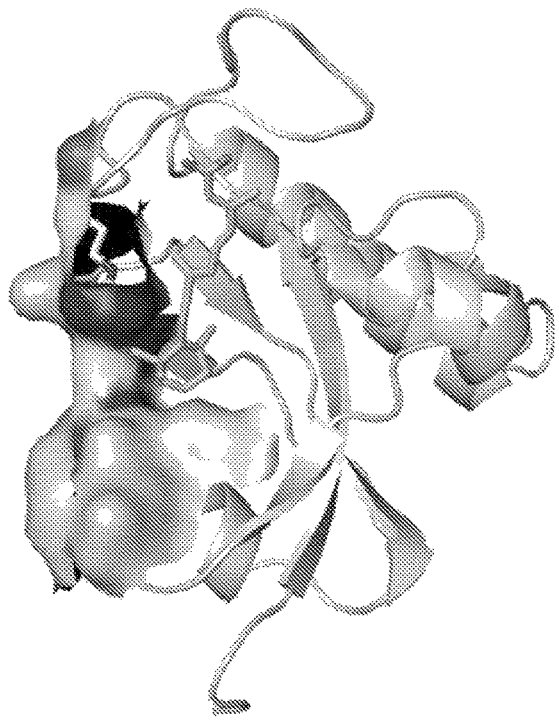
Figure 13

16A
Potential pocket P4 – within 8 Angstroms
(extended from K63, R68, R69 and S154)
Important residues:
| | | | |
|---|---|---|---|
| L61 | Q66 | P70 | D112 | S154 |
| V62 | S67 | S71 | Q131 | G155 |
| K63 | R68 | S72 | T152 | I156 |
| H64 | R69 | I78 | D153 | H157 |
16B
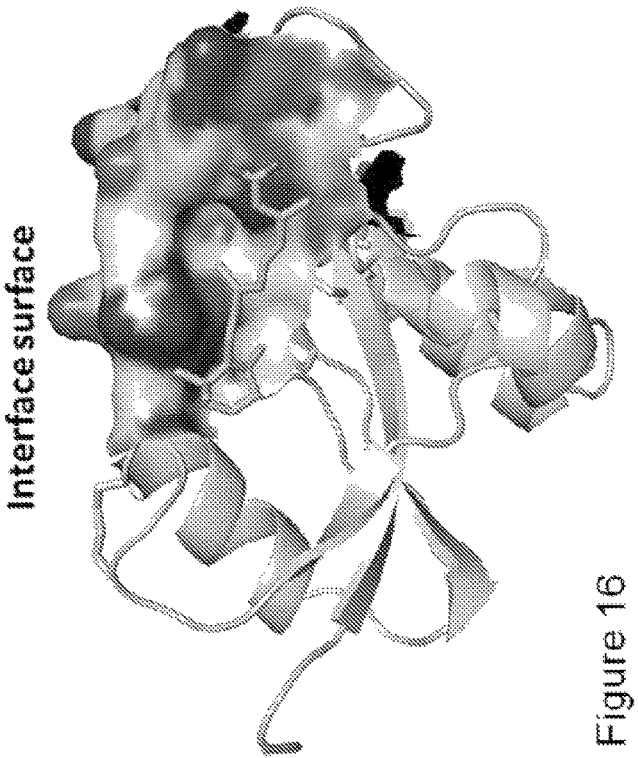
Interface surface
16C
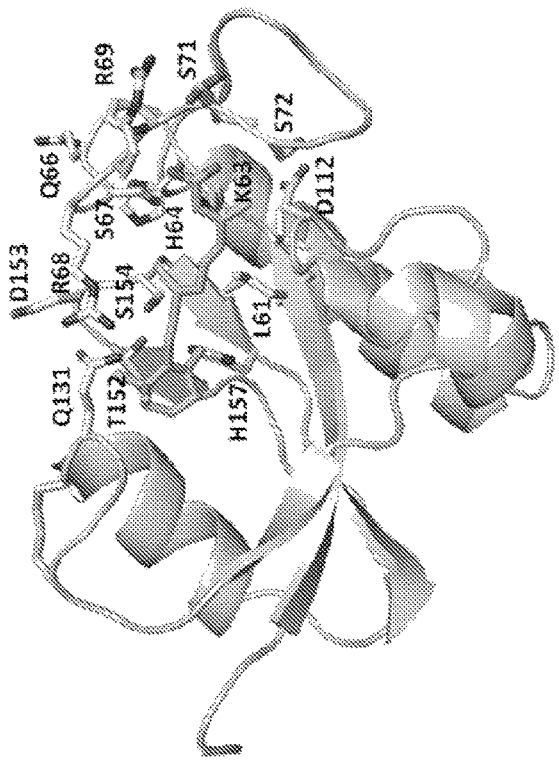
Residue sidechain distribution
Figure 16

17A
Potential pocket P5 - within 4 Angstroms
(extended from S71)
Important residues:
S71  Q75
S72  E76
W73  Q77
17B
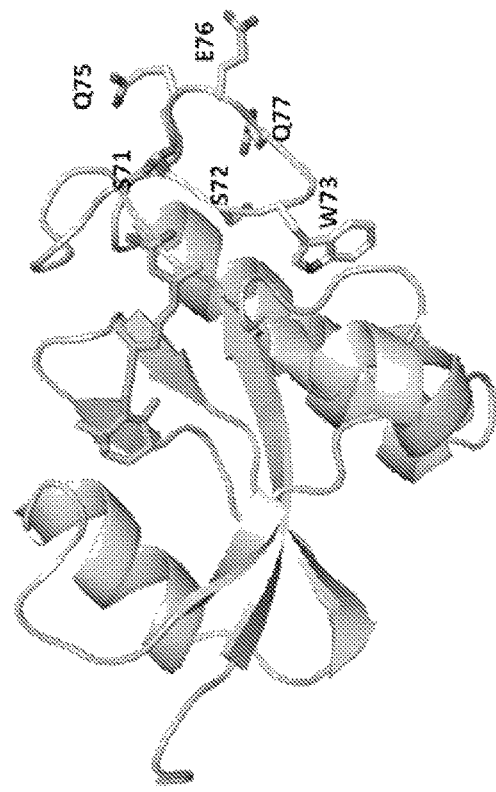
Interface surface
17C
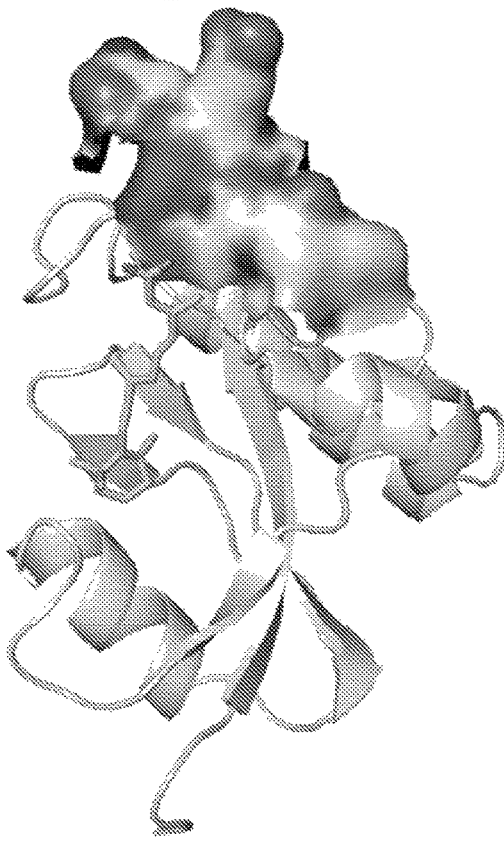
Residue sidechain distribution
Figure 17

18A
Potential pocket P5 - within 8 Angstroms
(extended from S71)
Important residues:
| K63 | S72 | E76 | D112 |
|-----|-----|-----|------|
| R69 | W73 | Q77 | S114 |
| P70 | R74 | I78 | |
| S71 | Q75 | T79 | |
18B
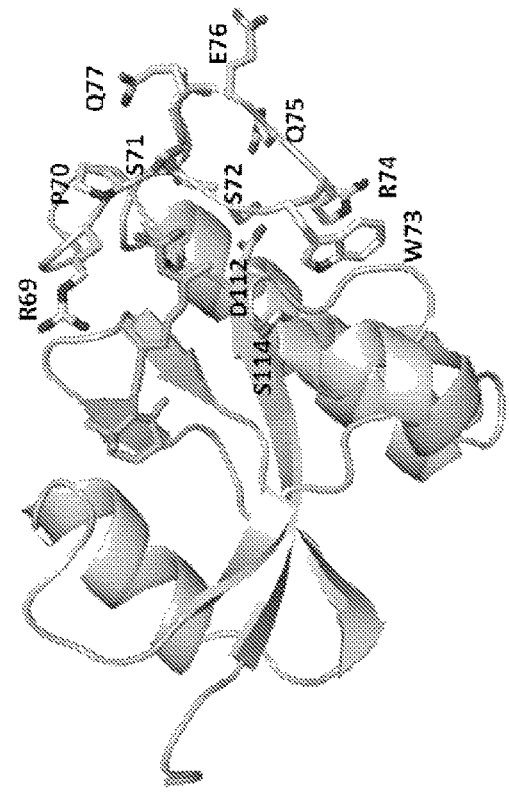
Interface surface
18C
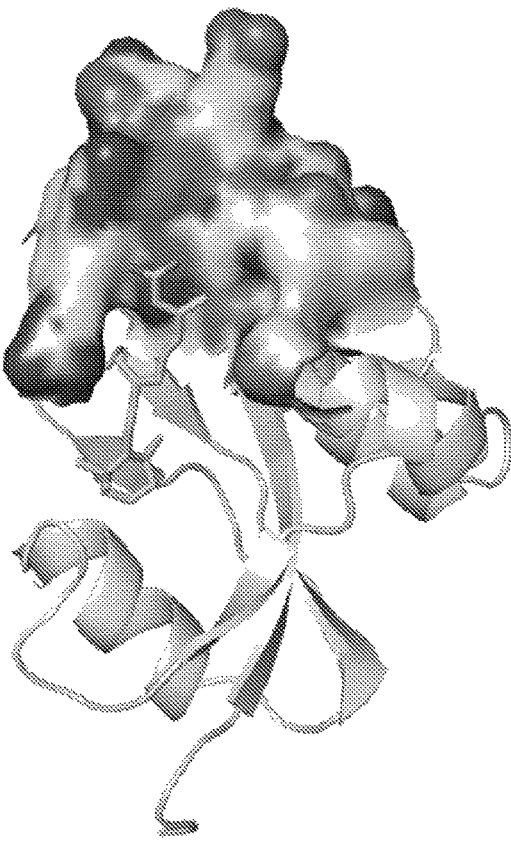
Residue sidechain distribution
Figure 18

Potential pocket P6 - within 4 Angstroms
(extended from S71)
Important residues:
S71  D112
S72  C113
W73  S114
19A
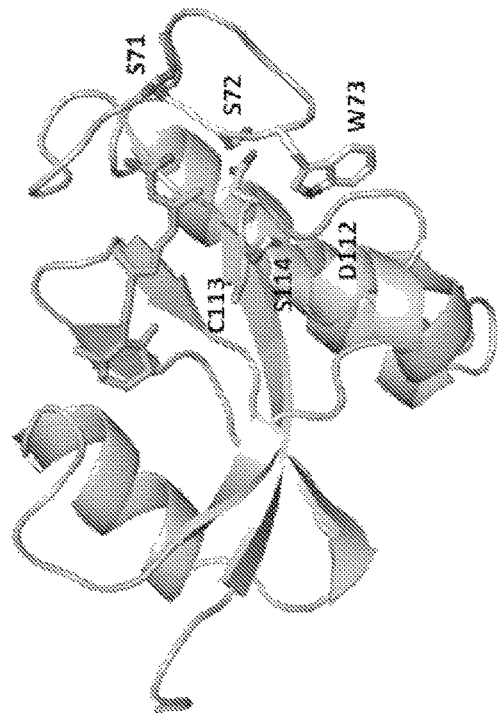
19C Residue sidechain distribution
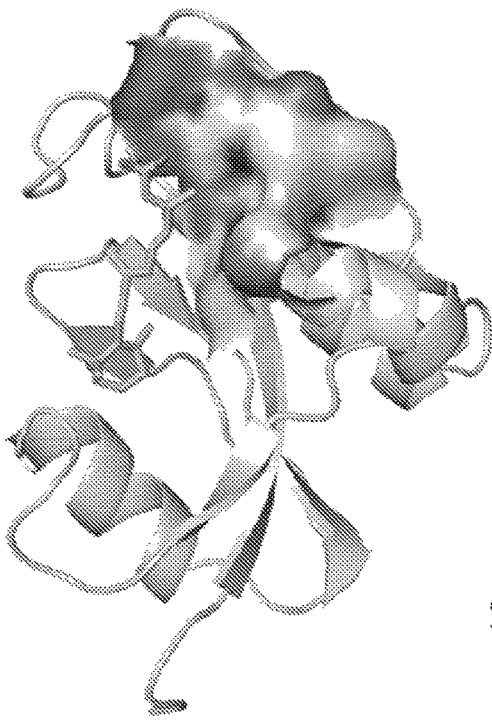
19B Interface surface
Figure 19

Potential pocket P6 - within 8 Angstroms
(extended from S71)
20A
Important residues:
| | | | | |
|---|---|---|---|---|
| S71 | E104 | S108 | D112 | A116 | G120 |
| S72 | S105 | Q109 | C113 | K117 |
| W73 | L106 | F110 | S114 | A118 |
| R74 | A107 | S111 | S115 | R119 |
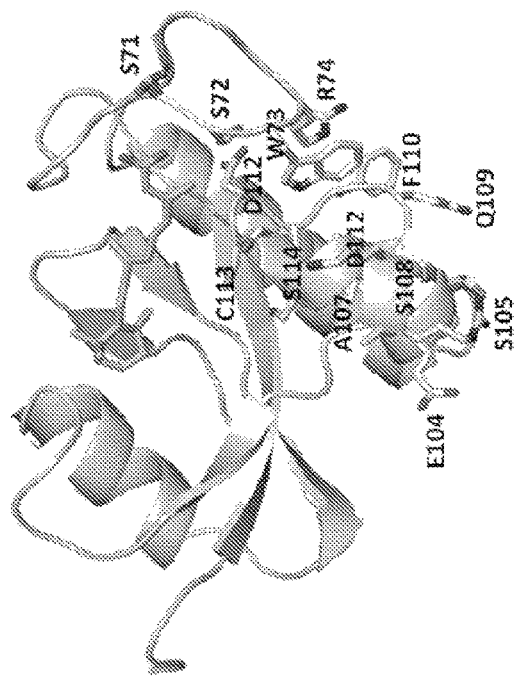
20C
Residue sidechain distribution
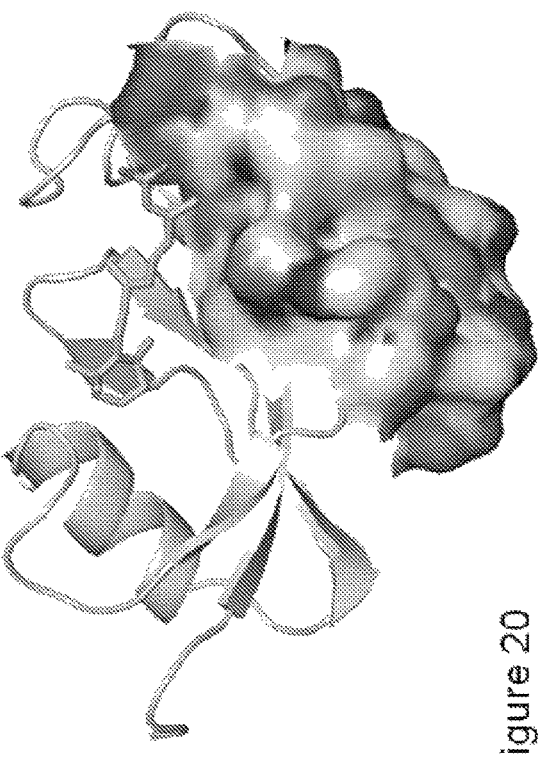
20B
Interface surface
Figure 20

23A

| Retinoid | Carboxylic group | % to ATRA |
|---|---|---|
| ATRA | Yes | 100 |
| 13cRA | Yes | 39 |
| Salicylic acid | Yes | 0 |
| Retinol | No | 0 |
| Retinyl acetate | No | 0 |
| Retinal | No | 0 |
| β-carotene | No | 0 |

| Next generation ATRA | Carboxylic group | % to ATRA |
|---|---|---|
| Acitretin | Yes | 64 |
| Fenretinide | No | 25 |
| Bexarotene | Yes | 28 |
| Tamibarotene | Yes | 63 |

| ATRA analog | Carboxylic group | % to ATRA |
|---|---|---|
| Indo-3-acetic acid | Yes | 0 |
| Pravastatin | Yes | 0 |

Figure 32

| | | | | |
|---|---|---|---|---|
| 47 | M | 82 | Bone marrow | APL |
| 48 | F | 78 | Bone marrow | APL |
| 49 | M | 22 | Bone marrow | APL |
| 50 | M | 31 | Bone marrow | Remission |
| 51 | F | 3 | Bone marrow | Remission |
| 52 | M | 7 | Bone marrow | Remission |
| 53 | M | 11 | Bone marrow | Remission |
| 54 | F | 19 | Bone marrow | Remission |
| 55 | F | 57 | Bone marrow | Remission |
| 56 | M | 58 | Bone marrow | Remission |
| 57 | M | 34 | Bone marrow | Remission |
| 58 | M | 31 | Bone marrow | Remission |
| 59 | M | 12 | Bone marrow | Remission |
| 60 | M | 10 | Bone marrow | Remission |
| 61 | M | 20 | Bone marrow | Remission |
| 62 | M | 50 | Bone marrow | Remission |
| 63 | M | 39 | Bone marrow | Remission |
| 64 | M | 54 | Bone marrow | Remission |
| 65 | F | 27 | Bone marrow | Remission |
| 66 | F | 51 | Bone marrow | Remission |

Figure 32 (cont.)

| No. | Sex | Age | Organ | Pathology diagnosis | Grade | Stage | TNM | ER | PR | HER |
|---|---|---|---|---|---|---|---|---|---|---|
| 1 | F | 40 | Breast | Invasive ductal carcinoma | 1 | IIB | T2N1M0 | - | - | - |
| 2 | F | 45 | Breast | Invasive ductal carcinoma | 1 | IIB | T3N0M0 | - | - | - |
| 3 | F | 39 | Breast | Invasive ductal carcinoma | 1 | IIA | T2N0M0 | - | - | - |
| 4 | F | 32 | Breast | Invasive ductal carcinoma | 1 | IIB | T2N1M0 | - | - | - |
| 5 | F | 68 | Breast | Invasive ductal carcinoma | 2 | IB | T1N1M0 | - | - | - |
| 6 | F | 45 | Breast | Invasive ductal carcinoma | 1 | IIA | T1N1M0 | - | - | - |
| 7 | F | 50 | Breast | Invasive ductal carcinoma | 2 | IIB | T2N1M0 | - | - | - |
| 8 | F | 54 | Breast | Invasive ductal carcinoma | 2 | IIIA | T2N2M0 | - | - | - |
| 9 | F | 37 | Breast | Invasive ductal carcinoma | 2 | IIB | T2N1M0 | - | - | - |
| 10 | F | 39 | Breast | Invasive ductal carcinoma | 2 | IIB | T4N2M0 | - | - | - |
| 11 | F | 52 | Breast | Invasive ductal carcinoma | 2 | IV | T3NxM1 | - | - | - |
| 12 | F | 58 | Breast | Invasive ductal carcinoma | 2 | IIB | T2N1M0 | - | - | - |
| 13 | F | 56 | Breast | Invasive ductal carcinoma | 2 | I | T1N0M0 | - | - | - |
| 14 | F | 45 | Breast | Invasive ductal carcinoma | 2 | IIA | T2N0M0 | - | - | 2+ |
| 15 | F | 60 | Breast | Invasive ductal carcinoma | 2 | IIIA | T3N1M0 | - | - | - |
| 16 | F | 66 | Breast | Invasive ductal carcinoma | 2 | IIIB | T4N1M0 | - | - | - |
| 17 | F | 32 | Breast | Invasive ductal carcinoma | 2 | IIIA | T2N2M0 | + | - | - |
| 18 | F | 41 | Breast | Invasive ductal carcinoma | 2 | IIB | T2N1M0 | - | - | - |
| 19 | F | 51 | Breast | Invasive ductal carcinoma | 2 | IIA | T2N0M0 | - | - | 3+ |
| 20 | F | 42 | Breast | Invasive ductal carcinoma | 2 | IIB | T2N1M0 | - | - | - |
| 21 | F | 79 | Breast | Invasive ductal carcinoma | 2 | IIB | T2N1M0 | - | - | - |
| 22 | F | 72 | Breast | Invasive ductal carcinoma (chronic mastitis) | - | IIB | T2N1M0 | - | - | - |
| 23 | F | 50 | Breast | Invasive ductal carcinoma | 2 | IIB | T2N1M0 | - | - | - |
| 24 | F | 68 | Breast | Invasive ductal carcinoma | 2 | IIA | T2N0M0 | - | - | - |
| 25 | F | 37 | Breast | Invasive ductal carcinoma | 2 | IIIA | T3N1M0 | - | - | - |
| 26 | F | 40 | Breast | Invasive ductal carcinoma | 2 | IIIB | T4N1M0 | - | - | - |
| 27 | F | 46 | Breast | Invasive ductal carcinoma | 2 | IIIA | T3N1M0 | - | - | - |
| 28 | F | 47 | Breast | Invasive ductal carcinoma | 3 | IIB | T2N1M0 | - | - | - |
| 29 | F | 40 | Breast | Invasive ductal carcinoma | 3 | IIB | T2N1M0 | - | - | - |
| 30 | F | 44 | Breast | Invasive ductal carcinoma | 3 | IIA | T2N0M0 | - | - | - |
| 31 | F | 47 | Breast | Invasive ductal carcinoma | 3 | IIIB | T4N0M0 | - | - | - |
| 32 | F | 57 | Breast | Invasive ductal carcinoma | 2 | IIA | T2N0M0 | - | - | - |
| 33 | F | 34 | Breast | Invasive ductal carcinoma | 3 | IIA | T2N0M0 | - | - | - |
| 34 | F | 51 | Breast | Invasive ductal carcinoma | 3 | IIB | T3N0M0 | - | - | - |
| 35 | F | 75 | Breast | Invasive ductal carcinoma | 3 | IIB | T2N1M0 | - | - | - |
| 36 | F | 48 | Breast | Invasive ductal carcinoma | 3 | IIB | T2N1M0 | - | - | - |
| 37 | F | 49 | Breast | Invasive ductal carcinoma | 3 | IIIA | T3N1M0 | - | - | - |
| 38 | F | 49 | Breast | Invasive ductal carcinoma | 3 | IIIB | T4N1M0 | - | - | - |
| 39 | F | 46 | Breast | Invasive ductal carcinoma | - | IIA | T2N0M0 | - | - | - |
| 40 | F | 45 | Breast | lobular ductal mixed carcinoma | 3 | IIA | T2N0M0 | - | - | - |
| 41 | F | 55 | Breast | lobular ductal mixed carcinoma | - | IIB | T2N1M0 | - | - | - |
| 42 | F | 34 | Breast | lobular ductal mixed carcinoma | - | IIB | T2N1M0 | + | - | - |
| 43 | F | 50 | Breast | Invasive lobular carcinoma | 3 | IIB | T2N1M0 | - | - | - |
| 44 | F | 74 | Breast | Invasive lobular carcinoma | - | IIB | T2N1M0 | - | - | - |
| 45 | F | 45 | Breast | Invasive lobular carcinoma | - | IIB | T2N1M0 | - | - | - |
| 46 | F | 51 | Breast | Medillary carcinoma | - | IIA | T2N0M0 | - | - | - |
| 47 | F | 45 | Breast | Medillary carcinoma | - | IIA | T2N0M0 | - | - | - |

Figure 35

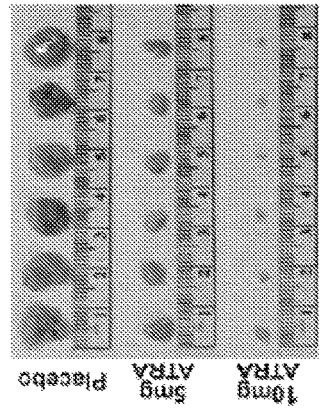
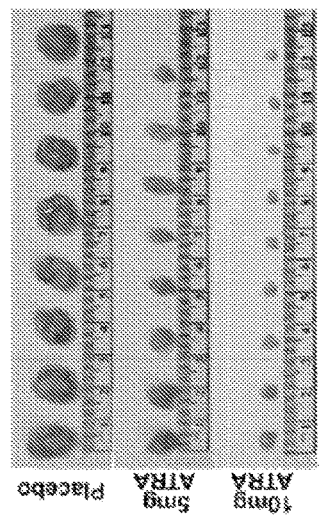
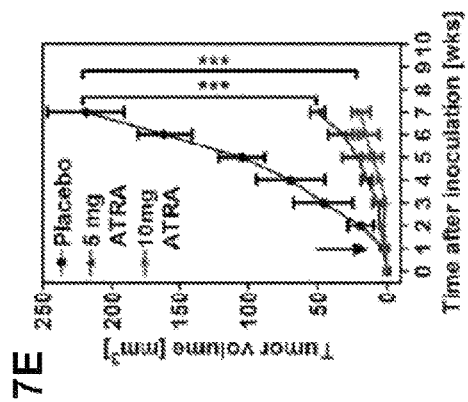
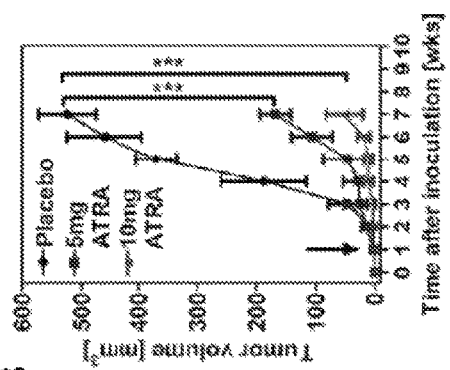
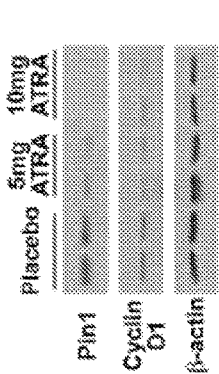
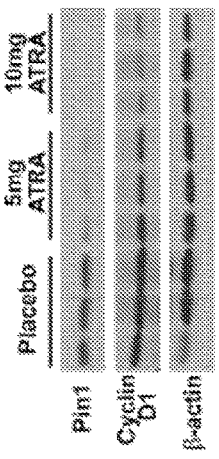
Figure 37

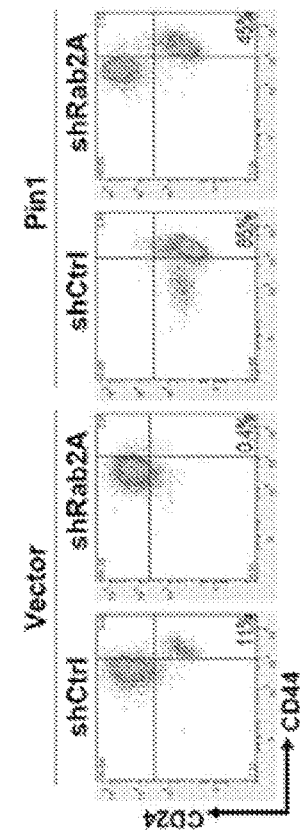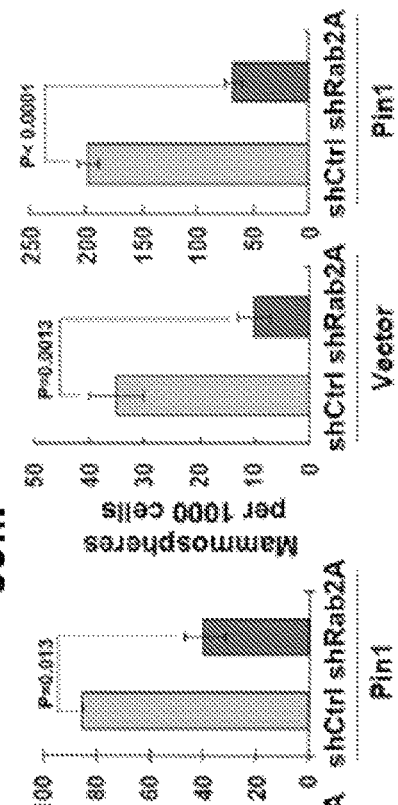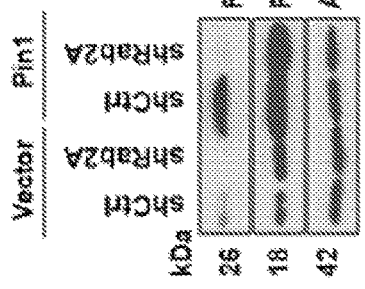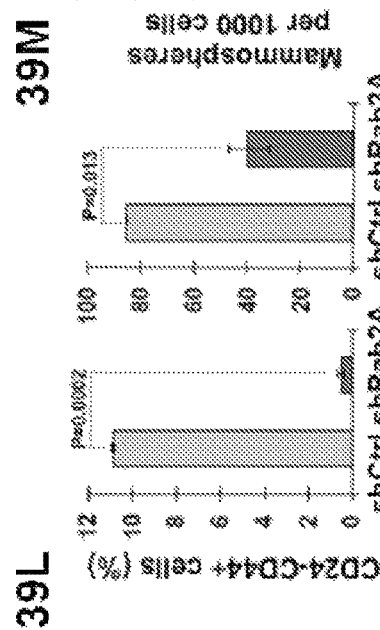
Figure 39

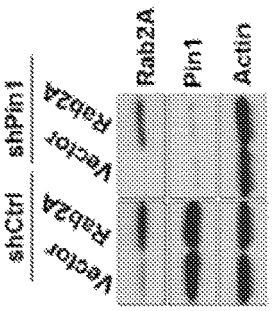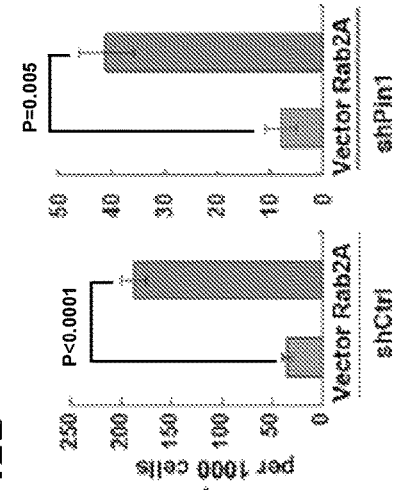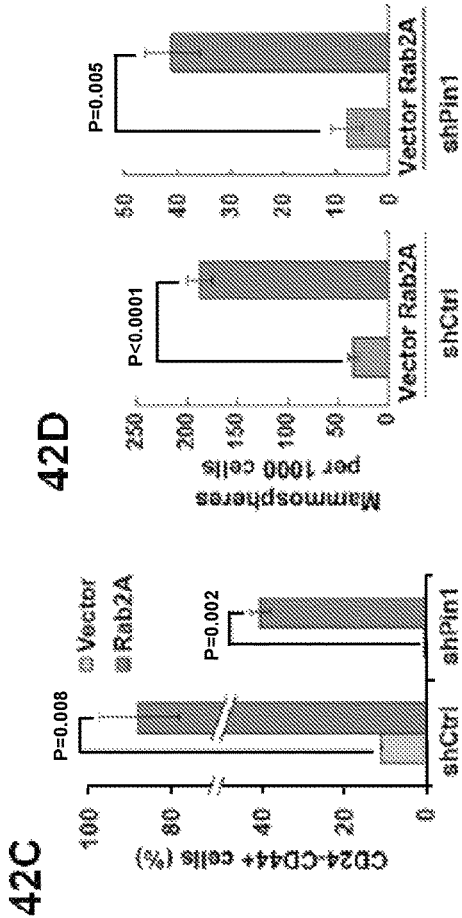
Figure 42

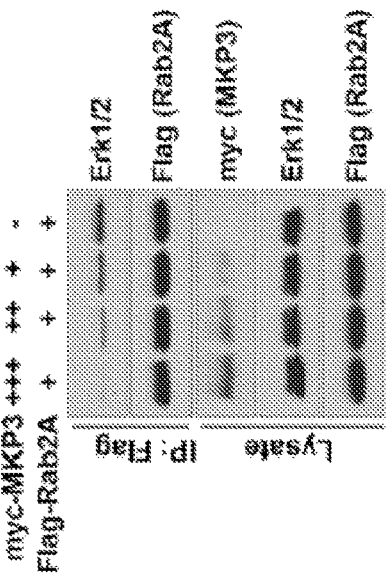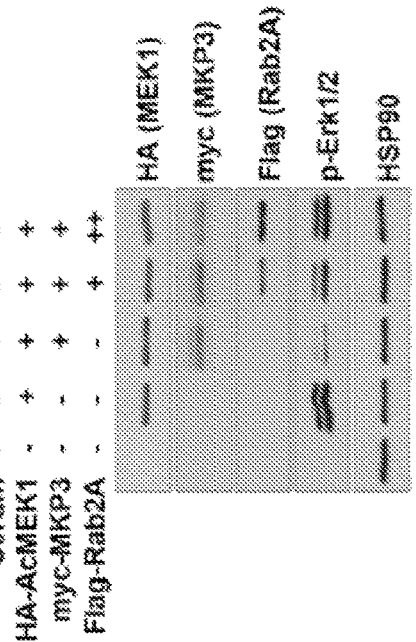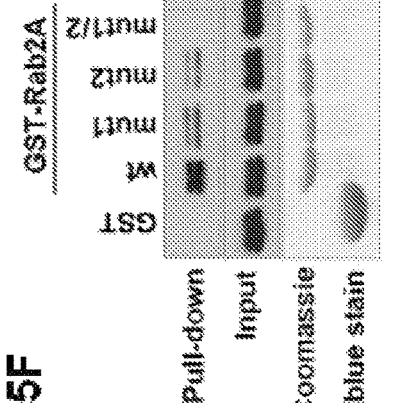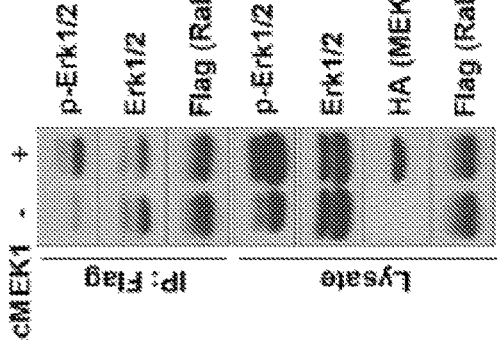
Figure 45

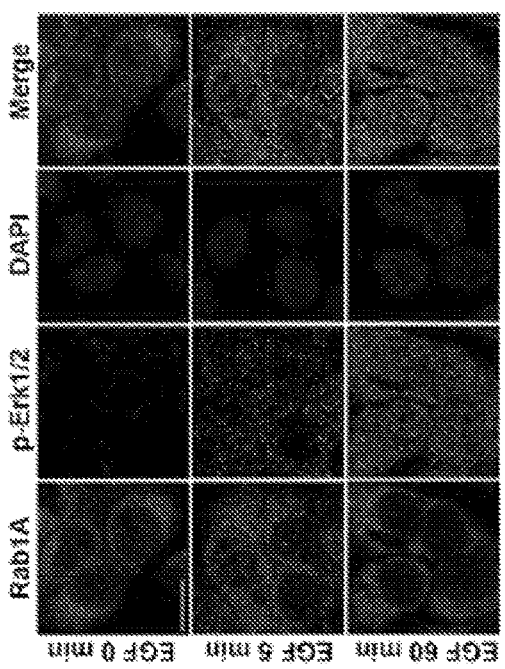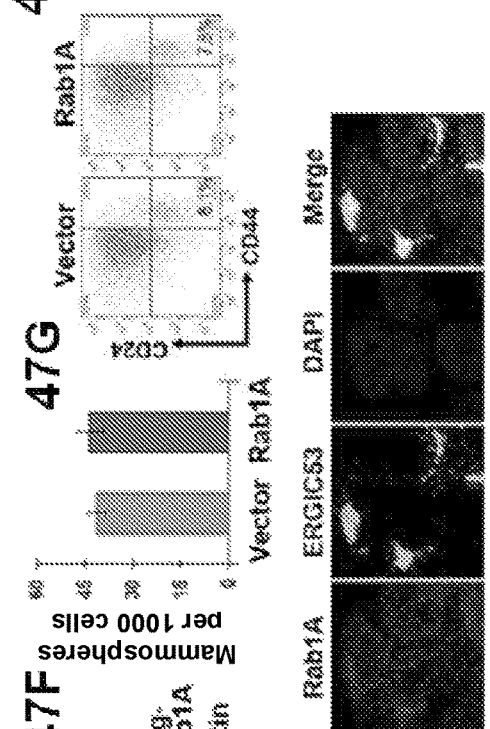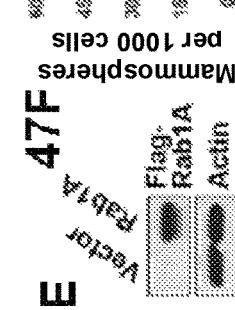
Figure 47

| Case No. | Age | Tumor size (cm) | ER | PR | HER | Grade | Lymph node | Stage | Lin⁻CD24⁻CD44⁺ |
|---|---|---|---|---|---|---|---|---|---|
| 1 | 35 | 3.8×3.0 | (+) | (+) | (-) | III | N1 | II | 1.35% |
| 2 | 44 | 3.6×2.8 | (+) | (-) | (+) | II | N2 | III | 28.61% |
| 3 | 40 | 4.5×2.6 | (-) | (-) | (-) | III | N2 | III | 14.00% |
| 4 | 48 | 3.3×2.3 | (+) | (+) | (+) | III | N1 | II | 5.22% |
| 5 | 42 | 3.6×2.8 | (+) | (-) | (-) | III | N2 | III | 4.61% |
| 6 | 43 | 4.3×2.9 | (+) | (-) | (-) | II | N2 | III | 2.07% |
| 7 | 45 | 3.0×1.8 | (-) | (-) | (-) | II | N1 | II | 1.99% |
| 8 | 40 | 3.9×2.5 | (-) | (-) | (-) | III | N1 | II | 23.54% |

Notes: All eight patients were diagnosed as invasive ductal breast cancer. The tumor size is the original tumor size measured after surgery. ER, Estrogen receptor, PR, progesteron receptor, HER2, Human Epidermal Growth Factor Receptor 2. The hormonal receptor status was determined by the immunohistochemistry, which were done on the paraffin-embedded sections of the primary tumors. The lymph node information is according to the breast cancer TNM staging system. The Lin⁻CD24⁻CD44⁺ cells were isolated for primary breast tumors.

Figure 51

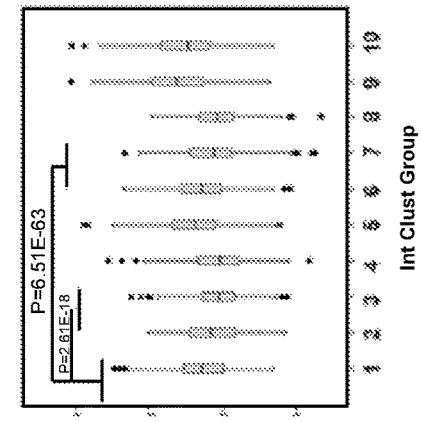
52B
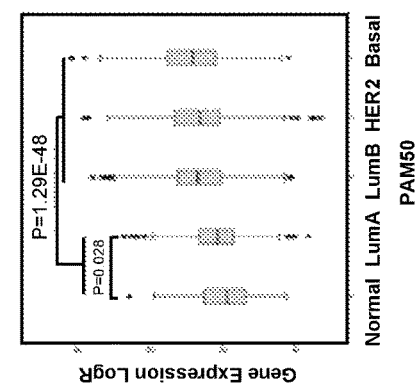
52C
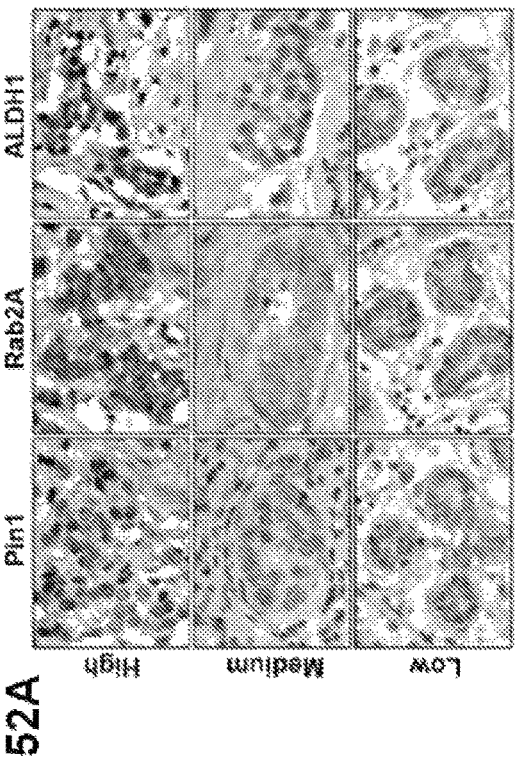
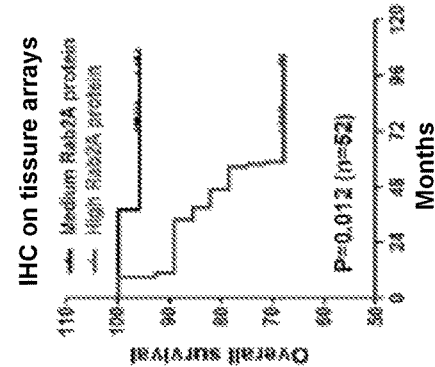
Figure 52

SEQUENCE LISTING

```
<160> NUMBER OF SEQ ID NOS: 66

<210> SEQ ID NO 1
<211> LENGTH: 119
<212> TYPE: PRT
<213> ORGANISM: Homo sapiens

<400> SEQUENCE: 1

Gly Lys Asn Gly Gln Gly Glu Pro Ala Arg Val Arg Cys Ser His Leu
1               5                   10                  15

Leu Val Lys His Ser Gln Ser Arg Pro Ser Ser Trp Arg Gln Glu
            20                  25                  30

Lys Ile Thr Arg Thr Lys Glu Glu Ala Leu Glu Leu Ile Asn Gly Tyr
        35                  40                  45

Ile Gln Lys Ile Lys Ser Gly Glu Glu Asp Phe Glu Ser Leu Ala Ser
    50                  55                  60
```

```
Gln Phe Ser Asp Cys Ser Ser Ala Lys Ala Arg Gly Asp Leu Gly Ala
 65                  70                  75                  80

Phe Ser Arg Gly Gln Met Gln Lys Pro Phe Glu Asp Ala Ser Phe Ala
             85                  90                  95

Leu Arg Thr Gly Glu Met Ser Gly Pro Val Phe Thr Asp Ser Gly Ile
            100                 105                 110

His Ile Ile Leu Arg Thr Glu
        115

<210> SEQ ID NO 2
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is phosphorylated Ser

<400> SEQUENCE: 2

Ala Xaa Pro Phe
1

<210> SEQ ID NO 3
<211> LENGTH: 4
<212> TYPE: PRT
<213> ORGANISM: Artificial Sequence
<220> FEATURE:
<223> OTHER INFORMATION: Synthetic Construct

<400> SEQUENCE: 3

Ala Glu Pro Phe
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Construct

<400> SEQUENCE: 4

Ala Ala Pro Phe
1

<210> SEQ ID NO 5
<211> LENGTH: 21
<212> TYPE: DNA
<213> ORGANISM: Artificial Sequence
<220> FEATURE:
<223> OTHER INFORMATION: Synthetic Construct

<400> SEQUENCE: 5
ccaccgtcac acagtattta t                                           21

<210> SEQ ID NO 6
<211> LENGTH: 21
<212> TYPE: DNA
<213> ORGANISM: Artificial Sequence
<220> FEATURE:
<223> OTHER INFORMATION: Synthetic Construct

<400> SEQUENCE: 6
gctcgaatga taactattga t                                           21
```

<210> SEQ ID NO 7
<211> LENGTH: 21
<212> TYPE: DNA
<213> ORGANISM: Artificial Sequence
<220> FEATURE:
<223> OTHER INFORMATION: Synthetic Construct

<400> SEQUENCE: 7
ccagtgcatg accttactat t                                              21

<210> SEQ ID NO 8
<211> LENGTH: 23
<212> TYPE: DNA
<213> ORGANISM: Artificial Sequence
<220> FEATURE:
<223> OTHER INFORMATION: Synthetic Construct

<400> SEQUENCE: 8
catgagaagt atgacaacag cct                                            23

<210> SEQ ID NO 9
<211> LENGTH: 22
<212> TYPE: DNA
<213> ORGANISM: Artificial Sequence
<220> FEATURE:
<223> OTHER INFORMATION: Synthetic Construct

<400> SEQUENCE: 9
agtccttcca cgataccaaa gt                                             22

<210> SEQ ID NO 10
<211> LENGTH: 19
<212> TYPE: DNA
<213> ORGANISM: Artificial Sequence
<220> FEATURE:
<223> OTHER INFORMATION: Synthetic Construct

<400> SEQUENCE: 10
gcctcacagt tcagcgact                                                 19

<210> SEQ ID NO 11
<211> LENGTH: 21
<212> TYPE: DNA
<213> ORGANISM: Artificial Sequence
<220> FEATURE:
<223> OTHER INFORMATION: Synthetic Construct

<400> SEQUENCE: 11
actcagtgcg gaggatgatg t                                              21

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
tgcccagaaa atgaaaaagg                                                20

<210> SEQ ID NO 13
<211> LENGTH: 20
<212> TYPE: DNA
<213> ORGANISM: Artificial Sequence
<220> FEATURE:

<223> OTHER INFORMATION: Synthetic Construct

<400> SEQUENCE: 13
gtgtatgtgg caatgcgttc                                                        20

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
acagtggcca cctacaaagg                                                        20

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15
ccgagatggg gttgataatg                                                        20

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
cagtgggaga cctcgagaag                                                        20

<210> SEQ ID NO 17
<211> LENGTH: 20
<212> TYPE: DNA
<213> ORGANISM: Artificial Sequence
<220> FEATURE:
<223> OTHER INFORMATION: Synthetic Construct

<400> SEQUENCE: 17
tccctcggaa catcagaaac                                                        20

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
gagaactttg ccgttgaagc                                                        20

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct

<400> SEQUENCE: 19
gcttcctgta ggtggcaatc                                                        20

```
<210> SEQ ID NO 20
<211> LENGTH: 23
<212> TYPE: DNA
<213> ORGANISM: Artificial Sequence
<220> FEATURE:
<223> OTHER INFORMATION: Synthetic Construct

<400> SEQUENCE: 20
tgggaaggca gatgtatctt tcg                                              23

<210> SEQ ID NO 21
<211> LENGTH: 22
<212> TYPE: DNA
<213> ORGANISM: Artificial Sequence
<220> FEATURE:
<223> OTHER INFORMATION: Synthetic Construct

<400> SEQUENCE: 21
tgttgactga aggtaggtct ga                                               22

<210> SEQ ID NO 22
<211> LENGTH: 23
<212> TYPE: DNA
<213> ORGANISM: Artificial Sequence
<220> FEATURE:
<223> OTHER INFORMATION: Synthetic Construct

<400> SEQUENCE: 22
aaccattaag gtgtcgtatg ctc                                              23

<210> SEQ ID NO 23
<211> LENGTH: 19
<212> TYPE: DNA
<213> ORGANISM: Artificial Sequence
<220> FEATURE:
<223> OTHER INFORMATION: Synthetic Construct

<400> SEQUENCE: 23
cgcccaaacc gagagaaca                                                   19

<210> SEQ ID NO 24
<211> LENGTH: 23
<212> TYPE: DNA
<213> ORGANISM: Artificial Sequence
<220> FEATURE:
<223> OTHER INFORMATION: Synthetic Construct

<400> SEQUENCE: 24
catccagcta atgtcatgtc tgt                                              23

<210> SEQ ID NO 25
<211> LENGTH: 23
<212> TYPE: DNA
<213> ORGANISM: Artificial Sequence
<220> FEATURE:
<223> OTHER INFORMATION: Synthetic Construct

<400> SEQUENCE: 25
ctctggtcac gggatagaat ttc                                              23

<210> SEQ ID NO 26
<211> LENGTH: 19
<212> TYPE: DNA
<213> ORGANISM: Artificial Sequence
<220> FEATURE:
<223> OTHER INFORMATION: Synthetic Construct
```

<400> SEQUENCE: 26
acgcaagctc tgccttttc                                                 19

<210> SEQ ID NO 27
<211> LENGTH: 23
<212> TYPE: DNA
<213> ORGANISM: Artificial Sequence
<220> FEATURE:
<223> OTHER INFORMATION: Synthetic Construct

<400> SEQUENCE: 27
cgtgaggact gaagtaccat aga                                            23

<210> SEQ ID NO 28
<211> LENGTH: 19
<212> TYPE: DNA
<213> ORGANISM: Artificial Sequence
<220> FEATURE:
<223> OTHER INFORMATION: Synthetic Construct

<400> SEQUENCE: 28
gcgaagccga aaaaggcag                                                 19

<210> SEQ ID NO 29
<211> LENGTH: 23
<212> TYPE: DNA
<213> ORGANISM: Artificial Sequence
<220> FEATURE:
<223> OTHER INFORMATION: Synthetic Construct

<400> SEQUENCE: 29
tccgcaggta agtcttcttt agt                                            23

<210> SEQ ID NO 30
<211> LENGTH: 20
<212> TYPE: DNA
<213> ORGANISM: Artificial Sequence
<220> FEATURE:
<223> OTHER INFORMATION: Synthetic Construct

<400> SEQUENCE: 30
atggtgacac ccagaccgat                                                20

<210> SEQ ID NO 31
<211> LENGTH: 22
<212> TYPE: DNA
<213> ORGANISM: Artificial Sequence
<220> FEATURE:
<223> OTHER INFORMATION: Synthetic Construct

<400> SEQUENCE: 31
gagaagccat aattggcctg at                                             22

<210> SEQ ID NO 32
<211> LENGTH: 20
<212> TYPE: DNA
<213> ORGANISM: Artificial Sequence
<220> FEATURE:
<223> OTHER INFORMATION: Synthetic Construct

<400> SEQUENCE: 32
tcccaaagat ctgccttcac                                                20

<210> SEQ ID NO 33
<211> LENGTH: 20

```
<212> TYPE: DNA
<213> ORGANISM: Artificial Sequence
<220> FEATURE:
<223> OTHER INFORMATION: Synthetic Construct

<400> SEQUENCE: 33
ttctgcattg tgctgagagg                                                 20

<210> SEQ ID NO 34
<211> LENGTH: 20
<212> TYPE: DNA
<213> ORGANISM: Artificial Sequence
<220> FEATURE:
<223> OTHER INFORMATION: Synthetic Construct

<400> SEQUENCE: 34
tcttcttttg aggccaggaa                                                 20

<210> SEQ ID NO 35
<211> LENGTH: 20
<212> TYPE: DNA
<213> ORGANISM: Artificial Sequence
<220> FEATURE:
<223> OTHER INFORMATION: Synthetic Construct

<400> SEQUENCE: 35
ggaaagacca agaaaagccc                                                 20

<210> SEQ ID NO 36
<211> LENGTH: 22
<212> TYPE: DNA
<213> ORGANISM: Artificial Sequence
<220> FEATURE:
<223> OTHER INFORMATION: Synthetic Construct

<400> SEQUENCE: 36
agttcggtgc tcgaatgata ac                                              22

<210> SEQ ID NO 37
<211> LENGTH: 22
<212> TYPE: DNA
<213> ORGANISM: Artificial Sequence
<220> FEATURE:
<223> OTHER INFORMATION: Synthetic Construct

<400> SEQUENCE: 37
aatacgacct tgtgatggaa cg                                              22

<210> SEQ ID NO 38
<211> LENGTH: 21
<212> TYPE: DNA
<213> ORGANISM: Artificial Sequence
<220> FEATURE:
<223> OTHER INFORMATION: Synthetic Construct

<400> SEQUENCE: 38
tgaatctcag ccagtggtct t                                               21

<210> SEQ ID NO 39
<211> LENGTH: 20
<212> TYPE: DNA
<213> ORGANISM: Artificial Sequence
<220> FEATURE:
<223> OTHER INFORMATION: Synthetic Construct

<400> SEQUENCE: 39
```
tcatcacttc ctacggcgat                                             20

<210> SEQ ID NO 40
<211> LENGTH: 22
<212> TYPE: DNA
<213> ORGANISM: Artificial Sequence
<220> FEATURE:
<223> OTHER INFORMATION: Synthetic Construct

<400> SEQUENCE: 40
ttccttttct ccgactctcc tt                                          22

<210> SEQ ID NO 41
<211> LENGTH: 21
<212> TYPE: DNA
<213> ORGANISM: Artificial Sequence
<220> FEATURE:
<223> OTHER INFORMATION: Synthetic Construct

<400> SEQUENCE: 41
ccccaagtac caagtgcatg t                                           21

<210> SEQ ID NO 42
<211> LENGTH: 21
<212> TYPE: DNA
<213> ORGANISM: Artificial Sequence
<220> FEATURE:
<223> OTHER INFORMATION: Synthetic Construct

<400> SEQUENCE: 42
tgccagccac ttactgtgaa a                                           21

<210> SEQ ID NO 43
<211> LENGTH: 22
<212> TYPE: DNA
<213> ORGANISM: Artificial Sequence
<220> FEATURE:
<223> OTHER INFORMATION: Synthetic Construct

<400> SEQUENCE: 43
gcctcaccaa caatacccca ta                                          22

<210> SEQ ID NO 44
<211> LENGTH: 23
<212> TYPE: DNA
<213> ORGANISM: Artificial Sequence
<220> FEATURE:
<223> OTHER INFORMATION: Synthetic Construct

<400> SEQUENCE: 44
agattggaca acctatggac tga                                         23

<210> SEQ ID NO 45
<211> LENGTH: 22
<212> TYPE: DNA
<213> ORGANISM: Artificial Sequence
<220> FEATURE:
<223> OTHER INFORMATION: Synthetic Construct

<400> SEQUENCE: 45
gcactctgtc gaactgaagt ta                                          22

<210> SEQ ID NO 46
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 46
gaggaggcgt ctccctattc                                              20

<210> SEQ ID NO 47
<211> LENGTH: 21
<212> TYPE: DNA
<213> ORGANISM: Artificial Sequence
<220> FEATURE:
<223> OTHER INFORMATION: Synthetic Construct

<400> SEQUENCE: 47
gcatctggtt gccctaaaa a                                             21

<210> SEQ ID NO 48
<211> LENGTH: 22
<212> TYPE: DNA
<213> ORGANISM: Artificial Sequence
<220> FEATURE:
<223> OTHER INFORMATION: Synthetic Construct

<400> SEQUENCE: 48
cctgtggtct ttttgaacag ag                                           22

<210> SEQ ID NO 49
<211> LENGTH: 20
<212> TYPE: DNA
<213> ORGANISM: Artificial Sequence
<220> FEATURE:
<223> OTHER INFORMATION: Synthetic Construct

<400> SEQUENCE: 49
caactggagg ccctgtatgt                                              20

<210> SEQ ID NO 50
<211> LENGTH: 26
<212> TYPE: DNA
<213> ORGANISM: Artificial Sequence
<220> FEATURE:
<223> OTHER INFORMATION: Synthetic Construct

<400> SEQUENCE: 50
acacacacat aaacagatca tctcgg                                       26

<210> SEQ ID NO 51
<211> LENGTH: 25
<212> TYPE: DNA
<213> ORGANISM: Artificial Sequence
<220> FEATURE:
<223> OTHER INFORMATION: Synthetic Construct

<400> SEQUENCE: 51
agtctctgaa cctgtcctgg ttctg                                        25

<210> SEQ ID NO 52
<211> LENGTH: 36
<212> TYPE: PRT
<213> ORGANISM: Homo sapiens

<400> SEQUENCE: 52

Ala Arg Met Ile Thr Ile Asp Gly Lys Gln Ile Lys Leu Gln Ile Trp
1               5                   10                  15

Asp Thr Ala Gly Gln Glu Ser Phe Arg Ser Ile Thr Arg Ser Tyr Tyr
```

Arg Gly Ala Ala
        35

<210> SEQ ID NO 53
<211> LENGTH: 36
<212> TYPE: PRT
<213> ORGANISM: Pan troglodytes

<400> SEQUENCE: 53

Ala Arg Met Ile Thr Ile Asp Gly Lys Gln Ile Lys Leu Gln Ile Trp
1               5                   10                  15

Asp Thr Ala Gly Gln Glu Ser Phe Arg Ser Ile Thr Arg Ser Tyr Tyr
            20                  25                  30

Arg Gly Ala Ala
        35

<210> SEQ ID NO 54
<211> LENGTH: 36
<212> TYPE: PRT
<213> ORGANISM: Bos taurus

<400> SEQUENCE: 54

Ala Arg Met Ile Thr Ile Asp Gly Lys Gln Ile Lys Leu Gln Ile Trp
1               5                   10                  15

Asp Thr Ala Gly Gln Glu Ser Phe Arg Ser Ile Thr Arg Ser Tyr Tyr
            20                  25                  30

Arg Gly Ala Ala
        35

<210> SEQ ID NO 55
<211> LENGTH: 36
<212> TYPE: PRT
<213> ORGANISM: Canis familiaris

<400> SEQUENCE: 55

Ala Arg Met Ile Thr Ile Asp Gly Lys Gln Ile Lys Leu Gln Ile Trp
1               5                   10                  15

Asp Thr Ala Gly Gln Glu Ser Phe Arg Ser Ile Thr Arg Ser Tyr Tyr
            20                  25                  30

Arg Gly Ala Ala
        35

<210> SEQ ID NO 56
<211> LENGTH: 36
<212> TYPE: PRT
<213> ORGANISM: Oryctolagus cuniculus

<400> SEQUENCE: 56

Ala Arg Met Ile Thr Ile Asp Gly Lys Gln Ile Lys Leu Gln Ile Trp
1               5                   10                  15

Asp Thr Ala Gly Gln Glu Ser Phe Arg Ser Ile Thr Arg Ser Tyr Tyr
            20                  25                  30

Arg Gly Ala Ala
        35

<210> SEQ ID NO 57
<211> LENGTH: 36
<212> TYPE: PRT
<213> ORGANISM: Mus musculus

```
<400> SEQUENCE: 57

Ala Arg Met Ile Thr Ile Asp Gly Lys Gln Ile Lys Leu Gln Ile Trp
1               5                   10                  15

Asp Thr Ala Gly Gln Glu Ser Phe Arg Ser Ile Thr Arg Ser Tyr Tyr
            20                  25                  30

Arg Gly Ala Ala
        35

<210> SEQ ID NO 58
<211> LENGTH: 36
<212> TYPE: PRT
<213> ORGANISM: Gallus gallus

<400> SEQUENCE: 58

Ala Arg Met Ile Thr Ile Asp Gly Lys Gln Ile Lys Leu Gln Ile Trp
1               5                   10                  15

Asp Thr Ala Gly Gln Glu Ser Phe Arg Ser Ile Thr Arg Ser Tyr Tyr
            20                  25                  30

Arg Gly Ala Ala
        35

<210> SEQ ID NO 59
<211> LENGTH: 36
<212> TYPE: PRT
<213> ORGANISM: Xenopus laevis

<400> SEQUENCE: 59

Ala Arg Met Ile Thr Ile Asp Gly Lys Gln Ile Lys Leu Gln Ile Trp
1               5                   10                  15

Asp Thr Ala Gly Gln Glu Ser Phe Arg Ser Ile Thr Arg Ser Tyr Tyr
            20                  25                  30

Arg Gly Ala Ala
        35

<210> SEQ ID NO 60
<211> LENGTH: 36
<212> TYPE: PRT
<213> ORGANISM: Danio rerio

<400> SEQUENCE: 60

Ala Arg Met Ile Thr Ile Asp Gly Lys Gln Ile Lys Leu Gln Ile Trp
1               5                   10                  15

Asp Thr Ala Gly Gln Glu Ser Phe Arg Ser Ile Thr Arg Ser Tyr Tyr
            20                  25                  30

Arg Gly Ala Ala
        35

<210> SEQ ID NO 61
<211> LENGTH: 36
<212> TYPE: PRT
<213> ORGANISM: Tetrahymena thermophila

<400> SEQUENCE: 61

Ala Arg Met Ile Ser Phe Asp Asn Lys Asn Ile Lys Leu Gln Ile Trp
1               5                   10                  15

Asp Thr Ala Gly Gln Glu Ser Phe Arg Ser Ile Thr Arg Ser Tyr Tyr
            20                  25                  30

Arg Ser Ala Ala
        35
```

```
<210> SEQ ID NO 62
<211> LENGTH: 11
<212> TYPE: PRT
<213> ORGANISM: Homo sapiens

<400> SEQUENCE: 62

Lys Arg Phe Gln Pro Val His Asp Leu Thr Ile
1               5                   10

<210> SEQ ID NO 63
<211> LENGTH: 10
<212> TYPE: PRT
<213> ORGANISM: Homo sapiens

<400> SEQUENCE: 63

Arg Arg Leu Gln Lys Gly Asn Leu Pro Val
1               5                   10

<210> SEQ ID NO 64
<211> LENGTH: 11
<212> TYPE: PRT
<213> ORGANISM: Homo sapiens

<400> SEQUENCE: 64

Lys Lys Val Thr Ser Ser Gly Val Leu Leu Leu
1               5                   10

<210> SEQ ID NO 65
<211> LENGTH: 9
<212> TYPE: PRT
<213> ORGANISM: Homo sapiens

<400> SEQUENCE: 65

Arg Arg Asp Ala Ala Asp Leu Leu Leu
1               5

<210> SEQ ID NO 66
<211> LENGTH: 8
<212> TYPE: PRT
<213> ORGANISM: Homo sapiens

<400> SEQUENCE: 66

Arg Lys Pro Arg Asp Leu Glu Leu
1               5
```

ENHANCED ATRA-RELATED COMPOUNDS FOR THE TREATMENT OF PROLIFERATIVE DISEASES, AUTOIMMUNE DISEASES, AND ADDICTION CONDITIONS

STATEMENT AS TO FEDERALLY SPONSORED RESEARCH

This invention was made with government support under Grant Nos. CA122434, CA167677, AG039405, DA031663, and HL111430 awarded by the National Institutes of Health. The government has certain rights in the invention.

STATEMENT AS TO JOINT RESEARCH AGREEMENT

This invention was made by or on behalf of the below listed parties to a joint research agreement. The joint research agreement was in effect on or before the date the claimed invention was made and the claimed invention was made as a result of activities undertaken within the scope of the joint research agreement. The parties to the joint research agreement are BETH ISRAEL DEACONESS MEDICAL CENTER and PINTEON THERAPEUTICS, INC.

FIELD OF THE INVENTION

In general, this invention relates to all-trans retinoic acid (ATRA)-related compounds for modulation of Pin1. The invention also relates to the treatment of proliferative disorders, autoimmune disorders, and addiction (e.g., disorders, diseases, and conditions characterized by elevated Pin1 marker levels) with retinoic acid compounds.

BACKGROUND OF THE INVENTION

Immune disorders are characterized by the inappropriate activation of the body's immune defenses. Rather than targeting infectious invaders, the immune response targets and damages the body's own tissues or transplanted tissues. The tissue targeted by the immune system varies with the disorder. For example, in multiple sclerosis, the immune response is directed against the neuronal tissue, while in Crohn's disease the digestive tract is targeted.

Immune disorders affect millions of individuals and include conditions such as asthma, allergic intraocular inflammatory diseases, arthritis, atopic dermatitis, atopic eczema, diabetes, hemolytic anaemia, inflammatory dermatoses, inflammatory bowel or gastrointestinal disorders (e.g., Crohn's disease and ulcerative colitis), multiple sclerosis, myasthenia gravis, pruritis/inflammation, psoriasis, rheumatoid arthritis, cirrhosis, and systemic lupus erythematosus.

A major cellular pathway in the pathogenesis of autoimmunity is the TLR/IRAK1/IRF/IFN pathway. For example, levels of IFNα (type I interferon) are elevated in patients with autoimmune diseases, including systemic lupus erythematosus (SLE), and are central to disease pathogenesis, correlating with autoantibodies and disease development. Recent genetic studies in SLE patients and lupus-prone mice have identified variants in the genes critical for the TLR/IRAK1/IRF/IFN pathways, including TLR7, IRAK1 and IRF5. In addition, several TLR inhibitors are in development for treatment of SLE. Notably, IRAK1 genetic variants have recently been identified in human SLE. IRAK1, a well-established pivotal player in TLRs and inflammation, is located on the X chromosome, which may help account for the fact that SLE is more common in women. Importantly, studies using mouse models, where the IRAK1 gene is removed, have demonstrated a key role for this kinase in the TLR7/9/IRF pathway that produces large quantities of IFNα in response to viral infection. IRAK1 gene deletion prevents TLR dependent activation of IRF5/7 in pDCs, the immune cells responsible for IFNα production. Significantly, autoantibody complexes obtained from SLE patients contain DNA and RNA and are taken up by pDCs to activate TLR7 and TLR9 leading to secretion of cytokines and IFNα. Moreover, TLR activation is known to inhibit activity of glucocorticoids, a frontline drug class used to treat SLE. Although IRAK1 activity is regulated by phosphorylation upon TLR activation, little is known about whether it is subject to further control after phosphorylation and whether such regulation has any role in SLE.

The prevalence of asthma is increasing in the developed world, but the underlying mechanisms are not fully understood, and therapeutic modalities remain limited. Asthma is a chronic inflammatory disease of the airways that is induced by overexpression of multiple proinflammatory genes regulated by various signal pathways in response to exposure to any of numerous allergens, including Toll-like receptor/interleukin-1 receptor (TLR/IL-1R) signaling activated by house dust mite (HDM) allergens and IL-33, respectively. A major regulatory mechanism in these signal pathways and gene activation is Pro-directed phosphorylation (pSer/Thr-Pro), but until recently little was known about whether and how they are regulated following phosphorylation.

Current treatment regimens for immune disorders typically rely on immunosuppressive agents. However, the effectiveness of these agents can vary and their use is often accompanied by adverse side effects. Thus, improved therapeutic agents and methods for the treatment of autoimmune disorders are needed.

In addition, drug addiction affects millions of individuals worldwide. The prevalence of cocaine addiction, for example, is estimated at over one million persons in the United States alone. Dopamine receptor signaling is understood to play a major role in addiction to drugs such as cocaine known to elicit dopamine responses. Dopamine induction is coupled to the phosphorylation of glutamate receptor protein mGluR5, which in turn potentiates NMDA receptor-mediated synaptic plasticity and thus cocaine-induced sensation. MAP Kinase phosphorylates mGluR5 where it binds the adaptor protein Homer and in so doing is thought to create a binding site for proteins that catalyze cis-trans isomerization of a phosphorylated serine-proline bond (pSer/Pro). Despite this recognition, there are presently no FDA-approved medications to treat cocaine addiction. Accordingly, there is a need to identify and develop therapeutic agents for the treatment of cocaine addiction.

The increased number of cancer cases reported in the United States, and, indeed, around the world, is also a significant concern. There are currently only a handful of detection and treatment methods available for some specific types of cancer, and these provide no absolute guarantee of success. In order to be most effective, these treatments require not only an early detection of the malignancy, but a reliable assessment of the severity of the malignancy.

It is apparent that the complex process of tumor development and growth must involve multiple gene products. It is therefore important to define the role of specific genes involved in tumor development and growth and identify those genes and gene products that can serve as targets for the diagnosis, prevention, and treatment of cancers.

In the realm of cancer therapy, it often happens that a therapeutic agent that is initially effective for a given patient becomes, over time, ineffective or less effective for that patient. The very same therapeutic agent may continue to be effective over a long period of time for a different patient. Further, a therapeutic agent that is effective, at least initially, for some patients can be completely ineffective from the outset or even harmful for other patients. Accordingly, it would be useful to identify genes and/or gene products that represent prognostic genes with respect to a given therapeutic agent or class of therapeutic agents. It then may be possible to determine which patients will benefit from a particular therapeutic regimen and, importantly, determine when, if ever, the therapeutic regime begins to lose its effectiveness for a given patient. The ability to make such reasoned predictions would make it possible to discontinue a therapeutic regime that was losing its effectiveness well before its loss of effectiveness becomes apparent by conventional measures.

Recent advances in the understanding of molecular mechanisms of oncogenesis have led to exciting new drugs that target specific molecular pathways. These drugs have transformed cancer treatments, especially for those caused by some specific oncogenic events, such as Herceptin for breast cancer, caused by HER2/Neu, and Gleevec® for chronic myelogenous leukemia caused by Bcr-Abl. However, it has been increasingly evident that, in many individual tumors, there are a large number of mutated genes that disrupt multiple interactive and/or redundant pathways. Thus, intervening in a single pathway may not be effective. Furthermore, cancer resistance to molecularly targeted drugs can develop through secondary target mutation or compensatory activation of alternative pathways, so-called "oncogenic switching." Thus, a major challenge remains how to simultaneously inhibit multiple oncogenic pathways either using a combination of multiple drugs, with each acting on a specific pathway, or using a single drug that concurrently blocks multiple pathways.

Cancer stem-like cells (CSCs) or tumor-initiating cells (TICs) have been hypothesized to retain the capacity of self-renewal and regeneration of the bulk of a heterogeneous tumor comprised of CSCs and non-stem cells. CSCs have important implications for understanding the molecular mechanisms of cancer progression and developing novel targets for cancer therapeutics because they are thought to be responsible for tumor initiation, progression, metastasis, relapse and drug resistance. A variety of regulators of breast cancer stem-like cells (BCSCs), notably transcription factors including Zeb1 and β-catenin, and miRNAs, have recently been identified. These modulators of transcription and/or translation are further regulated by upstream signaling pathways. For example, Erk signaling has been shown to regulate BCSCs by increasing transcription of Zeb1 and nuclear accumulation of unphosphorylated (active) β-catenin. However, regulatory pathways upstream of Erk signaling that regulates BCSCs are still not fully elucidated.

Among the small GTPase superfamily, Ras has been shown to induce epithelial mesenchymal transition (EMT) and confer CSC traits to breast cells in vitro and in vivo, while the Rho family GTPase Rac1 is involved in the maintenance and tumorigenicity of CSCs in non-small cell lung adenocarcinoma and glioma and is also required for intestinal progenitor cell proliferation and LGR5$^+$ intestinal stem cell expansion. Deletion of Rac1 in adult mouse epidermis stimulated stem cells to divide and undergo terminal differentiation. However, the roles of other GTPase family members in CSCs in solid tumors or adult stem cells are yet to be elucidated. For example, Rab2A, a small GTPase mainly localized to the ER-Golgi intermediate compartment (ERGIC), is essential for membrane trafficking between the ER and Golgi apparatus but has no known function in cancer or CSCs. As disclosed herein, we have unexpectedly found that Rab2A is a Pin1 transcriptional target that is activated via its gene amplification or mutation or Pin1 overexpression in breast cancer and promotes BCSC expansion in vitro and in vivo as well as in human primary normal and cancerous breast tissues. Mechanistically, Rab2A directly binds to Erk1/2 via a docking motif that is also used by an Erk1/2 phosphatase, MKP3 (MAP kinase phosphatase 3) to prevent Erk1/2 from being dephosphorylated/inactivated, leading to activation of the known BCSC regulators Zeb1 and β-catenin. We further describe a tight association of Rab2A overexpression with β-catenin or Zeb1 downstream target expression in human breast cancer tissues as well as with poor outcome of breast cancer patients, especially in the most common subtypes, as defined by HER2-negative or non-triple-negative breast cancer. Thus, the Pin1/Rab2A/Erk axis drives BCSC expansion and tumorigenicity, contributing to high mortality in patients. Similarly, Pin1 has also been identified as a critical regulator acting downstream of miR200c.

These and other results disclosed herein suggest that Pin1 inhibitors may have a major impact on treating cancers, especially aggressive and/or drug-resistant cancers. A common and central signaling mechanism in many oncogenic pathways is proline (Pro)-directed phosphorylation (pSer/Thr-Pro). Proline adopts cis and trans conformations, the isomerization of which is catalyzed by prolyl isomerases (PPIases) including Pin1. Phosphorylation on serine/threonine-proline motifs restrains cis/trans prolyl isomerization, and also creates a binding site for the essential protein Pin1. Pin1 binds and regulates the activity of a defined subset of phosphoproteins, as well as participating in the timing of mitotic progression. Both structural and functional analyses have indicated that Pin1 contains a phosphoserine/threonine-binding module that binds phosphoproteins, and a catalytic activity that specifically isomerizes the phosphorylated phosphoserine/threonine-proline. Both of these Pin1 activities are essential for Pin1 to carry out its function in vivo.

Pin1 has been implicated in autoimmune diseases and conditions such as SLE and asthma and in drug addiction pathways. Further, we and others have shown that Pin1 is prevalently overexpressed in human cancers and that high Pin1 marker levels correlate with poor clinical outcome in many cancers. In contrast, the Pin1 polymorphism that reduces Pin1 expression is associated with reduced cancer risk in humans. Significantly, Pin1 activates at least 32 oncogenes/growth enhancers, including β-catenin, cyclin D1, NF-κB, c-Jun, c-fos, AKT, A1B1, HER2/Neu, MC1-1, Notch, Raf-1, Stat3, c-Myb, Hbx, Tax, and v-rel, and also inactivates at least 19 tumor suppressors/growth inhibitors, including PML, SMRT, FOXOs, RARα, and Smad (FIG. 1). Whereas Pin1 overexpression causes cell transformation and tumorigenesis, Pin1 knockdown inhibits cancer cell growth in cell cultures and mice. Pin1-null mice are highly resistant to tumorigenesis induced either by oncogenes such as activated Ras or HER2/Neu, or tumor suppressors such as p53. Thus, Pin1 inhibitors may have the desirable property to suppress numerous oncogenic pathways simultaneously for treating cancers, especially those aggressive and/or drug-resistant cancers. Potent and selective Pin1 inhibitors having low toxicity, high cell permeability, and long half-lives in the body are particularly desirable.

Pin1 is highly conserved and contains active sites including a protein-interacting module, called the WW domain, and a catalytically active peptidyl-prolyl isomerase (PPIase) portion, each of which include at least one binding pocket. Pin1 is structurally and functionally distinct from members of two other well-characterized families of PPIases, the cyclophilins and the FKBPs. PPIases are ubiquitous enzymes that catalyze the typically slow prolyl isomerization of proteins, allowing relaxation of local energetically unfavorable conformational states. Phosphorylation on Ser/Thr residues immediately preceding Pro not only alters the prolyl isomerization rate, but also creates a binding site for the WW domain of Pin1. The WW domain acts as a novel phosphoserine-binding module targeting Pin1 to a highly conserved subset of phosphoproteins. Furthermore, Pin1 displays a unique phosphorylation-dependent PPIase that specifically isomerizes phosphorylated Ser/Thr-Pro bonds and regulates the function of phosphoproteins. The cis-trans isomerization of certain pSer/Thr-Pro motifs can be detected by cis- and trans-specific antibodies.

Taken together, these results indicate that the Pin1 subfamily of enzymes is a diagnostic and therapeutic target for diseases associated with signal pathways involving Pro-directed phosphorylation and characterized by uncontrolled cell proliferation, primarily malignancies.

We have surprisingly found that an approved anticancer reagent with an unknown mechanism, all-trans retinoic acid (ATRA), potently and reversibly binds and inhibits and ultimately induces degradation of active Pin1. The use of all-trans retinoic acid (ATRA) to treat acute promyelocytic leukemia (APL) is described as the first example of targeted therapy in human cancer. ATRA induces leukemia cell differentiation by activating RARα or the oncogene PML/RARα-dependent transcription and induces degradation of PML/RARα. However, the mechanism by which ATRA mediates these anticancer effects is unknown. Though RARα and PML have been described as Pin1 substrates, the link between ATRA and Pin1 is poorly understood. The establishment of the mechanism of interaction between ATRA and Pin1 could facilitate the development and identification of selective Pin1 inhibitors with low toxicity, high cell permeability, and long half-lives for use in the treatment of proliferative and other disorders. Accordingly, there is a need for an improved understanding of the binding interaction between ATRA and Pin1.

SUMMARY OF THE INVENTION

The present invention relates to all-trans retinoic acid (ATRA)-related compounds that act as Pin1 substrates and methods of treating a proliferative disorder, an autoimmune disorder, or an addiction condition with the retinoic acid compounds (e.g., ATRA-related compounds) of the invention.

In one aspect, the invention provides a method of treating a proliferative disease, an autoimmune disease, or an addiction condition in a subject comprising administering an ATRA-related compound of the invention to the subject in an amount sufficient to treat the subject, wherein the subject is determined to have elevated levels of a Pin1 marker (e.g., Ser71 phosphorylation or PML-RARα) prior to the administration.

In another aspect, the invention features a method of treating a proliferative disease, an autoimmune disease, or an addiction condition in a subject comprising determining Pin1 marker levels (e.g., reduced Ser71 phosphorylation or overexpression of PML-RARα) in a sample (e.g., tumor samples, blood, urine, biopsies, lymph, saliva, phlegm, and pus) from the subject and administering an ATRA-related compound of the invention to the subject if the sample is determined to have elevated Pin1 marker levels.

In a further aspect, the invention provides a method of treating a proliferative disease, an autoimmune disease, or an addiction condition in a subject previously treated with an ATRA-related compound and shown to have Pin1 degradation (e.g., by comparing a Pin1 marker level in a sample obtained from a subject before administration of the ATRA-related compound with a Pin1 marker level in a sample obtained from a subject after administration of the ATRA-related compound), the method comprising administering an ATRA-related compound of the invention to the subject in an amount sufficient to treat the subject.

In a related aspect, the invention provides a method of identifying a candidate for treatment with an ATRA-related compound, in which the candidate has a proliferative disease, an autoimmune disease, or an addiction condition and has previously been treated with (e.g., administered) an ATRA-related compound; the method comprising determining whether the subject has Pin1 degradation (e.g., Pin1 degradation resulting from the prior administration of an ATRA-related compound), where a candidate for treatment with an ATRA-related compound has Pin1 degradation.

In the context of the present invention, an "all-trans retinoic acid (ATRA)-related compound" refers to a compound that is structurally related to or an analog of ATRA. For example, a compound that is structurally related to or an analog of ATRA may have one or more components (e.g., one or more functional groups or structural motifs) in common with ATRA and/or may have one or more substitutions, elongations, eliminations, additions, or other differences relative to ATRA, e.g., as described herein. For example, one or more components, functional groups, or elements of ATRA may be modified, replaced, or eliminated, e.g., by adding, changing, or eliminating one or more substitutions, replacing one or more groups (e.g., replacing a carboxyl group with an ester group), and/or increasing or decreasing the size or length of a component of ATRA (e.g., replacing a six-membered ring with a seven-membered ring). An ATRA-related compound may differ from ATRA by as few as one group, element, or feature (e.g., a single isotopic substitution, a single methyl group or absence thereof, etc.). ATRA-related compounds may include isotopically substituted species (e.g., ATRA including one or more isotopic substitutions such as deuterium, tritium, $^{17}O$, $^{18}O$, $^{13}C$, $^{32}P$, $^{15}N$, and $^{18}F$), functionally substituted species (e.g., ATRA with one or more methyl groups eliminated or replaced by one or more other functional groups such as longer chain alkyl groups, hydroxyl groups, cycloalkyl groups, and other groups), and stereoisomers (e.g., ATRA including one or more cis alkene groups along its backbone).

An ATRA-related compound of the invention may include one or more unsaturations or substitutions (e.g., 1, 2, 3, 4, 5, 6, or more unsaturations or substitutions). An unsaturation may be a multiple bond such as a double bond (alkene) or triple bond (alkyne) or a ring structure. A substitution may be selected from the group consisting of, but not limited to, a halogen atom, a carboxylic acid, an alcohol (e.g., a hydroxyl), an ester, an aldehyde, a carbonyl, an acyl halide, a carbonate, an acetal, a phosphate, a thiol, a sulfoxide, a sulfinic acid, a sulfonic acid, a thial, a sulfate, a sulfonyl, an amide, an azido, a nitro, a cyano, isocyano, acyloxy, an amino, a carbamoyl, a sulfonamide, or another functional group, or an optionally substituted alkyl (e.g., $C_{1-10}$ alkyl), alkenyl (e.g., $C_{2-10}$ alkenyl), alkynyl (e.g., $C_{2-10}$ alkynyl), alkoxy (e.g., $C_{1-10}$ alkoxy), aryloxy (e.g., $C_{6-10}$ aryloxy), cycloalkyl (e.g., $C_{3-8}$ cycloalkyl), cycloalkoxy (e.g., $C_{3-8}$ cycloalkoxy), aryl (e.g., $C_{6-10}$ aryl), aryl-alkoxy (e.g., $C_{6-10}$ aryl-$C_{1-10}$ alkoxy), heterocyclyl or heterocycloalkyl (e.g., $C_{3-8}$ heterocycloalkyl), heterocycloalkenyl, (e.g., $C_{4-8}$ heterocycloalkenyl), or heteroaryl (e.g., $C_{6-10}$ heteroaryl). In some embodiments, the substituent groups themselves may be further substituted with, for example, 1, 2, 3, 4, 5, or 6 substituents as defined herein. For example, a $C_{1-6}$ alkyl, aryl, or heteroaryl group may be further substituted with 1, 2, 3, 4, 5, or 6 substituents as described herein. A heteroatom of a heteroaryl, heterocycloalkyl, heterocycloalkenyl, heterocycloalkynyl, or other group may be, for example, a sulfur atom, oxygen atom, or nitrogen atom. A functional group such as a heteroaryl, heterocycloalkyl, heterocycloalkenyl, heterocycloalkynyl, or other group may include more than one heteroatoms (e.g., one sulfur atom and one nitrogen atom, two nitrogen atoms, three nitrogen atoms, four nitrogen atoms, one sulfur atom and one oxygen atom, one nitrogen atom and one oxygen atom, or any other combination).

In some embodiments, an ATRA-related compound may include one or more rigid or sterically bulky groups such as one or more aryl, heteroaryl, cycloalkyl, cycloalkenyl, heterocycloakyl, or heterocycloalkenyl rings or a fusion thereof. For example, an ATRA-related compound may include, in place of the cyclohexenyl group of ATRA, a naphthyl or hydronaphthyl (e.g., di-, tri-, tetra-, penta-, hexa-, hepta-, octa-, nona-, or deca-hydronaphthyl) group. In some embodiments, an ATRA-related compound may include, in place of the cyclohexenyl group of ATRA, a single carbon ring including a single double bond (e.g., a cycloalkyl or cycloalkenyl group other than cyclohexene). In certain embodiments, an ATRA-related compound may include, in place of the cyclohexenyl group of ATRA, an optionally substituted cylcohexene group (e.g., a cyclohexene group having one or more additional, fewer, or different substitutions than the cyclohexenyl group of ATRA). In some preferred embodiments, substitutions on a ring (e.g., a ring such as those described herein in place of the cyclohexenyl group of ATRA) are not sterically bulky. For example, a ring preferably includes one or more short-chain alkyl (e.g., $C_{1-5}$ alkyl) substituents. In an embodiment, an ATRA-related compound includes a trimethylcyclohexene such as 1,3,3-trimethylcyclohexene.

In some embodiments, an ATRA-related compound includes a "backbone" carbon chain such as the backbone carbon chain of ATRA (e.g., the diterpene moiety). In certain embodiments, an ATRA-related compound includes, in place of the "backbone" moiety of ATRA, a carbon chain (e.g., an alkyl chain) including one or more rings. For example, an ATRA-related compound may include, in place of the "backbone" moiety of ATRA, an alkyl chain fused to an optionally substituted aryl, heteroaryl, cycloalkyl, cycloalkenyl, heterocycloalkyl, or heterocycloalkenyl group. In some embodiments, an ATRA-related compound includes a "backbone" moiety including one or more double bonds. In particular embodiments, the "backbone" moiety includes conjugation (e.g., alternating single and double bonds). For example, the "backbone" moiety may be 4-10 carbon chain 2-5 double bonds, such as octa-1,3,5,7-tetraene. In certain embodiments, the "backbone" moiety may include one or more isoprene units and be, e.g., a diterpene. In some embodiments, the "backbone" moiety includes one or more short-chain alkyl (e.g., $C_{1-5}$ alkyl) substituents. For instance, the backbone may be 2,6-dimethyl-octa-1,3,5,7-tetraene. As described above, all cis and trans isomers are contemplated.

In some embodiments, an ATRA-related compound includes a carboxylic acid group. In some embodiments, in place a carboxylic acid group, an ATRA-related compound includes one or more oxygen atoms and is a group selected from a hydroxyl, an ester, an aldehyde, a carbonyl, an acyl halide, a carbonate, an acetal, a phosphate, a sulfoxide, a sulfone, a sulfinic acid, a sulfonic acid, a sulfate, a sulfonyl, and an amide. In certain embodiments, an ATRA-related compound includes in place of the carboxylic group of ATRA a group selected from a hydroxyl, an ester, an aldehyde, a carbonyl, an acyl halide, a carbonate, and an amide. In some embodiments, in place of the carboxylic group of ATRA, an ATRA-related compound includes one or more optionally substituted aryl, heteroaryl, cycloalkyl, cycloalkenyl, heterocycloalkyl, or heterocycloalkenyl groups.

In some embodiments, an ATRA-related compound is a compound according to Formula II

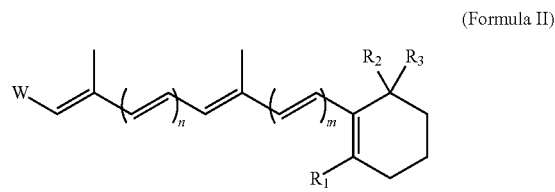

(Formula II)

wherein n and m are independently selected from 0, 1, and 2, and wherein W, $R_1$, $R_2$, and $R_3$ are independently selected from the group consisting of, but not limited to, a halogen atom, a carboxylic acid, an alcohol (e.g., a hydroxyl), an ester, an aldehyde, a carbonyl, an acyl halide, a carbonate, an acetal, a phosphate, a thiol, a sulfoxide, a sulfinic acid, a sulfonic acid, a thial, a sulfate, a sulfonyl, an amide, an azido, a nitro, a cyano, isocyano, acyloxy, an amino, a carbamoyl, a sulfonamide, or another functional group, or an optionally substituted alkyl (e.g., $C_{1-10}$ alkyl), alkenyl (e.g., $C_{2-10}$ alkenyl), alkynyl (e.g., $C_{2-10}$ alkynyl), alkoxy (e.g., $C_{1-10}$ alkoxy), aryloxy (e.g., $C_{6-10}$ aryloxy), cycloalkyl (e.g., $C_{3-8}$ cycloalkyl), cycloalkoxy (e.g., $C_{3-8}$ cycloalkoxy), aryl (e.g., $C_{6-10}$ aryl), aryl-alkoxy (e.g, $C_{6-10}$ aryl-$C_{1-10}$ alkoxy), heterocyclyl or heterocycloalkyl (e.g., $C_{3-8}$ heterocycloalkyl), heterocycloalkenyl, (e.g., $C_{4-8}$ heterocycloalkenyl), or heteroaryl (e.g., $C_{6-10}$ heteroaryl). In some embodiments, W is a bioisostere of a carboxyl group. For example, W can be selected from the group consisting of a phenolic group, a halophenolic group (e.g., 3-chloro-4-hydroxybenzyl), a heteroaryl group, a heterocycloalkyl group, a heterocycloalkenyl group, a sulfonamide, and a sulfonic acid. Any group may include one or more substitutions including halogen, hydroxyl, azido, and other substitutions described herein, or any additional substitution.

In certain embodiments, W is a carboxyl group. In some embodiments, $R_1$, $R_2$, and $R_3$ are independently selected from an optionally substituted alkyl (e.g., $C_{1-10}$ alkyl) group and an optionally substituted alkenyl (e.g., $C_{2-10}$ alkenyl) group.

In certain embodiments, $R_1$, $R_2$, and $R_3$ are independently selected from optionally substituted (e.g., with amino, alkoxy, carboxyl, or sulfonyl groups or other hydrophilic moieties) alkyl (e.g., $C_{1-10}$ alkyl) groups. In particular embodiments, $R_1$, $R_2$, and $R_3$ are methyl groups.

In some embodiments, n and m are independently selected from 0 and 1. In other embodiments, n and m are independently selected from 1 and 2. In certain embodiments, n and m are both 1.

In some embodiments, an ATRA-related compound is a compound according to Formula I

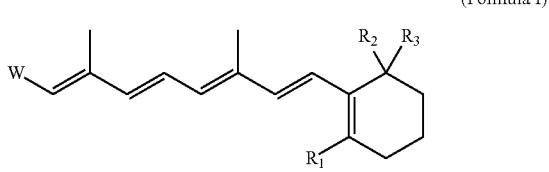

(Formula I)

wherein W, $R_1$, $R_2$, and $R_3$ are independently selected from the group consisting of, but not limited to, a halogen atom, a carboxylic acid, an alcohol (e.g., a hydroxyl), an ester, an aldehyde, a carbonyl, an acyl halide, a carbonate, an acetal, a phosphate, a thiol, a sulfoxide, a sulfinic acid, a sulfonic acid, a thial, a sulfate, a sulfonyl, an amide, an azido, a nitro, a cyano, isocyano, acyloxy, an amino, a carbamoyl, a sulfonamide, or another functional group, or an optionally substituted alkyl (e.g., $C_{1-10}$ alkyl), alkenyl (e.g., $C_{2-10}$ alkenyl), alkynyl (e.g., $C_{2-10}$ alkynyl), alkoxy (e.g., $C_{1-10}$ alkoxy), aryloxy (e.g., $C_{6-10}$ aryloxy), cycloalkyl (e.g., $C_{3-8}$ cycloalkyl), cycloalkoxy (e.g., $C_{3-8}$ cycloalkoxy), aryl (e.g., $C_{6-10}$ aryl), aryl-alkoxy (e.g, $C_{6-10}$ aryl-$C_{1-10}$ alkoxy), heterocyclyl or heterocycloalkyl (e.g., $C_{3-8}$ heterocycloalkyl), heterocycloalkenyl, (e.g., $C_{4-8}$ heterocycloalkenyl), or heteroaryl (e.g., $C_{6-10}$ heteroaryl).

In certain embodiments, one or more of $R_1$, $R_2$, and $R_3$ are methyl groups. In some embodiments, $R_1$ is a methyl group. In some embodiments, $R_2$ is a methyl group. In some embodiments, $R_3$ is a methyl group. In some embodiments, $R_1$ and $R_2$ are methyl groups. In some embodiments, $R_2$ and $R_3$ are methyl groups.

In some embodiments, W is an group including one or more electronegative atoms (e.g., a carboxylic acid, alcohol, ester, aldehyde, carbonyl, acyl halide, carbonate, acetal, phosphate, thiol, sulfoxide, sulfinic acid, sulfonic acid, thial, sulfate, sulfonyl, thioketone, thioaldehyde, or amide). In particular embodiments, W is a carboxylic acid group.

As used herein, the term "acyl" represents an alkyl group or hydrogen that is attached to a parent molecular group through a carbonyl group. Examples include formyl, acetyl, and propionyl groups.

As used herein, the term "acyloxy" represents a group of the form —OC(O)R, in which R is a carbon-containing group such as an alkyl group, as defined herein.

As used herein, the term "acetal" represents a group of the form —C(OR')$_2$R", in which each OR' are alkoxy groups, as defined herein, and R" is a carbon-containing group such as an alkyl group, as defined herein. The alkoxy groups of an acetal group may be the same (e.g., a symmetric acetal) or different (e.g., a mixed acetal).

As used herein, the term "aldehyde" represents an acyl group having the structure —CHO.

As used herein, the term "carbonyl" represents a —C(O) group, alternatively represented by C=O.

As used herein, the term "alkoxy" represents a group of the formula —OR, where R is an alkyl group of any length (e.g., $C_{1-10}$ alkyl). Examples include methoxy, ethoxy, propoxy (e.g., n-propoxy and isoproxy) groups. The alkyl portion of an alkoxy group may include any additional substitution as defined herein.

As used herein, the term "alkyl" includes straight chain and branched chain saturated groups including between 1 and 20 carbon atoms, unless otherwise specified. Examples include methyl, ethyl, n-propyl, and isopropyl. An alkyl group may be optionally substituted with one or more substituents as defined herein.

As used herein, the term "alkenyl" represents an alkyl group including one or more double bonds. An alkene or alkenyl group may be a straight or branched alkyl chain with two or more hydrogen atoms removed. Examples include methylene, ethylene, and isopropylene. An alkenyl group may include between 2 and 20 carbon atoms, unless otherwise specified, and may be optionally substituted as defined herein. Alkenyls include both cis and trans isomers. For example, 2-butene includes cis-but-2-ene [(Z)-but-2-ene] and trans-but-2-ene [(E)-but-2-ene].

As used herein, the term "alkynyl" represents an alkyl group including one or more triple bonds. An alkyne or alkynyl group may be a straight or branched alkyl chain with four or more hydrogen atoms removed. Examples include acetylene (ethyne), propyne, and butyne. An alkynyl group may include between 2 and 20 carbon atoms, unless otherwise specified, and may be optionally substituted as defined herein.

As used herein, the term "cycloalkyl" represents a saturated or unsaturated non-aromatic cyclic hydrocarbon group including 3, 4, 5, 6, 7, 8, or more carbon atoms, unless otherwise specified. A cycloalkyl group may optionally include one or more substitutions, as defined herein. Examples include cyclopropyl, cyclobutyl, cyclopentyl, cyclohexyl, cycloheptyl, and cyclooctyl groups. In some embodiments, the cycloalkyl is a polycyclic (e.g., adamantyl). A cycloalkyl group including one or more double bonds is referred to as a "cycloalkenyl" group. Examples of cycloalkenyl groups include cyclopentenyl, cyclohexenyl, cycloheptenyl, and cyclooctenyl groups.

As used herein, the term "cycloalkoxy" represents a substituent of the form —OR, where R is a cycloalkyl grup, as defined herein.

As used herein, the term "aryl" represents a mono-, bi-, or multi-cyclic carbocyclic ring system having one or more aromatic rings. For example, an aryl group may be a mono- or bicyclic $C_6$-$C_{14}$ group with [4n+2]π electrons in conjugation and where n is 1, 2, or 3. Phenyl is an aryl group where n is 1. Aryl groups also include ring systems where the ring system having [4n+2]π electrons is fused to a non-aromatic cycloalkyl or a non-aromatic heterocyclyl. Examples include phenyl, naphthyl, 1,2-dihydronaphthyl, 1,2,3,4-tetrahydronaphthyl, anthracenyl, and indenyl. An aryl group may optionally include one or more substitutions, as defined herein.

As used herein, the term "heterocycloalkyl" or "heterocyclyl" represents a cycloalkyl (e.g., a non-aromatic ring) group including one or more heteroatoms independently selected from the group consisting of nitrogen, oxygen, and sulfur. A heterocycloalkyl group including one or more double bonds is referred to as a "heterocycloalkenyl" group.

A heterocyclyl group may be a multicyclic structure (e.g., a bicyclic structure or a bridged multicyclic structure). Examples of heterocycles include piperidinyl, pyrrolidinyl, and tetrahydrofuryl groups. Heterocyclyl groups may be unsubstituted or substituted with, e.g., 1, 2, 3, or 4 substituent groups as defined herein.

As used herein, the term "heteroaryl" represents an aryl (e.g., aromatic) group including one or more heteroatoms independently selected from the group consisting of nitrogen, oxygen, and sulfur. Heteroaryls may be monocycles, bicycles, tricycles, or tetracycles in which any aromatic ring is fused to one, two, or three heterocyclic or carbocyclic rings (e.g., an aryl ring). Examples of heterocyclic aromatic molecules include furan, thiophene, pyrrole, thiadiazole (e.g., 1,2,3-thiadiazole or 1,2,4-thiadiazole), oxadiazole (e.g., 1,2,3-oxadiazole or 1,2,5-oxadiazole), oxazole, isoxazole, isothiazole, pyrazole, thiazole, triazole (e.g., 1,2,4-triazole or 1,2,3-triazole), pyridine, pyrimidine, pyrazine, pyrazine, triazine (e.g, 1,2,3-triazine 1,2,4-triazine, or 1,3,5-triazine), 1,2,4,5-tetrazine, indolyl, quinolinyl, isoquinolinyl, benzimidazolyl, benzothiazolyl, and benzoxazolyl. Heteroaryls may be unsubstituted or substituted with, e.g., 1, 2, 3, or 4 substituents groups as defined herein.

As used herein, the term "fused" refers to one or more chemical elements that are connected to one another by one or more chemical bonds. In particular, two rings (e.g, cycloalkyl or aryl groups) may be fused to one another, as described above. Examples include indolyl, quinolyl, and isoquinolyl groups.

As used herein, the term "alkaryl" represents an aryl group, as defined herein, attached to a parent molecular group through an alkyl group, as defined herein.

As used herein, the term "aryl-alkoxy" represents an alkaryl group, as defined herein, attached to a parent molecular group through an oxygen atom.

As used herein, the term "aryloxy" represents a group of the form —OR, where R is an aryl group, as defined herein.

As used herein, the term "halo" represents a halogen selected from the group consisting of bromine, chlorine, iodine, and fluorine.

As used herein, the term "carboxylic acid" or "carboxy" represents a group of the form —C(O)OH, also represented as —CO$_2$H.

As used herein, the term "ester" represents a group of the form —C(O)O—.

As used herein, the term "acyl halide" represents a group of the form —C(O)X, in which X is a halide selected from bromide, fluoride, chloride, and iodide.

As used herein, the term "carbonate" represents a group of the form —OC(O)O—.

As used herein, the term "alcohol" or "hydroxyl" represents a group of the form —OH. As used herein, the term "phosphate" represents an P(O)$_4^{3-}$ group.

As used herein, the term "thiol" represents an —SH group.

As used herein, the term "thial" represents an —C(S)H group.

As used herein, the term "sulfoxide" represents an —S(O)— group.

As used herein, the term "sulfonyl" represents an —S(O)$_2$— group.

As used herein, the term "sulfinic acid" represents an —S(O)OH group.

As used herein, the term "sulfonic acid" represents an —S(O)$_2$OH group.

As used herein, the term "sulfate" represents an S(O)$_4^{2-}$ group.

As used herein, the term "sulfonamide" represents a group of the form —S(O)$_2$NR$_2$ or —N(R)S(O)$_2$R, wherein each R is independently optionally substituted alkyl, aryl, cycloalkyl, cycloaryl, or another group.

As used herein, the term "amide" represents a group of the form —C(O)NR$_2$, or —N(R)C(O)R, wherein each R is independently optionally substituted alkyl, aryl, cycloalkyl, cycloaryl, or another group.

As used herein, the term "amino" represents an —NR$_2$ group, wherein each R is independently optionally substituted alkyl, aryl, cycloalkyl, cycloaryl, or another group.

As used herein, the term "azido" represents an —N$_3$ group.

As used herein, the term "nitro" represents an —NO$_2$ group.

As used herein, the term "cyano" represents a —CN group, while the term "isocyano" represents an —NC group.

As used herein, the term "carbamoyl" represents a group of the form —OC(O)NR$_2$ or —N(R)C(O)OR, wherein each R is independently optionally substituted alkyl, aryl, cycloalkyl, cycloaryl, or another group.

In some embodiments, an ATRA-related compound of the invention may include one or more isotopic substitutions, including deuterium, tritium, $^{17}$O, $^{18}$O, $^{13}$C, $^{32}$P, $^{15}$N, and $^{18}$F. An ATRA-related compound may have any stereochemistry. All possible isomeric and conformational forms of ATRA-related compounds (e.g., those disclosed herein) are contemplated, including diastereomers, enantiomers, and/or conformers of a given structure. Different tautomeric forms are also contemplated. The invention includes protonated, deprotonated, and solvated species, as well as salts of the compounds of the invention. n some embodiments, an ATRA-related compound is a compound according to Formula Ia

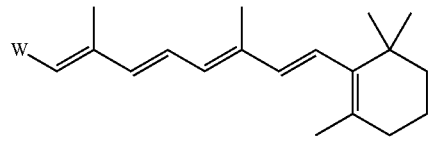

(Formula Ia)

wherein W comprises one or more optionally substituted (e.g., with one or more halogen, carbonyl, hydroxyl, alkoxy, amino, amide, sulfonyl, or other groups, such as those described herein) aryl or heteroaryl groups or one or more optionally substituted cycloalkyl, heterocycloalkyl, cycloalkenyl, or heterocycloalkenyl groups. For example, an ATRA-related compound may be selected from compounds 1-101 of Table 1.

TABLE 1
ATRA-related compounds of the invention including substitutions at W.
| Compound Number | Compound | MMGBSA dG Bind |
|---|---|---|
| 1 | 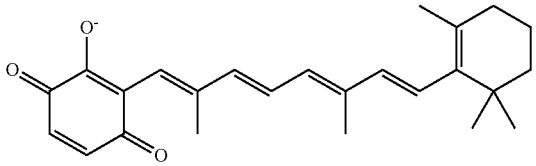 [SMILES: CC1=C(/C=C/C(C)=C/C=C/C(C)=C/C2=C([O-])C(=O)C=CC2=O)C(C)(C)CCC1] | −42.523 |
| 2 | 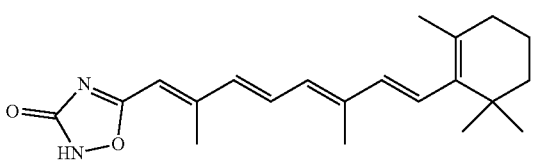 [SMILES: CC1=C(/C=C/C(C)=C/C=C/C(C)=C/c2nc(=O)[nH]o2)C(C)(C)CCC1] | −41.676 |
| 3 | 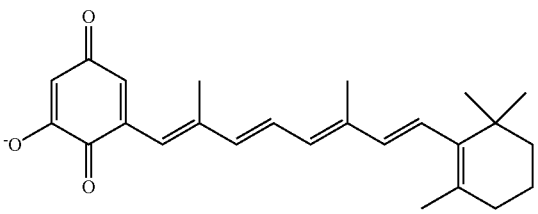 | −40.719 |
| 4 | 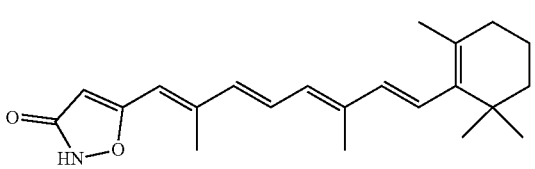 [SMILES: CC1=C(/C=C/C(C)=C/C=C/C(C)=C/c2cc(=O)[nH]o2)C(C)(C)CCC1] | −40.448 |
| 5 | 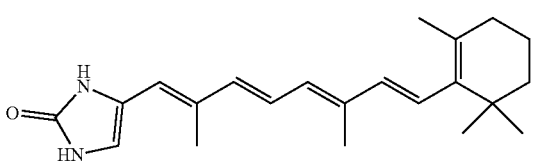 [SMILES: CC1=C(/C=C/C(C)=C/C=C/C(C)=C/c2c[nH]c(=O)[nH]2)C(C)(C)CCC1] | −40.365 |
| 6 | 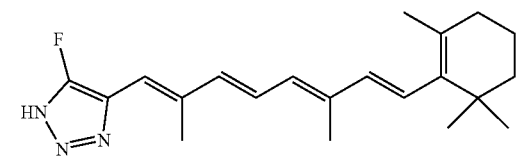 [SMILES: CC1=C(/C=C/C(C)=C/C=C/C(C)=C/c2nn[nH]c2F)C(C)(C)CCC1] | −40.345 |
| 7 | 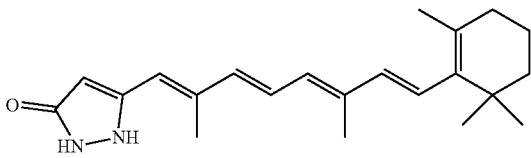 [SMILES: CC1=C(/C=C/C(C)=C/C=C/C(C)=C/c2cc(=O)[nH][nH]2)C(C)(C)CCC1] | −40.249 |
| 8 | 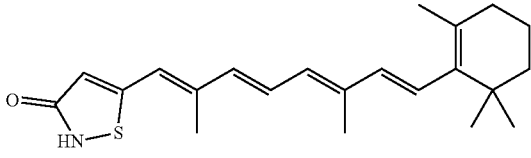 [SMILES: CC1=C(/C=C/C(C)=C/C=C/C(C)=C/c2cc(=O)[nH]s2)C(C)(C)CCC1] | −39.417 |

TABLE 1-continued
ATRA-related compounds of the invention including substitutions at W.
| Compound Number | Compound | MMGBSA dG Bind |
|---|---|---|
| 9 | 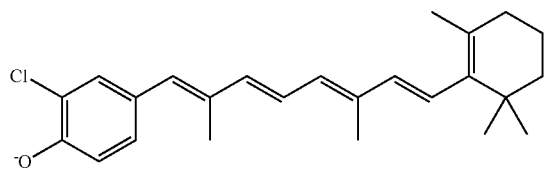 | −39.232 |
| 10 | 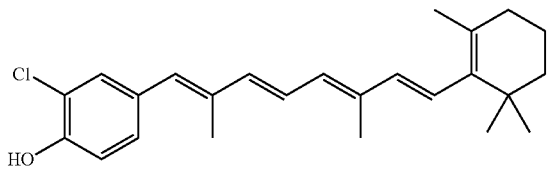 [SMILES: CC1=C(/C=C/C(C)=C/C=C/C(C)=C/c2ccc(O)c(Cl)c2)C(C)(C)CCC1] | −39.050 |
| 11 | 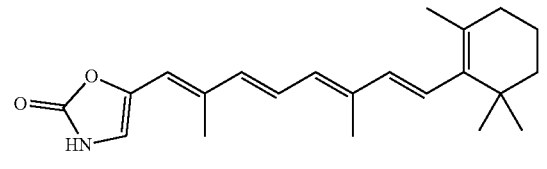 [SMILES: CC1=C(/C=C/C(C)=C/C=C/C(C)=C/c2c[nH]c(=O)o2)C(C)(C)CCC1] | −38.984 |
| 12 | 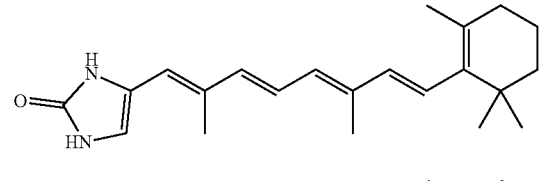 | −38.958 |
| 13 | 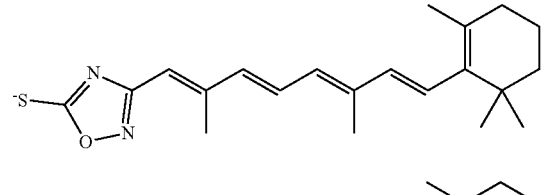 | −38.818 |
| 14 | 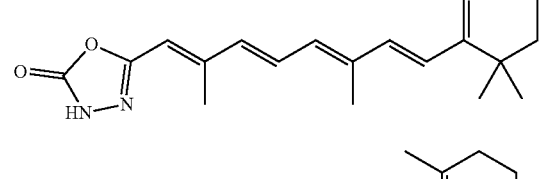 | −38.817 |
| 15 | 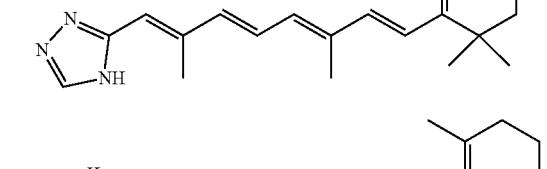 | −38.742 |
| 16 | 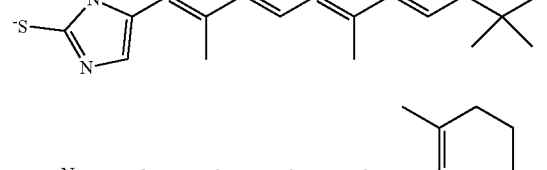 | −38.627 |
| 17 |  | −38.309 |

TABLE 1-continued

ATRA-related compounds of the invention including substitutions at W.

| Compound Number | Compound | MMGBSA dG Bind |
|---|---|---|
| 18 | | −38.247 |
| 19 | | −38.124 |
| 20 | | −37.847 |
| 21 | | −37.846 |
| 22 | | −37.804 |
| 23 | | −37.628 |
| 24 | | −37.601 |
| 25 | | −37.585 |
| 26 | | −37.568 |

TABLE 1-continued

ATRA-related compounds of the invention including substitutions at W.

| Compound Number | Compound | MMGBSA dG Bind |
|---|---|---|
| 27 | | −37.558 |
| 28 | | −37.542 |
| 29 | | −37.485 |
| 30 | | −37.460 |
| 31 | | −37.390 |
| 32 | | −37.361 |
| 33 | | −37.135 |
| 34 | | −36.909 |
| 35 | | −36.848 |

TABLE 1-continued

ATRA-related compounds of the invention including substitutions at W.

| Compound Number | Compound | MMGBSA dG Bind |
|---|---|---|
| 36 | | −36.903 |
| 37 | | −36.761 |
| 38 | | −36.718 |
| 39 | | −36.588 |
| 40 | | −36.555 |
| 41 | | −36.527 |
| 42 | | −36.516 |
| 43 | | −36.418 |
| 44 | | −36.392 |

TABLE 1-continued

ATRA-related compounds of the invention including substitutions at W.

| Compound Number | Compound | MMGBSA dG Bind |
|---|---|---|
| 45 | | −36.388 |
| 46 | | −36.384 |
| 47 | | −36.256 |
| 48 | | −36.247 |
| 49 | | −36.061 |
| 50 | | −35.965 |
| 51 | | −35.875 |
| 52 | | −35.849 |

TABLE 1-continued

ATRA-related compounds of the invention including substitutions at W.

| Compound Number | Compound | MMGBSA dG Bind |
|---|---|---|
| 53 | | −35.784 |
| 54 | | −35.682 |
| 55 | | −35.677 |
| 56 | | −35.622 |
| 57 | | −35.513 |
| 58 | | −35.493 |
| 59 | | −35.321 |
| 60 | | −35.277 |

TABLE 1-continued

ATRA-related compounds of the invention including substitutions at W.

| Compound Number | Compound | MMGBSA dG Bind |
|---|---|---|
| 61 | | −35.303 |
| 62 | | −35.186 |
| 63 | | −35.164 |
| 64 | | −35.152 |
| 65 | | −35.142 |
| 66 | | −34.986 |
| 67 | | −34.949 |
| 68 | | −34.940 |
| 69 | | −34.843 |

TABLE 1-continued
ATRA-related compounds of the invention including substitutions at W.
| Compound Number | Compound | MMGBSA dG Bind |
|---|---|---|
| 70 | 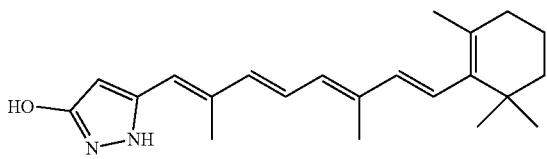 [SMILES: CC1=C(/C=C/C(C)=C/C=C/C(C)=C/c2cc(O)n[nH]2)C(C)(C)CCC1] | −34.823 |
| 71 | 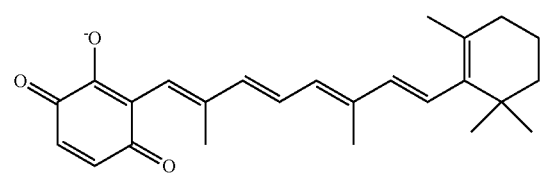 | −34.762 |
| 72 | 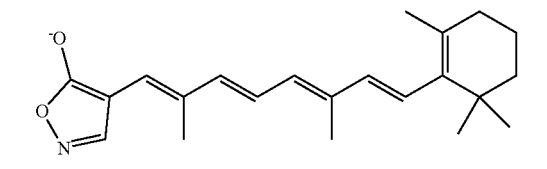 | −34.648 |
| 73 | 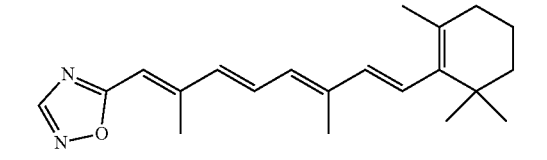 [SMILES: CC1=C(/C=C/C(C)=C/C=C/C(C)=C/c2ncno2)C(C)(C)CCC1] | −34.522 |
| 74 | 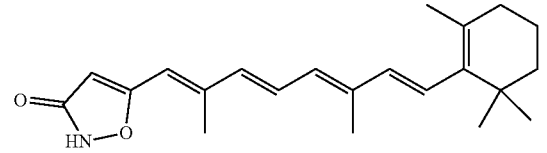 | −34.465 |
| 75 | 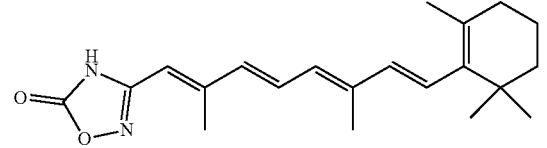 [SMILES: CC1=C(/C=C/C(C)=C/C=C/C(C)=C/c2noc(=O)[nH]2)C(C)(C)CCC1] | −34.303 |
| 76 | 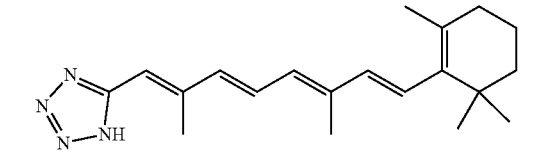 | −34.217 |
| 77 | 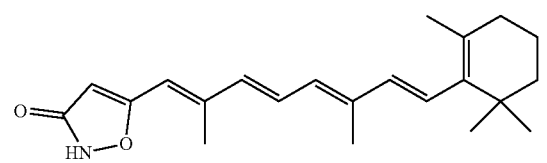 [SMILES: CC1=C(/C=C/C(C)=C/C=C/C(C)=C/c2cc(=O)[nH]o2)C(C)(C)CCC1] | −34.173 |
| 78 | 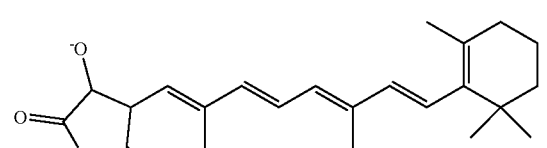 | −34.134 |

TABLE 1-continued
ATRA-related compounds of the invention including substitutions at W.
| Compound Number | Compound | MMGBSA dG Bind |
|---|---|---|
| 79 | 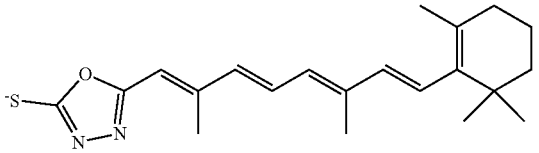 | −34.042 |
| 80 | 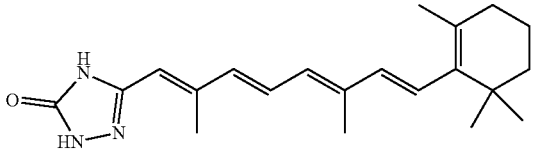 | −34.010 |
| 81 | 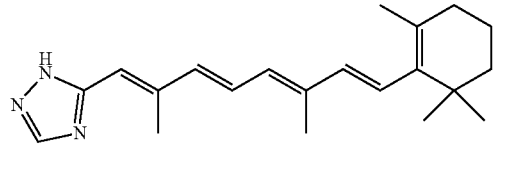 [SMILES: CC1=C(/C=C/C(C)=C/C=C/C(C)=C/c2ncn[nH]2)C(C)(C)CCC1] | −33.982 |
| 82 | 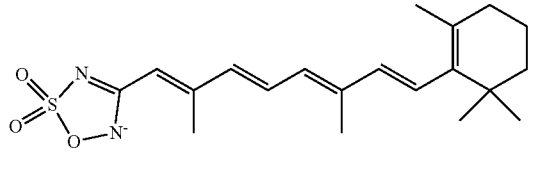 [SMILES: CC1=C(/C=C/C(C)=C/C=C/C(C)=C/C2=NS(=O)(=O)O[N-]2)C(C)(C)CCC1] | −33.971 |
| 83 | 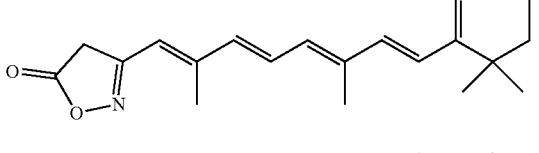 | −33.948 |
| 84 | 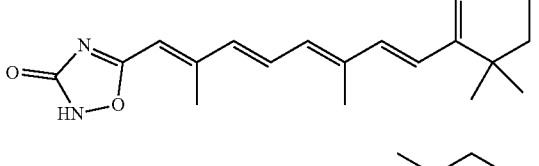 | −33.573 |
| 85 | 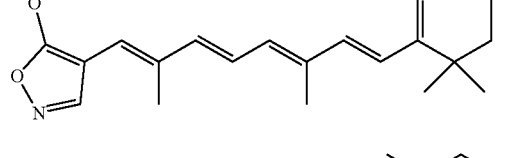 | −33.498 |
| 86 | 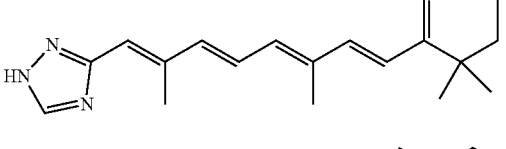 | −32.867 |
| 87 | 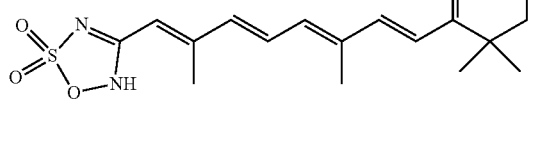 | −32.431 |

TABLE 1-continued

ATRA-related compounds of the invention including substitutions at W.

| Compound Number | Compound | MMGBSA dG Bind |
|---|---|---|
| 88 | | −32.106 |
| 89 | | −32.103 |
| 90 | | −31.917 |
| 91 | | −31.769 |
| 92 | | −31.700 |
| 93 | | −31.628 |
| 94 | | −31.591 |
| 95 | | −31.533 |
| 96 | | −31.228 |

TABLE 1-continued

ATRA-related compounds of the invention including substitutions at W.

| Compound Number | Compound | MMGBSA dG Bind |
|---|---|---|
| 97 | 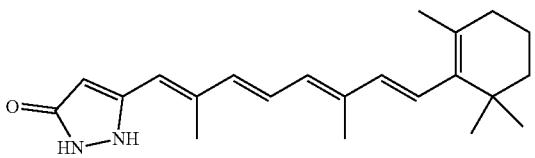 | −30.921 |
| 98 | 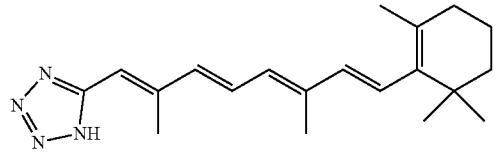 [SMILES: CC1=C(/C=C/C(C)=C/C=C/C(C)=C/c2nnn[n-]2)C(C)(C)CCC1] | −30.851 |
| 99 | 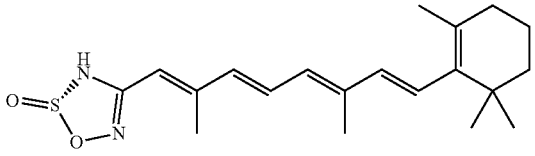 [SMILES: CC1=C(/C=C/C(C)=C/C=C/C(C)=C/C2=NO[S@](=O)N2)C(C)(C)CCC1] | −30.640 |
| 100 | 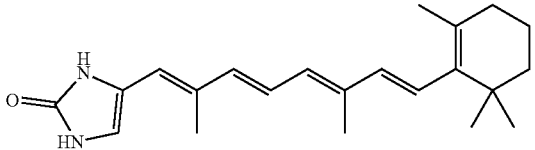 [SMILES: CC1=C(/C=C/C(C)=C/C=C/C(C)=C/c2c[nH]c(=O)[nH]2)C(C)(C)CCC1] | −30.511 |
| 101 | 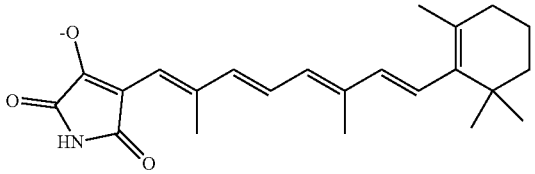 | −30.252 |

In Tables 1-5, the MMGBSA dG Bind values are calculated binding energies. These binding energies may not match the absolute values of experimental binding affinities but should agree reasonably well with rankings based on experimental binding affinities. A more negative value indicates stronger binding.

In some embodiments, an ATRA-related compound is a compound according to Formula Ib (Formula Ib)

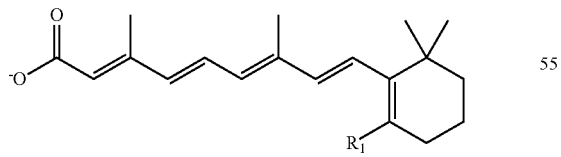

$R_1$ includes a substitution such as any disclosed herein. $R_1$ may comprise one or more halogen, carbonyl, hydroxyl, alkoxy, amino, amide, sulfonyl, or other groups, such as those described herein; one or more optionally substituted aryl or heteroaryl groups; or one or more optionally substituted cycloalkyl, heterocycloalkyl, cycloalkenyl, or heterocycloalkenyl groups. For example, an ATRA-related compound may be selected from compounds 102-125 of Table 2.

TABLE 2

ATRA-related compounds of the invention including substitutions at $R_1$.

| Compound Number | Compound | MMGBSA dG Bind |
|---|---|---|
| 102 | | −41.258 |
| 103 | | −40.318 |
| 104 | | −37.914 |
| 105 | | −37.502 |
| 106 | | −37.178 |
| 107 | | −37.014 |

TABLE 2-continued
ATRA-related compounds of the invention including substitutions at $R_1$.
| Compound Number | Compound | MMGBSA dG Bind |
|---|---|---|
| 108 | 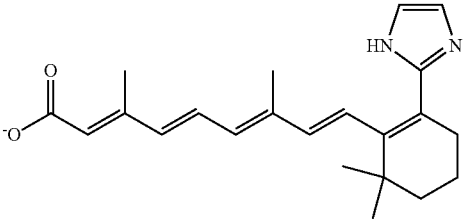 | −36.647 |
| 109 | 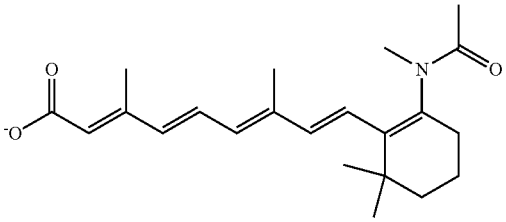 | −36.455 |
| 110 | 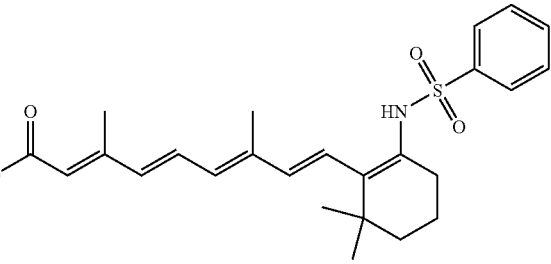 | −36.050 |
| 111 | 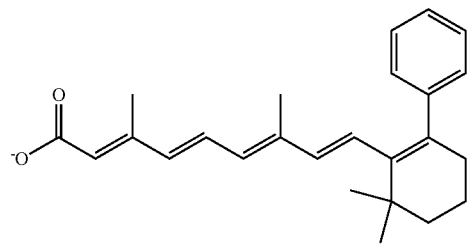 | −35.993 |
| 112 | 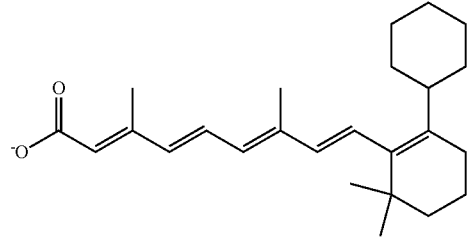 | −35.993 |
| 113 | 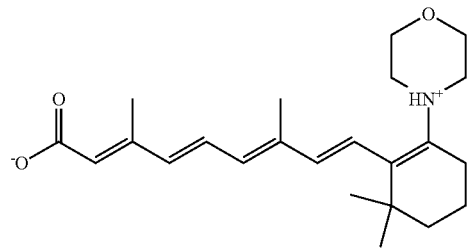 | −34.396 |

TABLE 2-continued

ATRA-related compounds of the invention including substitutions at $R_1$.

| Compound Number | Compound | MMGBSA dG Bind |
|---|---|---|
| 114 | | −33.971 |
| 115 | | −33.970 |
| 116 | | −33.501 |
| 117 | | −33.395 |
| 118 | | −33.298 |
| 119 | | −32.812 |

TABLE 2-continued

ATRA-related compounds of the invention including substitutions at $R_1$.

| Compound Number | Compound | MMGBSA dG Bind |
|---|---|---|
| 120 | | −32.087 |
| 121 | | −30.415 |
| 122 | | −30.228 |
| 123 | | −30.154 |
| 124 | | −30.137 |
| 125 | | −30.052 |

In some embodiments, an ATRA-related compound is a compound according to Formula I Ic

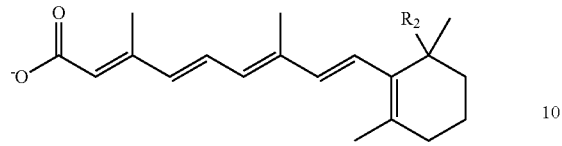

(Formula Ic)

wherein $R_2$ includes a substitution such as any disclosed herein. $R_2$ may comprise one or more halogen, carbonyl, hydroxyl, alkoxy, amino, amide, sulfonyl, or other groups, such as those described herein; one or more optionally substituted aryl or heteroaryl groups; or one or more optionally substituted cycloalkyl, heterocycloalkyl, cycloalkenyl, or heterocycloalkenyl groups. For example, an ATRA-related compound may be selected from compounds 126-150 of Table 3.

TABLE 3

ATRA-related compounds of the invention including substitutions at $R_2$.

| Compound Number | Compound | MMGBSA dG Bind |
|---|---|---|
| 126 | | −38.710 |
| 127 | | −38.225 |
| 128 | | −37.131 |
| 129 | | −36.785 |

TABLE 3-continued

ATRA-related compounds of the invention including substitutions at $R_2$.

| Compound Number | Compound | MMGBSA dG Bind |
|---|---|---|
| 130 | | −36.314 |
| 131 | | −35.906 |
| 132 | | −35.695 |
| 133 | | −35.669 |
| 134 | | −35.419 |
| 135 | | −35.284 |
| 136 | | −34.966 |

TABLE 3-continued
ATRA-related compounds of the invention including substitutions at $R_2$.
| Compound Number | Compound | MMGBSA dG Bind |
|---|---|---|
| 137 | 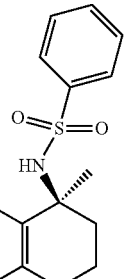 | −34.466 |
| 138 | 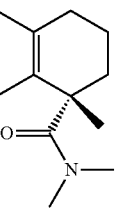 | −34.411 |
| 139 | 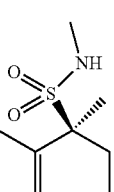 | −34.268 |
| 140 | 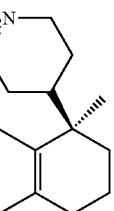 | −34.256 |
| 141 | 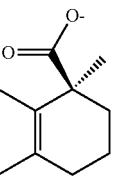 | −33.085 |
| 142 | 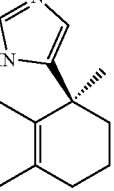 | −32.963 |

TABLE 3-continued

ATRA-related compounds of the invention including substitutions at R$_2$.

| Compound Number | Compound | MMGBSA dG Bind |
|---|---|---|
| 143 | | −32.080 |
| 144 | | −31.664 |
| 145 | | −30.991 |
| 146 | | −30.819 |
| 147 | | −30.766 |
| 148 | | −30.370 |
| 149 | | −30.318 |

TABLE 3-continued

ATRA-related compounds of the invention including substitutions at $R_2$.

| Compound Number | Compound | MMGBSA dG Bind |
|---|---|---|
| 150 | | −30.111 |

In some embodiments, an ATRA-related compound is a compound according to Formula Id

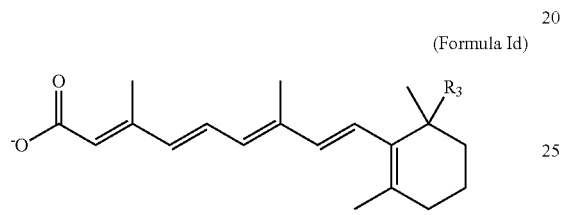

(Formula Id)

wherein $R_3$ includes a substitution such as any disclosed herein. $R_3$ may comprise one or more halogen, carbonyl, hydroxyl, alkoxy, amino, amide, sulfonyl, or other groups, such as those described herein; one or more optionally substituted aryl or heteroaryl groups; or one or more optionally substituted cycloalkyl, heterocycloalkyl, cycloalkenyl, or heterocycloalkenyl groups. For example, an ATRA-related compound may be selected from compounds 151-176 of Table 4.

TABLE 4

ATRA-related compounds of the invention including substitutions at $R_3$.

| Compound Number | Compound | MMGBSA dG Bind |
|---|---|---|
| 151 | | −43.497 |
| 152 | | −41.832 |

TABLE 4-continued

ATRA-related compounds of the invention including substitutions at $R_3$.

| Compound Number | Compound | MMGBSA dG Bind |
|---|---|---|
| 153 | | −40.871 |
| 154 | | −39.638 |
| 155 | | −38.360 |
| 156 | | −38.167 |
| 157 | | −37.593 |
| 158 | | −37.523 |
| 159 | | −37.214 |

TABLE 4-continued

ATRA-related compounds of the invention including substitutions at $R_3$.

| Compound Number | Compound | MMGBSA dG Bind |
|---|---|---|
| 160 | | −36.927 |
| 161 | | −36.711 |
| 162 | | −36.274 |
| 163 | | −35.940 |
| 164 | | −35.824 |
| 165 | | −35.720 |

TABLE 4-continued

ATRA-related compounds of the invention including substitutions at R₃.

| Compound Number | Compound | MMGBSA dG Bind |
|---|---|---|
| 166 | | −35.322 |
| 167 | | −34.656 |
| 168 | | −34.565 |
| 169 | | −33.968 |
| 170 | | −32.483 |
| 171 | | −31.386 |

TABLE 4-continued

ATRA-related compounds of the invention including substitutions at $R_3$.

| Compound Number | Compound | MMGBSA dG Bind |
|---|---|---|
| 172 | | -31.339 |
| 173 | | -31.060 |
| 174 | | -30.951 |
| 175 | | -30.670 |
| 176 | | -30.553 |

In some embodiments, an ATRA-related compound is a compound according to formula I wherein one or more of $R_1$, $R_2$, $R_3$, and W includes a substitution such as any disclosed herein. For example, an ATRA-related compound may include one or more methyl groups at one or more of $R_1$, $R_2$, and $R_3$ and a carboxylic acid group at W. In some embodiments, ATRA-related compounds include two methyl groups at two of $R_1$, $R_2$, and $R_3$ and an optionally substituted aryl, heteroaryl, cycloalkyl, cycloalkenyl, heterocycloalkyl, or heterocycloalkenyl group at W. Examples of ATRA-related compounds according to the present invention are included Table 5.

TABLE 5

ATRA-related compounds of the invention including substitutions at one or more of R$_1$, R$_2$, R$_3$, and W.

| Compound Number | Compound | MMGBSA dG Bind |
|---|---|---|
| 177 | | −48.677 |
| 178 | | −48.019 |
| 179 | | −47.880 |
| 180 | | −47.752 |
| 181 | | −47.697 |
| 182 | | −47.360 |
| 183 | | −47.269 |

TABLE 5-continued

ATRA-related compounds of the invention including substitutions at one or more of $R_1$, $R_2$, $R_3$, and W.

| Compound Number | Compound | MMGBSA dG Bind |
|---|---|---|
| 184 | | −46.786 |
| 185 | | −46.761 |
| 186 | | −46.392 |
| 187 | | −45.617 |
| 188 | | −45.455 |
| 189 | | −45.187 |
| 190 | | −44.921 |

TABLE 5-continued

ATRA-related compounds of the invention including substitutions at one or more of R₁, R₂, R₃, and W.

| Compound Number | Compound | MMGBSA dG Bind |
|---|---|---|
| 191 | | −44.915 |
| 192 | | −44.866 |
| 193 | | −44.729 |
| 194 | | −44.709 |
| 195 | | −44.707 |
| 196 | | −44.652 |
| 197 | | −44.554 |

TABLE 5-continued

ATRA-related compounds of the invention including substitutions at one or more of R$_1$, R$_2$, R$_3$, and W.

| Compound Number | Compound | MMGBSA dG Bind |
|---|---|---|
| 198 | | −44.505 |
| 199 | | −44.358 |
| 200 | | −44.353 |
| 201 | | −44.219 |
| 202 | | −44.152 |
| 203 | | −44.021 |
| 204 | | −43.946 |

TABLE 5-continued

ATRA-related compounds of the invention including substitutions at one or more of R₁, R₂, R₃, and W.

| Compound Number | Compound | MMGBSA dG Bind |
|---|---|---|
| 205 | | −43.886 |
| 206 | | −43.798 |
| 207 | | −43.743 |
| 208 | | −43.716 |
| 209 | | −43.575 |
| 210 | | −43.424 |

TABLE 5-continued

ATRA-related compounds of the invention including substitutions at one or more of $R_1$, $R_2$, $R_3$, and W.

| Compound Number | Compound | MMGBSA dG Bind |
|---|---|---|
| 211 | | −43.403 |
| 212 | | −43.270 |
| 213 | | −42.985 |
| 214 | | −42.595 |
| 215 | | −42.420 |
| 216 | | −42.360 |

TABLE 5-continued

ATRA-related compounds of the invention including substitutions at one or more of $R_1$, $R_2$, $R_3$, and W.

| Compound Number | Compound | MMGBSA dG Bind |
|---|---|---|
| 217 | | −42.289 |
| 218 | | −42.244 |
| 219 | | −41.962 |
| 220 | | −41.884 |
| 221 | | −41.661 |
| 222 | | −41.517 |

TABLE 5-continued

ATRA-related compounds of the invention including substitutions at one or more of R₁, R₂, R₃, and W.

| Compound Number | Compound | MMGBSA dG Bind |
|---|---|---|
| 223 | | −41.502 |
| 224 | | −40.866 |
| 225 | | −40.861 |
| 226 | | −40.804 |
| 227 | | −40.611 |
| 228 | | −40.470 |

TABLE 5-continued

ATRA-related compounds of the invention including substitutions at one or more of R₁, R₂, R₃, and W.

| Compound Number | Compound | MMGBSA dG Bind |
|---|---|---|
| 229 | | −39.952 |
| 230 | | −39.895 |
| 231 | | −39.785 |
| 232 | | −39.704 |
| 233 | | −39.520 |
| 234 | | −39.409 |

TABLE 5-continued
ATRA-related compounds of the invention including substitutions at one or more of $R_1$, $R_2$, $R_3$, and W.
| Compound Number | Compound | MMGBSA dG Bind |
|---|---|---|
| 235 | 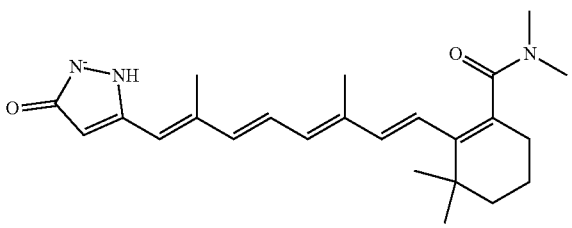 [SMILES: CC(/C=C/C1=C(C(=O)N(C)C)CCCC1(C)C)=C\C=C\C(C)=C\c1cc(=O)[n-][nH]1] | −39.169 |
| 236 | 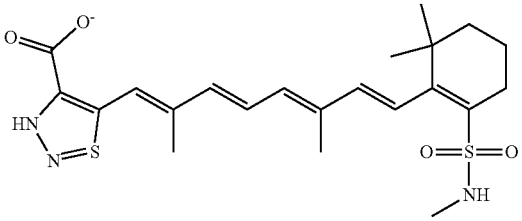 | −39.122 |
| 237 | 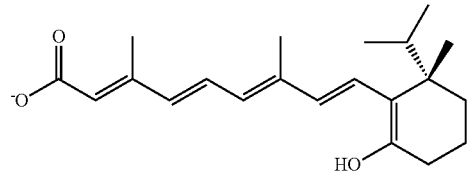 | −38.985 |
| 238 | 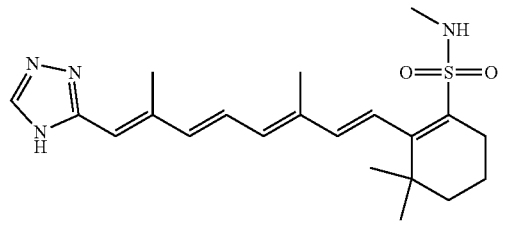 [SMILES: CNS(=O)(=O)C1=C(/C=C/C(C)=C/C=C/C(C)=C/c2nnc[nH]2)C(C)(C)CCC1] | −38.949 |
| 239 | 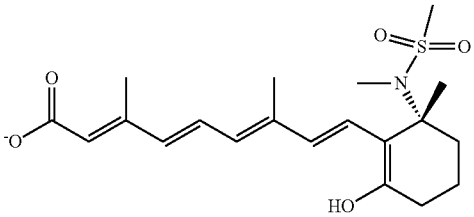 | −38.918 |
| 240 | 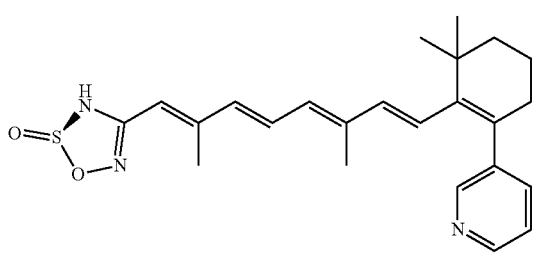 [SMILES: CC(/C=C/C1=C(c2cccnc2)CCCC1(C)C)=C\C=C\C(C)=C\C1=NO[S@@](=O)N1] | −38.495 |

TABLE 5-continued

ATRA-related compounds of the invention including substitutions at one or more of R₁, R₂, R₃, and W.

| Compound Number | Compound | MMGBSA dG Bind |
|---|---|---|
| 241 | | −38.478 |
| 242 | | −38.423 |
| 243 | | −38.203 |
| 244 | | −38.198 |
| 245 | | −37.907 |
| 246 | | −37.747 |
| 247 | | −37.674 |

TABLE 5-continued

ATRA-related compounds of the invention including substitutions at one or more of $R_1$, $R_2$, $R_3$, and W.

| Compound Number | Compound | MMGBSA dG Bind |
|---|---|---|
| 248 | | −37.617 |
| 249 | | −37.559 |
| 250 | | −37.499 |
| 251 | | −37.379 |
| 252 | | −37.159 |
| 253 | | −36.667 |

TABLE 5-continued
ATRA-related compounds of the invention including substitutions at one or more of $R_1$, $R_2$, $R_3$, and W.
| Compound Number | Compound | MMGBSA dG Bind |
|---|---|---|
| 254 | 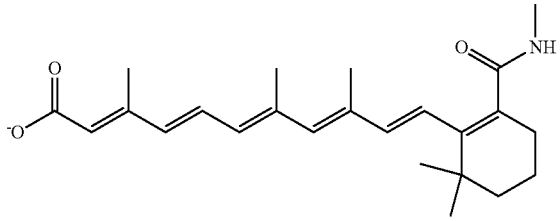 | −36.467 |
| 255 | 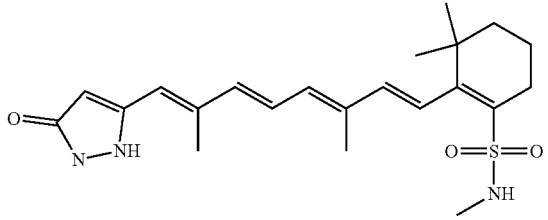 [SMILES: CNS(=O)(=O)C1=C(/C=C/C(C)=C/C=C/C(C)=C/c2cc(=O)[nH][nH]2)C(C)(C)CCC1] | −35.928 |
| 256 | 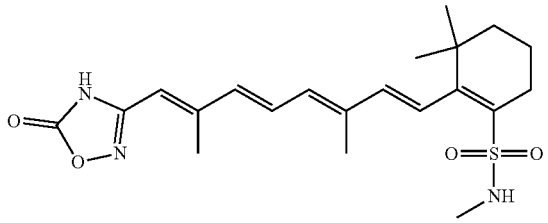 [SMILES: CNS(=O)(=O)C1=C(/C=C/C(C)=C/C=C/C(C)=C/c2noc(=O)[nH]2)C(C)(C)CCC1] | −35.741 |
| 257 | 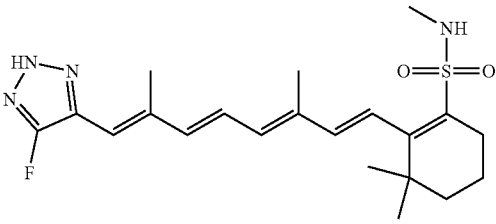 [SMILES: CNS(=O)(=O)C1=C(/C=C/C(C)=C/C=C/C(C)=C/c2n[nH]nc2F)C(C)(C)CCC1] | −35.403 |
| 258 | 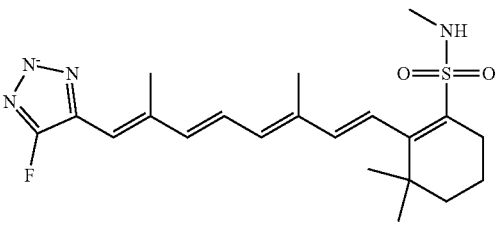 [SMILES: CNS(=O)(=O)C1=C(/C=C/C(C)=C/C=C/C(C)=C/c2n[n-]nc2F)C(C)(C)CCC1] | −35.039 |
| 259 | 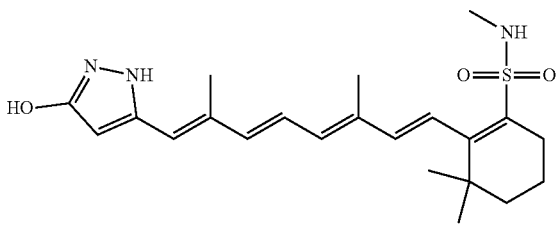 [SMILES: CNS(=O)(=O)C1=C(/C=C/C(C)=C/C=C/C(C)=C/c2cc(O)n[nH]2)C(C)(C)CCC1] | −34.906 |

TABLE 5-continued
ATRA-related compounds of the invention including substitutions at one or more of R₁, R₂, R₃, and W.
| Compound Number | Compound | MMGBSA dG Bind |
|---|---|---|
| 260 | 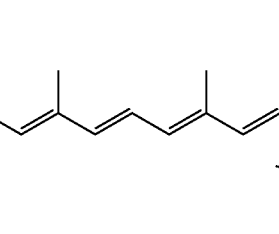 | −34.492 |
| 261 | 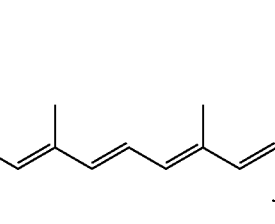 | −32.922 |
| 262 | 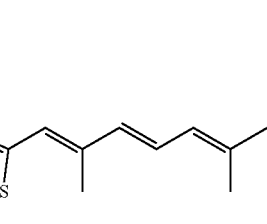 | −32.805 |
| 263 | 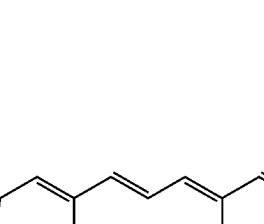 | −32.786 |
| 264 | 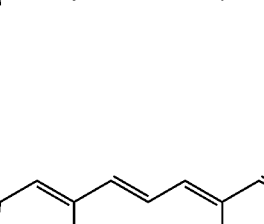 | −32.382 |
| 265 | 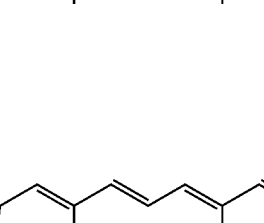 | −31.879 |

TABLE 5-continued

ATRA-related compounds of the invention including substitutions at one or more of R₁, R₂, R₃, and W.

| Compound Number | Compound | MMGBSA dG Bind |
|---|---|---|
| 266 | | −31.566 |
| 267 | | −31.378 |
| 268 | | −31.366 |
| 269 | | −31.288 |
| 270 | | −30.991 |
| 271 | | −30.938 |

TABLE 5-continued

ATRA-related compounds of the invention including substitutions at one or more of $R_1$, $R_2$, $R_3$, and W.

| Compound Number | Compound | MMGBSA dG Bind |
|---|---|---|
| 272 | (structure) | −30.652 |

As used herein, ATRA-related compounds do not include: ATRA, 13cRA, retinal, retinol, retinyl acetate, AC-55649, β-carotene, adapalene (e.g., in combination with clindamycin hydrochloride), alitretinoin, bexarotene, isotretinoin, tamibarotene, tazarotene, tretinoin (e.g., in combination with clindamycin phosphate), adapalene (e.g., in combination with benzoyl peroxide), peretinoin, NRX-4204, seocalcitol, 9cUAB-30, RXR agonists (e.g., those described by Okayama University), palovarotene, talarozole, AGN-193174, AGN-194301, AHPN analogs, BMS-181163, E-6060, I-arglitazar, Farnesoid X receptor agonists, GW-0791, HX-600, LG-100754, LG-101506, LG-268, NRX-4310, Ro-13-6307, PA-452, RAR alpha agonists (e.g., those described by Allergan and Eisai), RAR beta agonists (e.g., those described by MD Anderson), RAR-binding retinoids (e.g., those described by Galderma), retinoic acid receptor antagonists (e.g., those described by Allergan), retinoic acid receptor substrates (e.g., those described by Bristol-Myers Squibb), RWJ-23989, RXR modulators (e.g., those described by Ligand/Eli Lilly), SR-11238, amsilarotene, MX-781, SR-11237, acitretin, BMS 194753, AGN 195183, AM580 (CD365), BMS 209641, BMS 238987, AGN-153639, CD586, AC261066, BMS 189981, CD 666, AHPN (CD437), CH55, LGD 1550, TTNPB (RO139410), AGN-194310, BMS 204493, AGN 195109, BMS 206005, Ro 41-5251, BMS 195634, CD2565, or the compounds included in Table 6. Further, ATRA-related compounds of the invention do not include compounds having the structure $R^1$—$Ar^1$-$L^1Ar^2$-$L^2$-$C(=O)R^3$ (Formula I), in which $Ar^1$ and $Ar^2$ are, independently, optionally substituted aryl or an optionally substituted heteroaryl; $R^1$ is H, an optionally substituted alkyl group, an optionally substituted alkenyl group, or an optionally substituted alkynyl group; each of $L^1$ and $L^2$ is selected, independently, from a covalent bond, an optionally substituted $C_{1-10}$ alkylene, an optionally substituted $C_{2-10}$ alkenylene (e.g., —CH=CH—, —COCH=CH—, —CH=CHCO—, a dienyl group, or a trienyl group), optionally substituted $C_{2-10}$ alkynylene (e.g., —C≡C—), or —$(CHR^4)_n$$CONR^5$—, —$NR^5CO$—, where n is 0 or 1, $R^4$ is H or OH, and $R^5$ is H or optionally substituted alkyl; and $R^3$ is H, $OR^4$, or $N(R^4)_2$, where each $R^4$ is selected, independently, from H, optionally substituted alkyl, or optionally substituted heteroalkyl.

Table 6 includes examples of retinoic acid compounds that are not ATRA-related compounds of the invention.

TABLE 6

Excluded compounds structurally similar to retinoic acid.

| CID | IUPAC | Other names |
|---|---|---|
| 444795 | (2E,4E,6E,8E)-3,7-dimethyl-9-(2,6,6-trimethylcyclohexen-1-yl)nona-2,4,6,8-tetraenoic acid | Retinoic acid; tretinoin; Vitamin A acid |
| 25145416 | (2Z,4E,6Z,8Z)-3,7-dimethyl-9-(2,6,6-trimethylcyclohexen-1-yl)nona-2,4,6,8-tetraenoic acid | |
| 23275881 | (2Z,4Z,6E,8Z)-3,7-dimethyl-9-(2,6,6-trimethylcyclohexen-1-yl)nona-2,4,6,8-tetraenoic acid | |
| 12358678 | (2E,4E,6E,8Z)-3,7-dimethyl-9-(2,6,6-trimethylcyclohexen-1-yl)nona-2,4,6,8-tetraenoic acid | CHEMBL44478; CHEBI: 168407; AC-540 |
| 10881132 | (2Z,4Z,6E,8E)-3,7-dimethyl-9-(2,6,6-trimethylcyclohexen-1-yl)nona-2,4,6,8-tetraenoic acid | |
| 10638113 | (2E,4E,6E,8E)-3,7-dimethyl-9-(2,6,6-trimethylcyclohexen-1-yl)nona-2,4,6,8-tetraenoic acid | |
| 9861147 | (2E,4Z,6Z,8E)-3,7-dimethyl-9-(2,6,6-trimethylcyclohexen-1-yl)nona-2,4,6,8-tetraenoic acid | |
| 9796370 | (2E,4Z,6E,8E)-3,7-dimethyl-9-(2,6,6-trimethylcyclohexen-1-yl)nona-2,4,6,8-tetraenoic acid | 1tyr; (11Z)-retinoic acid; 11-cis-Retinoic acid |
| 6603983 | (2E,4Z,6E,8Z)-3,7-dimethyl-9-(2,6,6-trimethylcyclohexen-1-yl)nona-2,4,6,8-tetraenoic acid | Tocris-0695; Lopac-R-2625; Lopac-R-3255 |

TABLE 6-continued

Excluded compounds structurally similar to retinoic acid.

| CID | IUPAC | Other names |
|---|---|---|
| 6419708 | (2Z,4E,6Z,8E)-3,7-dimethyl-9-(2,6,6-trimethylcyclohexen-1-yl)nona-2,4,6,8-tetraenoic acid | 9,13-di-cis-RA; 9,13-Di-cis-retinoic acid; 9-cis,13-cis-Retinoic acid |
| 5282379 | (2Z,4E,6E,8E)-3,7-dimethyl-9-(2,6,6-trimethylcyclohexen-1-yl)nona-2,4,6,8-tetraenoic acid | Isotretinoin; 13-cis-Retinoic acid; Accutan |
| 449171 | (2E,4E,6Z,8E)-3,7-dimethyl-9-(2,6,6-trimethylcyclohexen-1-yl)nona-2,4,6,8-tetraenoic acid | Alitretinoin; Panretin; 9-CIS-RETINOIC ACID |
| 5538 | 3,7-dimethyl-9-(2,6,6-trimethylcyclohexen-1-yl)nona-2,4,6,8-tetraenoic acid | Spectrum_001676; SpecPlus_000696; AC1L1KKH |
| 54305566 | 2,4-dideuterio-7-methyl-3-(trideuteriomethyl)-9-(2,6,6-trimethylcyclohexen-1-yl)nona-2,4,6,8-tetraenoic acid | |
| 54305565 | 9-[3,3-dideuterio-6,6-dimethyl-2-(trideuteriomethyl)cyclohexen-1-yl]-3,7-dimethylnona-2,4,6,8-tetraenoic acid | |
| 10566385 | (2E,4E,6Z,8E)-7-methyl-3-(trideuteriomethyl)-9-(2,6,6-trimethylcyclohexen-1-yl)nona-2,4,6,8-tetraenoic acid | |
| 10518761 | (2E,4E,6Z,8E)-7-methyl-9-(2,6,6-trimethylcyclohexen-1-yl)-3-(tritritiomethyl)nona-2,4,6,8-tetraenoic acid | |
| 10470200 | (2E,4Z,6Z,8E)-4,5-dideuterio-3,7-dimethyl-9-(2,6,6-trimethylcyclohexen-1-yl)nona-2,4,6,8-tetraenoic acid | |
| 10425032 | (2E,4E,6Z,8E)-4,5-dideuterio-3,7-dimethyl-9-(2,6,6-trimethylcyclohexen-1-yl)nona-2,4,6,8-tetraenoic acid | |
| 10357701 | (2E,4E,6Z,8E)-3,7-dimethyl-9-(2,6,6-trimethyl-4,5-ditritiocyclohexen-1-yl)nona-2,4,6,8-tetraenoic acid | |
| 10267048 | (2E,4E,6Z,8E)-3,7-dimethyl-9-(2,6,6-trimethylcyclohexen-1-yl)-4,5-ditritionona-2,4,6,8-tetraenoic acid | |
| 10086398 | (2Z,4Z,6Z,8E)-3,7-dimethyl-9-(2,6,6-trimethylcyclohexen-1-yl)-4,5-ditritionona-2,4,6,8-tetraenoic acid | |
| 10086397 | (2E,4E,6Z,8E)-3,7-dimethyl-9-(2,6,6-trimethyl-3,4-ditritiocyclohexen-1-yl)nona-2,4,6,8-tetraenoic acid | |
| 10063649 | (2E,4E,6Z,8E)-9-[2,6-dimethyl-6-(trideuteriomethyl)cyclohexen-1-yl]-3,7-dimethylnona-2,4,6,8-tetraenoic acid | |
| 10040620 | (2E,4E,6Z,8E)-9-(4,5-dideuterio-2,6,6-trimethylcyclohexen-1-yl)-3,7-dimethylnona-2,4,6,8-tetraenoic acid | |
| 10017935 | (2Z,4E,6E,8E)-3,7-dimethyl-9-(2,6,6-trimethylcyclohexen-1-yl)-4,5-ditritionona-2,4,6,8-tetraenoic acid | |
| 10017822 | (2E,4E,6Z,8E)-9-(3,4-dideuterio-2,6,6-trimethylcyclohexen-1-yl)-3,7-dimethylnona-2,4,6,8-tetraenoic acid | |
| 9995220 | (2E,4Z,6Z,8E)-3,7-dimethyl-9-(2,6,6-trimethylcyclohexen-1-yl)-4,5-ditritionona-2,4,6,8-tetraenoic acid | |
| 9972327 | (2Z,4Z,6E,8E)-3,7-dimethyl-9-(2,6,6-trimethylcyclohexen-1-yl)-4,5-ditritionona-2,4,6,8-tetraenoic acid | |
| 9972326 | (2E,4Z,6E,8E)-3,7-dimethyl-9-(2,6,6-trimethylcyclohexen-1-yl)-4,5-ditritionona-2,4,6,8-tetraenoic acid | |
| 9839397 | (2E,4E,6Z,8E)-3,7-dimethyl-9-(2,6,6-trimethylcyclohexen-1-yl)-5-tritionona-2,4,6,8-tetraenoic acid | |
| 6913160 | (2Z,4E,6Z,8E)-3,7-dimethyl-9-(2,6,6-trimethylcyclohexen-1-yl)-5-tritionona-2,4,6,8-tetraenoic acid | Retinoic-11-t acid; AC1OC7MJ; all-trans-(11-3H)-Retinoic acid |
| 6913136 | (2Z,4E,6Z,8E)-3,7-dimethyl-9-(2,6,6-trimethylcyclohexen-1-yl)-4,5-ditritionona-2,4,6,8-tetraenoic acid | AC1OC7KP; Retinoic-11,12-t2 acid; 11,12-3H-Retinoic acid |
| 6913131 | (2Z,4E,6Z,8E)-3,7-dimethyl-9-(2,6,6-trimethylcyclohexen-1-yl)-5,6-ditritionona-2,4,6,8-tetraenoic acid | AC1OC7KA; Retinoic-10,11-t2 acid; all-trans-(10,11-3H2)-Retinoic acid |
| 6439661 | (2Z,4E,6Z,8E)-3,7-dimethyl-9-(2,6,6-trimethylcyclohexen-1-yl)nona-2,4,6,8-tetraenoic acid | |
| 134262 | 3,7-dimethyl-9-(2,6,6-trimethylcyclohexen-1-yl)nona-2,4,6,8-tetraenoic acid | SHGAZHPCJJPHSC-SPLUINJESA-N; FDEFF7D13961B766CC9FE8A740623243 |
| 56684147 | (2E,6Z,8E)-3,7-dimethyl-9-(2,6,6-trimethylcyclohexen-1-yl)nona-2,6,8-trienoic acid | |
| 54219808 | 3,6,7-trimethyl-9-(2,6,6-trimethylcyclohexen-1-yl)nona-2,4,6,8-tetraenoic acid | |
| 53936974 | 3,7-dimethyl-9-(2,6,6-trimethylcyclohexen-1-yl)nona-2,6,8-trienoic acid | |
| 53740187 | 3,7-dimethyl-9-(2,6,6-trimethylcyclohexen-1-yl)nona-2,4,6-trienoic acid | |

TABLE 6-continued

Excluded compounds structurally similar to retinoic acid.

| CID | IUPAC | Other names |
|---|---|---|
| 44725022 | (Z)-3-[(E)-2-(2,6,6-trimethylcyclohexen-1-yl)ethenyl]hept-2-enoic acid | AC1Q2V68; (2Z)-3-[(E)-2-(2,6,6-trimethylcyclohex-1-en-1-yl)ethenyl]hept-2-enoic acid |
| 21590819 | (2Z,4E,8E)-3-methyl-7-methylidene-9-(2,6,6-trimethylcyclohexen-1-yl)nona-2,4,8-trienoic acid | CHEMBL182393 |
| 11738545 | (2E,4E,6E,8E)-3,7-dimethyl-9-(2,6,6-trimethylcyclohexen-1-yl)deca-2,4,6,8-tetraenoic acid | |
| 10518336 | (2E,4E,8E)-3-methyl-7-methylidene-9-(2,6,6-trimethylcyclohexen-1-yl)nona-2,4,8-trienoic acid | CHEMBL426963 |
| 10380944 | (2E,4E,6Z,8E)-3-ethyl-7-methyl-9-(2,6,6-trimethylcyclohexen-1-yl)nona-2,4,6,8-tetraenoic acid | |
| 10335106 | (2E,4E,6E)-3,7-dimethyl-9-(2,6,6-trimethylcyclohexen-1-yl)nona-2,4,6-trienoic acid | CHEMBL487208 |
| 10286439 | (2E,4E,6Z,8E)-7-ethyl-3-methyl-9-(2,6,6-trimethylcyclohexen-1-yl)nona-2,4,6,8-tetraenoic acid | |
| 10149682 | (2E,4E,6Z,8E)-3,6,7-trimethyl-9-(2,6,6-trimethylcyclohexen-1-yl)nona-2,4,6,8-tetraenoic acid | |
| 10041353 | (2E,4E,6E,8E)-3-ethyl-7-methyl-9-(2,6,6-trimethylcyclohexen-1-yl)nona-2,4,6,8-tetraenoic acid | |
| 6439749 | (2E,4E,6E,8E)-9-(2-ethyl-6,6-dimethylcyclohexen-1-yl)-3,7-dimethylnona-2,4,6,8-tetraenoic acid | SRI 2712-24; 2,4,6,8-Nonatetracenoic acid, AC1NUZ8L |
| 5496917 | (2E,4Z,6E)-3,7-dimethyl-9-(2,6,6-trimethylcyclohexen-1-yl)nona-2,4,6-trienoic acid | |
| 5326825 | (2Z,4Z,6E)-3,7-dimethyl-9-(2,6,6-trimethylcyclohexen-1-yl)nona-2,4,6-trienoic acid | AC1NS159 |
| 4136524 | 3-[2-(2,6,6-trimethylcyclohexen-1-yl)ethenyl]hept-2-enoic acid | AC1N4YDA |
| 135317 | 9-(2-ethyl-6,6-dimethylcyclohexen-1-yl)-3,7-dimethylnona-2,4,6,8-tetraenoic acid | |
| 54525370 | 13-(2,6,6-trimethylcyclohexen-1-yl)trideca-2,4,6,8,10,12-hexaenoic acid | |
| 54472611 | 4,7-dimethyl-9-(2,6,6-trimethylcyclohexen-1-yl)nona-2,4,6,8-tetraenoic acid | |
| 54398880 | 3-methyl-5-[2-[2-(2,6,6-trimethylcyclohexen-1-yl)ethenyl]cyclopenten-1-yl]penta-2,4-dienoic acid | |
| 54044750 | 11-(2,6,6-trimethylcyclohexen-1-yl)undeca-2,4,6,8,10-pentaenoic acid | |
| 53876852 | 3,7-dimethyl-9-(2,4,6,6-tetramethylcyclohexen-1-yl)nona-2,4,6,8-tetraenoic acid | |
| 53790569 | 9-(2,6,6-trimethylcyclohexen-1-yl)nona-2,4,6,8-tetraenoic acid | |
| 53743104 | 5,9-dimethyl-11-(2,6,6-trimethylcyclohexen-1-yl)undeca-2,4,6,8,10-pentaenoic acid | |
| 44579060 | (2E,4E,6Z,8E)-9-(2-butyl-6,6-dimethylcyclohexen-1-yl)-3,7-dimethylnona-2,4,6,8-tetraenoic acid | CHEMBL518436 |
| 44393163 | (2Z,4E,8E)-7-methylidene-9-(2,6,6-trimethylcyclohexen-1-yl)nona-2,4,8-trienoic acid | |
| 25141345 | (2E,4E,6E,8E)-9-(2-butyl-6,6-dimethylcyclohexen-1-yl)-3,7-dimethylnona-2,4,6,8-tetraenoic acid | |
| 19609253 | (2E,4E)-3-methyl-5-[2-[(E)-2-(2,6,6-trimethylcyclohexen-1-yl)ethenyl]cyclopenten-1-yl]penta-2,4-dienoic acid | |
| 14731990 | (2E,4E,6E,8E)-7-methyl-9-(2,6,6-trimethylcyclohexen-1-yl)nona-2,4,6,8-tetraenoic acid | |
| 11141121 | (2E,4E,6E,8E)-4,7-dimethyl-9-(2,6,6-trimethylcyclohexen-1-yl)nona-2,4,6,8-tetraenoic acid | |
| 10712359 | (2E,4E,6Z)-3-methyl-7-[(E)-2-(2,6,6-trimethylcyclohexen-1-yl)ethenyl]undeca-2,4,6-trienoic acid | |
| 10474100 | (2E,4E,6E,8E,10E,12E)-3,7,11-trimethyl-13-(2,6,6-trimethylcyclohexen-1-yl)trideca-2,4,6,8,10,12-hexaenoic acid | |
| 10426543 | (E,4E)-3-methyl-4-[3-[(E)-2-(2,6,6-trimethylcyclohexen-1-yl)ethenyl]cyclohex-2-en-1-ylidene]but-2-enoic acid | |
| 10358907 | (Z,4E)-3-methyl-4-[(4E)-3-methyl-4-[(2,6,6-trimethylcyclohexen-1-yl)methylidene]cyclohexa-2,5-dien-1-yl)methylidene] | |
| 10314319 | (2E,4E,6E,8E,10E)-5,9-dimethyl-11-(2,6,6-trimethylcyclohexen-1-yl)undeca-2,4,6,8,10-pentaenoic acid | CHEMBL225948 |
| 10286753 | (2E,4E,6Z,8E)-7-tert-butyl-3-methyl-9-(2,6,6-trimethylcyclohexen-1-yl)nona-2,4,6,8-tetraenoic acid | |
| 10266931 | (2E,4E,6Z)-3-methyl-7-[(E)-2-(2,6,6-trimethylcyclohexen-1-yl)ethenyl]deca-2,4,6-trienoic acid | CHEMBL507779 |
| 10125803 | (2E,4E,6Z)-3-methyl-7-[(E)-2-(2,6,6-trimethylcyclohexen-1-yl)ethenyl]deca-2,4,6-trienoic acid | |
| 10087786 | (Z,4E)-3-methyl-4-[3-[(E)-2-(2,6,6-trimethylcyclohexen-1-yl)ethenyl]cyclohex-2-en-1-ylidene]but-2-enoic acid | |
| 10015486 | (2E,4E,6E)-5-methyl-7-(2,6,6-trimethylcyclohexen-1-yl)hepta-2,4,6-trienoic acid | |

TABLE 6-continued

Excluded compounds structurally similar to retinoic acid.

| CID | IUPAC | Other names |
|---|---|---|
| 9929074 | (2E,4E,6E,8E)-3,7-dimethyl-9-(2,6,6-trimethylcyclohexen-1-yl)nona-2,4,6,8-tetraenoic acid | |
| 9860303 | (2E,4E,6E,8E)-9-(2,6,6-trimethylcyclohexen-1-yl)nona-2,4,6,8-tetraenoic acid | |
| 5355027 | (2E,4E)-3-methyl-5-(2,6,6-trimethylcyclohexen-1-yl)penta-2,4-dienoic acid | C15 acid; AC1NS6O9; NSC23978 |
| 167095 | 3-methyl-5-(2,6,6-trimethylcyclohexen-1-yl)penta-2,4-dienoic acid | AC1L4ZB4 |
| 56606832 | 3,7-dimethyl-9-(9,9,11-trimethylspiro[2.5]oct-10-en-10-yl)nona-2,4,6,8-tetraenoic acid | |
| 54548815 | 3,7,11,11-tetramethyldodeca-2,4-dienoic acid | |
| 54515105 | 7-methyl-3-[2-(2,6,6-trimethylcyclohexen-1-yl)ethenyl]nona-2,5-dienoic acid | YLWKTERFWUXEBW-UHFFFAOYSA-N; 005B26AC36D10A0C9DB5EF006864943F |
| 54358950 | 3-methyl-5-[2-[2-(2,6,6-trimethylcyclohexen-1-yl)ethenyl]cyclohepten-1-yl]penta-2,4-dienoic acid | |
| 54353726 | 3,7,11,11-tetramethyltrideca-2,4-dienoic acid | |
| 54193713 | 3-methyl-5-[2-[2-(2,6,6-trimethylcyclohexen-1-yl)ethenyl]cycloocten-1-yl]penta-2,4-dienoic acid | |
| 53946778 | 2,3,7-trimethyl-9-(2,6,6-trimethylcyclohexen-1-yl)nona-2,4,6,8-tetraenoic acid | |
| 53944823 | 9-(6,6-dimethylcyclohexen-1-yl)-3,7-dimethylnona-2,4,6,8-tetraenoic acid | JAIGDKSXLVOFMH-UHFFFAOYSA-N; F42136BEED6C5A3745B9BA23356D7830 |
| 53921377 | 3-methyl-5-[2-[2-(2,6,6-trimethylcyclohexen-1-yl)ethenyl]cyclohexen-1-yl]penta-2,4-dienoic acid | |
| 44579100 | (2E,4E,6Z,8E)-9-[6,6-dimethyl-2-(2-methylpropyl)cyclohexen-1-yl]-3,7-dimethylnona-2,4,6,8-tetraenoic acid | CHEMBL476773 |
| 44579056 | (2E,4E,6E,8E)-9-[6,6-dimethyl-2-(2-methylpropyl)cyclohexen-1-yl]-3,7-dimethylnona-2,4,6,8-tetraenoic acid | CHEMBL476348 |
| 44314230 | (2Z,5E)-7-methyl-3-[(E)-2-(2,6,6-trimethylcyclohexen-1-yl)ethenyl]nona-2,5-dienoic acid | CHEMBL75548; CHEBI: 220121 |
| 25011742 | (2E,8E)-3,7-dimethyl-9-(2,6,6-trimethylcyclohexen-1-yl)nona-2,8-dienoic acid | |
| 22646220 | (2E,4E,6E,8E)-2,3-dimethyl-9-(2,6,6-trimethylcyclohexen-1-yl)nona-2,4,6,8-tetraenoic acid | |
| 20830941 | (2E,4E,6E,8E)-2,3-dimethyl-9-(2,6,6-trimethylcyclohexen-1-yl)nona-2,4,6,8-tetraenoic acid | |
| 19609240 | (2E,4E)-3-methyl-5-[(1Z)-2-[(E)-2-(2,6,6-trimethylcyclohexen-1-yl)ethenyl]cycloocten-1-yl]penta-2,4-dienoic acid | |
| 18977383 | (2E,4E,6E,8E)-3,7-dimethyl-9-(2,5,6,6-tetramethylcyclohexen-1-yl)nona-2,4,6,8-tetraenoic acid | |
| 15125883 | (2Z,4E,6E,8E)-2,3,7-trimethyl-9-(2,6,6-trimethylcyclohexen-1-yl)nona-2,4,6,8-tetraenoic acid | |
| 15125882 | (2E,4E,6E,8E)-2,3,7-trimethyl-9-(2,6,6-trimethylcyclohexen-1-yl)nona-2,4,6,8-tetraenoic acid | CHEMBL153895; 14-methyl-all-trans-retinoic acid; LMPR01090034 |
| 11266097 | (2Z,4E,8E)-3-methyl-9-(2,6,6-trimethylcyclohexen-1-yl)nona-2,4,8-trien-6-ynoic acid | |
| 11000660 | (2E,4E,6Z,8E)-9-(6,6-dimethylcyclohexen-1-yl)-3,7-dimethylnona-2,4,6,8-tetraenoic acid | |
| 10733921 | (2E,4E,6Z)-7-(8,8-dimethyl-4,5,6,7-tetrahydro-3H-naphthalen-2-yl)-3-methylocta-2,4,6-trienoic acid | |
| 10636975 | (2E,4E,6E,8E)-9-(6,6-dimethylcyclohexen-1-yl)-3,7-dimethylnona-2,4,6,8-tetraenoic acid | |
| 10591236 | (2E,4E,6Z)-7-(4a,8-dimethyl-4,5,6,7-tetrahydro-3H-naphthalen-2-yl)-3-methylocta-2,4,6-trienoic acid | |
| 10404132 | (Z,4E)-3-methyl-4-[(4E)-3-methyl-4-[(2,6,6-trimethylcyclohexen-1-yl)methylidene]cyclohex-2-en-1-ylidene]but-2-enoic acid | |
| 10314318 | (E,4E)-3-methyl-4-[(4E)-3-methyl-4-[(2,6,6-trimethylcyclohexen-1-yl)methylidene]cyclohex-2-en-1-ylidene]but-2-enoic acid | |
| 10215224 | (2E,4E,6Z,8E)-3-methyl-7-propan-2-yl-9-(2,6,6-trimethylcyclohexen-1-yl)nona-2,4,6,8-tetraenoic acid | |
| 10193246 | (2E,4E)-3-methyl-6-[1-[(E)-2-(2,6,6-trimethylcyclohexen-1-yl)ethenyl]cyclopropyl]hexa-2,4-dienoic acid | |
| 9841547 | (2E,4E)-3-methyl-5-[2-[(E)-2-(2,6,6-trimethylcyclohexen-1-yl)ethenyl]cyclohepten-1-yl]penta-2,4-dienoic acid | |
| 9830767 | (2Z,4E,6Z,8E)-9-(6,6-dimethylcyclohexen-1-yl)-3,7-dimethylnona-2,4,6,8-tetraenoic acid | |

TABLE 6-continued

Excluded compounds structurally similar to retinoic acid.

| CID | IUPAC | Other names |
|---|---|---|
| 9819335 | (2E,4E)-3-methyl-5-[2-[(E)-2-(2,6,6-trimethylcyclohexen-1-yl)ethenyl]cyclohexen-1-yl]penta-2,4-dienoic acid | Ro 25-6603; 173792-73-9 |
| 56667667 | (2E,4E,6Z,8E)-3,7-dimethyl-9-(6-methyl-3-prop-1-en-2-ylcyclohexen-1-yl)nona-2,4,6,8-tetraenoic acid | CHEMBL455993; CHEMBL455994 |
| 54758572 | (2Z,4E,6Z,8E)-3,7-dimethyl-9-(2,6,6-trimethylcyclohexen-1-yl)nona-2,4,6,8-tetraenoate | 9-cis-Retinoate; CPD-13549 |
| 54426679 | 2,7-dimethyl-9-(2,6,6-trimethylcyclohexen-1-yl)nona-2,4,6,8-tetraenoic acid | |
| 54325149 | 6-chloro-3,7-dimethyl-9-(2,6,6-trimethylcyclohexen-1-yl)nona-2,4,6,8-tetraenoic acid | |
| 53702687 | 6-iodo-3,7-dimethyl-9-(2,6,6-trimethylcyclohexen-1-yl)nona-2,4,6,8-tetraenoic acid | |
| 29986894 | (2E,4Z,6E,8E)-3,7-dimethyl-9-(2,6,6-trimethylcyclohexen-1-yl)nona-2,4,6,8-tetraenoate | ZINC22066351 |
| 29927144 | (2E,4E,6E,8Z)-3,7-dimethyl-9-(2,6,6-trimethylcyclohexen-1-yl)nona-2,4,6,8-tetraenoate | ZINC21992287 |
| 24916820 | (2E,4E,6E)-3,7-dimethyl-9-(2,6,6-trimethylcyclohexen-1-yl)nona-2,4,6-trienoate | 2g78 |
| 24771817 | 3,7-dimethyl-9-(2,6,6-trimethylcyclohexen-1-yl)nona-2,4,6,8-tetraenoate | CHEBI: 15036 |
| 21917290 | (2E,4E,6E,8E)-9-(5-tert-butyl-2,6,6-trimethylcyclohexen-1-yl)-3,7-dimethylnona-2,4,6,8-tetraenoic acid | |
| 19609245 | (2E,4E,6E,8E)-6-chloro-3,7-dimethyl-9-(2,6,6-trimethylcyclohexen-1-yl)nona-2,4,6,8-tetraenoic acid | |
| 19609224 | (2E,4E,6E,8E)-6-iodo-3,7-dimethyl-9-(2,6,6-trimethylcyclohexen-1-yl)nona-2,4,6,8-tetraenoic acid | |
| 10924150 | (2E,4E,6Z,8E)-9-(2,6-dimethylcyclohexen-1-yl)-3,7-dimethylnona-2,4,6,8-tetraenoic acid | |
| 10613228 | (2E,4E,6E,8E)-9-(2,6-dimethylcyclohexen-1-yl)-3,7-dimethylnona-2,4,6,8-tetraenoic acid | |
| 10469989 | (2E,6Z,8E)-3,7-dimethyl-9-(2,6,6-trimethylcyclohexen-1-yl)nona-2,6,8-trien-4-ynoic acid | |
| 10334998 | (2E,4E)-3-methyl-5-[2-[(E)-2-(2,6,6-trimethylcyclohexen-1-yl)ethenyl]cyclopropyl]penta-2,4-dienoic acid | |
| 9904356 | (2Z,4E,6Z)-3,7-dimethyl-9-(2,6,6-trimethylcyclohexen-1-yl)nona-2,4,6-trien-8-ynoic acid | |
| 7364357 | (2E,4E,6Z,8E)-3,7-dimethyl-9-(2,6,6-trimethylcyclohexen-1-yl)nona-2,4,6,8-tetraenoate | AC1OKKW8; ZINC12661824; 13-cis-retinoate; ZINC03792789 |
| 7048538 | (2Z,4E,6E,8E)-3,7-dimethyl-9-(2,6,6-trimethylcyclohexen-1-yl)nona-2,4,6,8-tetraenoate | |
| 6440565 | 2E,4E,6E)-3,7-dimethyl-9-(2,6,6-trimethylcyclohexen-1-yl)nona-2,4,6-trien-8-ynoic acid | 7,8-Dehydroretinoic acid; 7,8-Didehydroretinoic acid |
| 6419707 | (2E,4E,6E,8E)-3,7-dimethyl-9-(2,6,6-trimethylcyclohexen-1-yl)nona-2,4,6,8-tetraenoate | Retinoate; all-trans-Retinoate; Tretinoine |
| 5771658 | (Z)-3-(2,6,6-trimethylcyclohexen-1-yl)prop-2-enoic acid | NSC-202789; AC1NY9IQ; NCGC00014560 |
| 5383969 | (E)-3-(2,6,6-trimethylcyclohexen-1-yl)prop-2-enoic acid | NSC202789; NSC-20278 |
| 5353358 | (2Z,4E)-3-methyl-6-(2,7,7-trimethyl-3-methylidene-1,4,5,6-tetrahydroinden-2-yl)hexa-2,4-dienoic acid | AC1NS43Q |
| 5289278 | (2E,4E)-3-methyl-6-[(2R)-2,7,7-trimethyl-3-methylidene-1,4,5,6-tetrahydroinden-2-yl]hexa-2,4-dienoic acid | NSC202789; 3-(2,6,6-trimethyl-1-cyclohexen-1-yl)acrylic acid; AC1L77HZ |
| 305742 | 3-(2,6,6-trimethylcyclohexen-1-yl)prop-2-enoic acid | NSC202789; 3-(2,6,6-trimethyl-1-cyclohexen-1-yl)acrylic acid; AC1L77HZ |
| 1851 | 3-methyl-6-(2,7,7-trimethyl-3-methylidene-1,4,5,6-tetrahydroinden-2-yl)hexa-2,4-dienoic acid | AC1L1CDO |
| 54399542 | 6-bromo-3,7-dimethyl-9-(2,6,6-trimethylcyclohexen-1-yl)nona-2,4,6,8-tetraenoic acid | |
| 54233476 | 3,7-dimethyl-5-oxo-9-(2,6,6-trimethylcyclohexen-1-yl)nona-2,6,8-trienoic acid | |
| 54033110 | 2,5,9-trimethyl-11-(2,6,6-trimethylcyclohexen-1-yl)undeca-2,4,6,8,10-pentaenoic acid | |
| 53936708 | 3-methyl-5-[2-[2-(2,6,6-trimethylcyclohexen-1-yl)ethynyl]cyclopenten-1-yl]penta-2,4-dienoic acid | |
| 44314320 | (2Z,4E)-3-methyl-5-[2-[(E)-2-(3,3,6,6-tetramethylcyclohexen-1-yl)ethenyl]cyclopropyl]penta-2,4-dienoic acid | CHEMBL73973; CHEBI: 220303 |

TABLE 6-continued

Excluded compounds structurally similar to retinoic acid.

| CID | IUPAC | Other names |
|---|---|---|
| 44314319 | (2E,4E)-3-methyl-5-[2-[(E)-2-(3,3,6,6-tetramethylcyclohexen-1-yl)ethenyl]cyclopropyl]penta-2,4-dienoic acid | CHEMBL74331; CHEBI: 220301 |
| 22373193 | (2E,4E)-3-methyl-5-[2-[2-(2,6,6-trimethylcyclohexen-1-yl)ethynyl]cyclopenten-1-yl]penta-2,4-dienoic acid | |
| 21145248 | (2Z,4E,6E,8E)-3,7-dimethyl-9-(2,6,6-trimethylcyclohexen-1-yl)nona-2,4,6,8-tetraenoic acid | |
| 20151571 | (2E,4E,6E,8E)-3,7-dimethyl-9-(2,6,6-trimethylcyclohexen-1-yl)nona-2,4,6,8-tetraenoic acid | |
| 19609231 | (2E,4E,6E,8E)-6-bromo-3,7-dimethyl-9-(2,6,6-trimethylcyclohexen-1-yl)nona-2,4,6,8-tetraenoic acid | |
| 16727824 | (2E,4E,6Z,8E)-3,7-dimethyl-9-(2,6,6-trimethylcyclohexen-1-yl)nona-2,4,6,8-tetraenoic acid | All-trans-Retinoic acid & 9-cis-Retinoic Acid |
| 11015604 | (2E,4E,6E,8E,10E,12E,14E,16E)-2,6,11,15-tetramethyl-17-(2,6,6-trimethylcyclohexen-1-yl)-3-tritioheptadeca-2,4,6,8-trimethylcyclyhexen-1-yl)-3-tritioheptadeca-2,4,6,8,10,12,14,16-octaenoic acid | |
| 10406618 | (2E,4Z,6E,8E,10E,12E)-2,7,11-trimethyl-13-(2,6,6-trimethylcyclohexen-1-yl)trideca-2,4,6,8,10,12-hexanoic acid | |
| 9976193 | (2E,4E,6E,8E,10E,12E)-2,7,11-trimethyl-13-(2,6,6-trimethylcyclohexen-1-yl)trideca-2,4,6,8,10,12-hexanoic acid | |
| 9843074 | (2E,4E,6E)-3-methyl-7-(4,4,7,7-tetramethyl-2-pentyl-1,3,5,6-tetrahydroinden-2-yl)hepta-2,4,6-trienoic acid | |
| 6439881 | (2Z,4E,6Z,8E)-9-(3,3-difluoro-2,6,6-trimethylcyclohexen-1-yl)-3,7-dimethylnona-2,4,6,8-tetraenoic acid | DFRA; 4,4-Difluororetinoic acid; AC1O5SM |
| 6436320 | (2E,4E,6Z,8E,10E,12E,14E,16E)-2,6,11,15-tetramethyl-17-(2,6,6-trimethylcyclohexen-1-yl)heptadeca-2,4,6,8,10,12,14,16-octaenoic acid | AC1O5LFK; beta-apo-8'-Carotenoic acid; 8'-Apo-beta,psi-carotenoic acid |
| 5387557 | (2Z)-2-[5-(2,6,6-trimethylcyclohexen-1-yl)-3-[(E)-2-(2,6,6-trimethylcyclohexen-1-yl)ethenyl]cyclohexanoic acid | NSC624510; AC1NTSHG; AC1Q5T6Y |
| 5366642 | (2E,4E,6E,8E)-9-(3,3-difluoro-2,6,6-trimethylcyclohexen-1-yl)-3,7-dimethylnona-2,4,6,8-tetraenoic acid | 4,4-Difluororetinoic acid; AC1NSNWF; 4,4-Difluororetinoic acid (all-trans) |
| 361473 | 2-[5-(2,6,6-trimethylcyclohexen-1-yl)-3-[2-(2,6,6-trimethylcyclohexen-1-yl)ethenyl]cyclohex-2-en-1-yl]heptadeca-2,4,6,8,10,12,14,16-octaenoic acid | AC1L7IQC; NCI60_007432; 2-[5-(2,6,6-trimethylcyclohexen-1-yl)-3-[2-(2,6,6-trimethylcyclohexen-1-yl)ethenyl]cyclohex-2-en-1-ylidene]acetic acid |
| 146218 | 9-(3,3-difluoro-2,6,6-trimethylcyclohexen-1-yl)-3,7-dimethylnona-2,4,6,8-tetraenoic acid | |
| 56660872 | (2E,4E,6Z,8E)-3,7-dimethyl-9-(2-methyl-5-prop-1-en-2-ylcyclohexen-1-yl)nona-2,4,6,8-tetraenoic acid | CHEMBL457645; CHEMBL513434 |
| 54587023 | (2E,4E,6Z,8E)-3,7-dimethyl-9-[(3S,6R)-3-methyl-6-prop-1-en-2-ylcyclohexen-1-yl]nona-2,4,6,8-tetraenoic acid | CHEMBL1773351 |
| 54586043 | (2E,4E,6Z)-3-methyl-7-[(3R,6S)-3-methyl-6-propan-2-ylcyclohexen-1-yl]octa-2,4,6-trienoic acid | CHEMBL1773361 |
| 54310202 | 7-ethyl-3,11-dimethyltrideca-2,4-dienoic acid | |
| 54177995 | 8-(3-ethyl-2-propan-2-ylcyclohex-2-en-1-ylidene)-3,7-dimethylocta-2,4,6-trienoic acid | OZUIXDDSOLQKNK-UHFFFAOYSA-N; 982DADEA9DC5579A132BDF2AD7FA647A |
| 54012267 | 3,8,12-trimethyltrideca-2,4-dienoic acid | |
| 53787191 | 3,8,13-trimethyltetradeca-2,4-dienoic acid | |
| 53743194 | 4-methyl-6-(2,6,6-trimethylcyclohexen-1-yl)hex-2-enoic acid | |
| 53710521 | 3,7,13-trimethyltetradeca-2,4-dienoic acid | |
| 53707670 | 3,7-dimethyl-8-(3-methyl-2-propan-2-ylcyclohex-2-en-1-ylidene)octa-2,4,6-trienoic acid | BYHSFJNWVLBCIM-UHFFFAOYSA-N; 14B10A34153F37A66327788679FAC42F |
| 53666154 | 3,7,11-trimethyltrideca-2,4-dienoic acid | |
| 53438161 | 3,7,11-trimethyltetradeca-2,4-dienoic acid | |
| 53427754 | 7,7-dimethylicosa-2,4-dienoic acid | |
| 52952998 | (2E,4E,6Z,8E)-3,7-dimethyl-9-[(3R,6S)-3-methyl-6-prop-1-en-2-ylcyclohexen-1-yl]nona-2,4,6,8-tetraenoic acid | CHEMBL1773352 |

TABLE 6-continued

Excluded compounds structurally similar to retinoic acid.

| CID | IUPAC | Other names |
|---|---|---|
| 44631433 | (2Z,4E)-3-methyl-5-(2,2,4-trimethylcyclohex-3-en-1-yl)penta-2,4-dienoic acid | FZFFLFPGBIXCKI-STRRHFTISA-CHEMBL43954 |
| 44291210 | (2Z,4Z,6Z,8E)-8-(3-ethyl-2-propan-2-ylcyclohex-2-en-1-ylidene)-3,7-dimethylocta-2,4,6-trienoic acid | |
| 44290946 | (2E,4Z,6Z,8E)-8-(3-ethyl-2-propan-2-ylcyclohex-2-en-1-ylidene)-3,7-dimethylocta-2,4,6-trienoic acid | CHEMBL43833; CHEBI: 167938 |
| 24845989 | sodium (2Z,4E,6Z,8E)-3,7-dimethyl-9-(2,6,6-trimethylcyclohexen-1-yl)nona-2,4,6,8-tetraenoate | LS-143475 |
| 23670222 | potassium (2E,4E,6E,8E)-3,7-dimethyl-9-(2,6,6-trimethylcyclohexen-1-yl)nona-2,4,6,8-tetraenoate | |
| 23665641 | sodium (2E,4E,6E,8E)-3,7-dimethyl-9-(2,6,6-trimethylcyclohexen-1-yl)nona-2,4,6,8-tetraenoate | Sodium retinoate; Retinoic acid, sodium salt; Vitamin A acid sodium sal |
| 23265304 | (2E,4E)-3-methyl-5-(2,2,4-trimethylcyclohex-3-en-1-yl)penta-2,4-dienoic acid | |
| 21437585 | (2E,4E)-3,8,12-trimethyltrideca-2,4-dienoic acid | |
| 21437539 | (2E,4E)-3,8,13-trimethyltetradeca-2,4-dienoic acid | |
| 21437504 | (2E,4E)-3,7,13-trimethyltetradeca-2,4-dienoic acid | |
| 21158960 | (2E,4E)-7,7-dimethylicosa-2,4-dienoic acid | |
| 20270951 | (6E,8E)-2,7-dimethyl-9-(2,6,6-trimethylcyclohexen-1-yl)nona-2,3,6,8-tetraenoic acid | |
| 19609232 | (2E,4E)-3-methyl-5-[2-[(E)-2-(2,6,6-trimethylcyclohexen-1-yl)ethenyl]cyclohexen-1-yl]penta-2,4-dienoic acid | |
| 11130378 | (2E,4E,6E,8E)-3,7-dimethyl-9-(2,6,6-trimethylcyclohex-2-en-1-yl)nona-2,4,6,8-tetraenoic acid | |
| 11066537 | (2Z,4E,6E,8E)-3,7-dimethyl-9-(2,6,6-trimethylcyclohex-2-en-1-yl)nona-2,4,6,8-tetraenoic acid | |
| 10470917 | (2Z,4E,6Z,8E)-8-(3-ethyl-2-propan-2-ylcyclohex-2-en-1-ylidene)-3,7-dimethylocta-2,4,6-trienoic acid | |
| 10402558 | (2Z,4E,6E,8E)-3,7-dimethyl-8-(3-methyl-2-propan-2-ylcyclohex-2-en-1-ylidene)octa-2,4,6-trienoic acid | |
| 10357464 | (2E,4E,6E,8E)-3,7-dimethyl-8-(3-methyl-2-propan-2-ylcyclohex-2-en-1-ylidene)octa-2,4,6-trienoic acid | |
| 10086191 | (2E,4E,6E,8E)-3,7-dimethyl-8-(3-methyl-2-propan-2-ylcyclohex-2-en-1-ylidene)octa-2,4,6-trienoic acid | CHEMBL333032; CHEBI: 299410 |
| 10086189 | (2Z,4E,6E,8E)-3,7-dimethyl-8-(3-methyl-2-propan-2-ylcyclohex-2-en-1-ylidene)octa-2,4,6-trienoic acid | |
| 9972952 | (2Z,4E,6E,8E)-8-(3-ethyl-2-propan-2-ylcyclohex-2-en-1-ylidene)-3,7-dimethylocta-2,4,6-trienoic acid | CHEMBL44582; CHEBI: 168408 |
| 9972949 | (2E,4E,6Z,8E)-8-(3-ethyl-2-propan-2-ylcyclohex-2-en-1-ylidene)-3,7-dimethylocta-2,4,6-trienoic acid | |
| 9883342 | (2E,4E,6E,8E)-8-(3-ethyl-2-propan-2-ylcyclohex-2-en-1-ylidene)-3,7-dimethylocta-2,4,6-trienoic acid | CHEMBL46398; CHEBI: 168441 |
| 5372326 | (E)-3-methyl-5-(2,6,6-trimethylcyclohexen-1-yl)pent-2-enoic acid | AC1NSY3I; 2-Pentenoic acid, 3-methyl-5-(2,6,6-trimethyl-1-cyclohexenyl); (E)-3-methyl-5-(2,6,6-trimethylcyclohexen-1-yl)pent-2-enoic acid |
| 445560 | (2E,4E,6Z,8E)-3,7-dimethyl-9-(2,6,6-trimethylcyclohex-2-en-1-yl)nona-2,4,6,8-tetraenoic acid | AC1L9I79 |
| 56667221 | (2E,4E,6Z,8E)-3,7-dimethyl-9-(3-methyl-6-propan-2-ylcyclohexen-1-yl)nona-2,4,6,8-tetraenoic acid | CHEMBL508378 |
| 54585066 | (2E,4E,6Z,8E)-3,7-dimethyl-9-[(1S,4R,5R)-4,6,6-trimethyl-3-bicyclo[3.1.1]hept-2-enyl]nona-2,4,6,8-tetraenoic acid | CHEMBL1773358 |
| 54585064 | (2E,4E,6Z,8E)-3,7-dimethyl-9-[(3R)-3-methyl-6-propan-2-ylidenecyclohexen-1-yl]nona-2,4,6,8-tetraenoic acid | CHEMBL1773355 |
| 54582176 | (2E,4E,6Z,8E)-3,7-dimethyl-9-[(3S)-3-methyl-6-propan-2-ylidenecyclohexen-1-yl]nona-2,4,6,8-tetraenoic acid | CHEMBL1773354 |
| 54581148 | (2E,4E,6Z,8E)-3,7-dimethyl-9-[(1R,2R,5S)-2-methyl-5-propan-2-yl-3-bicyclo[3.1.0]hex-3-enyl]nona-2,4,6,8-tetraenoic acid | CHEMBL1773360 |
| 54542310 | 3,4,4-trimethyltetradec-2-enoic acid | |
| 54521054 | 3,4,4-trimethyloctadec-2-enoic acid | |
| 54518673 | 3,7-dimethyl-9-(2,6,6-trimethyl-5-oxocyclohexen-1-yl)nona-2,4,6,8-tetraenoic acid | |
| 54348687 | 3,7,10,11-tetramethyldodeca-2,4-dienoic acid | |
| 54325421 | 3,4,4-trimethylheptadec-2-enoic acid | |
| 54316493 | 3,4,4-trimethylpentadec-2-enoic acid | |
| 54305044 | 2-ethyl-3,7-dimethyl-9-(2,6,6-trimethylcyclohexen-1-yl)nona-2,4,6,8-tetraenoic acid | |

TABLE 6-continued

Excluded compounds structurally similar to retinoic acid.

| CID | IUPAC | Other names |
|---|---|---|
| 54265680 | 3,7,11,15-tetramethylhexadeca-2,4-dienoic acid | |
| 54194359 | 3,7-dimethyl-9-(2,6,6-trimethyl-4-oxocyclohexen-1-yl)nona-2,4,6,8-tetraenoic acid | |
| 54170467 | 3,7,11,15-tetramethylhexadeca-2,4,6,14-tetraenoic acid | |
| 54167172 | 3,4,4-trimethylhexadec-2-enoic acid | |
| 54105865 | 3,7,7,11,11-pentamethyldodec-2-enoic acid | |
| 54064253 | 2-ethyl-5,9-dimethyl-3-(2,6,6-trimethylcyclohexen-1-yl)undeca-2,4,6,8,10-pentaenoic acid | |
| 53961371 | 3,7,11-trimethyldodeca-2,4,11-trienoic acid | |
| 53936602 | 9-[5-(2-cyclohexylethyl)-2,6,6-trimethylcyclohexen-1-yl]-3,7-dimethylnona-2,4,6,8-tetraenoic acid | |
| 53825233 | 3,7,11,15,19-pentamethylicosa-2,4,6,10,18-pentaenoic acid | |
| 53801569 | 3-methyl-5-[2-[2-(2,6,6-trimethylcyclohexen-1-yl)ethynyl]cyclohepten-1-yl]penta-2,4-dienoic acid | |
| 53725805 | 3,7-dimethyldodeca-2,4-dienoic acid | |
| 53700416 | 3,7,11,15-tetramethylhexadeca-2,4,6-trienoic acid | |
| 52953080 | (2E,4E,6Z,8E)-3,7-dimethyl-9-[(3S,6R)-3-methyl-6-propan-2-ylcyclohexen-1-yl]nona-2,4,6,8-tetraenoic acid | CHEMBL1773353 |
| 52952997 | (2E,4E,6Z,8E)-3,7-dimethyl-9-[(1R,4S,5S)-4,6,6-trimethyl-3-bicyclo[3.1.1]hept-2-enyl]nona-2,4,6,8-tetraenoic acid | CHEMBL1773357 |
| 52921782 | (2E,5R,10E,12E)-3,5,15-trimethyl-7-methylidenehexadeca-2,10,12-trienoic acid | LMFA01020367; 16:3(2E,10E,12E)(3Me,5Me[R],7My,15Me) |
| 46178652 | (2E,4E)-5-[(1R)-2,2-dimethyl-6-methylidenecyclohexyl]-3-methylpenta-2,4-dienoic acid | |
| 44579059 | (2E,4E,6Z,8E)-3,7-dimethyl-9-(2,2,6-trimethylcyclohexyl)nona-2,4,6,8-tetraenoic acid | CHEMBL451158 |
| 25147656 | (2E,4E,6Z,8E)-3,7-dimethyl-9-[(3R,6S)-3-methyl-6-propan-2-ylcyclohexen-1-yl]nona-2,4,6,8-tetraenoic acid | CHEMBL508378 |
| 22168242 | (2E,4E,6E,10E)-3,7,11,15,19-pentamethylicosa-2,4,6,10,18-pentaenoic acid | |
| 22168239 | (2E,4E,6E)-3,7,11,15-tetramethylhexadeca-2,4,6-trienoic acid | |
| 22168234 | (2E,4E,6E)-3,7,11,15-tetramethylhexadeca-2,4,6,14-tetraenoic acid | |
| 21764469 | (2E,4E)-3-methyl-5-[(1R)-2,6,6-trimethylcyclohex-2-en-1-yl]penta-2,4-dienoic acid | |
| 21650797 | acetyl(2E,4E,6E,8E)-3,7-dimethyl-9-(2,6,6-trimethylcyclohexen-1-yl)nona-2,4,6,8-tetraeneperoxoate | |
| 21525820 | (2E,4E)-7,11,11-trimethyldodeca-2,4-dienoic acid | |
| 21525806 | (2E,4E)-3,7-dimethyldodeca-2,4-dienoic acid | |
| 21291068 | (E)-3,4,4-trimethylhexadec-2-enoic acid | |
| 21291063 | (E)-3,4,4-trimethyltetradec-2-enoic acid | |
| 21291060 | (E)-3,4,4-trimethylpentadec-2-enoic acid | |
| 21291047 | (E)-3,4,4-trimethylheptadec-2-enoic acid | |
| 21291045 | (E)-3,4,4-trimethyloctadec-2-enoic acid | |
| 20830940 | (2E,4E,6Z,8E)-3,7-dimethyl-9-(2,5,6,6-tetramethylcyclohexen-1-yl)nona-2,4,6,8-tetraenoate | |
| 20306860 | (2E,4E)-3,7,11-trimethyldodeca-2,4,11-trienoic acid | |
| 20027300 | azanium(2E,4E,6E,8E)-3,7-dimethyl-9-(2,6,6-trimethylcyclohexen-1-yl)nona-2,4,6,8-tetraenoate | |
| 19609235 | (2E,4E)-2-iodo-3-methyl-5-(2,6,6-trimethylcyclohexen-1-yl)penta-2,4-dienoic acid | |
| 19606927 | (2E,4E,6E,8E)-3,7-dimethyl-9-(2,6,6-trimethyl-4-oxocyclohexen-1-yl)nona-2,4,6,8-tetraenoic acid | |
| 18977382 | (2E,4E,6E,8E)-3,7-dimethyl-9-(2,5,6,6-tetramethylcyclohexen-1-yl)nona-2,4,6,8-tetraenoate | |
| 16061319 | (2Z,4E,6Z,8E)-7-(hydroxymethyl)-3-methyl-9-(2,6,6-trimethylcyclohexen-1-yl)nona-2,4,6,8-tetraenoic acid | 19-Hydroxy-13-cis-retinoic acid; LMPR01090029 |
| 16061318 | (2E,4E,6Z,8E)-7-(hydroxymethyl)-3-methyl-9-(2,6,6-trimethylcyclohexen-1-yl)nona-2,4,6,8-tetraenoic acid | 19-Hydroxy-all-trans-retinoic acid; LMPR01090028 |
| 15125888 | (2E,4E,6E,8E)-2-ethyl-3,7-dimethyl-9-(2,6,6-trimethylcyclohexen-1-yl)nona-2,4,6,8-tetraenoic acid | CHEMBL154239 |
| 11747707 | (2E,4E,6Z,8E)-3,7-dimethyl-9-(6-methylcyclohexen-1-yl)nona-2,4,6,8-tetraenoic acid | |
| 11602784 | (2E,4E)-3-methyl-5-[2-[2-(2,6,6-trimethylcyclohexen-1-yl)ethynyl]cyclohepten-1-yl]penta-2,4-dienoic acid | |
| 10516342 | (2E,4E,6E,8E)-3,7-dimethyl-9-(6-methylcyclohexen-1-yl)nona-2,4,6,8-tetraenoic acid | |
| 10354668 | (Z,4E)-4-(3-ethyl-2-propan-2-ylcyclohex-2-en-1-ylidene)-3-methylbut-2-enoic acid | |

TABLE 6-continued

Excluded compounds structurally similar to retinoic acid.

| CID | IUPAC | Other names |
|---|---|---|
| 10053647 | (2Z,4Z,6E,8E,10E,12E,14E,16E,18E,20E,22E,24E)-2,6,10,14,19,23-hexamethyl-25-(2,6,6-trimethylcyclohexen-1-yl)pentacosa-2,4,6,8,10,12,14,16,18,20,22,24-dodecaenoic acid | |
| 9995780 | (2Z,4E,6E,8E)-3,7-dimethyl-9-(2,6,6-trimethyl-5-oxocyclohexen-1-yl)nona-2,4,6,8-tetraenoic acid | Oxo-13-cis-retinoate; 4-keto-13-cis-retinoate |
| 9949957 | (2E,4E,6E,8E)-3,7-dimethyl-8-[3-(2-methylpropyl)-2-propan-2-ylcyclohex-2-en-1-ylidene]octa-2,4,6-trienoic acid | |
| 9948768 | (2E,4E,6Z,8E)-3,7-dimethyl-9-(2,6,6-trimethyl-5-oxocyclohexen-1-yl)nona-2,4,6,8-tetraenoic acid | |
| 9829386 | (2E,4Z,6E,8E,10E,12E,14E,16E,18E,20E,22E,24E)-2,6,10,14,19,23-hexamethyl-25-(2,6,6-trimethylcyclohexen-1-yl)pentacosa-2,4,6,8,10,12,14,16,18,20,22,24-dodecaenoic acid | |
| 6477090 | (2Z,4Z,6Z,8E,10Z,12Z,14E,16Z,18Z,20E,22Z,24E)-2,6,10,14,19,23-hexamethyl-25-(2,6,6-trimethylcyclohexen-1-yl)pentacosa-2,4,6,8,10,12,14,16,18,20,22,24-dodecaenoic acid | AC1O53P5; 3',4'-Didehydro-,,psi.-caroten-16'-oic acid |
| 6439734 | (2Z,4E,6Z,8E)-3,7-dimethyl-9-(2,2,6-trimethylcyclohexyl)nona-2,4,6,8-tetraenoic acid | 7,8-Dihydroretinoic acid |
| 6437018 | (2Z,4E)-3,7,11-trimethyldodeca-2,4-dienoic acid | AC1O5MUO; EINECS 258-354-9 |
| 6437016 | (2E,4E)-3,7,11-trimethyldodeca-2,4-dienoic acid | AC1O5MUI; CHEMBL37590 |
| 5476505 | (2E,4E)-3-methyl-5-(2,6,6-trimethylcyclohex-2-en-1-yl)penta-2,4-dienoic acid | AC1O5MUI; CHEMBL37590 |
| 5460164 | (2E,4E,6E,8E)-3,7-dimethyl-9-(2,2,6-trimethylcyclohexyl)nona-2,4,6,8-tetraenoic acid | Retinyl ester; all-trans-Retinyl ester |
| 5281248 | (2E,4E,6E,8E,10E,12E,14E,16E,18E,20E,22E,24E)-2,6,10,14,19,23-hexamethyl-25-(2,6,6-trimethylcyclohexanoic acid | NSC635690; Torularhodin; AC1NQY9 |
| 637039 | 2E,4E,6E,8E,10E,12E,14E,16E,18E,20E)-2,6,10,15,19-pentamethyl-21-(2,6,6-trimethylcyclohexen-1-yl)hexanoic acid | Neurosporaxanthin; all-trans-Neurosporaxanthin |
| 428485 | 3-methyl-5-(2,6,6-trimethylcyclohex-2-en-1-yl)penta-2,4-dienoic acid | AC1L8LML; 3-methyl-5-(2,6,6-trimethylcyclohex-2-en-1-yl)penta-2,4-dienoic acid |
| 103723 | 3,7,11-trimethyldodeca-2,4-dienoic acid | |
| 94165 | 2,6,10,14,19,23-hexamethyl-25-(2,6,6-trimethylcyclohexen-1-yl)pentacosa-2,4,6,8,10,12,14,16,18,20,22,24-dodecanenoic acid | AC1L3RN8; NCI60_011910 |
| 56661049 | (2E,4E,6Z,8E)-3,7-dimethyl-9-(4,4,6,6-tetramethyl-2-bicyclo[3.1.1]hept-2-enyl)nona-2,4,6,8-tetraenoic acid | CHEMBL455992 |
| 54581147 | (2E,4E,6Z,8E)-9-[(1S,5R)-6,6-dimethyl-4-bicyclo[3.1.1]hept-3-enyl]-3,7-dimethylnona-2,4,6,8-tetraenoic acid | CHEMBL1773359 |
| 54478024 | 3,4,4-trimethylnon-2-enoic acid | |
| 54476971 | 3,4,4-trimethylundec-2-enoic acid | |
| 54287870 | 3-formyl-7-methyl-9-(2,6,6-trimethylcyclohexen-1-yl)nona-2,4,6,8-tetraenoic acid | RVKZSGIKOAAYJJ-UHFFFAOYSA-N; 293564D2B64FAC5F524A1B691CBF7C6B |
| 54116397 | 3,7-dimethyl-2-propan-2-yl-9-(2,6,6-trimethylcyclohexen-1-yl)nona-2,4,6,8-tetraenoic acid | NKQIYDSGIYJXSA-UHFFFAOYSA-N; 5597749F477D668D55E163C44DA1F3EB |
| 54073647 | 3,4,4-trimethyldec-2-enoic acid | |
| 53995964 | 3-methyl-5-[2-[2-(2,6,6-trimethylcyclohexen-1-yl)ethenyl]cyclohexyl]penta-2,4-dienoic acid | |
| 53919798 | 3,4,4-trimethyldodec-2-enoic acid | |
| 53889922 | 3,7-dimethyl-9-(2,4,4,6,6-pentamethyl-3-oxocyclohexen-1-yl)nona-2,4,6,8-tetraenoic acid | |
| 53887460 | 4-(hydroxymethyl)-3,7-dimethyl-9-(2,6,6-trimethylcyclohexen-1-yl)nona-2,4,6,8-tetraenoic acid | |
| 53854796 | 3-methyl-6-(3,3,7,7-tetramethyl-3a,4,5,6-tetrahydroinden-2-ylidene)hexa-2,4-dienoic acid | |
| 53754609 | 2-ethyl-5,9-dimethyl-11-(2,6,6-trimethylcyclohexen-1-yl)undeca-2,4,6,8,10-pentaenoic acid | |
| 50925583 | (2E,4E,6E,8E)-9-[(1R,2R,4aS,8aR)-1,6-dimethyl-2-propyl-4a,5,8,8a-tetrahydro-2H-naphthalen-1-yl]-8-methylnona-2,4,6,8-tetraenoic acid | |
| 45039634 | (2E,4E,6E,8E)-9-[6,6-dimethyl-3-oxo-2-(trideuteriomethyl)cyclohexen-1-yl]-3,7-dimethylnona-2,4,6,8-tetraenoic acid | |

TABLE 6-continued

Excluded compounds structurally similar to retinoic acid.

| CID | IUPAC | Other names |
|---|---|---|
| 21291081 | (E)-3,4,4-trimethyldec-2-enoic acid | |
| 21291044 | (E)-3,4,4-trimethyldodec-2-enoic acid | |
| 21291042 | (E)-3,4,4-trimethylnon-2-enoic acid | |
| 21291032 | (E)-3,4,4-trimethylundec-2-enoic acid | |
| 19384872 | (E)-4-[(2E,4E,6E,8E)-3,7-dimethyl-9-(2,6,6-trimethylcyclohexen-1-yl)nona-2,4,6,8-tetraenoyl]oxy-4-oxobut-2-enoic acid | |
| 16061321 | (2Z,4E,6Z,8E)-7-formyl-3-methyl-9-(2,6,6-trimethylcyclohexen-1-yl)nona-2,4,6,8-tetraenoic acid | 19-Oxo-9-cis-retinoic acid; LMPR01090031 |
| 16061320 | (2E,4E,6Z,8E)-7-formyl-3-methyl-9-(2,6,6-trimethylcyclohexen-1-yl)nona-2,4,6,8-tetraenoic acid | 19-Oxo-all-trans-retinoic acid; LMPR01090030 |
| 15125894 | (2E,4E,6E,8E)-3,7-dimethyl-2-propan-2-yl-9-(2,6,6-trimethylcyclohexen-1-yl)nona-2,4,6,8-tetraenoic acid | CHEMBL153894 |
| 10043037 | (2E,4E,6E,8E)-3,7-dimethyl-9-(2,4,4,6,6-pentamethyl-3-oxocyclohexen-1-yl)nona-2,4,6,8-tetraenoic acid | CHEMBL103068 |
| 9972939 | (2E,4E,6Z,8E)-3,7-dimethyl-9-(2,6,6-trimethyl-3-oxocyclohexen-1-yl)nona-2,4,6,8-tetraenoic acid | |
| 9906064 | (2E,4E)-3-methyl-5-[(1R)-2-[(E)-2-(2,6,6-trimethylcyclohexen-1-yl)ethenyl]cyclohexyl]penta-2,4-dienoic acid | |
| 9902057 | (2Z,4E,6Z,8E)-4-(hydroxymethyl)-3,7-dimethyl-9-(2,6,6-trimethylcyclohexen-1-yl)nona-2,4,6,8-tetraenoic acid | |
| 6437087 | (2Z,4E,6E,8E)-3,7-dimethyl-9-(2,6,6-trimethyl-3-oxocyclohexen-1-yl)nona-2,4,6,8-tetraenoic acid | Oxoretinoic acid; 4-Oxo-isotretinoin |
| 6437063 | (2E,4E,6E,8E)-3,7-dimethyl-9-(2,6,6-trimethyl-3-oxocyclohexen-1-yl)nona-2,4,6,8-tetraenoic acid | 4-Oxoretinoic acid; 4-Ketoretinoic acid |
| 447276 | (2E,4E,6E,8E)-3,7-dimethyl-9-(2,6,6-trimethylcyclohexa-1,3-dien-1-yl)nona-2,4,6,8-tetraenoic acid | Vitamin A2 acid; 3,4-Didehydroretinoic acid |
| 104857 | 3,7-dimethyl-9-(2,6,6-trimethyl-3-oxocyclohexen-1-yl)nona-2,4,6,8-tetraenoic acid | |

Thus, in some embodiments, the invention provides a method of treating a condition selected from the group consisting of a proliferative disease, an autoimmune disease, or an addiction condition in a subject having elevated levels of a Pin1 marker, said method comprising administering an ATRA-related compound to said subject in an amount sufficient to treat said subject, wherein said ATRA-related compound is a compound according to Formula I wherein W, $R_1$, $R_2$, and $R_3$ are independently selected from the group consisting of, but not limited to, the groups described herein (e.g., a halogen atom, a carboxylic acid, an alcohol, an ester, an aldehyde, a carbonyl, an acyl halide, a carbonate, an acetal, a phosphate, a thiol, a sulfoxide, a sulfinic acid, a sulfonic acid, a thial, a sulfate, a sulfonyl, an amide, an azido, a nitro, a cyano, isocyano, acyloxy, an amino, a carbamoyl, a sulfonamide, or another functional group, or an optionally substituted alkyl (e.g., $C_{1-10}$ alkyl), alkenyl (e.g., $C_{2-10}$ alkenyl), alkynyl (e.g., $C_{2-10}$ alkynyl), alkoxy (e.g., $C_{1-10}$ alkoxy), aryloxy (e.g., $C_{6-10}$ aryloxy), cycloalkyl (e.g., $C_{3-8}$ cycloalkyl), cycloalkoxy (e.g., $C_{3-8}$ cycloalkoxy), aryl (e.g., $C_{6-10}$ aryl), aryl-alkoxy (e.g, $C_{6-10}$ aryl-$C_{1-10}$ alkoxy), heterocyclyl or heterocycloalkyl (e.g., $C_{3-8}$ heterocycloalkyl), heterocycloalkenyl, (e.g., $C_{4-8}$ heterocycloalkenyl), or heteroaryl (e.g., $C_{6-10}$ heteroaryl) group).

The invention further provides a method of treating a condition selected from the group consisting of a proliferative disease, an autoimmune disease, or an addiction condition in a subject, said method comprising determining Pin1 marker levels in a sample from said subject and administering an ATRA-related compound to said subject if said sample is determined to have elevated Pin1 marker levels, wherein said ATRA-related compound is a compound according to Formula I wherein W, $R_1$, $R_2$, and $R_3$ are independently selected from the group consisting of, but not limited to, the groups described herein.

The invention also provides a method of treating a condition selected from the group consisting of a proliferative disease, an autoimmune disease, or an addiction condition in a subject previously treated with an ATRA-related compound and having Pin1 degradation (e.g., Pin1 degradation that resulted from the administration of the ATRA-related compound), said method comprising administering an ATRA-related compound to said subject in an amount sufficient to treat said subject, wherein said ATRA-related compound is a compound according to Formula I wherein W, $R_1$, $R_2$, and $R_3$ are independently selected from the group consisting of, but not limited to, the groups described herein.

The invention additionally provides a method of identifying a candidate for treatment with an ATRA-related compound, wherein said candidate has a condition selected from the group consisting of a proliferative disease, an autoimmune disease, or an addiction condition and has previously been administered said ATRA-related compound, said method comprising determining whether said subject has Pin1 degradation, wherein a candidate for treatment with said ATRA-related compound has Pin1 degradation, and wherein said ATRA-related compound is a compound according to Formula I wherein W, $R_1$, $R_2$, and $R_3$ are independently selected from the group consisting of, but not limited to, the groups described herein.

In any of the methods described herein, one or more of $R_1$, $R_2$, and $R_3$ can be methyl groups.

In any of the methods described herein, W can be a carboxylic acid group.

In any of the methods described herein, an ATRA-related compound can be selected from the group consisting of Compounds 1-272.

In any of the methods described herein, an ATRA-related compound can be a compound according to Formula Ia. In some embodiments, the ATRA-related compound is selected from the group consisting of Compounds 1-10.

In any of the methods described herein, an ATRA-related compound can be a compound according to Formula Ib. In some embodiments, the ATRA-related compound is selected from the group consisting of Compounds 102-111.

In any of the methods described herein, an ATRA-related compound can be a compound according to Formula Ic. In some embodiments, the ATRA-related compound is selected from the group consisting of Compounds 126-135.

In any of the methods described herein, an ATRA-related compound can be a compound according to Formula Id. In some embodiments, the ATRA-related compound is selected from the group consisting of Compounds 151-160.

In any of the methods described herein, an ATRA-related compound can be selected from the group consisting of Compounds 177-186. In any of the methods described herein, an ATRA-related compound can be selected from the group consisting of Compounds 187-196.

In the methods described herein, a Pin1 marker can be reduced Ser71 phosphorylation of Pin1. In some embodiments, a Pin1 marker is overexpression of PML-RARα. In some embodiments, an elevated Pin1 marker level is due to an inherited trait or somatic mutation.

In certain embodiments, a method of treatment or identifying a candidate for treatment further comprises determining Pin1 marker levels in said sample after said administration of said ATRA-related compound. In particular embodiments, a sample is selected from the group consisting of tumor samples, blood, urine, biopsies, lymph, saliva, phlegm, and pus.

In any of the methods described herein, an ATRA-related compound can be administered in combination with a second therapeutic compound (e.g., any described herein, such as an anti-proliferative, anti-inflammatory, anti-microbial, or anti-viral compound). In some embodiments, a second therapeutic compound is administered at a low dosage or at a different time (e.g., separate administration). In other embodiments, a second therapeutic compound is formulated together with the ATRA-related compound (e.g., in a single formulation). In some embodiments, the second therapeutic compound is formulated as a liposomal formulation or a controlled release formulation. In some embodiments, a second therapeutic compound may be another ATRA-related compound. A second therapeutic compound may be, for example, an anti-proliferative, anti-inflammatory, anti-microbial, or anti-viral compound. In some embodiments, the second therapeutic compound is an anti-proliferative compound (e.g., at a low dosage) or anti-cancer compound (e.g., an anti-angiogenic compound). Examples of anti-proliferative compounds useful in the methods of the invention include, but are not limited to: MK-2206, ON 013105, RTA 402, BI 2536, Sorafenib, ISIS-STAT3Rx, a microtubule inhibitor, a topoisomerase inhibitor, a platin, an alkylating agent, an anti-metabolite, paclitaxel, gemcitabine, doxorubicin, vinblastine, etoposide, 5-fluorouracil, carboplatin, altretamine, aminoglutethimide, amsacrine, anastrozole, azacitidine, bleomycin, busulfan, carmustine, chlorambucil, 2-chlorodeoxyadenosine, cisplatin, colchicine, cyclophosphamide, cytarabine, cytoxan, dacarbazine, dactinomycin, daunorubicin, docetaxel, estramustine phosphate, floxuridine, fludarabine, gentuzumab, hexamethylmelamine, hydroxyurea, ifosfamide, imatinib, interferon, irinotecan, lomustine, mechlorethamine, melphalen, 6-mercaptopurine, methotrexate, mitomycin, mitotane, mitoxantrone, pentostatin, procarbazine, rituximab, streptozocin, tamoxifen, temozolomide, teniposide, 6-thioguanine, topotecan, trastuzumab, vincristine, vindesine, and/or vinorelbine.

Examples of anti-inflammatory compounds useful in the methods of the invention include, but are not limited to: corticosteroids, NSAIDs (e.g., naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid (salsalate), fenoprofen, flurbiprofen, ketoprofen, meclofenamate sodium, meloxicam, oxaprozin, sulindac, and tolmetin), COX-2 inhibitors (e.g., rofecoxib, celecoxib, valdecoxib, and lumiracoxib), biologics (e.g., inflixamab, adelimumab, etanercept, CDP-870, rituximab, and atlizumab), small molecule immunomodulators (e.g., VX 702, SCIO 469, doramapimod, RO 30201195, SCIO 323, DPC 333, pranalcasan, mycophenolate, and merimepodib), non-steroidal immunophilin-dependent immunosuppressants (e.g., cyclosporine, tacrolimus, pimecrolimus, and ISAtx247), 5-amino salicylic acid (e.g., mesalamine, sulfasalazine, balsalazide disodium, and olsalazine sodium), DMARDs (e.g., methotrexate, leflunomide, minocycline, auranofin, gold sodium thiomalate, aurothioglucose, and azathioprine), hydroxychloroquine sulfate, and penicillamine By "corticosteroid" is meant any naturally occurring or synthetic steroid hormone which can be derived from cholesterol and is characterized by a hydrogenated cyclopentanoperhydrophenanthrene ring system. Naturally occurring corticosteroids are generally produced by the adrenal cortex. Synthetic corticosteroids may be halogenated. Functional groups required for activity include a double bond at Δ4, a C3 ketone, and a C20 ketone. Corticosteroids may have glucocorticoid and/or mineralocorticoid activity. Exemplary corticosteroids include algestone, 6-alpha-fluoroprednisolone, 6-alpha-methylprednisolone, 6-alpha-methylprednisolone 21-acetate, 6-alpha-methylprednisolone 21-hemisuccinate sodium salt, 6-alpha,9-alpha-difluoroprednisolone 21-acetate 17-butyrate, amcinafal, beclomethasone, beclomethasone dipropionate, beclomethasone dipropionate monohydrate, 6-beta-hydroxycortisol, betamethasone, betamethasone-17-valerate, budesonide, clobetasol, clobetasol propionate, clobetasone, clocortolone, clocortolone pivalate, cortisone, cortisone acetate, cortodoxone, deflazacort, 21-deoxycortisol, deprodone, descinolone, desonide, desoximethasone, dexamethasone, dexamethasone-21-acetate, dichlorisone, diflorasone, diflorasone diacetate, diflucortolone, doxibetasol, fludrocortisone, flumethasone, flumethasone pivalate, flumoxonide, flunisolide, fluocinonide, fluocinolone acetonide, 9-fluorocortisone, fluorohydroxyandrostenedione, fluorometholone, fluorometholone acetate, fluoxymesterone, flupredidene, fluprednisolone, flurandrenolide, formocortal, halcinonide, halometasone, halopredone, hyrcanoside, hydrocortisone, hydrocortisone acetate, hydrocortisone butyrate, hydrocortisone cypionate, hydrocortisone sodium phosphate, hydrocortisone sodium succinate, hydrocortisone probutate, hydrocortisone valerate, 6-hydroxydexamethasone, isoflupredone, isoflupredone acetate, isoprednidene, meclorisone, methylprednisolone, methylprednisolone acetate, methylprednisolone sodium succinate, paramethasone, paramethasone acetate, prednisolone, prednisolone acetate, prednisolone metasulphobenzoate, prednisolone sodium phosphate, prednisolone tebutate, prednisolone-21-hemisuccinate free acid, prednisolone-21-acetate, prednisolone-21(beta-D-glucuronide), prednisone, prednylidene, procinonide, tralonide, triamcinolone, triamcinolone acetonide, triamcinolone acetonide 21-palmitate, triamcinolone diacetate, triamcinolone hexacetonide, and wortmannin Desirably, the corticosteroid is fludrocortisone or prednisolone.

Examples of anti-microbial agents useful in the methods of the invention include, but are not limited to: penicillins (e.g., penicillin G, ampicillin, methicillin, oxacillin, and amoxicillin), cephalosporins (e.g., cefadroxil, ceforanid, cefotaxime, and ceftriaxone), tetracyclines (e.g., doxycycline, minocycline, and tetracycline), aminoglycosides (e.g., amikacin, gentamycin, kanamycin, neomycin, streptomycin, and tobramycin), macrolides (e.g., azithromycin, clarithromycin, and erythromycin), fluoroquinolones (e.g., ciprofloxacin, lomefloxacin, and norfloxacin), and other antibiotics including chloramphenicol, clindamycin, cycloserine, isoniazid, rifampin, and vancomycin. Particularly useful formulations contain aminoglycosides, including for example amikacin, gentamicin, kanamycin, neomycin, netilmicin, paromomycin, streptomycin, and tobramycin.

Examples of anti-viral agents useful in the methods of the invention include, but are not limited to: 1-D-ribofuranosyl-1,2,4-triazole-3 carboxamide, 9->2-hydroxy-ethoxy methylguanine, adamantanamine, 5-iodo-2'-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir.

By the term "proliferative disorder" is meant a disorder characterized by inappropriate accumulation of a cell population in a tissue (e.g., by abnormal cell growth). This inappropriate accumulation may be the result of a genetic or epigenetic variation that occurs in one or more cells of the cell population. This genetic or epigenetic variation causes the cells of the cell population to grow faster, die slower, or differentiate slower or in a different manner than the surrounding, normal tissue. The cell population includes cells of hematopoietic, epithelial, endothelial, or solid tissue origin.

As used herein, the term "abnormal cell growth" is intended to include cell growth which is undesirable or inappropriate. Abnormal cell growth also includes proliferation which is undesirable or inappropriate (e.g., unregulated cell proliferation or undesirably rapid cell proliferation). Abnormal cell growth can be benign and result in benign masses of tissue or cells, or benign tumors. Many art-recognized conditions are associated with such benign masses or benign tumors including diabetic retinopathy, retrolental fibrioplasia, neovascular glaucoma, psoriasis, angiofibromas, rheumatoid arthrtis, hemangiomas, and Karposi's sarcoma. Abnormal cell growth can also be malignant and result in malignancies, malignant masses of tissue or cells, or malignant tumors. Many art-recognized conditions and disorders are associated with malignancies, malignant masses, and malignant tumors including cancer and carcinoma.

As used herein, the term "tumor" is intended to encompass both in vitro and in vivo tumors that form in any organ of the body. Tumors may be associated with benign abnormal cell growth (e.g., benign tumors) or malignant cell growth (e.g., malignant tumors). The tumors which are described herein are preferably sensitive to the Pin1 inhibitors of the present invention. Examples of the types of tumors intended to be encompassed by the present invention include those tumors associated with breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys.

The proliferative disorder of any of the foregoing methods can be, but is not limited to: leukemias, polycythemia vera, lymphomas, Waldenstrom's macroglobulinemia, heavy chain disease, and solid tumors. Specifically, proliferative disorders include: acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), Hodgkin's disease, non-Hodgkin's disease, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma. In particular embodiments, a proliferative disease may be selected from the group consisting of leukemias, polycythemia vera, lymphomas, Waldenstrom's macroglobulinemia, heavy chain disease, and solid tumors. In certain embodiments, the proliferative disease is breast cancer.

By the term "immune disorder" or "immune disease" is meant a disorder characterized by dysfunction of the immune system Immune disorders often involve deregulation of Toll like receptor and/or type 1 interferon.

By "autoimmune disorder" or "autoimmune disease" is meant any disease, disorder, or condition associated with an immune response against substances normally present in the body (e.g., compounds, polypeptides, nucleic acids, cells, tissues, and organs).

The immune disorder of any of the foregoing methods can, e.g., result from disregulation of Toll-like receptor signaling or type I interferon-mediated immunity. The immune disorder of any of the foregoing methods can be, but is not limited to: acne vulgaris; acute respiratory distress syndrome; Addison's disease; adrenocortical insufficiency; adrenogenital ayndrome; agammaglbulinemia; allergic conjunctivitis; allergic rhinitis; allergic intraocular inflammatory diseases; alopecia areata; amyotrophic lateral sclerosis; ANCA-associated small-vessel vasculitis; angioedema; ankylosing spondylitis; antiphospholipid syndrome; anti-synthetase syndrome; aphthous stomatitis; arthritis, asthma; atherosclerosis; atopic allergy; atopic dermatitis; autoimmune aplastic anemia; autoimmune cardiomyopathy; autoimmune disease; autoimmune enteropathy; autoimmune hemolytic anemia; autoimmune hepatitis; autoimmune inner ear disease; autoimmune lymphoproliferative syndrome; autoimmune peripheral neuropathy; autoimmune pancreatitis; autoimmune polyendocrine syndrome; autoimmune progesterone dermatitis; autoimmune thrombocytopenic purpura; autoimmune urticaria; autoimmune uveitis; Balo concentric sclerosis; Behcet's disease; Bell's palsy; Berger's disease; berylliosis; Bickerstaff's encephalitis; Blau syndrome; bronchial asthma; bullous herpetiformis dermatitis; bullous pemphigoid; Castleman's disease; carditis; celiac disease; cerebral ischaemia; Chagas disease; chronic bronchitis; chronic inflammatory demyelinating polyneuropathy; chronic obstructive pulmonary disease (COPD); chronic recurrent multifocal osteomyelitis; chronic sinusitis; Churg-Strauss syndrome; cicatricial pemphigoid; cirrhosis; Cogan's syndrome; cold agglutinin disease; complement component 2 deficiency; contact dermatitis; cranial arteritis; CREST syndrome; Crohn's disease; Cushing's syndrome; cutaneous leukocytoclastic vasculitis; Dego's disease; Dercum's disease; dermatitis herpetiformis; dermatomyositis; diabetes mellitus type 1; diffuse cutaneous systemic sclerosis; Dressler's syndrome; drug-induced lupus; eczema; encephalomyelitis; discoid lupus erythematosus; endometriosis; enthesitis-related arthritis; eosinophilic fasciitis; eosinophilic gastroenteritis; epicondylitis; epidermolysis bullosa acquisita; erythema nodosum; erythroblastosis fetalis; essential mixed cryoglobulinemia; Evan's syndrome; exfoliative dermatitis; fibrodysplasia ossificans progressive; fibromyalgia; fibrosing alveolitis; focal glomerulosclerosis; gastritis; gastrointestinal pemphigoid; giant cell arteritis; glomerulonephritis; Goodpasture's syndrome; gout; gouty arthritis; graft-versus-host disease; Grave's disease; Guillain-Barre syndrome; hand eczema; Hashimoto's encephalopathy; Hashimoto's thyroiditis; Henoch-Schonlein purpura; herpes gestationis; hidradenitis suppurativa; hirsutism; Hughes-Stovin syndrome; hypersensitivity drug reactions; hypertension; hypogammaglobulinemia; idiopathic ceratoscleritis; idiopathic inflammatory demyelinating diseases; idiopathic pulmonary fibrosis; idiopathic thrombocytopenic purpura; IgA nephropathy; inclusion body myositis; inflammatory bowel or gastrointestinal disorders, inflammatory dermatoses; interstitial cystitis; juvenile idiopathic arthritis; juvenile rheumatoid arthritis; Kawasaki's disease; Lambert-Eaton myasthenic syndrome; laryngeal edema; leukocytoclastic vasculitis; lichen planus; lichen sclerosus; linear IgA disease; Loeffler's syndrome; lupus erythematosus; lupus nephritis; lupus vulgaris; lymphomatous tracheobronchitis; macular edema; Majeed syndrome; Meniere's disease; microscopic polyangiitis; mixed connective tissue disease; morphea; Mucha-Habermann disease; multiple sclerosis; musculoskeletal and connective tissue disorder; myasthenia gravis; myositis; narcolepsy; neuromyelitis optica; neuromyotonia; obstructive pulmonary disease; ocular cicatricial pemphigoid; ocular inflammation; opsoclonus myoclonus syndrome; Ord's thyroiditis; organ transplant rejection; osteoarthritis; palindromic rheumatism; pancreatitis; PANDAS; paraneoplastic cerebellar degeneration; paroxysmal nocturnal hemoglobinuria; Parry Romberg syndrome; Parsonage-Turner syndrome; pars planitis; pemphigoid gestationis; pemphigus vulgaris; pernicious anaemia; perivenous encephalomyelitis; peripheral vascular disease; POEMS syndrome; polyarteritis nodosa; polymyalgia rheumatica; polymyositis; primary adrenocortical insufficiency; primary billiary cirrhosis; primary sclerosing cholangitis; progressive inflammatory neuropathy; pruritus scroti; pruritis/inflammation, psoriasis; psoriatic arthritis; pyoderma gangrenosum; pure red cell aplasia; Rasmussen's encephalitis; raynaud phenomenon; Reiter's disease; relapsing polychondritis; restless leg syndrome; retroperitoneal fibrosis; rheumatic carditis; rheumatic fever; rheumatoid arthritis; rosacea caused by sarcoidosis; rosacea caused by scleroderma; rosacea caused by Sweet's syndrome; rosacea caused by systemic lupus erythematosus; rosacea caused by urticaria; rosacea caused by zoster-associated pain; sarcoidosis; Schnitzler syndrome; scleritis; scleroderma; segmental glomerulosclerosis; septic shock syndrome; serum sickness; shoulder tendinitis or bursitis; Sjogren's syndrome; spondyloarthropathy; stiff person syndrome; Still's disease; stroke-induced brain cell death; subacute bacterial endocarditis; Susac's syndrome; Sweet's disease; sympathetic ophthalmia; systemic dermatomyositis; systemic lupus erythematosus; systemic sclerosis; Takayasu's arteritis; temporal arteritis; thrombocytopenia; thyroiditis; Tolosa-Hunt syndrome; toxic epidermal necrolysis; transverse myelitis; tuberculosis; type-1 diabetes; ulcerative colitis; undifferentiated connective tissue disease; undifferentiated spondyloarthropathy; uveitis; vasculitis; vitiligo; and Wegener's granulomatosis. The autoimmune disorder of any of the foregoing methods can be, but is not limited to: multiple sclerosis (MS); encephalomyelitis; Addison's disease; agammaglbulinemia; alopecia areata; amyotrophic lateral sclerosis; ankylosing spondylitis; antiphospholipid syndrome; antisynthetase syndrome; atopic allergy; atopic dermatitis; autoimmune aplastic anemia; autoimmune cardiomyopathy; autoimmune enteropathy; autoimmunehemolytic anemia; autoimmune hepatitis; autoimmune inner ear disease; autoimmune lymphoproliferative syndrome; autoimmune peripheral neuropathy; autoimmune pancreatitis; autoimmune polyendocrine syndrome; autoimmune progesterone dermatitis; autoimmune thrombocytopenic purpura; autoimmune urticaria; autoimmune uveitis; Balo concentric sclerosis; Behcet's disease; Berger's disease; Bickerstaff's encephalitis; Blau syndrome; bullous pemphigoid; chronic bronchitis; Castleman's disease; Chagas disease; chronic inflammatory demyelinating polyneuropathy; chronic recurrent multifocal osteomyelitis; chronic obstructive pulmonary disease; Churg-Strauss syndrome; cicatricial pemphigoid; Cogan syndrome; cold agglutinin disease; complement component 2 deficiency; contact dermatitis; cranial arteritis; CREST syndrome; Crohn's disease; Cushing's syndrome; cutaneous leukocytoclastic vasculitis; Dego's disease; Dercum's disease; dermatitis herpetiformis; dermatomyositis; diabetes mellitus type 1; diffuse cutaneous systemic sclerosis; Dressler's syndrome; drug-induced lupus; discoid lupus erythematosus; eczema; endometriosis; enthesitis-related arthritis; eosinophilic fasciitis; eosinophilic gastroenteritis; epidermolysis bullosa acquisita; erythema nodosum; erythroblastosis fetalis; essential mixed cryoglobulinemia; Evan's syndrome; fibrodysplasia ossificans progressive; fibrosing alveolitis; gastritis; gastrointestinal pemphigoid; giant cell arteritis; glomerulonephritis; Goodpasture's syndrome; Grave's disease; Guillain-Barre syndrome; Hashimoto's encephalopathy; Hashimoto's thyroiditis; Henoch-Schonlein purpura; herpes gestationis; hidradenitis suppurativa; Hughes-Stovin syndrome; hypertension; hypogammaglobulinemia; idiopathic inflammatory demyelinating diseases; idiopathic pulmonary fibrosis; idiopathic thrombocytopenic purpura; IgA nephropathy; inclusion body myositis; chronic inflammatory demyelinating polyneuropathy; interstitial cystitis; juvenile idiopathic arthritis; Kawasaki's disease; Lambert-Eaton myasthenic syndrome; leukocytoclastic vasculitis; lichen planus; lichen sclerosus; linear IgA disease; lupus erythematosus; Majeed syndrome; Meniere's disease; microscopic polyangiitis; mixed connective tissue disease; morphea; Mucha-Habermann disease; myasthenia gravis; myositis; narcolepsy; neuromyelitis optica; neuromyotonia; ocular cicatricial pemphigoid; opsoclonus myoclonus syndrome; Ord's thyroiditis; palindromic rheumatism; PANDAS; paraneoplastic cerebellar degeneration; paroxysmal nocturnal hemoglobinuria; Parry Romberg syndrome; Parsonage-Turner syndrome;

pars planitis; pemphigus vulgaris; pernicious anaemia; perivenous encephalomyelitis; peripheral vascular disease; POEMS syndrome; polyarteritis nodosa; polymyalgia rheumatic; polymyositis; primary biliary cirrhosis; primary sclerosing cholangitis; progressive inflammatory neuropathy; psoriatic arthritis; psoriasis; pyoderma gangrenosum; pure red cell aplasia; Rasmussen's encephalitis; raynaud phenomenon; relapsing polychondritis; Reiter's syndrome; restless leg syndrome; retroperitoneal fibrosis; rheumatic fever; rheumatoid arthritis; Schnitzler syndrome; scleritis; scleroderma; serum sickness; chronic sinusitis; Sjogren's syndrome; spondyloarthropathy; stiff person syndrome; subacute bacterial endocarditis; Susac's syndrome; Sweet's syndrome; sympathetic ophthalmia; Takayasu's arteritis; temporal arteritis; thrombocytopenia; Tolosa-Hunt syndrome; transverse myelitis; ulcerative colitis; undifferentiated connective tissue disease; undifferentiated spondyloarthropathy; vitiligo; and Wegener's granulomatosis. The invention also features the treatment of immune disorders that increase susceptibility to microbial or viral infection, including HIV. In particular embodiments, the autoimmune disease is lupus erythematosus. In certain embodiments, the autoimmune disease is asthma.

By the term "addiction disorder" or "addiction condition" is meant a compulsive disorder or condition characterized by impulsive behavior. Addiction conditions include substance use disorders, eating disorders, sexual addictions, and other conditions characterized by pathological or compulsive gambling, electronic device use, spending, arson (e.g, pyromania), theft (e.g., kleptomania), hair pulling (e.g., trichotillomania), overworking, overexercising, and other behaviors. In particular embodiments, an addiction condition is a substance use disorder. A substance use disorder may involve dependence or abuse of one or more substances with or without physiological dependence. Such substances include, but are not limited to, alcohol, amphetamines or amphetamine-like substances, inhalants, caffeine, *cannabis*, cocaine, hallucinogens, inhalants, nicotine, opioids, phencyclidine and phencyclidine-like compounds, sedative-hyptnotics, benzodiazepines, and combinations thereof. In particular embodiments, the methods of the invention are used to treat cocaine addiction. Substance use disorders may encompass drug withdrawal disorders and symptoms including headaches, delirium, perceptual disturbances, mood disorders (e.g., anxiety), sleep disorders (e.g., insomnia), fatigue, sweating, vomiting, diarrhea, nausea, irritability, shaking, difficulty concentrating, and cravings.

As used herein, the term "Pin1 marker" refers to a marker which is capable of being indicative of Pin1 activity levels in a sample of the invention. Pin1 markers include nucleic acid molecules (e.g., mRNA, DNA) which corresponds to some or all of a Pin1 gene, peptide sequences (e.g., amino acid sequences) which correspond to some or all of a Pin1 protein, nucleic acid sequences which are homologous to Pin1 gene sequences, peptide sequences which are homologous to Pin1 peptide sequences, antibodies to Pin1 protein, substrates of Pin1 protein, binding partners of Pin1 protein, and activity of Pin1.

By "elevated levels of a Pin1 marker" is meant a level of Pin1 marker that is altered thereby indicating elevated Pin1 activity. "Elevated levels of a Pin1 marker" include levels at least 5%, 6%, 7%, 8%, 9%, 10%, 15%, 20%, 25%, 30%, 40%, 50%, 60%, 70%, 80%, 90%, 100%, 200%, 500%, 1000%, or greater than, or 5%, 6%, 7%, 8%, 9%, 10%, 15%, 20%, 25%, 30%, 40%, 50%, 60%, 70%, 80%, 90%, 100% less than the marker levels measured in a normal, disease fee subject or tissue.

By "Pin1 degradation" is meant a reduction in a level of Pin1 marker. For example, a patient treated with a Pin1 substrate (e.g., catalytic inhibitor) may exhibit a lower level of a Pin1 marker prior to treatment than after treatment, indicating that the substrate degraded Pin1. Pin1 degradation includes changes in a level of a Pin1 marker of less than 5%, or at least 5%, 6%, 7%, 8%, 9%, 10%, 15%, 20%, 25%, 30%, 40%, 50%, 60%, 70%, 80%, 90%, 100%, 200%, 500%, 1000%, or 5%, 6%, 7%, 8%, 9%, 10%, 15%, 20%, 25%, 30%, 40%, 50%, 60%, 70%, 80%, 90%, 100%.

By "active site" is meant a portion of a protein where a ligand, substrate, or inhibitor associates. For example, Pin1 has at least two active sites including a WW domain and a peptidyl-prolyl isomerase (PPIase) domain that catalyzes the prolyl isomerization of proteins. An active site of Pin1 may include one or more "binding pockets" with which a substrate (e.g., catalytic inhibitor) can interact (e.g., bind, associate, or participate in a chemical reaction or change). For example, a portion of an active site of Pin1 may be a binding pocket. As described herein, the PPIase active site of Pin1 includes multiple Pin1 binding pockets such as a phosphate or carboxyl binding pocket (e.g., a high electron density binding pocket) and a cyclohexenyl or hydrophobic binding pocket. Association of a substrate with Pin1 or a portion thereof (e.g., one or more binding pockets of an active site) may involve non-covalent intermolecular interactions such as electrostatic, van der Waals, hydrogen bonding, and hydrophobic interactions. A substrate having high affinity for Pin1 or a portion thereof may associate strongly and/or efficiently with all or a portion of Pin1 (e.g., with one or more binding pockets of one or more active sites). As used herein, a substrate with a "high affinity" for Pin1 or a portion thereof has a low picomolar to submicromolar $K_i$ and/or $K_d$ value as measured by, for example, a Pin1 fluorescence polarization assay, Pin1 photolabeling, a Pin1 PPIase enzymatic assay, isothermal titration calorimetry, microscale thermophoresis, or a thermal shift assay. Affinity for Pin1 or a portion thereof may also be determined by, for example, a binding energy determined with molecular modeling (e.g., a protein-ligand docking program). Affinities and binding energies determined with molecular modeling may differ from or be the same as or similar to experimental values, though relative values should be similar. For example, a ranking of compounds by affinities or binding energies determined with molecular modeling is likely to be the same as a ranking of the same compounds based on affinities or binding energies determined experimentally, e.g., as described herein. A substrate may alternately be referred to as an inhibitor (e.g., a catalytic inhibitor), binder, or ligand herein.

As used herein, a "co-crystal" is a crystalline solid including two or more components. For example, a co-crystal may include a protein, such as Pin1, and a molecule, such as ATRA or an ATRA-related compound. Without wishing to be bound by theory, components of a co-crystal tend to have one or more hydrogen bonding or solvent-mediated hydrogen bonding interactions, which aids in the formation of the co-crystal. A co-crystal may be formed by, for example, combining a solution containing a first component (e.g., Pin1) with a solution containing a second component (e.g., ATRA), optionally incubating, and performing vapor diffusion (e.g., in a hanging-drop or sitting-drop format).

A co-crystal or portion thereof may be interrogated and characterized with crystallographic methods such as X-ray, neutron, or electron diffraction. An X-ray (e.g., a synchrotron), neutron, or electron source can be used to produce a diffraction pattern from a co-crystal or portion thereof according to methods known in the art. Subsequently, a computer model or program can be used to derive structural coordinates for components of the co-crystal or portion thereof. Derived structural coordinates (e.g., Cartesian or "xyz" coordinates) can be used to generate a three-dimensional visualization or visual or graphical representation of a co-crystal or portion thereof. Such representations can facilitate the identification of binding pockets and to make inferences about the intermolecular forces between the components of the co-crystal (e.g., between Pin1 and ATRA). A three-dimensional visual representation may include an electron density map and may be generated using a computer program, model, or platform, such as those known in the art. Software for generating visual representations from structural coordinates are widely available and include programs such as Mercury, Diamond, CrystalMaker, and VESTA.

The ATRA-related compounds of the invention inhibit Pin1 activity (e.g., as determined by the fluorescence polarization-based displacement assay or PPIase assay as describe herein). This inhibition can be, e.g., greater than 20%, 30%, 40%, 50%, 60%, 70%, 80%, 90%, 95%, 99%, or greater.

The term "anti-proliferative compound" is intended to include chemical reagents which inhibit the growth of proliferating cells or tissues wherein the growth of such cells or tissues is undesirable. Chemotherapeutic agents are well known in the art (as well as described herein), and are typically used to treat neoplastic diseases, tumors, and cancers. Anti-proliferative compounds can be, for example, any anti-proliferative compound described herein.

The term "anti-microbial compound" is intended to include agents that inhibit the growth of or kill microorganisms. Anti-microbial compounds may be anti-bacterial compounds (e.g., compounds useful against bacteria), anti-fungal compounds (e.g., compounds useful against fungi), anti-viral compounds, anti-parasitic compounds, disinfectants, and anti-septics. Anti-microbial compounds can be, for example, any anti-microbial compound described herein.

The term "anti-viral compound" is intended to include agents useful for treating viral infections, e.g., by inhibiting the development of a pathogen. Anti-viral compounds can be, for example, any anti-viral compound described herein.

The term "anti-inflammatory compound" is intended to include agents useful for reducing inflammation or swelling. Anti-inflammatory compounds can be, for example, any anti-inflammatory compound described herein.

"Treatment," as used herein, is defined as the application or administration of a therapeutic agent (e.g., a retinoic acid compound) to a patient (e.g., a subject), or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease, or to slow the progression of the disease.

As used herein, the terms "sample" and "biological sample" include samples obtained from a mammal or a subject containing Pin1 which can be used within the methods described herein, e.g., tissues, cells and biological fluids isolated from a subject, as well as tissues, cells and fluids present within a subject. Typical samples from a subject include tissue samples, tumor samples, blood, urine, biopsies, lymph, saliva, phlegm, pus, and the like.

By a "low dosage" or "low concentration" is meant at least 5% less (e.g., at least 10%, 20%, 50%, 80%, 90%, or even 95%) than the lowest standard recommended dosage or lowest standard recommended concentration of a particular compound formulated for a given route of administration for treatment of any human disease or condition. For example, a low dosage of an anti-proliferative compound formulated for oral administration will differ from a low dosage of an anti-proliferative compound formulated for intravenous administration.

Standard one-letter amino acid abbreviations are used herein. For example, K corresponds to lysine, R corresponds to arginine, L corresponds to leucine, M corresponds to methionine, Q corresponds to glutamine, and F corresponds to phenylalanine. A residue denoted "M130" indicates a methionine at position 130 of an amino acid sequence.

BRIEF DESCRIPTION OF THE DRAWINGS

In FIG. 2L, the middle and right panels show that ATRA-Pin1 binding is mediated by salt bridges between the carboxylic acid of ATRA and K63 and R69 residues, while the hydrophobic interaction between the cyclohexenyl moiety of ATRA and L122, M130, Q131 and F134 residues are shown in the left panel.

FIG. 3A shows the Pin1 residues within 4 Angstroms (Å) of ATRA, including H59, K63, R68, R69, S71, S72, D112, L122, M130, Q131, F134, S154 and H157, while FIG. 3B shows the interface surface of those residues with ATRA and FIG. 3C shows the side chain distribution of those residues.

FIG. 4A shows the Pin1 residues within 8 Å of ATRA, including H59, L60, L61, K63, S67, R68, R69, P70, S71, S72, W73, R74, Q75, E76, I78, S111, D112, C113, S114, S115, L122, F125, Q129, M130, Q131, K132, P133, F134, E135, S138, V150, T152, D153, S154, G155, I156, H157 and I159, while FIG. 4B shows the interface surface of those residues with ATRA and FIG. 4C shows the side chain distribution of those residues.

FIG. 5A shows the Pin1 residues within 4 Å of the cyclohexenyl-moiety of ATRA, including H59, R68, L122, M130, Q131, F134, S154, and H157, as well as their side chain distribution of those residues.

FIG. 5B shows the Pin1 residues within 8 Å of the cyclohexenyl-moiety of ATRA, including H59, L60, L61, K63, R68, R69, D112, C113, S115, L122, F125, Q129, M130, Q131, K132, P133, F134, E135, S138, V150, T152, D153, S154, G155, I156, H157, and I159, as well as their side chain distribution of those residues.

FIG. 6A shows the Pin1 residues within 4 Å of the double bond moiety of ATRA, including K63, R68, R69, S71, S72, D112 and S154, and the side chain distribution of those residues.

FIG. 6B shows the Pin1 residues within 8 Å of the double bond moiety of ATRA, including H59, L61, K63, R68, R69, P70, S71, S72, W73, R74, Q75, I78, S111, D112, C113, S114, S115, L122, F125, Q129, M130, Q131, F134, T152, D153, S154, G155, and H157, and the side chain distribution of those residues.

FIG. 7A shows the Pin1 residues within 4 Å of the carboxylic moiety of ATRA, including K63, R69, and S71, and the side chain distribution of those residues.

FIG. 7B shows the Pin1 residues within 8 Å of the carboxylic moiety of ATRA, including H59, L60, L61, K63, S67, R68, R69, P70, S71, S72, W73, R74, Q75, E76, I78, S111, D112, C113, S114, S115, L122, F125, Q129, M130, Q131, K132, P133, F134, E135, S138, V150, T152, D153, S154, G155, I156, H157, and I159, and the side chain distribution of those residues.

FIG. 9A shows the Pin1 residues in the potential pocket P1 within 4 Å of ATRA, including C113, S114, S115, A116, K117, A118, R119, G120, D121, and L122, while FIG. 9B shows the interface surface of those residues with ATRA and FIG. 9C shows the side chain distribution of those residues. Potential pocket P1 is the extension pocket from the ATRA-interacting residue L122 listed in FIG. 3.

FIG. 10A shows the Pin1 residues in the potential pocket P1 within 8 Å of ATRA, including C57, H59, L61, D112, C113, S114, S115, A116, K117, A118, R119, G120, D121, L122, G123, A124, F125, Q129, M130, and F134, while FIG. 10B shows the interface surface of those residues with ATRA and FIG. 10C shows the side chain distribution of those residues. Potential pocket P1 is the extension pocket from the ATRA-interacting residue L122 listed in FIG. 3.

FIG. 11A shows the Pin1 residues in the potential pocket P2 within 4 Å of ATRA, including H59, R68, L122, M130, Q131, F134, S154, and H157, while FIG. 11B shows the interface surface of those residues with ATRA and FIG. 11C shows the side chain distribution of those residues. Potential pocket P2 is the extension pocket from the ATRA-interacting residues R68, L122, M130, Q131, and F134 listed in FIG. 3.

FIG. 12A shows the Pin1 residues in the potential pocket P2 within 8 Å of ATRA, including H59, L60, L61, V62, K63, R68, R69, D112, C113, S115, L122, F125, Q129, M130, Q131, K132, P133, F134, E135, S138, V150, T152, D153, S154, G155, I156, H157, and I159, while FIG. 12B shows the interface surface of those residues with ATRA and FIG. 12C shows the side chain distribution of those residues.

Figure 3:
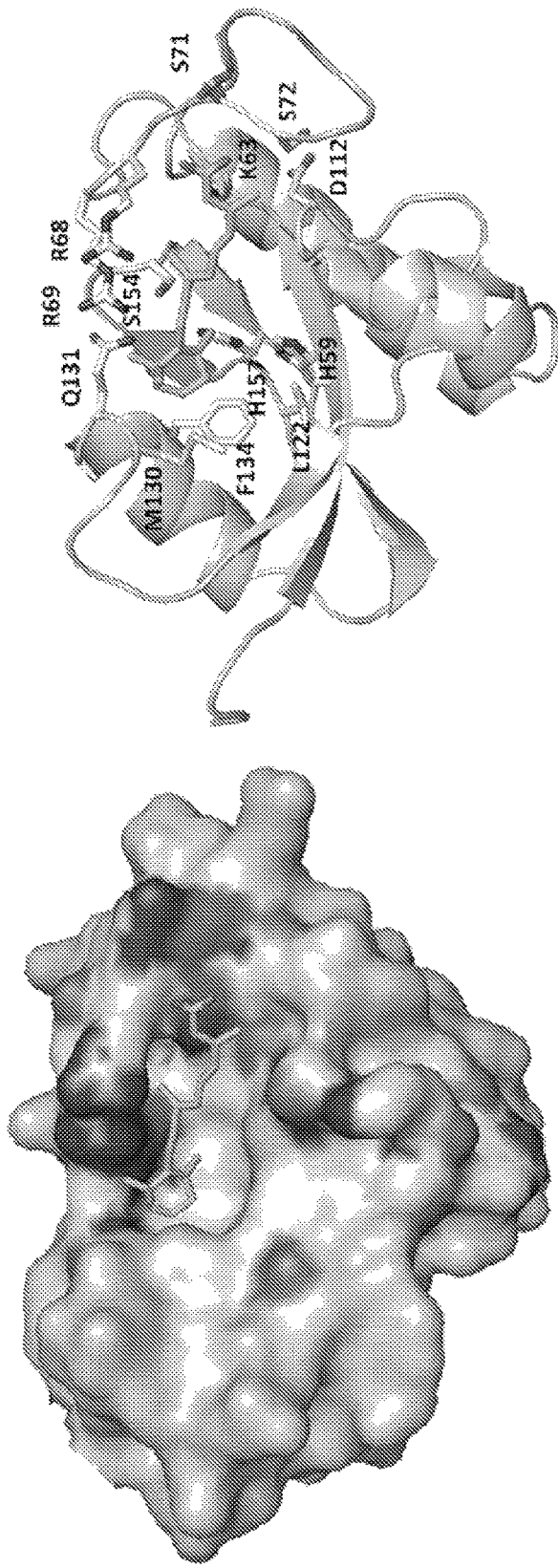

Potential pocket P2 is the extension pocket from the ATRA-interacting residues R68, L122, M130, Q131, and F134 listed in FIG. 3.

FIG. 13A shows the Pin1 residues in the potential pocket P3 within 4 Å of ATRA, including R68, Q129, M130, Q131, K132, and D153, while FIG. 13B shows the interface surface of those residues with ATRA and FIG. 13C shows the side chain distribution of those residues. Potential pocket P3 is the extension pocket from the ATRA-interacting residues R68, M130, and Q131 listed in FIG. 3.

Figure 14:
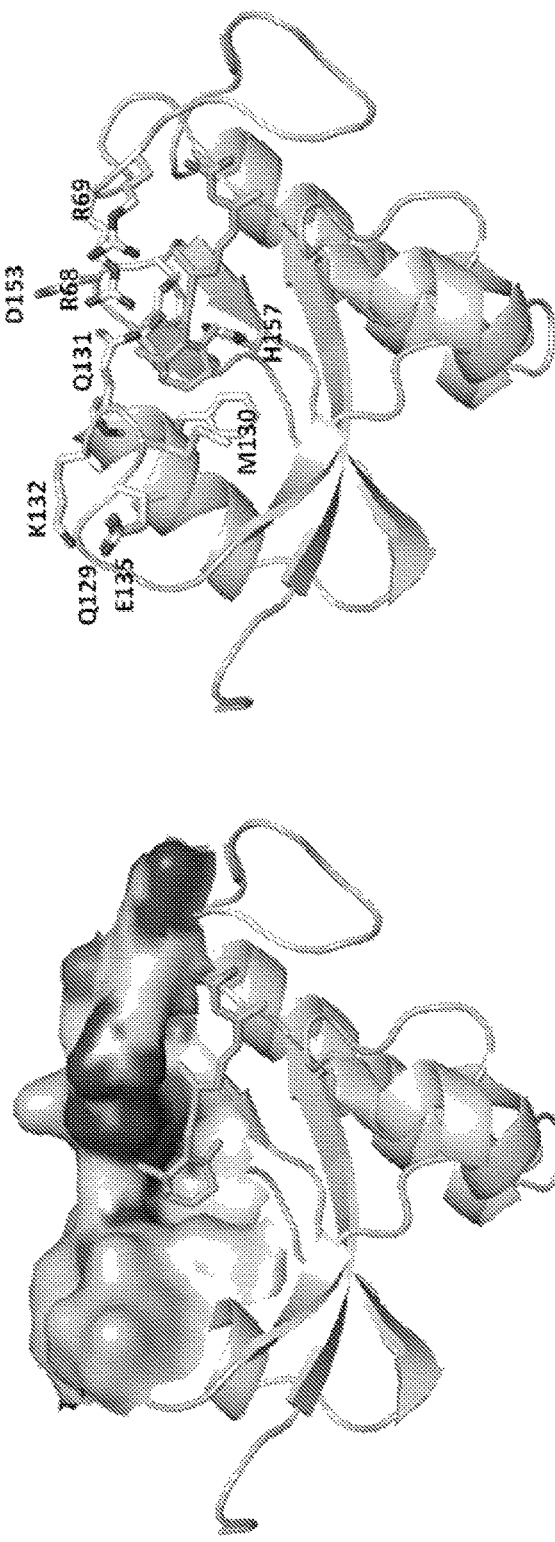

FIG. 14A shows the Pin1 residues in the potential pocket P3 within 8 Å of ATRA, including R68, R69, G128, Q129, M130, Q131, K132, P133, F134, E135, F151, T152, D153, S154, G155, and H157, while FIG. 14B shows the interface surface of those residues with ATRA and FIG. 14C shows the side chain distribution of those residues. Potential pocket P3 is the extension pocket from the ATRA-interacting residues R68, M130, and Q131 listed in FIG. 3.

Figure 15:
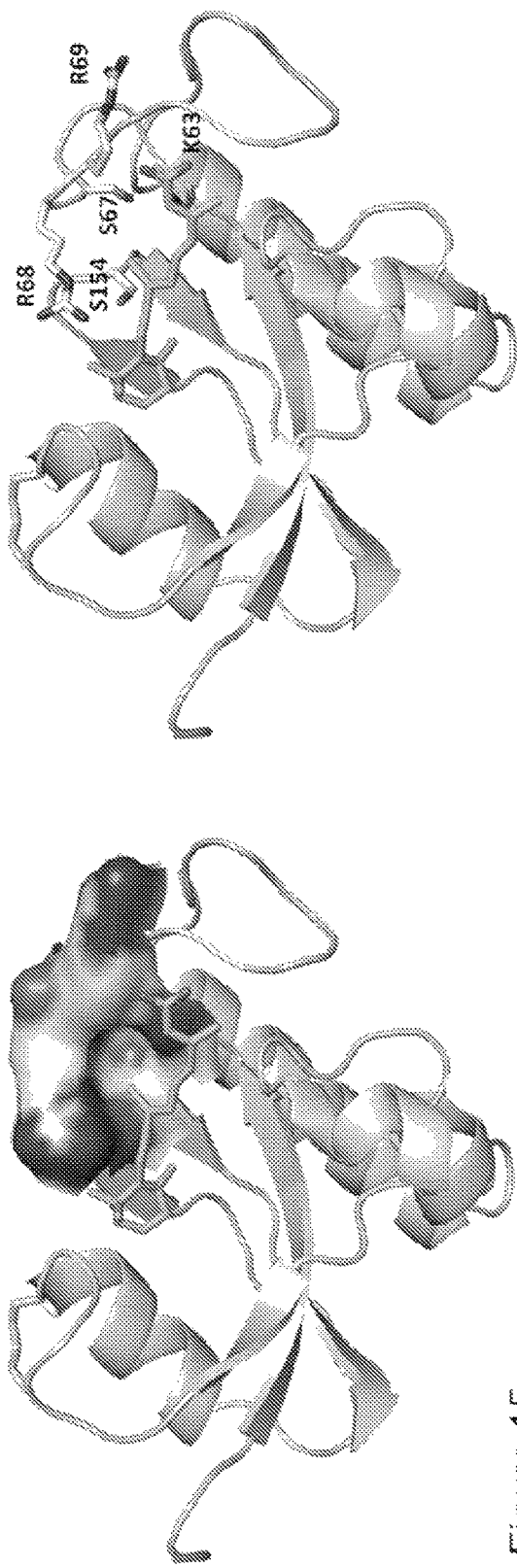

FIG. 15A shows the Pin1 residues in the potential pocket P4 within 4 Å of ATRA, including K63, S67, R68, R69, and S154, while FIG. 15B shows the interface surface of those residues with ATRA and FIG. 15C shows the side chain distribution of those residues. Potential pocket P4 is the extension pocket from the ATRA-interacting residues K63, R68, and R69 listed in FIG. 3.

FIG. 16A shows the Pin1 residues in the potential pocket P4 within 8 Å of ATRA, including L61, V62, K63, H64, Q66, S67, R68, R69, P70, S71, S72, 178, D112, Q131, T152, D153, S154, G155, I156, and H157, while FIG. 16B shows the interface surface of those residues with ATRA and FIG. 16C shows the side chain distribution of those residues. Potential pocket P4 is the extension pocket from the ATRA-interacting residues K63, R68, and R69 listed in FIG. 3.

FIG. 17A shows the Pin1 residues in the potential pocket P5 within 4 Å of ATRA, including S71, S72, W73, Q75, E76, and Q77, while FIG. 17B shows the interface surface of those residues with ATRA and FIG. 17C shows the side chain distribution of those residues. Potential pocket P5 is the first extension pocket from the ATRA-interacting residue S71 listed in FIG. 3.

FIG. 18A shows the Pin1 residues in the potential pocket P5 within 8 Å of ATRA, including K63, R69, P70, S71, S72, W73, R74, Q75, E76, Q77, I78, T79, D112, and S114, while FIG. 18B shows the interface surface of those residues with ATRA and FIG. 18C shows the side chain distribution of those residues. Potential pocket P5 is the first extension pocket from the ATRA-interacting residue S71 listed in FIG. 3.

FIG. 19A shows the Pin1 residues in the potential pocket P6 within 4 Å of ATRA, including S71, S72, W73, D112, C113, and S114, while FIG. 19B shows the interface surface of those residues with ATRA and FIG. 19C shows the side chain distribution of those residues. Potential pocket P6 is the second extension pocket from the ATRA-interacting residue S71 listed in FIG. 3.

FIG. 20A shows the Pin1 residues in the potential pocket P6 within 8 Å of ATRA, including S71, S72, W73, R74, E104, S105, L106, A107, S108, Q109, F110, S111, D112, C113, S114, S115, A116, K117, A118, R119, and G120, while FIG. 20B shows the interface surface of those residues with ATRA and FIG. 20C shows the side chain distribution of those residues. Potential pocket P6 is the second extension pocket from the ATRA-interacting residue S71 listed in FIG. 3.

Figure 21:
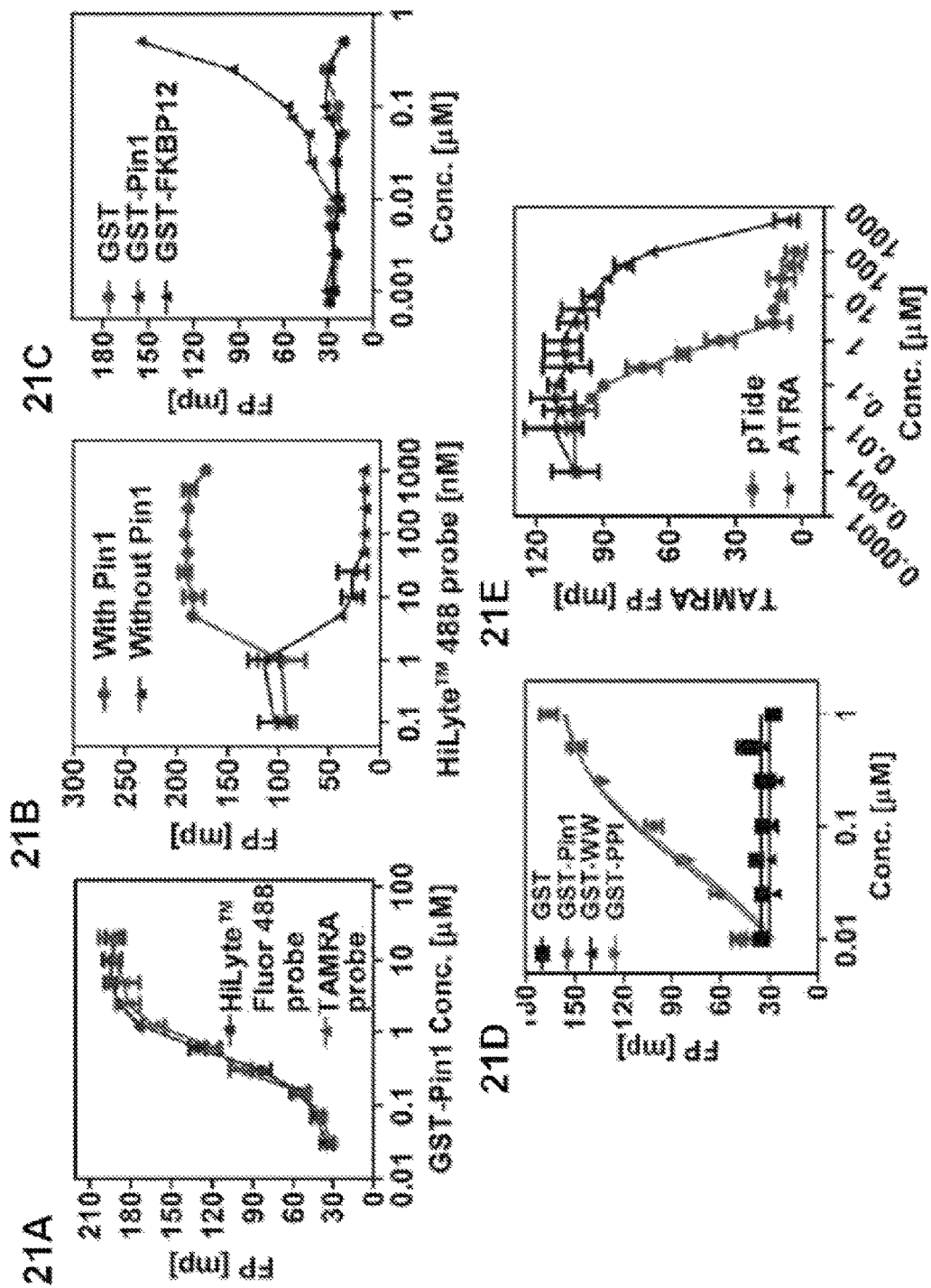

FIGS. 21A, 21B, 21C, 21D, and 21E plot fluorescence polarization against concentrations for various components measured in an FP assay. FIG. 21A depicts HiLyte™ Fluor 488- or TAMRA-conjugated pTide probe interacting with Pin1 in a dose-dependent manner, while FIG. 21B shows the binding curve between HiLyte™ Fluor 488-conjugated pTide with or without Pin1. FIGS. 21C and 21D demonstrate the specif interaction of the HiLyte™ Fluor 488 probe pTide with Pin1 but not FKBP12 (21C) and with the catalytic PPIase domain of Pin1 but not the WW domain of Pin1 (21D). FIG. 21E shows that ATRA was competitive with the interaction between TAMRA-conjugated pTide and Pin1.

Figure 22:
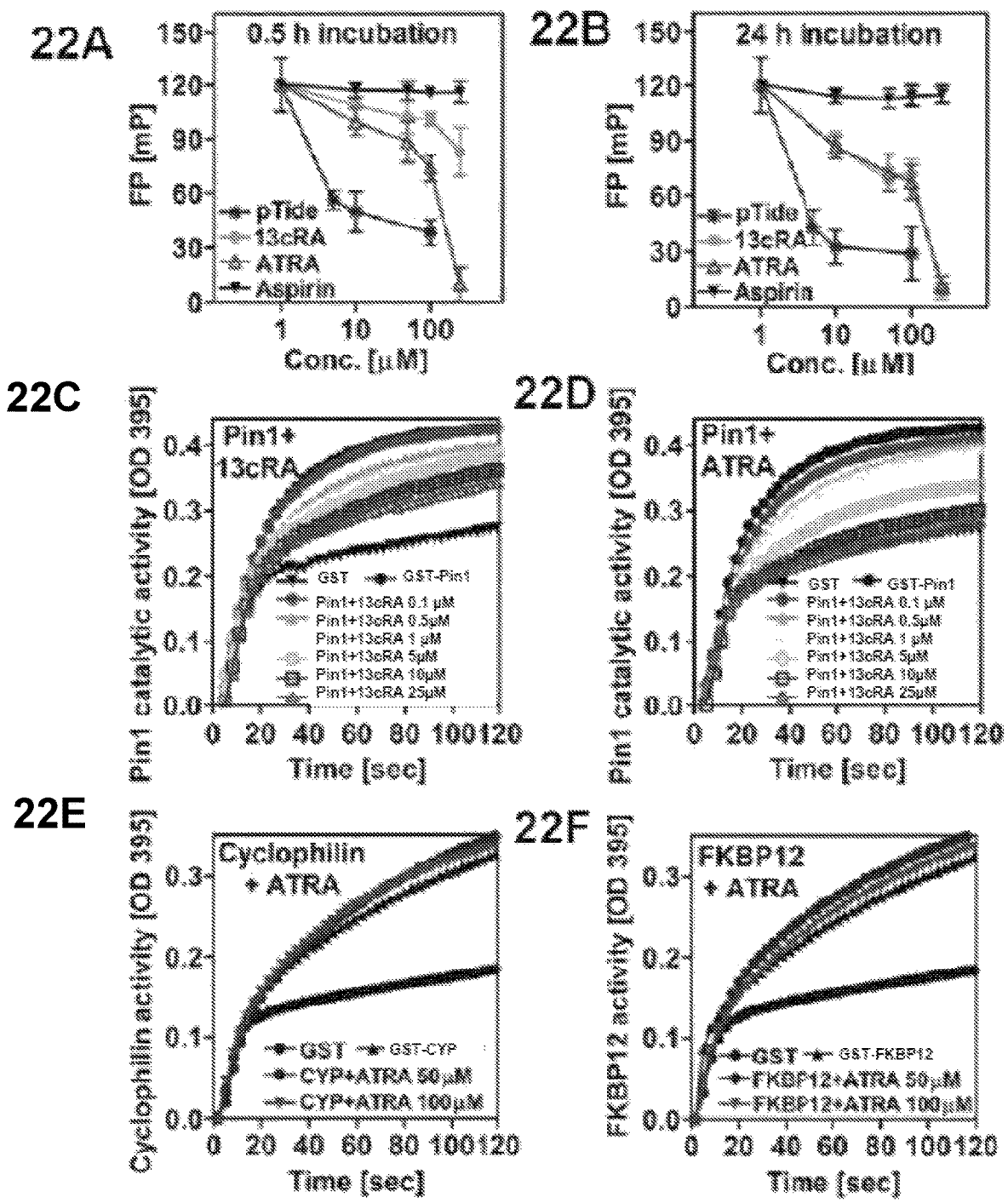

FIGS. 22A and 22B are FP plots showing the inhibition of Pin1 after adding HiLyte™ Fluor 488-pTide and incubating for 0.5 (22A) or 24 hours (22B) with different concentrations of cold pTide, ATRA, 13cRA, or salicylic acid.

FIGS. 22C and 22D are plots of Pin1 catalytic activity measured in an in vitro PPIase assay for varying concentrations of 13cRA (22C) and ATRA (22D) and demonstrate the dose-dependent inhibition of Pin1 catalytic activity by retinoic acids.

Figure 23:
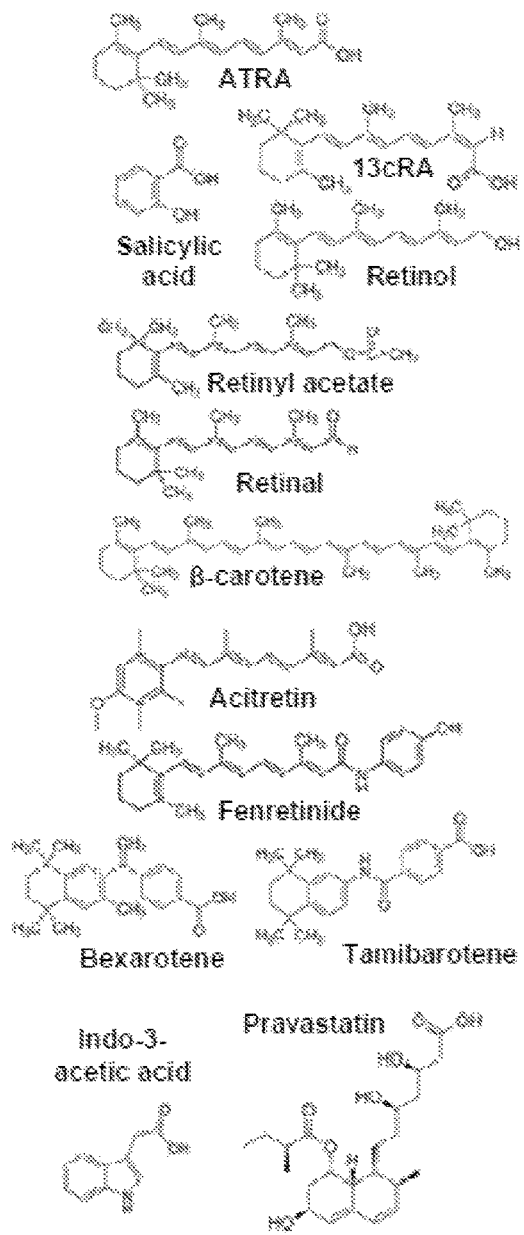
Figure 23:
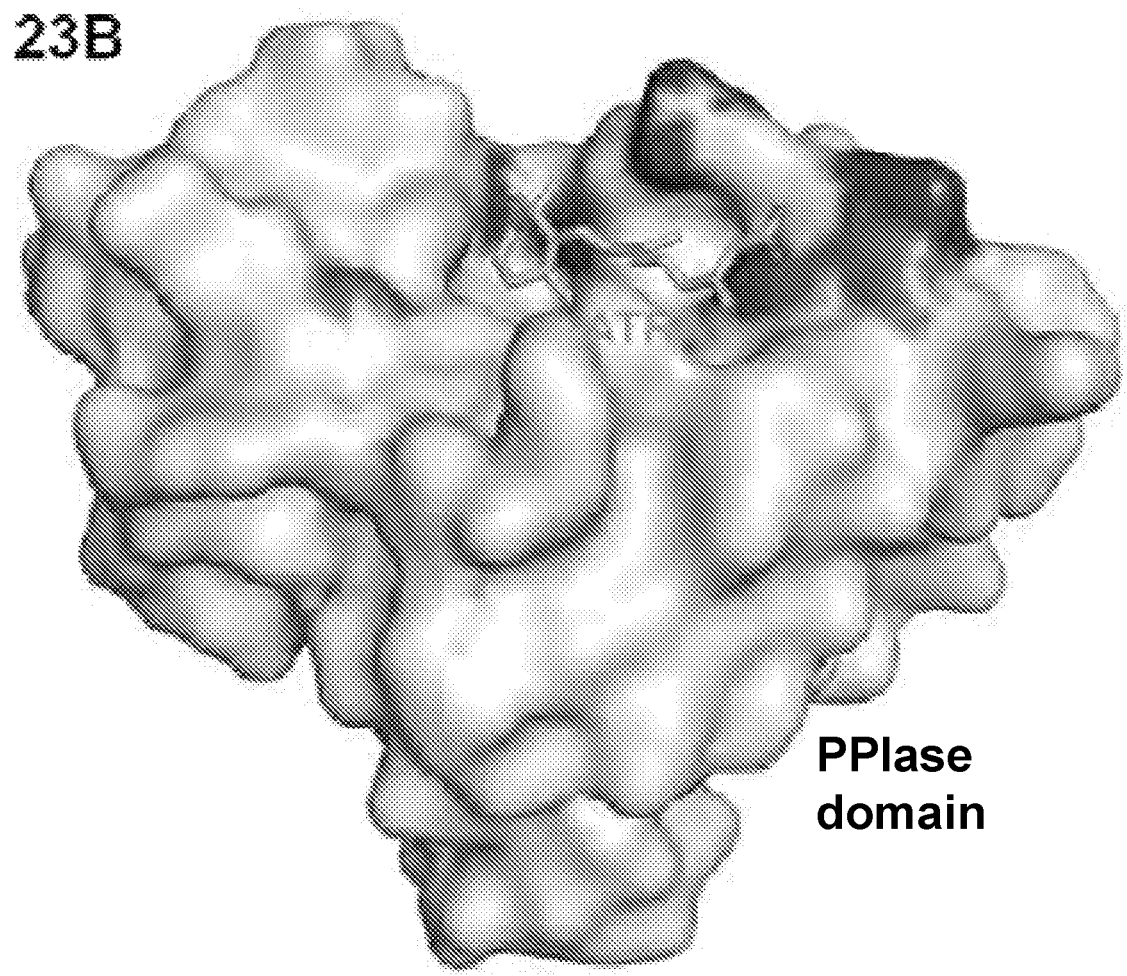

FIGS. 22E and 22F are plots of cyclophilin (22E) and FKBP12 (22F) activity measured in an in vitro PPIase assay with different concentrations of ATRA. ATRA is unable to inhibit these isomerase families FIG. 23A shows the structures of selected ATRA-related compounds including bexarotene, fenretinide, acitretin, tamibarotene, pravastatin, indo-3-acetic acid, retinal, retinol, salicylic acid, retinyl acetate, β-carotene, ATRA, and 13cRA. The inset table shows the percentage of Pin1 inhibition measured relative to ATRA as measured with an FP assay.

FIG. 23B shows a full view of the co-crystal structure of ATRA and the Pin1 PPIase domain.

Figure 24:
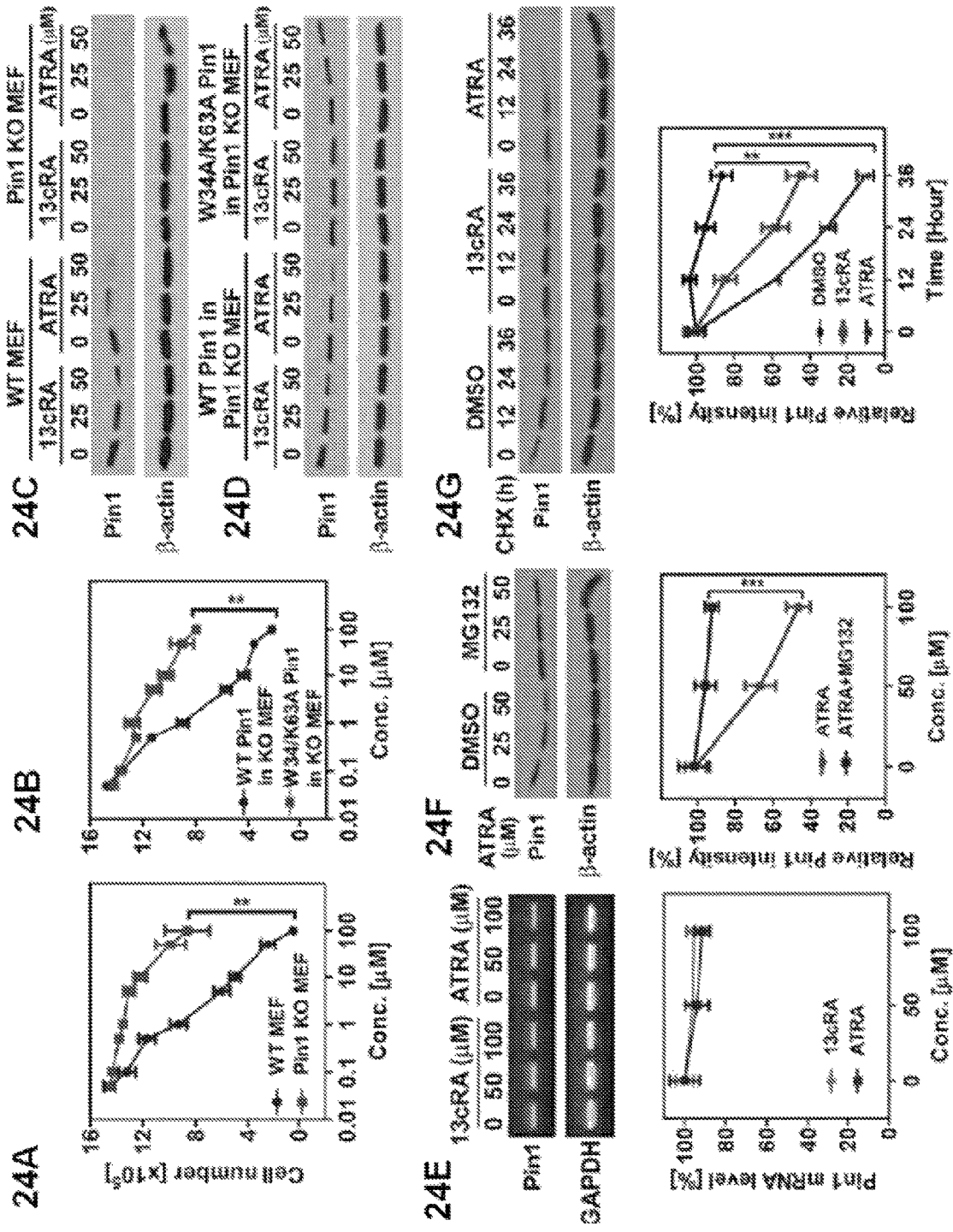
Figure 24:
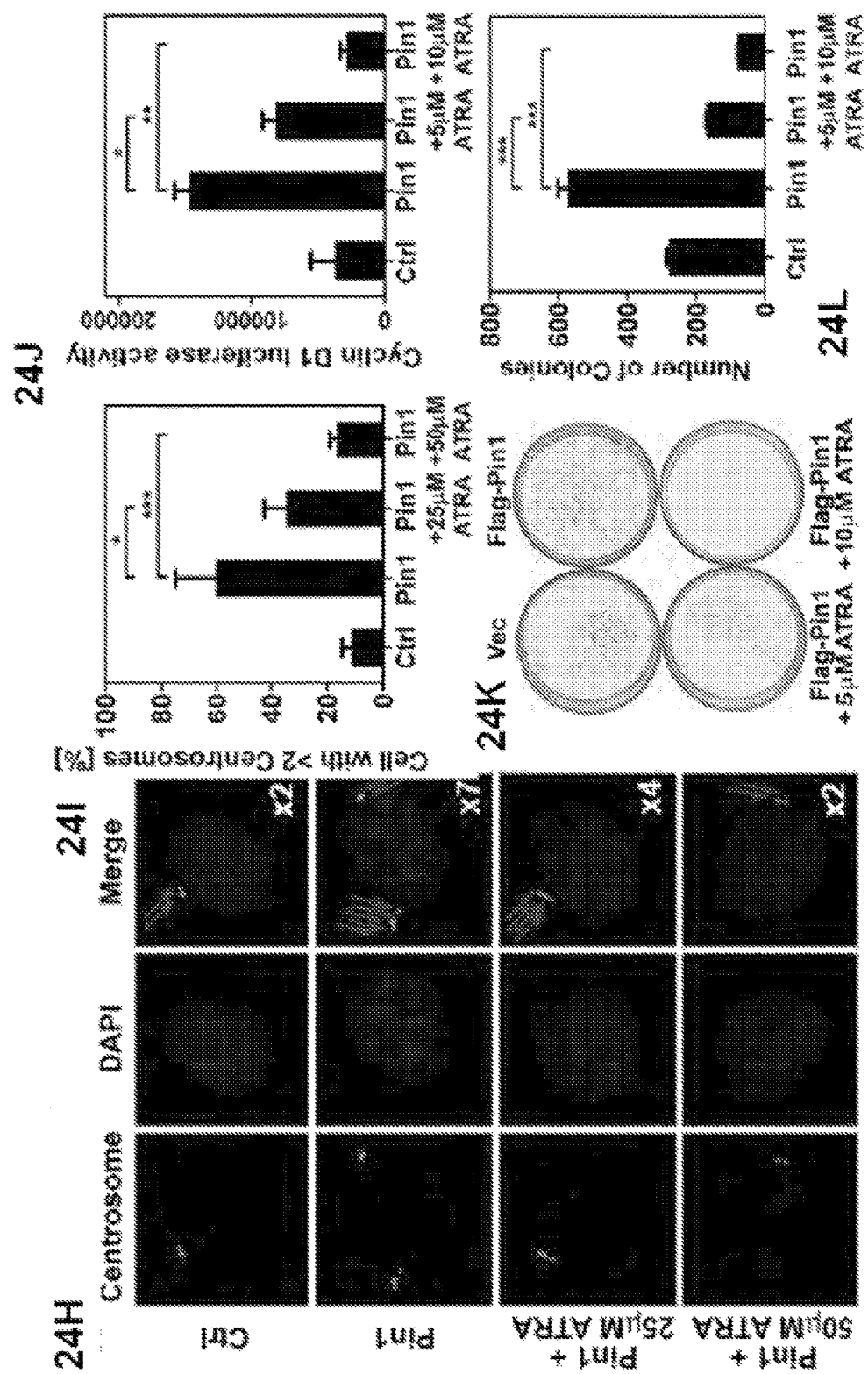

FIGS. 24A and 24B are plots of changes in cell growth with increasing ATRA for WT and Pin1 KO MEFs (24A) or Pin1 KO MEFs reconstituted with WT- or W34/K63APin1 (24B).

FIGS. 24C and 24D are immunoblots showing changes in the relative amounts of Pin1 in WT and Pin1 KO MEFs (24C) or Pin1 KO MEFs reconstituted with WT- or W34/K63APin1 (24D) after treatment with different concentrations of 13cRA or ATRA.

FIG. 24E shows quantitative RT-PCR readouts for Pin1 mRNA in MEFs treated with ATRA or 13cRA, with quantification being shown (n=3).

FIG. 24F shows immunoblots of MEFs treated with ATRA in the presence or absence of MG132, with quantification being shown (n=3).

FIG. 24G shows immunoblots of MEFs treated with ATRA or 13cRA, followed by CHX chase to detect Pin1 stability, with quantification being shown (n=3).

FIGS. 24H and 24I show fluorescence micrographs of NIH3T3 cells stably expressing Flag-tagged Pin1 or vectors treated with ATRA for 72 hours and subsequently immunostained with γ-tubulin to detect centrosomes (24H), with cells containing over 2 centrosomes being quantified from 3 independent experiments with over 100 cells in each (24I).

FIG. 24J is a plot showing cyclin D1 promoter luciferase activity in SKBR3 cells co-transfected with cyclin D1 promoter luciferase and Flag-Pin1 or control vector and subsequently treated with ATRA for 72 hours.

FIGS. 24K and 24L show colony growth of SKBR3 cells co-transfected with Flag-Pin1 or control vector, and subsequently treated with ATRA and assayed with a foci formation assay (24K), with foci counts being shown in (24L) (n=3).

Figure 25:
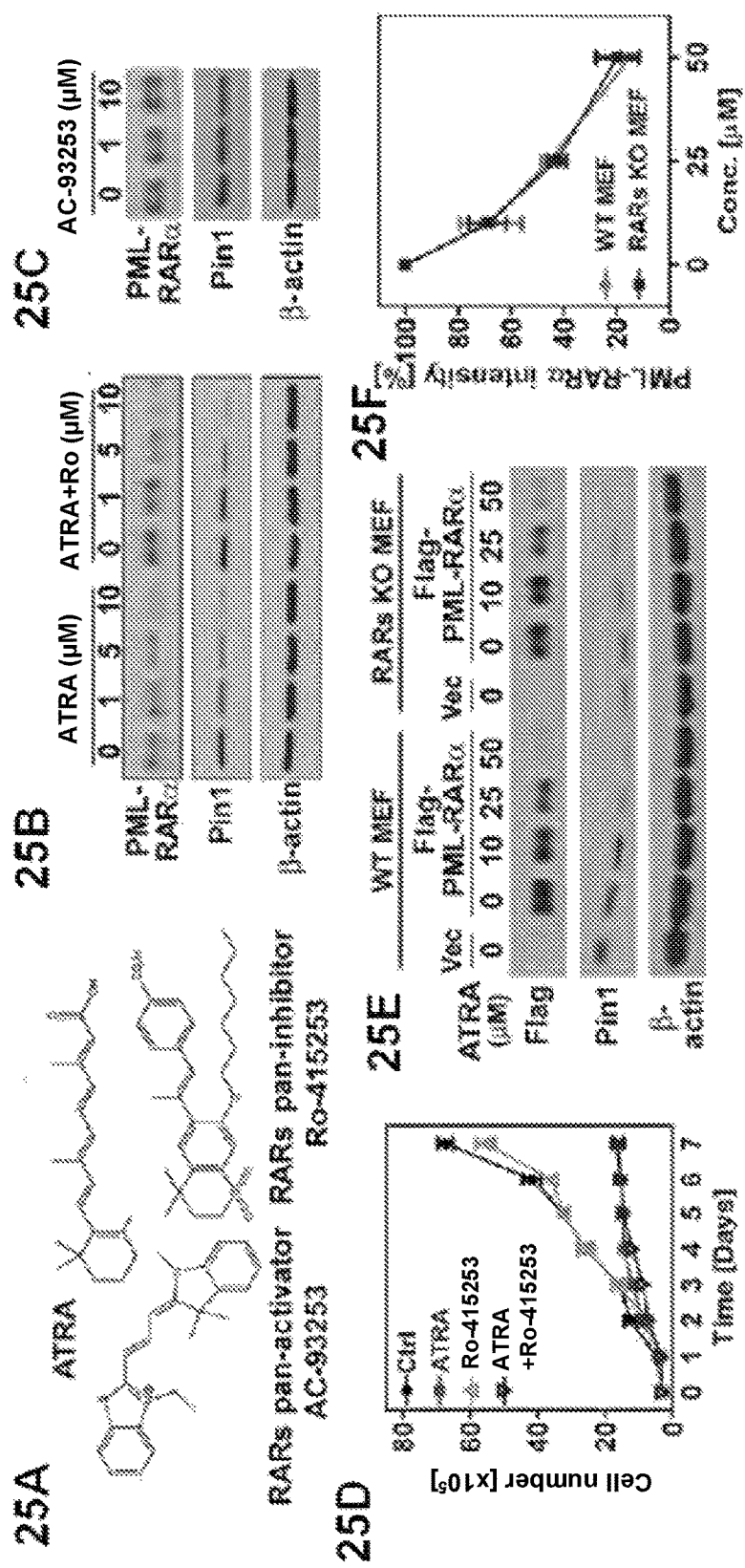
Figure 25:
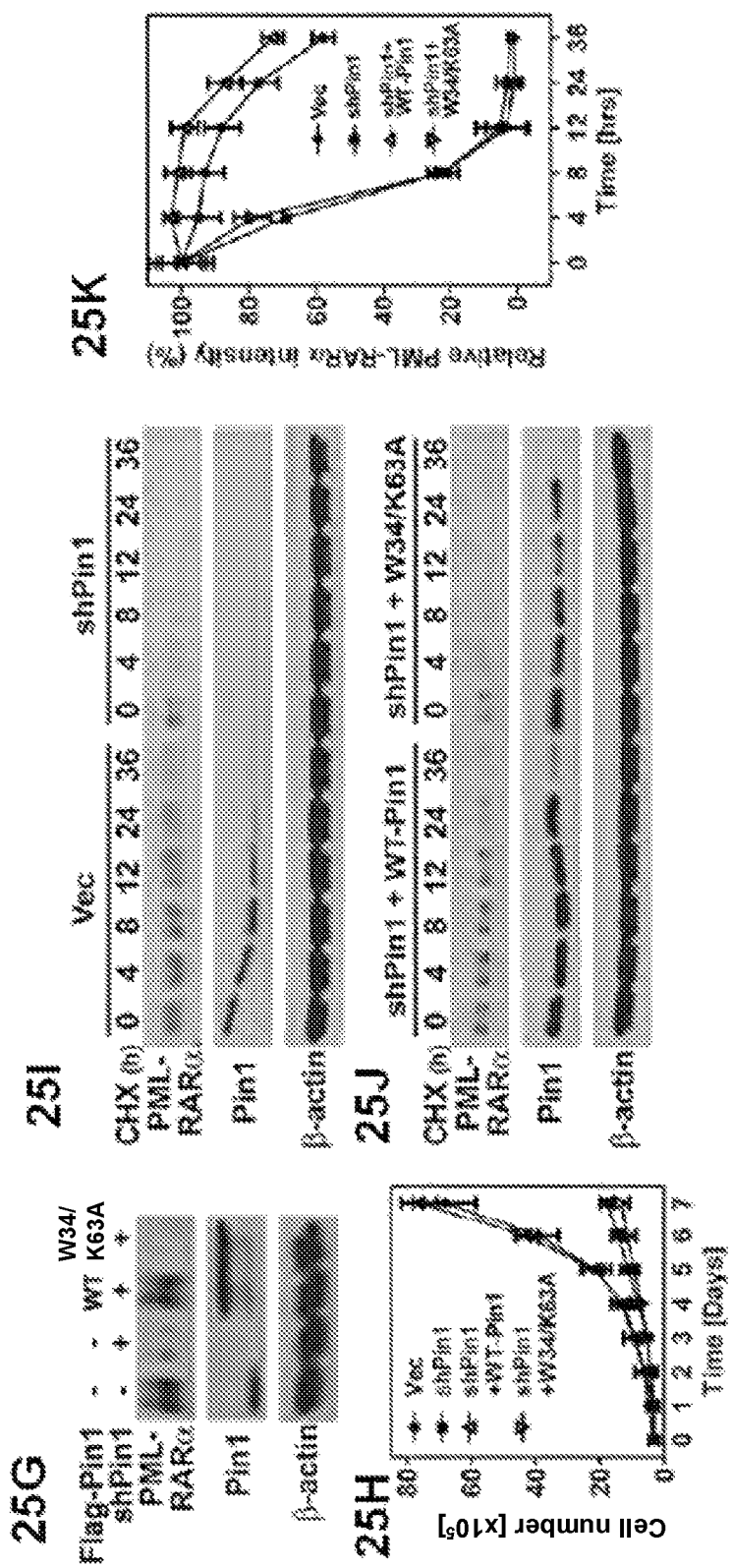
Figure 25:
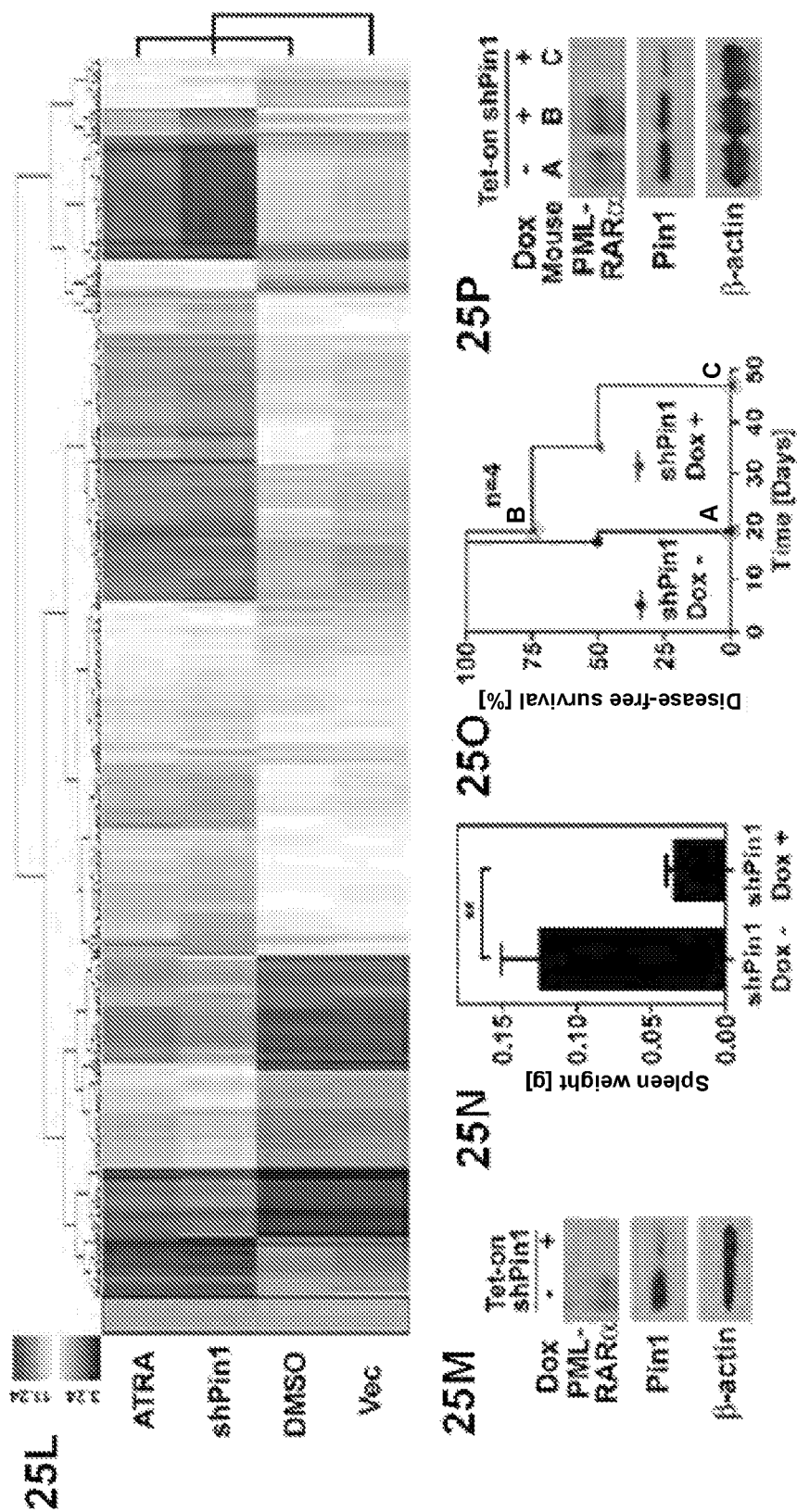

FIG. 25A shows the structures of pan-RARs activator, AC-93253, and pan-RARs inhibitor, Ro-415253.

FIG. 25B is an immunoblot demonstrating that Pan-RARs inhibitor Ro-415253 is unable to restore ATRA-mediated Pin1 degradation.

FIG. 25C is an immunoblot demonstrating that Pan-RARs activator AC-93253 is unable to lead to Pin1 degradation in NB4 cells.

FIG. 25D is a plot showing how cell growth changes in time NB4 cells suppressed by ATRA. Pan-RARs inhibitor Ro-415253 was unable to rescue NB4 cell proliferation suppressed by ATRA.

FIGS. 25E and 25F show immunoblots (25E) and a corresponding intensity plot (25F) demonstrating that ATRA causes degradation of Flag-PML-RARα and Pin1 in both WT and RARs triple KO MEFs.

FIG. 25G shows immunoblots (25G) demonstrating that NB4 cells were stably infected by lentivirus expressing shPin1 and WT or W34/K63A Flag-Pin1. FIG. 25H is a corresponding plot of cell count over time.

FIGS. 25I, 25J, and 25K are immunoblots (25I and 25J) and a corresponding intensity plot (25K) showing the result of subjecting NB4 cells stably infected by lentivirus expressing shPin1 and WT or W34/K63A Flag-Pin1 to the CHX chase, with quantification in (25K) (n=3).

FIG. 25L shows a hierarchical cluster of the differential expression profiling showed similar profiles in ATRA treated and Pin1 KO NB4 cells.

FIGS. 25M, 25N, 25O, and 25P are plots showing the results of transplanting immunodeficient NSG mice with $5 \times 10^5$ human APL NB4 cells stably carrying inducible Tet-on shPin1 and providing doxycycline food to induce Pin1 KD, followed by examining PML-RARα and Pin1 in the bone marrow (25M) and the effects on spleen size (25N) and disease-free survival time (25O) of transplanted mice. Bone marrow samples from the mice labeled with A, B, C in panel 25O were subjected to immunobloting for PML-RARα and Pin1 (25P).

Figure 26:
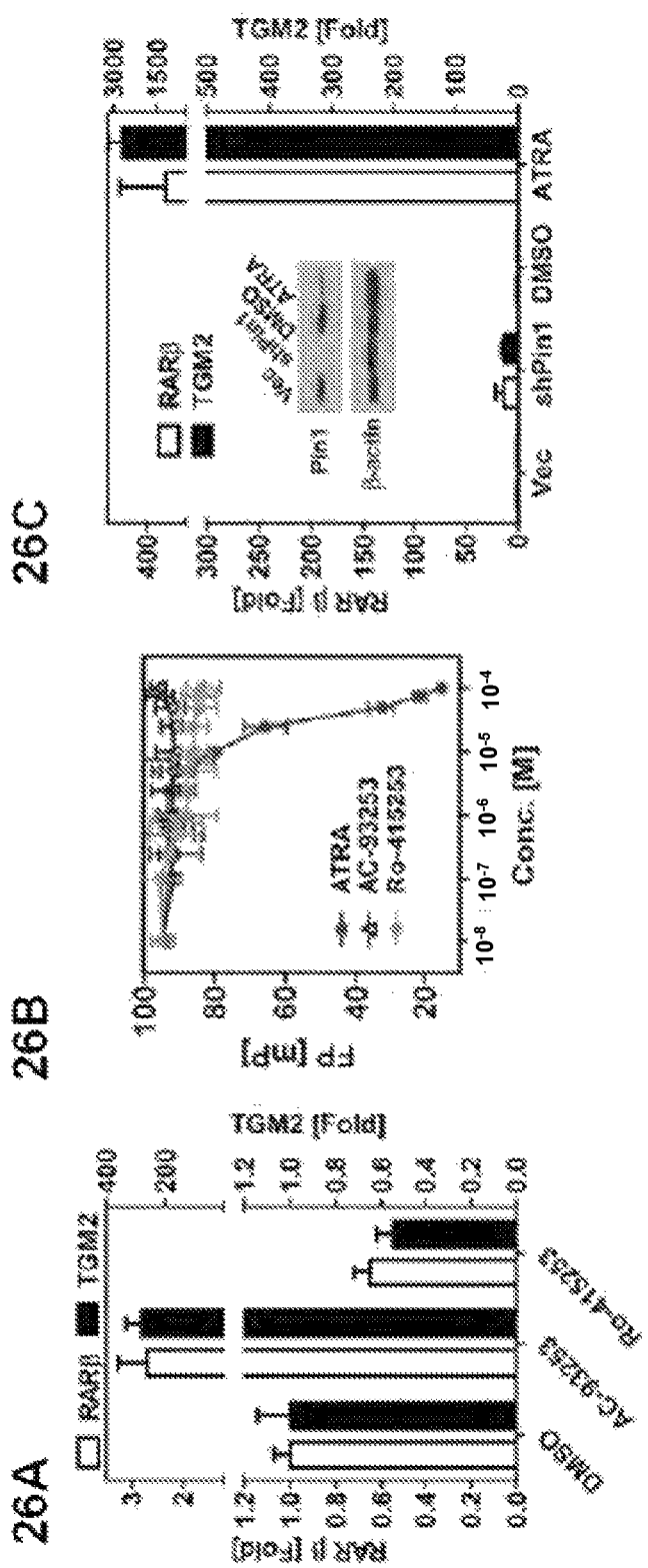

FIGS. 26A, 26B, and 26C are plots showing the activating or inhibitory effects of the pan-RAR activator AC-93253, the pan-RAR inhibitor Ro-415253, and ATRA on Pin1 binding and transactivation of RAR downstream target genes. FIG. 26A shows the expected behavior of the activator and inhibitor:

AC-93253 effectively induces transactivation of the RAR downstreams RARβ and TGM2, while Ro-415253 suppresses it. FIG. 26B shows that neither the activator nor the inhibitor interact with Pin1 while ATRA does interact with Pin1, and FIG. 26C shows that ATRA effectively and significantly induces transactivation of RAR downstreams while Pin1 KD only marginally induced it. The inset is an immunoblot showing the Pin1 level in response to different treatments.

Figure 27:
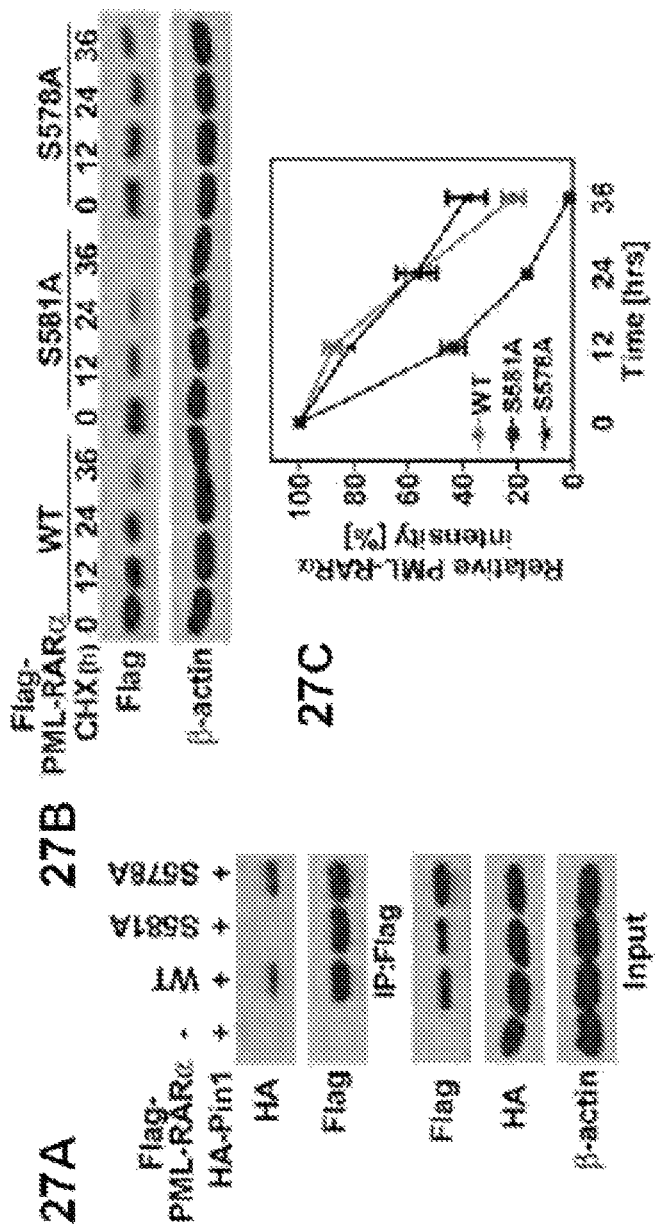

FIGS. 27A, 27B, and 27C show immunoblots (27A and 27B) and a corresponding intensity plot (27C) demonstrating that Pin1 interacts with PML-RARα containing S581 and increases PML-RARα protein stability in NB4 cells. HA-Pin1 Co-IPed with FLAG-PML-RARα but not its S581A mutant (27A), while S581A Flag-PML-RARα demonstrated a shortened protein half-life relative to that of the WT of S578A mutant Flag-PML-RARα (27B and 27C).

Figure 28:
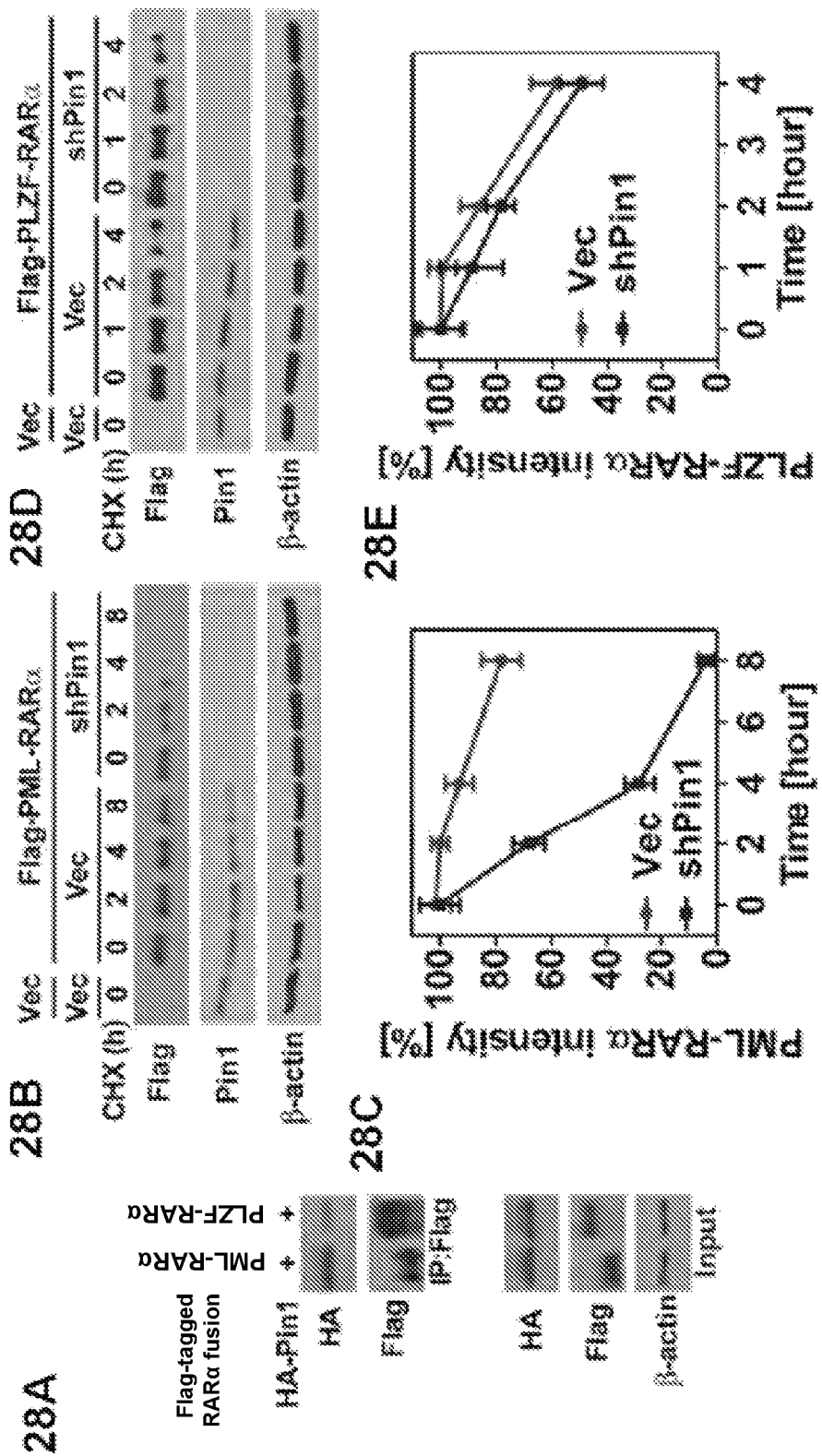

FIGS. 28A, 28B, 28C, 28D, and 28E show that Pin1 interacts much less with PLZF-RARα than with PML-RARα, and that Pin1 knockdown reduces the protein stability of PLZF-RARα much less than that of PML-RARα in NB4 cells. FIG. 28A shows immunoblots showing that HA-Pin1 co-immunoprecipitated with Flag-PML-RARα more than Flag-PLZF-RARα. Flab-PML-RARα (28B and 28C) but not Flag-PLZF-RARα (28D and 28E) demonstrated significantly shorter protein half-life in Pin1 knockdown in NB4 cells.

Figure 29:
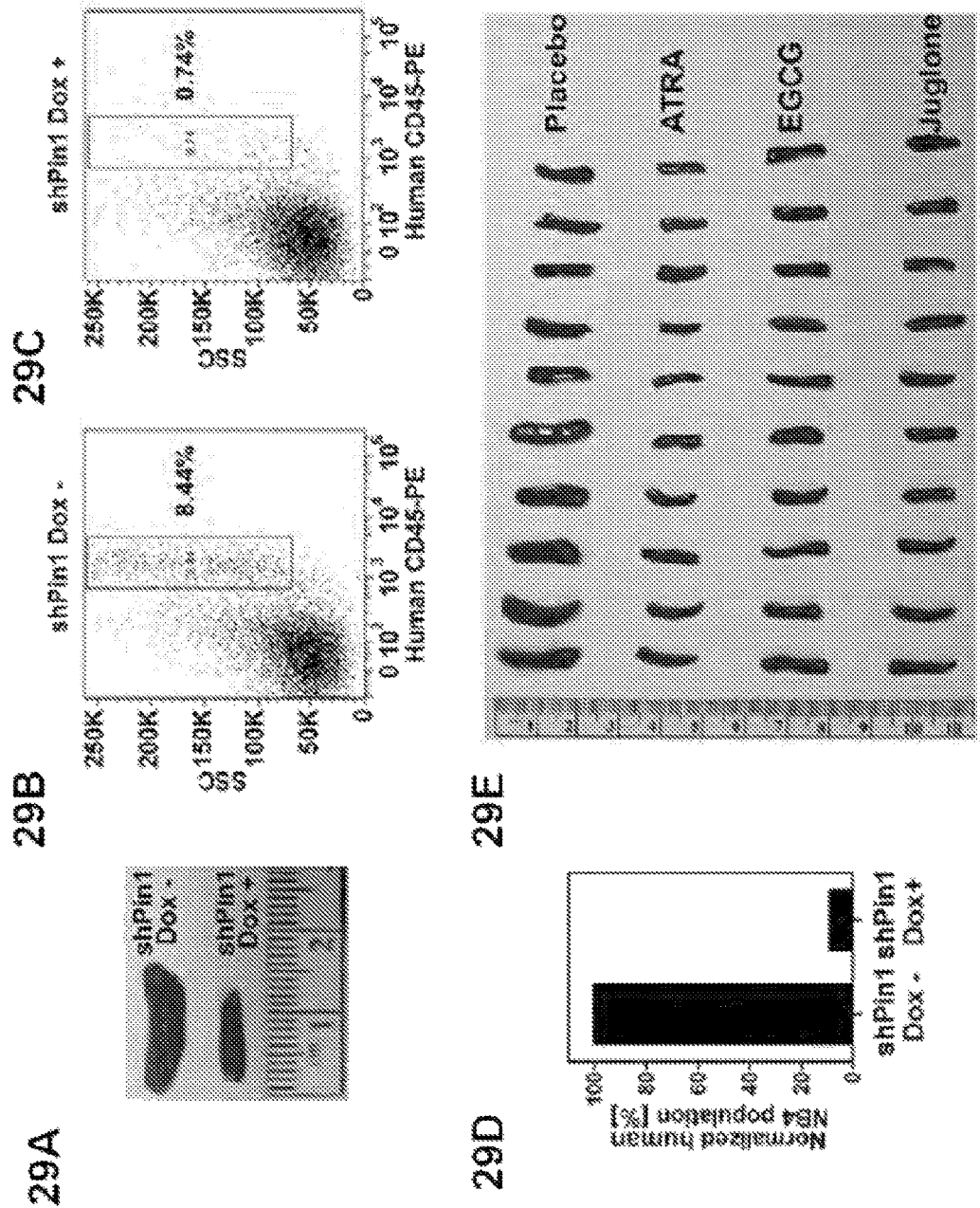

FIG. 29A shows that the spleen sizes of mice fed with doxycycline food were smaller than those fed with regular food.

FIGS. 29B and 29C are plots showing that the NB4 cell number transplanted into the mice fed with doxycycline food was significantly less than those in the mice fed with regular food. FIG. 29D presents quantification results.

FIG. 29E shows that Pin1 inhibitors EGCG and Juglone affected spleen sizes in the same manner as ATRA.

Figure 30:
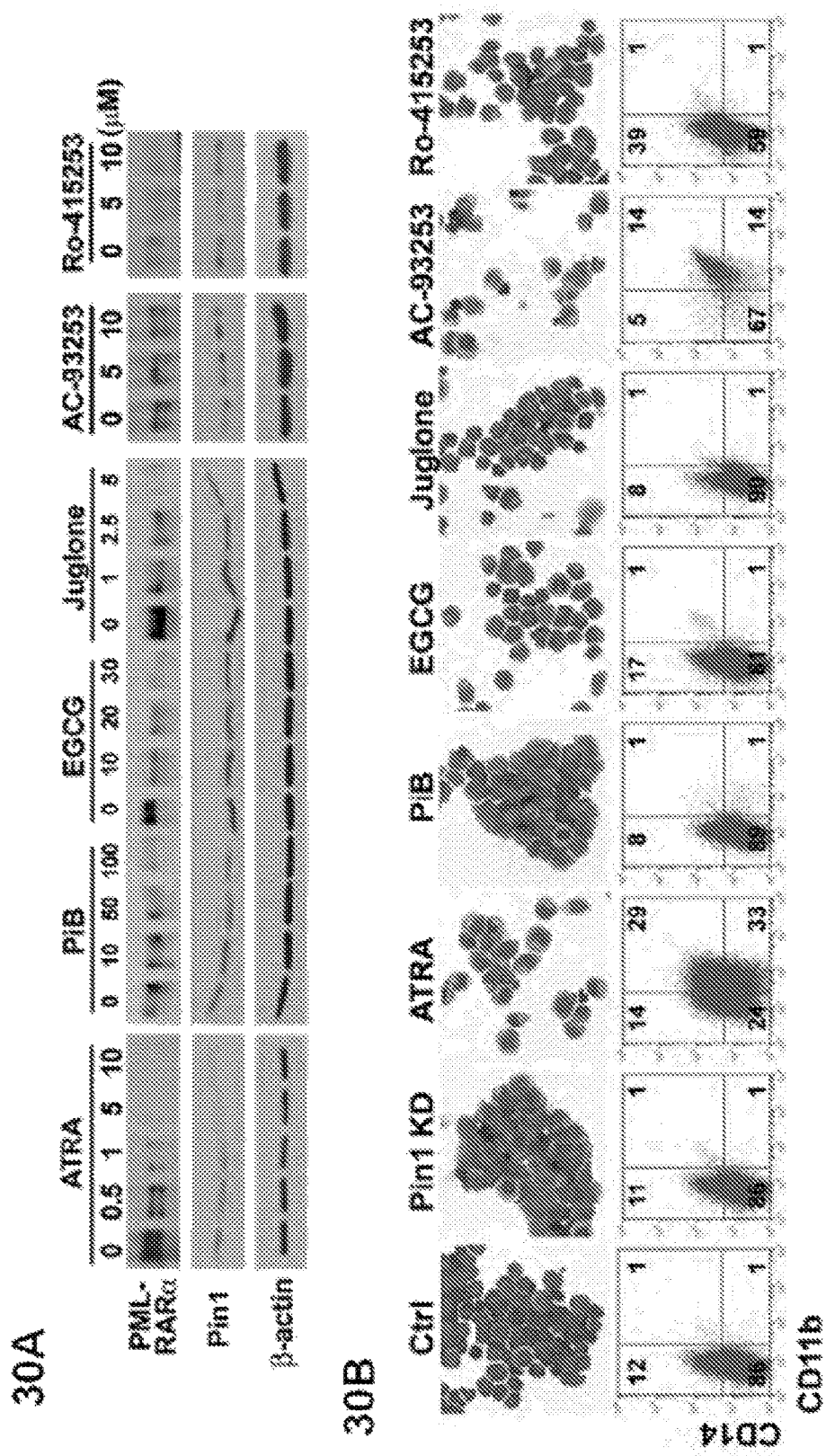
Figure 30:
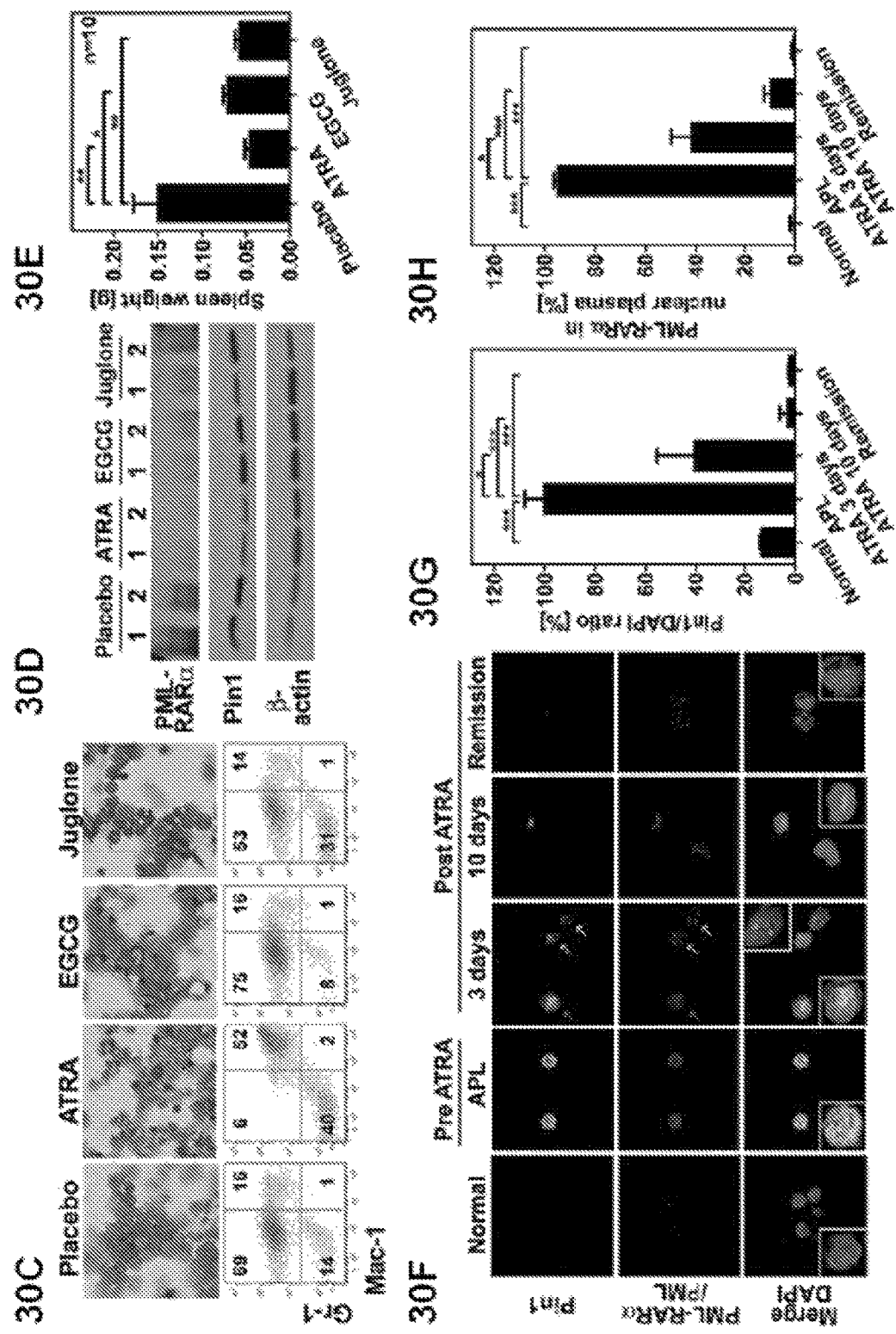

FIG. 30A shows immunoblots demonstrating the effect of treating NB4 cells with ATRA, various Pin1 inhibitors, RAR inhibitors, or RAR activator for 72 hours.

FIG. 30B shows NB4 cells treated with ATRA, various Pin1 inhibitors, RAR inhibitors, or RAR activator for 72 hours and subsequently Giemsa stained (upper panel) or fluorescence-activated cell sorting (FACS) results with CD14 and CD11 b (lower panel) for detecting APL cell differentiation.

FIGS. 30C, 30D, and 30E show the effects of transplanting sublethally irradiated C57BL/6J mice with $1 \times 10^6$ APL cells isolated from the hCG-PML-RARα transgenic mice and, 5 days after, treating with ATRA-releasing implants, EGCG, Juglone or placebo for 3 weeks, followed by determining APL cell differentiation status with Giemsa staining (upper panel) or FACS with Gr-1 and Mac-1 (lower panel) (30C), PML-RARα and Pin1 expression in the bone marrow (n=10) (30D), and the size of the spleen in mice (30E).

FIGS. 30F, 30G, and 30H show bone marrow samples from normal controls (n=24) or APL patients before (n=19) or after the treatment with ATRA for 3 (n=3) or 10 days (n=3) or APL patients in complete remission (n=17) immunostained with anti-Pin1 and anti-PML antibodies (30F). Relative levels of Pin1 (30G) in the nucleus and PML-RARα in the nuclear plasma outside of the PML nuclear body (30H) were semi-quantified (n=3). Note that PML-RARα/PML was still diffusely distributed to the entire nucleus in APL cells that contained more Pin1 (red arrows), but almost exclusively localized to the PML body (likely reflecting endogenous PML) in APL cells that contained much less Pin1 (yellow arrows).

Figure 31:
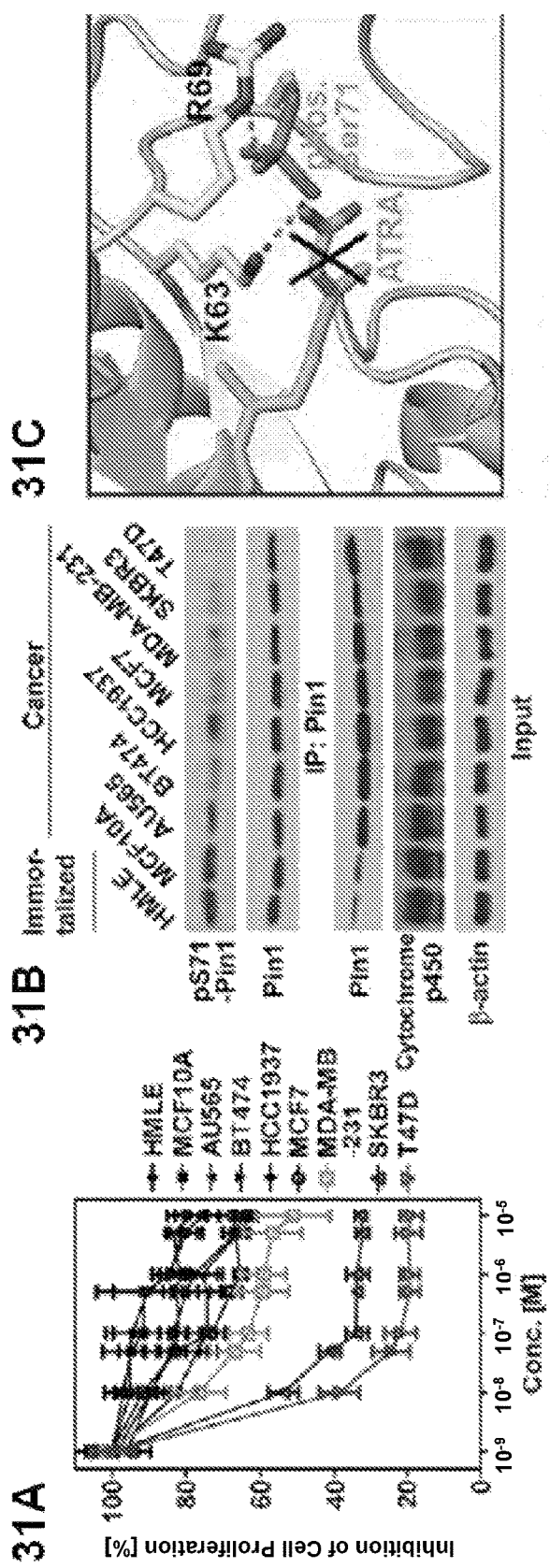
Figure 31:
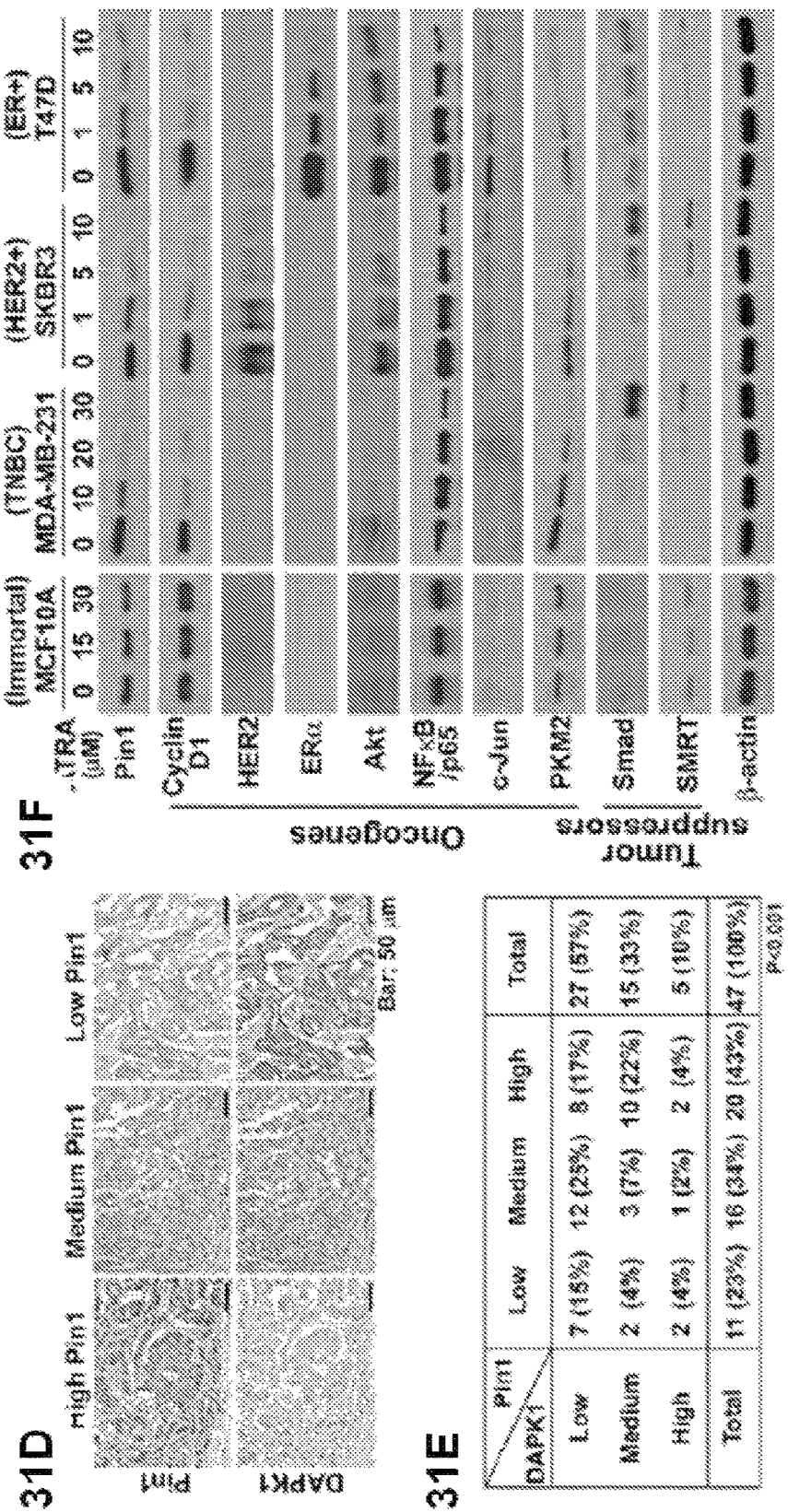
Figure 31:
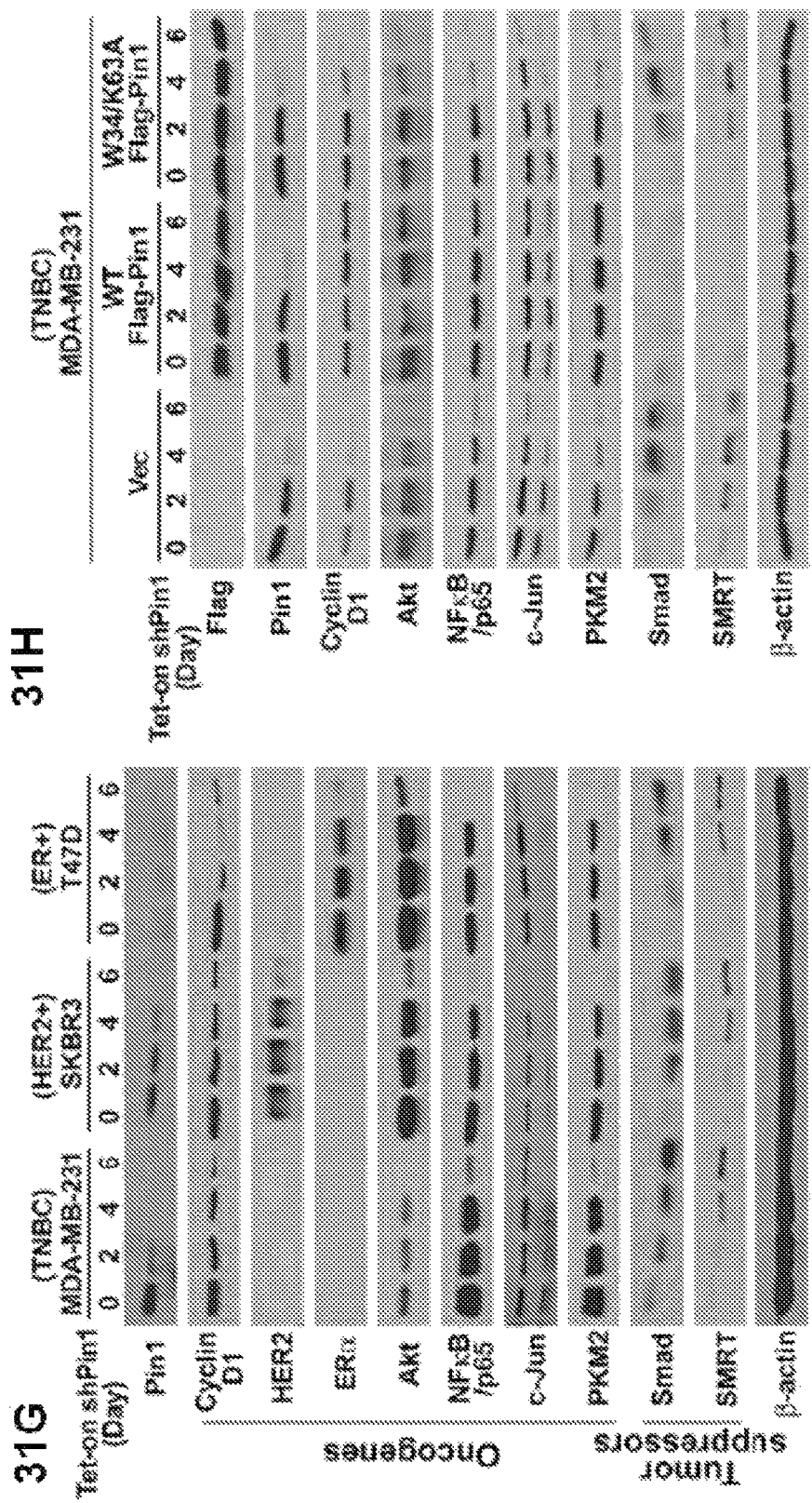

FIGS. 31A and 31B show human normal and breast cancer cells either treated with ATRA for 72 hours and subsequently examined for cell growth (31A) or directly subjected without the treatment to IP/IB for detecting Pin1 and its S71 phosphorylation (31B).

FIG. 31C is a schematic showing that S71 phosphorylation results in hydrogen bonds with R69 and K63 in the Pin1 active site and prevents the carboxylic acid of ATRA from binding to the same active site residues.

FIGS. 31D and 31E depict the inverse correlation of Pin1 and DAPK1 in human triple negative breast cancer tissues (31D), with quantification in (31E) (n=47).

FIG. 31F shows immunoblots for different breast cells treated with different concentrations of ATRA for 72 hours and assayed with IB for detecting different proteins.

FIG. 31G shows immunoblots for different breast cells stably expressing Tet-inducible Pin1 shRNA and treated with tetracycline for different times to induce Pin1 KD and assayed with IB for detecting different proteins.

FIG. 31H shows immunoblots for different breast cells after reconstitution of shRNA-resistant Pin1 or its W34/K63A mutant assayed by IB for detecting different proteins.

Figure 32:
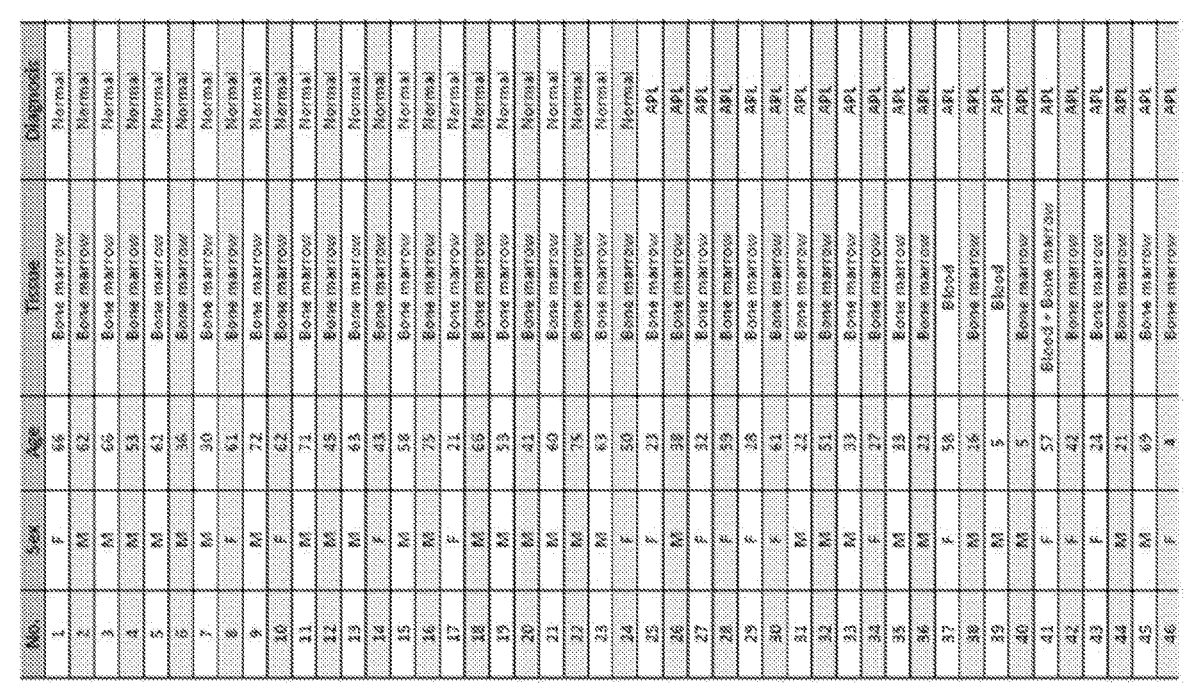

FIG. 32 depicts patient information for APL human samples.

Figure 33:
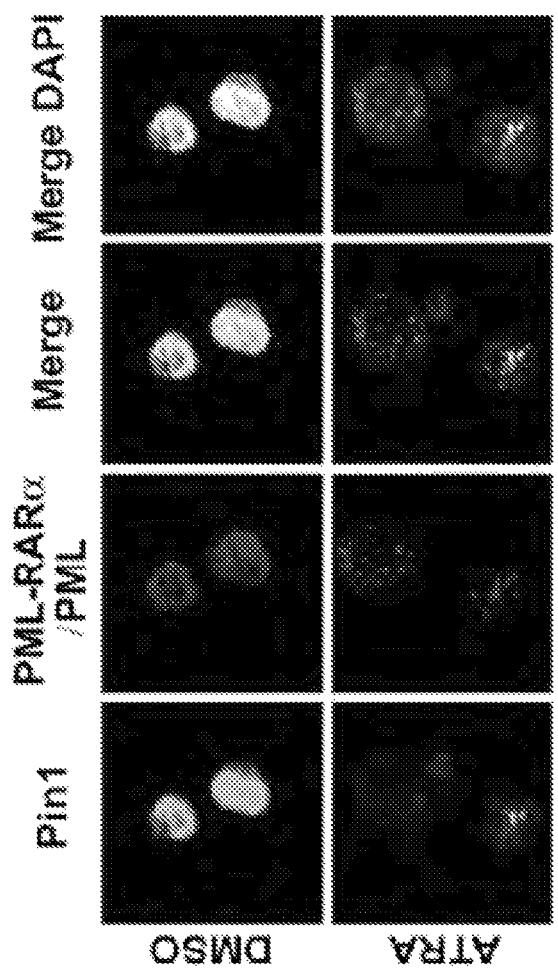

FIG. 33 is a series of micrographs showing that APL NB4 cells that received 10 μM of ATRA for 96 hours exhibited reduced Pin1 and PML-RARα expression.

Figure 34:
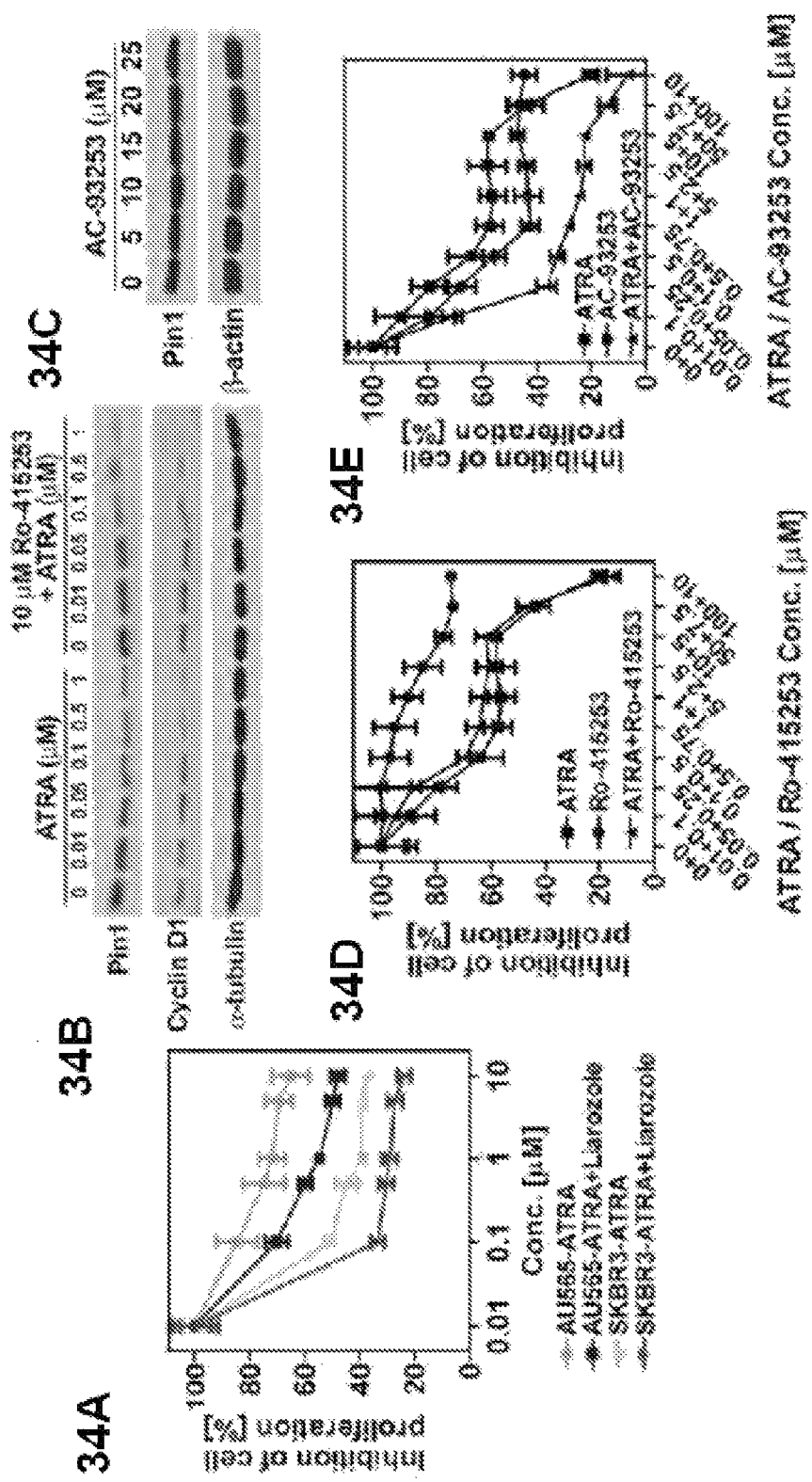

FIG. 34A is a plot showing the enhancement of inhibition of cell proliferation for ATRA-irresponsive AU565 or ATRA-responsive SKBR3 cells treated with ATRA and the cytochrome p450 inhibitor liarozole.

FIGS. 34B, 34C, 34D, and 34E are immunoblots and corresponding plots of inhibition of cell proliferation demonstrating that the pan-RARs inhibitor cannot reverse ATRA-incuded Pin1 or cyclin D1 dgradation in T47D cells (34B) and is unable to rescue ATRA-mediated anti-proliferative effects (34D) while the pan-RARs activator cannot trigger Pin1 degradation in T47D cells (34C), and co-treatment with ATRA and the pan-RARs activator can have an additive effect on cell growth in T47D cells.

FIG. 35 depicts patient information on triple negative breast cancer human samples.

Figure 36:
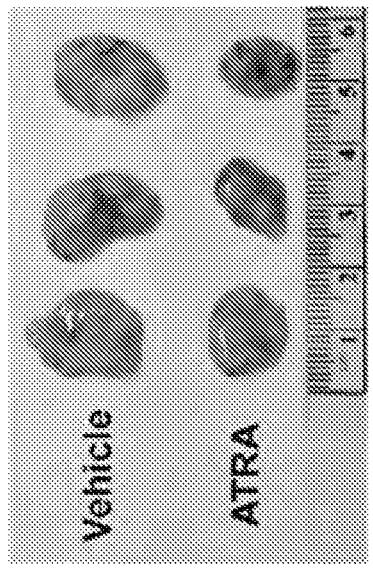

FIG. 36 shows tumor sizes of MDA-MB-231-based xenograft tumors treated with placebo or ATRA intraperitoneally, demonstrating that ATRA has moderate antitumor activity.

Figure 37:
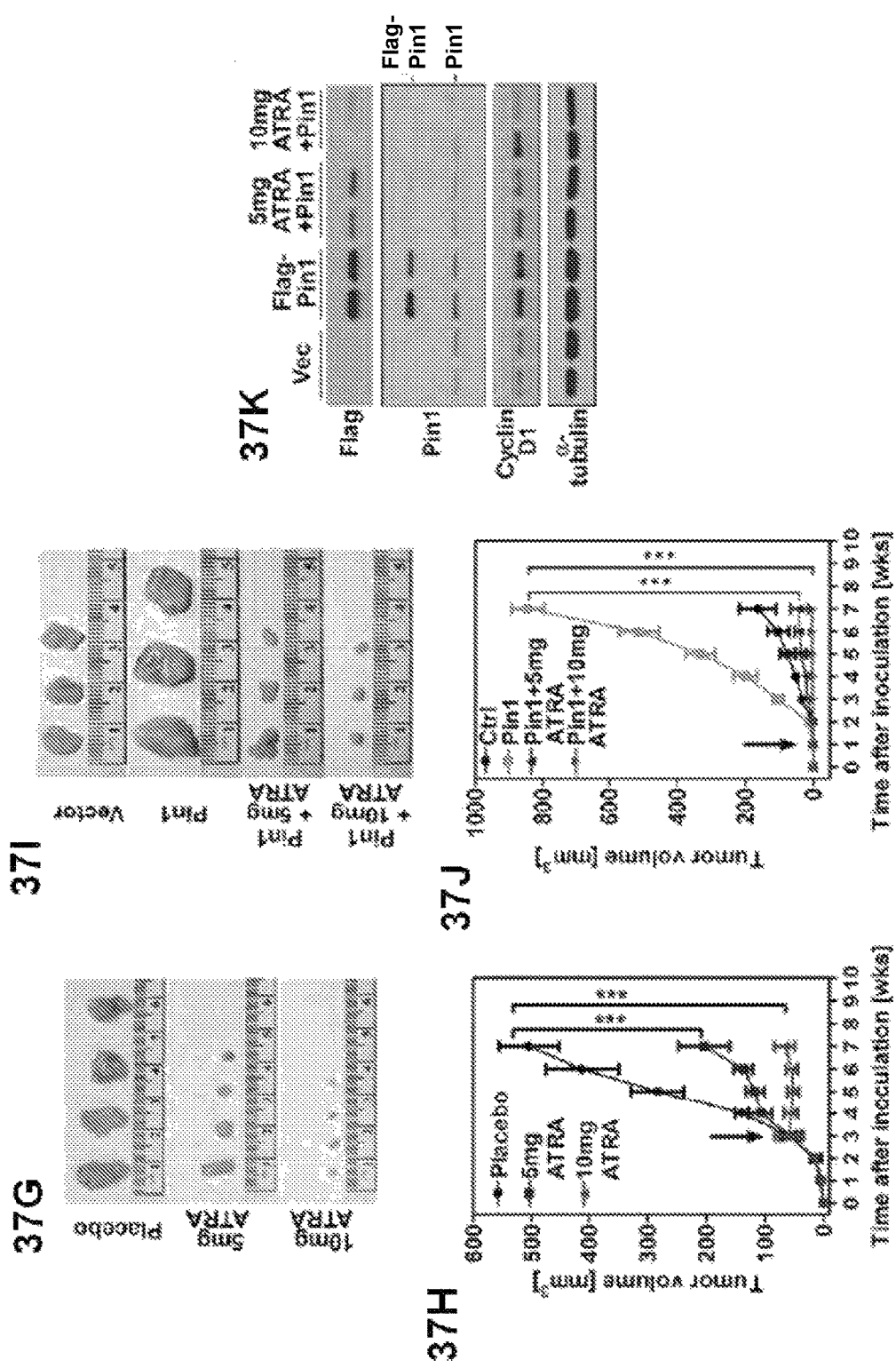

FIGS. 37A, 37B, and 37C show the results on tumor size, Pin1 levels, and cyclin-D1 levels of flank-inoculating female nude mice with $2 \times 10^6$ MDA-MB-231 cells and, 1 week later, implanting them with 5 or 10 mg 21 day ATRA-releasing or placebo pellets. Tumor sizes were measured weekly and mice were sacrificed after 7 weeks to collect tumor tissues (37A). Curves of tumor volume are plotted over time in FIG. 37B. Pin1 and cyclin D1 in xenograft tumors were assayed by IB (37C).

FIGS. 37D, 37E, and 37F show the results on tumor size, Pin1 levels, and cyclin-D1 levels of flank-inoculating female nude mice with $2 \times 10^6$ MDA-MB-468 cells and, 1 week later, implanting them with 5 or 10 mg 21 day ATRA-releasing or placebo pellets. Tumor sizes were measured weekly and mice were sacrificed after 7 weeks to collect tumor tissues (37D). Curves of tumor volume are plotted over time in FIG. 37E. Pin1 and cyclin D1 in xenograft tumors were assayed by IB (37F).

FIGS. 37G and 37H shows the results on tumor size of flank-inoculating female nude mice with $2 \times 10^6$ MDA-MB-231 cells and, 3 weeks later (arrow), implanted with 5 or 10 mg 21 day ATRA-releasing or placebo pellets. Tumor sizes were measured weekly and mice were sacrificed after 7 weeks to collect tumor tissues (37G). Curves of tumor volume are plotted over time in FIG. 37H.

FIGS. 37I, 37J, and 37K show the results on tumor size of inoculating MDA-MB-231 cells stably expressing Flag-Pin1 or control vector into nude mice, and 1 week later, treating with ATRA implants for 7 weeks before collecting tumors (37I). Quantitative curves of tumor volume are plotted in FIG. 37J. Exogenous and endogenous Pin1 along with cyclin D1 in xenograft tumors were assayed by IB (37K).

Figure 38:
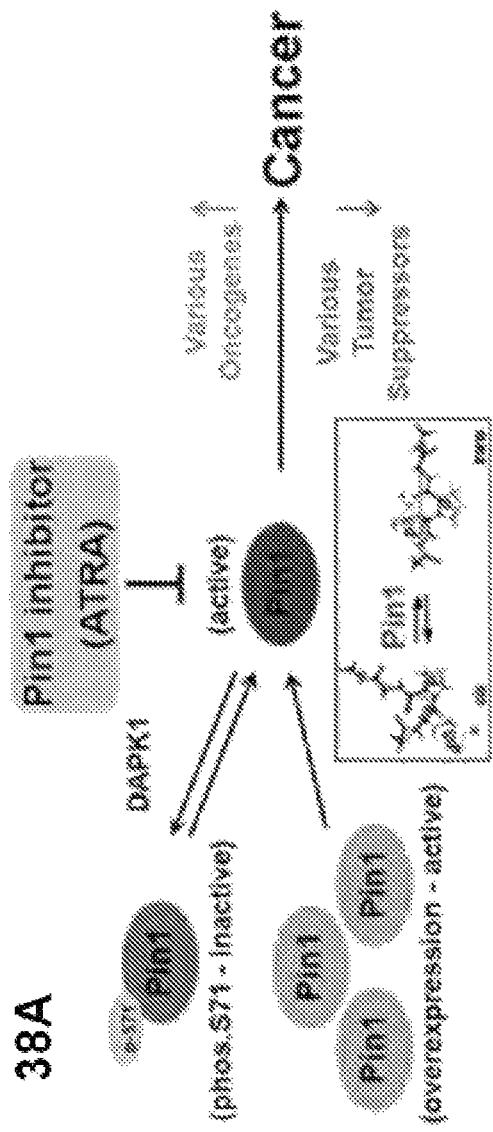
Figure 38:
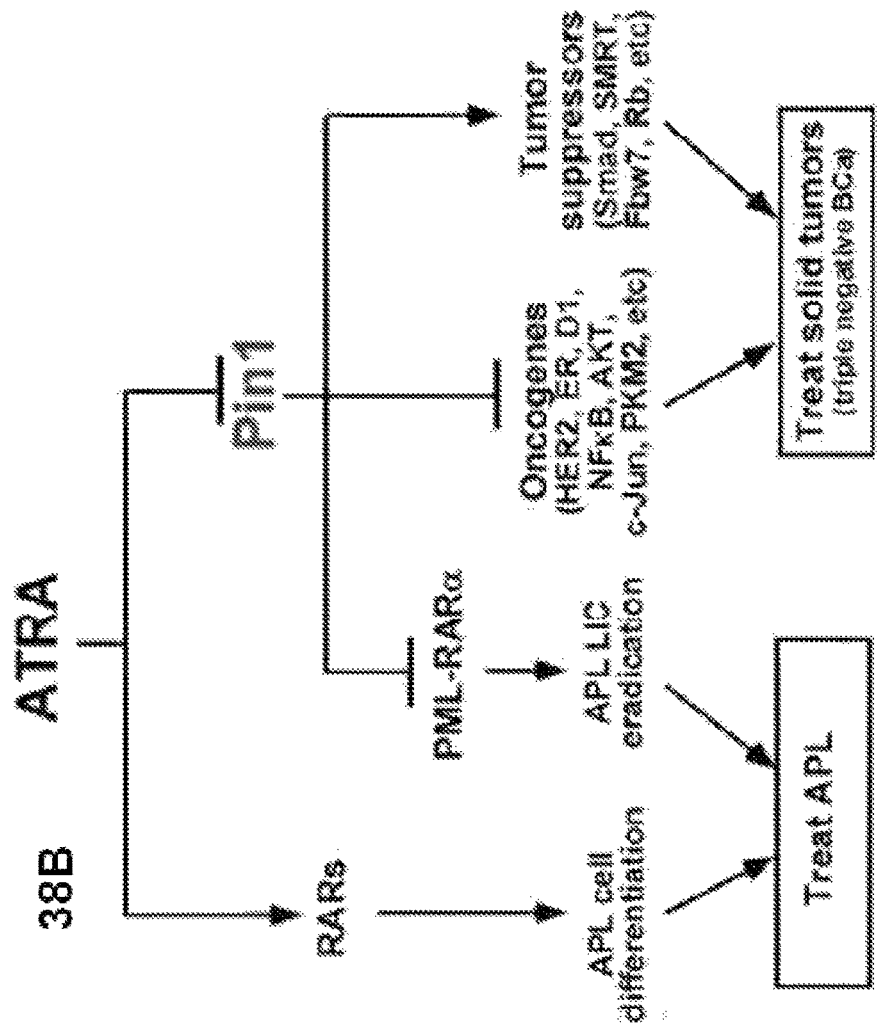

FIGS. 38A and 38B show schematics depicting the activity of Pin1. In cancers, Pin1 becomes activated due to loss of the inhibitory kinase and tumor suppressor DAPK1 and/or overexpression, thereby activating many oncogenes and inactivating many tumor suppressors to promote tumorigenesis by catalyzing cis-trans isomerization of specific pSer/Thr-Pro motifs. ATRA directly binds, inhibits and ultimately degrades the active Pin1 selectively in cancer cells to exert potent anticancer activity against both APL and triple negative breast cancer by blocking multiple cancer-driving pathways simultaneously.

Figure 39:
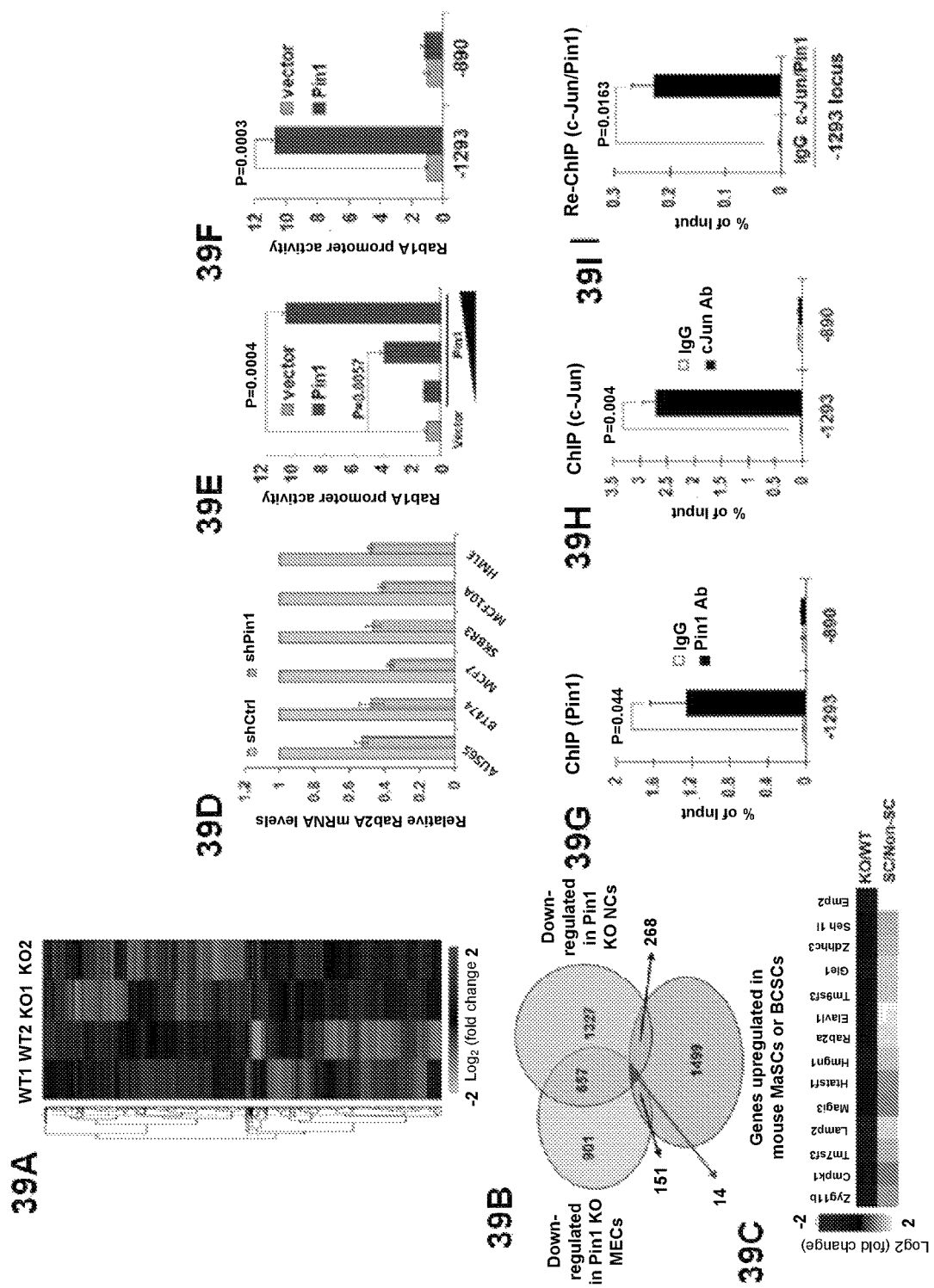
Figure 39:
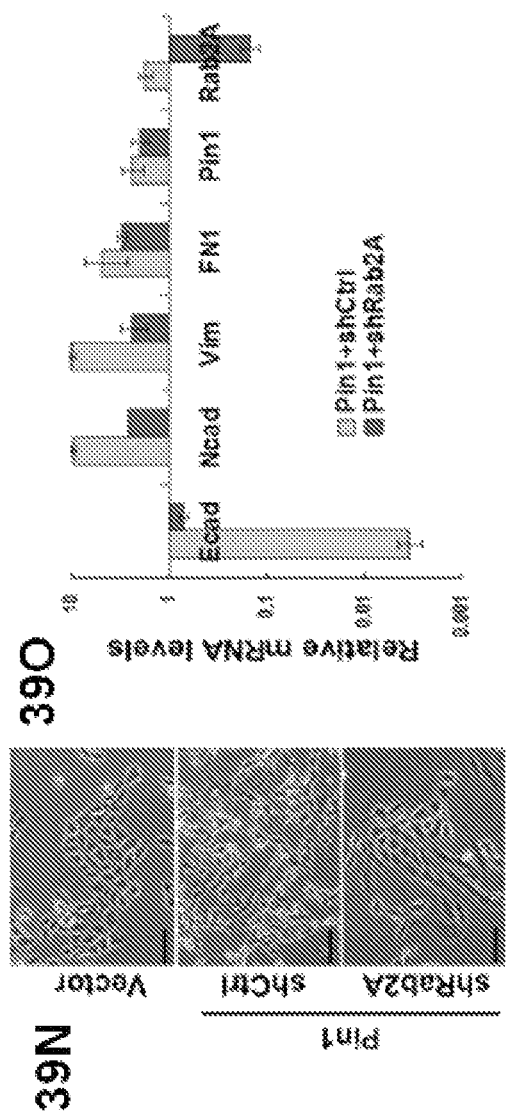

FIG. 39A shows a hierarchical cluster of the microarray data of Lin—population of mammary epithelial cells in two pairs of WT and Pin1 KO littermates.

FIG. 39B show that genomic profiling identified 14 potential target genes that were downregulated in Pin1 KO MECs and neuron cells (NCs), but upregulated in mouse MaSCs or BCSCs. 657 downregulated genes identified from MECs and NCs in Pin1 KO mice were compared with 1499 upregulated genes in mouse MaSCs or BCSCs.

FIG. 39C is a heatmap depicting the fold changes of 14 candidate genes, which were downregulated in Pin1 KO cells (presented by KO/WT ratio), but upregulated in either mouse MaSCs or BCSCs (presented by SC/Non-SC ratio).

FIG. 39D is a graph showing real-time PCR results demonstrating that Pin1 KD reduced Rab2A mRNA in human breast cancer lines.

FIGS. 39E and 39F are plots of a Rab2A promoter luciferase reporter assay showing that Pin1 activated the Rab2A promoter in a dose-dependent manner using a long fragment that contains an AP-1 binding site (−1293) (39E), but not a shorter promoter fragment (−890) (39F).

FIGS. 39G, 39H, 39I, and 39J demonstrate that both Pin1 and c-Jun bound to the Rab2A promoter as shown by ChIP and Re-ChIP analyses. Pin1 antibody (39G) or c-Jun antibody (39H) showed appreciable binding to the −1293 locus. Re-ChIP analysis using c-Jun antibody followed by Pin1 antibody demonstrated that both proteins were present in the same complex on the −1293 locus (39I). Real-time PCR data were calibrated to IgG control and normalized with sample inputs of chromatin harvested prior to immunoprecipitation (39J). Rab2A was knocked down in vector control and Pin1-overexpressing HMLE cells, as confirmed by immunoblot.

FIGS. 39K and 39L show that Rab2A KD in HMLE cells reduced the CD24−CD44+ population and suppressed the ability of Pin1 overexpression to increase the CD24−CD44+ population.

FIG. 39M includes plots demonstrating that Rab2A KD in HMLE cells reduced mammosphere-forming activity and impaired the ability of Pin1 overexpression to increase mammosphere-forming activity.

FIGS. 39N and 39O demonstrate Rab2A KD impaired the ability of Pin1 overexpression to induce the EMT in HMLE cells, as shown by cell morphology (39N) or upregulation of E-cadherin and downregulation of N-cadherin, fibronectin, and vimentin, determined by real-time RT-PCR (39O). GAPDH expression was used to normalize the variability in template loading. (Scale bar, 100 □m)

Figure 40:
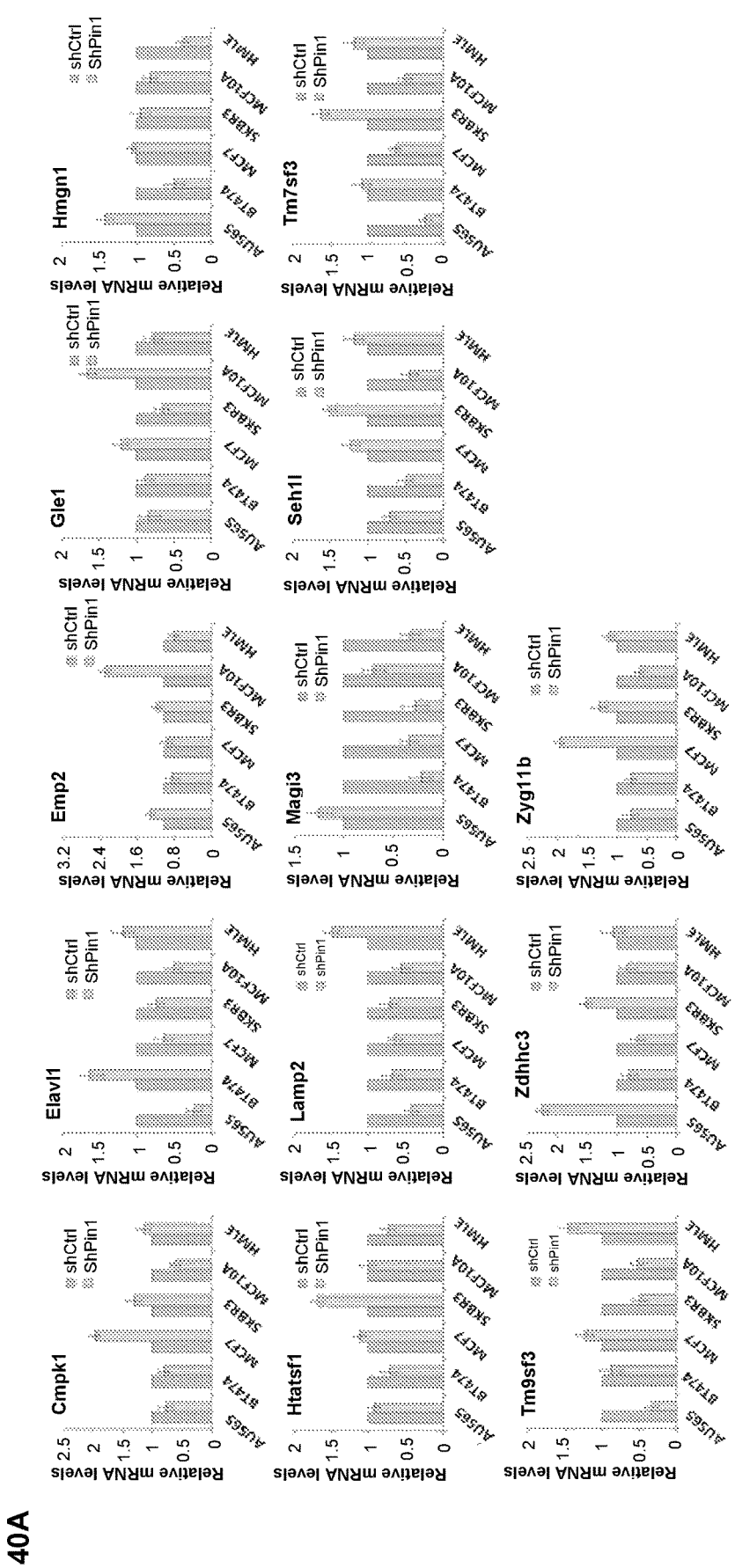
Figure 40:
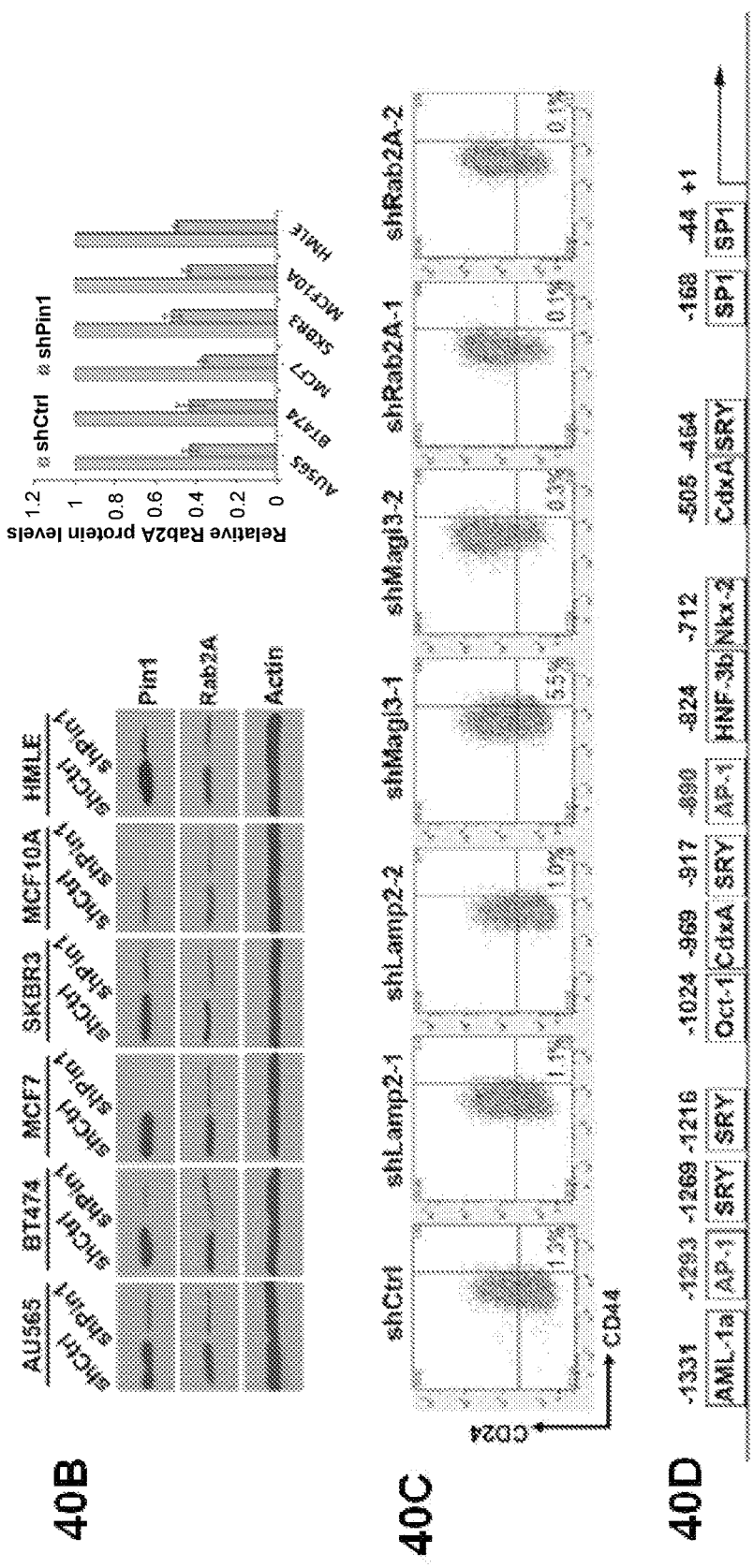

FIG. 40A shows real-time PCR results of mRNA expression of 13 candidate genes in six Pin1 KD breast cell lines.

FIG. 40B includes a series of blots and a corresponding plot demonstrating that Pin1 KD reduced Rab2A expression in six human breast cancer cells at the protein level.

FIG. 40C shows that Lamp2, Magi3, and Rab2A expressions were knocked down by two shRNAs in MCF10A cells. Only Rab2A, but not Lamp2 or Magi3 knockdown, consistently reduced the CD24−CD44+ population.

FIG. 40D is a schematic representation of Rab2A promoter with predicted transcription factor binding sites in TFsearch.

Figure 41:
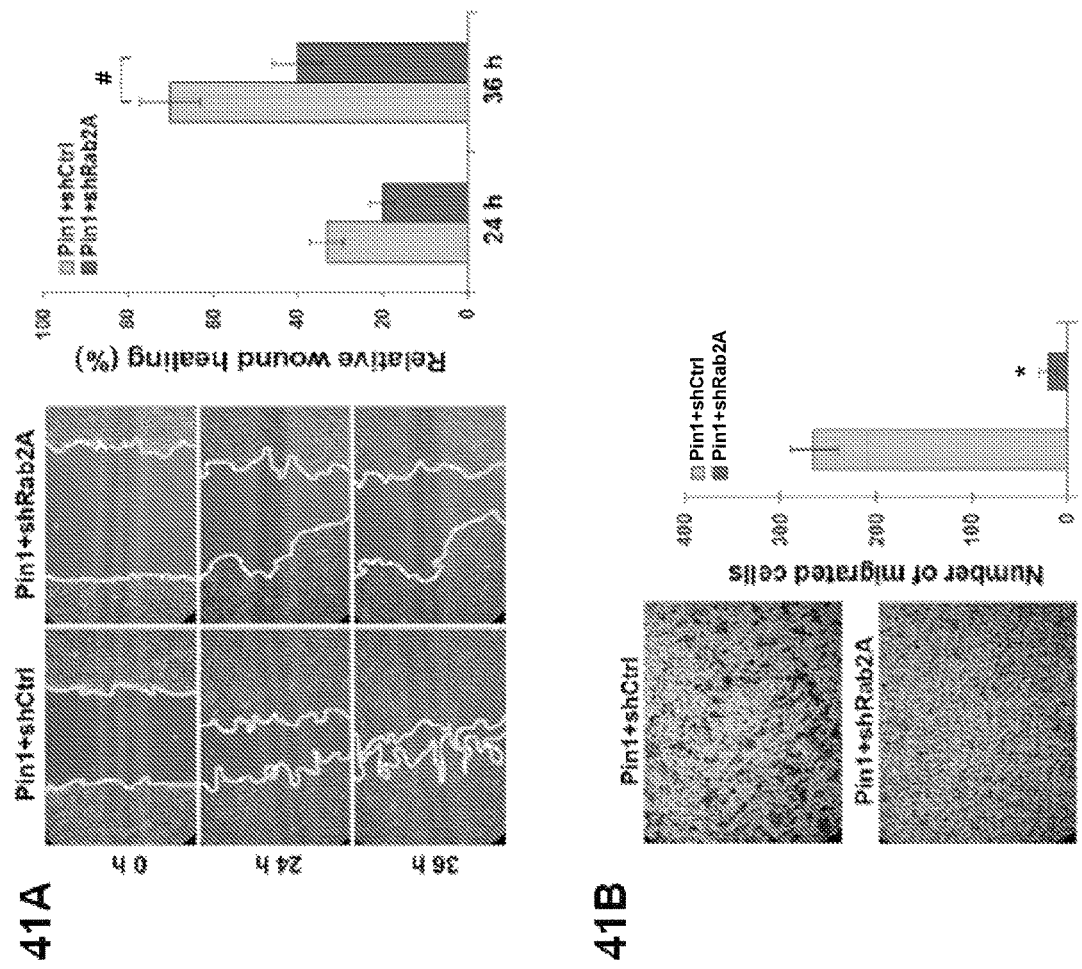

FIG. 41A shows that Rab2A knockdown in Pin1-overexpressing HMLE cells impaired would healing capability.

FIG. 41B shows that Rab2 knockdown impaired the ability of Pin1 overexpression to increase cell migration, as measured by the transwell assay.

Figure 42:
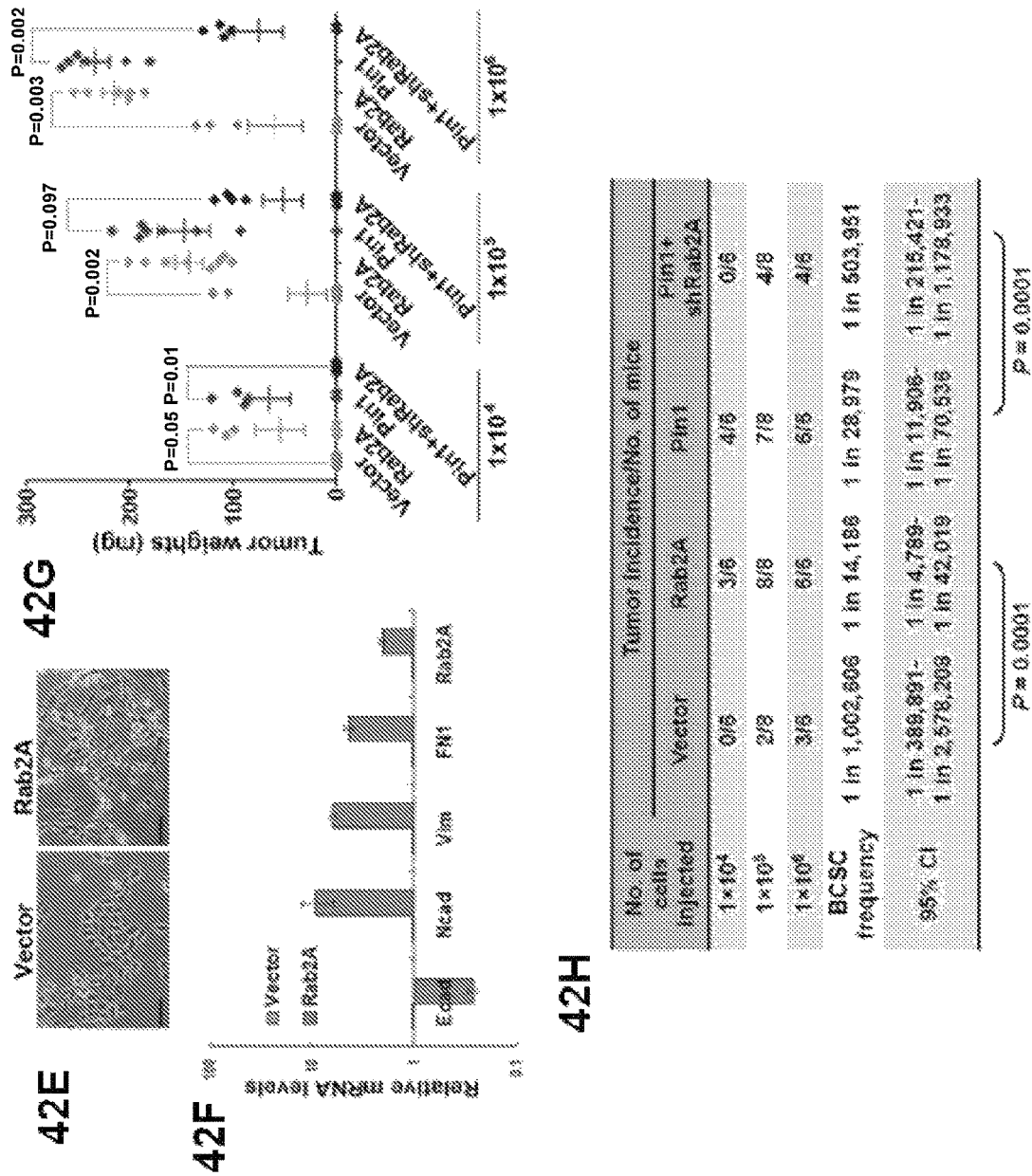
Figure 42:
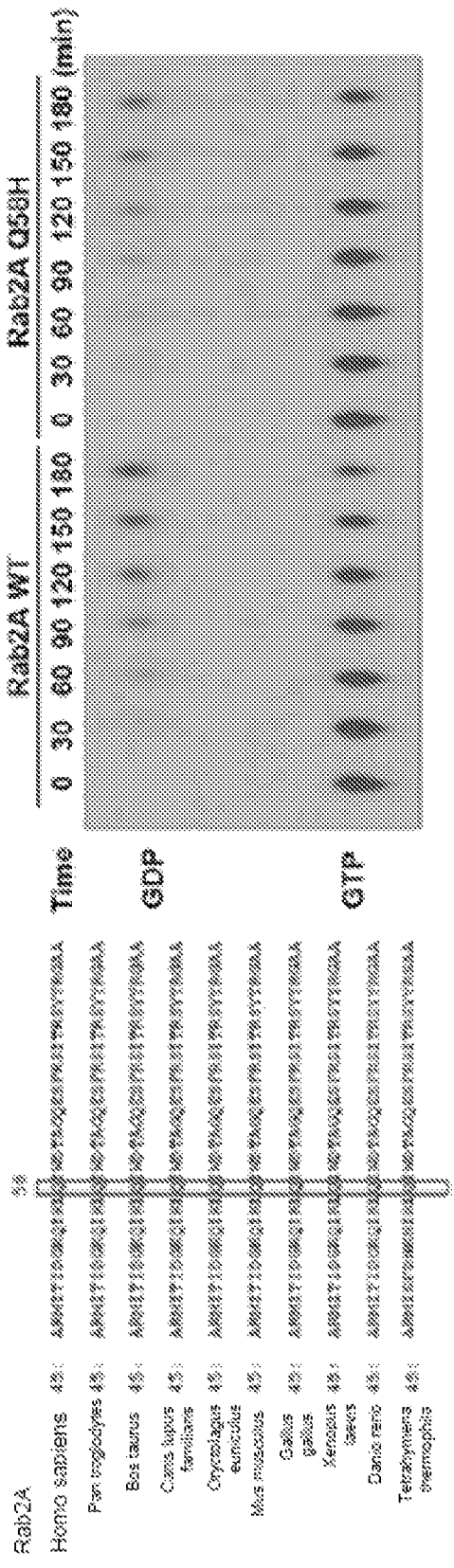
Figure 42:
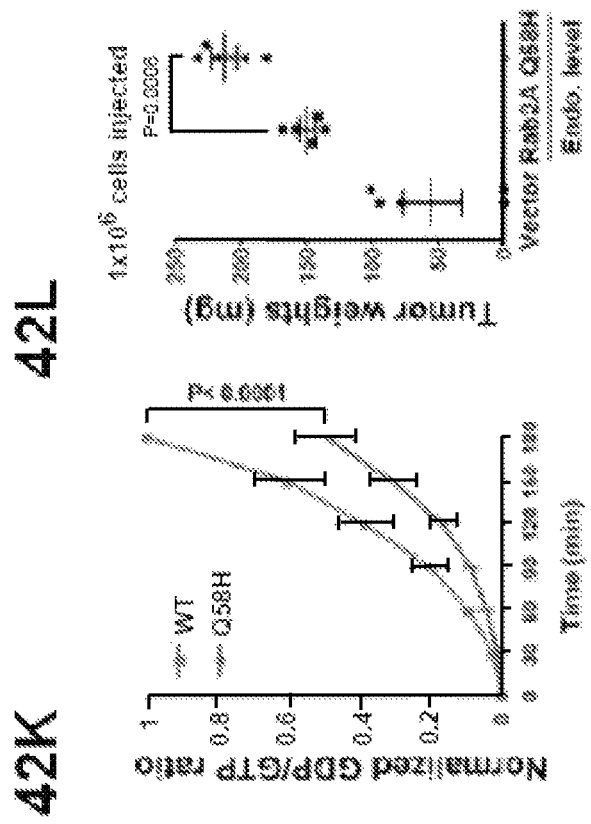

FIG. 42A shows Rab2A gene amplification in a wide range of human cancers reported in cBioPortal for Cancer Genomics, with the highest amplification frequency of ~9.5% (72 out of 760) in invasive breast carcinoma patients.

FIG. 42B is an immunoblot showing the stable overexpression of Rab2A in Pin1 KD or control HMLE cells using retrovirus-mediated gene transfer.

FIG. 42C shows the results of an FACS analysis and demonstrates the overexpression of Rab2A in HMLE cells potently induced the CD24$^-$CD44$^+$ population and rescued the phenotypes inhibited by Pin1 KD.

FIG. 42D shows that overexpression of Rab2A increased the mammosphere formation in shCtrl HMLE cells and rescued the phenotypes inhibited by Pin1 KD.

FIGS. 42E and 42F show that overexpression of Rab2A potently induced the EMT in HMLE cells, as assayed by cell morphology (42E) and real-time RT-PCR of the marker expressions (42F).

FIGS. 42G and 42H demonstrate that Rab2A overexpression increased tumorigenicity of BCSCs, while its KD impaired the ability of Pin1 overexpression to increase tumorigenicity of BCSCs, as measured by limiting dilution tumor-initiation assay in nude mice. HMLE-Ras cells infected with indicated lentivirus were injected into subcutaneous sites of nude mice at a series of limiting dilutions. Two months later, mice were sacrificed and evaluated for tumor weight (42G) and tumor incidence (42H).

FIG. 42I shows that Q58 in Rab2A is evolutionarily conserved across species.

FIGS. 42J and 42K demonstrate that the Q58H mutant displayed decreased GTP hydrolysis activity, relative to the WT Rab2A protein in the in vitro GTPase assay, as monitored by $\alpha$-$^{32}$P-labeled GTP hydrolysis (42J), and quantified by densitometry of three independent experiments (42K).

FIG. 42L is a plot showing that HMLE-Ras cells infected with Rab2A Q58H were more potent in forming tumors than those infected with WT Rab2A when overexpressed at endogenous levels. $1 \times 10^6$ cells were injected into subcutaneous sites of nude mice. Two months later, mice were sacrificed and evaluated for tumor weights.

Figure 43:
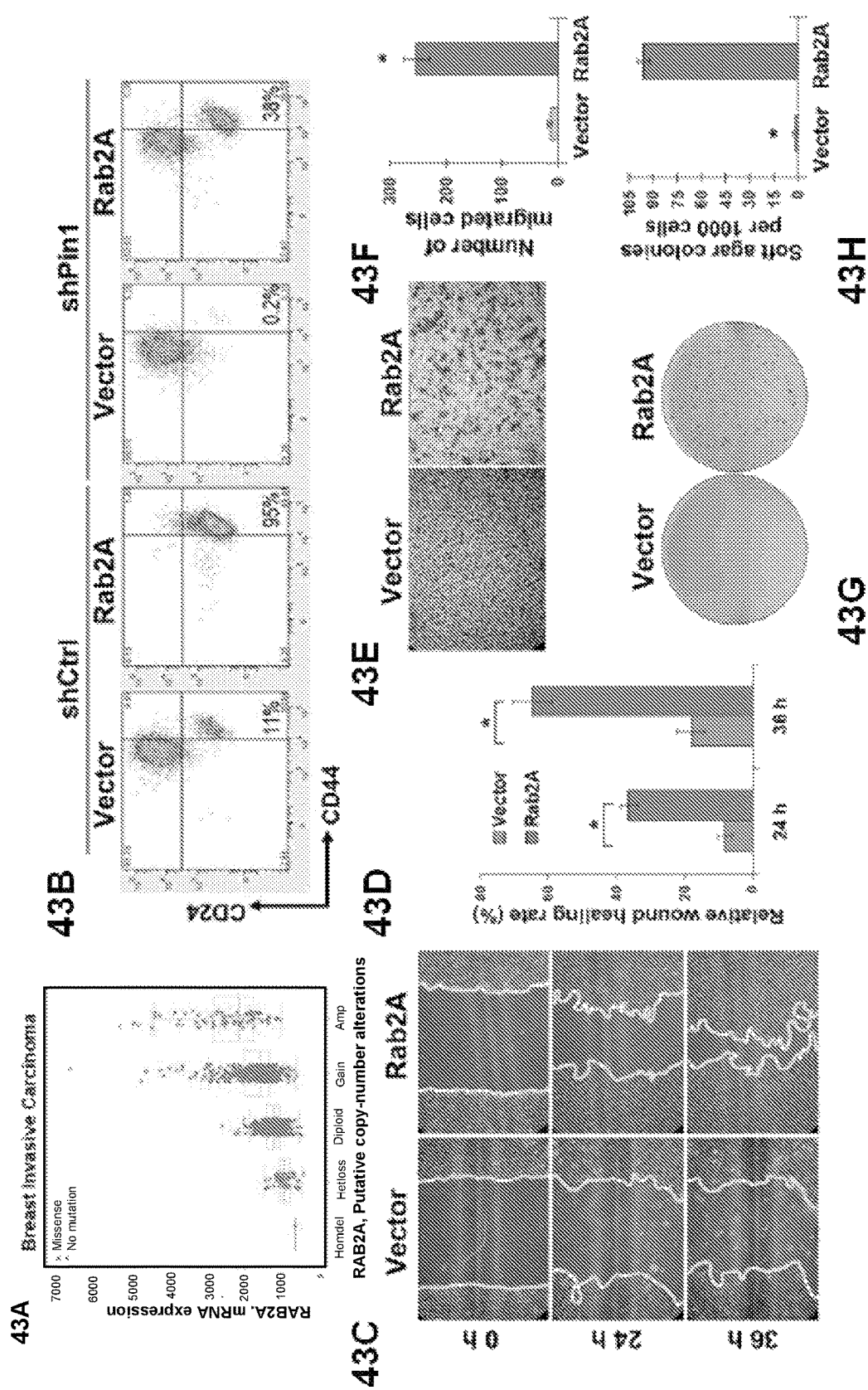
Figure 43:
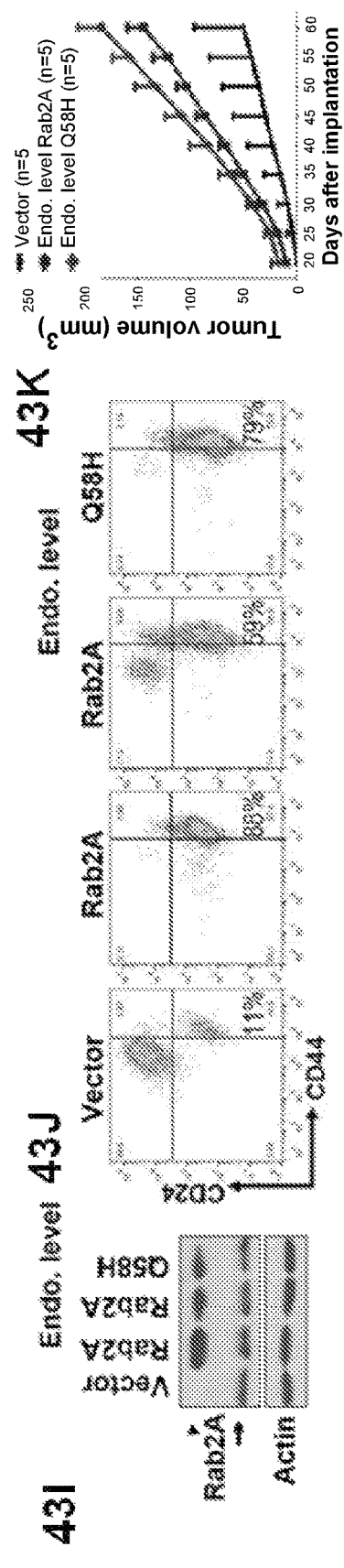

FIG. 43A is a plot showing that increased Rab2A copy number is associated with higher mRNA levels in the breast cancer (TCGA, Provisional) (P=1.56E-84).

FIG. 43B demonstrates that Rab2A overexpression in HMLEs increased the CD24−CD44+ population and rescued the phenotypes inhibited by Pin1 KD.

FIGS. 43C, 43D, 43E, and 43F demonstrate that Rab2A overexpression enhances cell migration, as measured by wound healing assay (43C and 43D) and transwell migration assay (43E and 43F).

FIGS. 43G and 43H show that Rab2A overexpression potently increased cology formation in soft agar.

FIG. 43I is a plot showing that lentivirus mediated overexpression of Flag-Rab2A and its Q58H mutant at levels similar to or three times over the endogenous level in HMLEs. The arrowhead indicates exogenous Flag-Rab2A, while the arrow indicates endogenous Rab2A.

FIG. 43J shows that overexpressed Rab2A Q58H mutant in HMLE cells at the endogenous level increased the CD24−CD44+ population as potently as Rab2A overexpressed at three times over the endogenous level.

FIG. 43K shows that subcutaneous tumors in nude mice formed by HMLE cells infected with endogenous levels of Q58H mutant grew faster than those infected with WT Rab2A.

Figure 44:
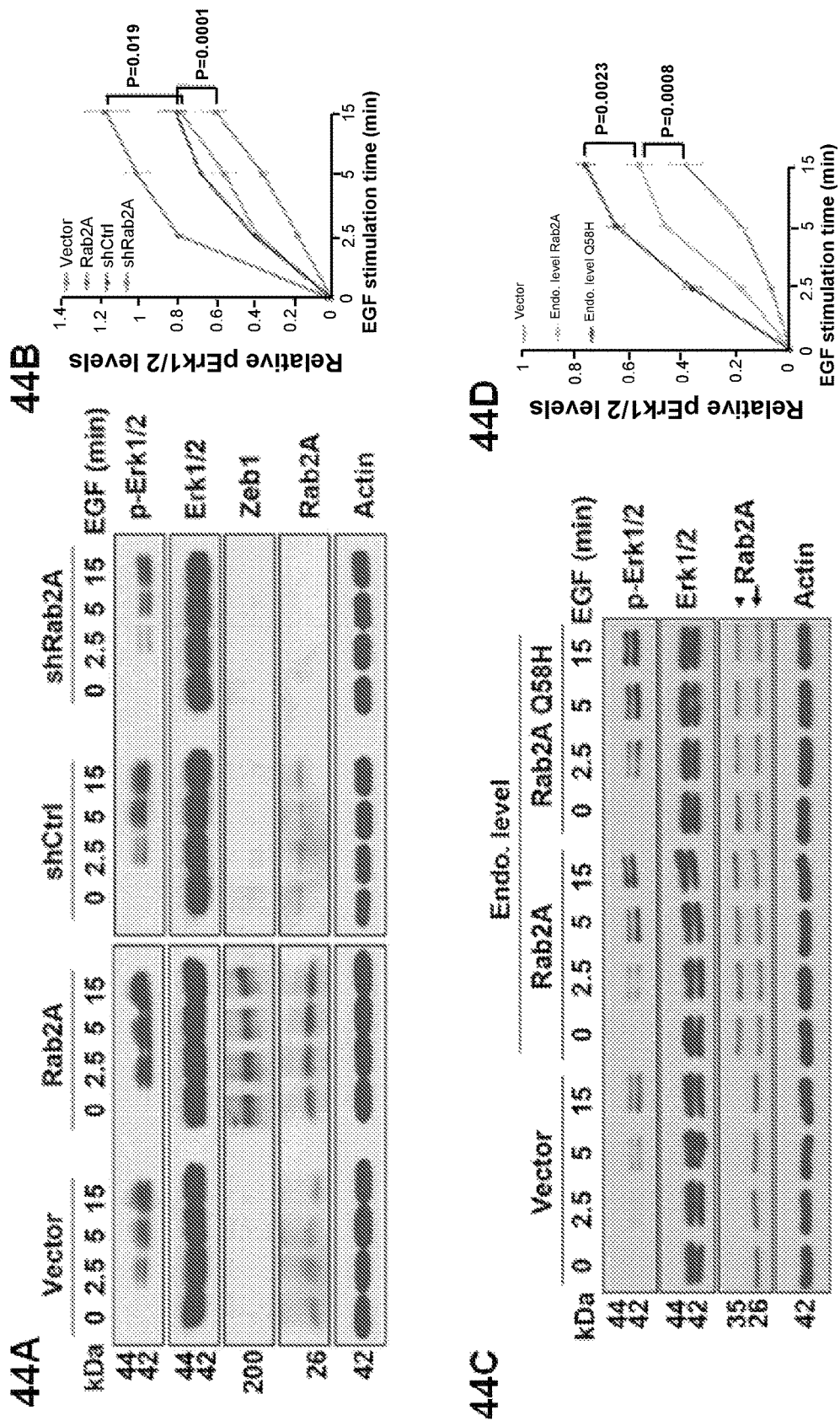
Figure 44:
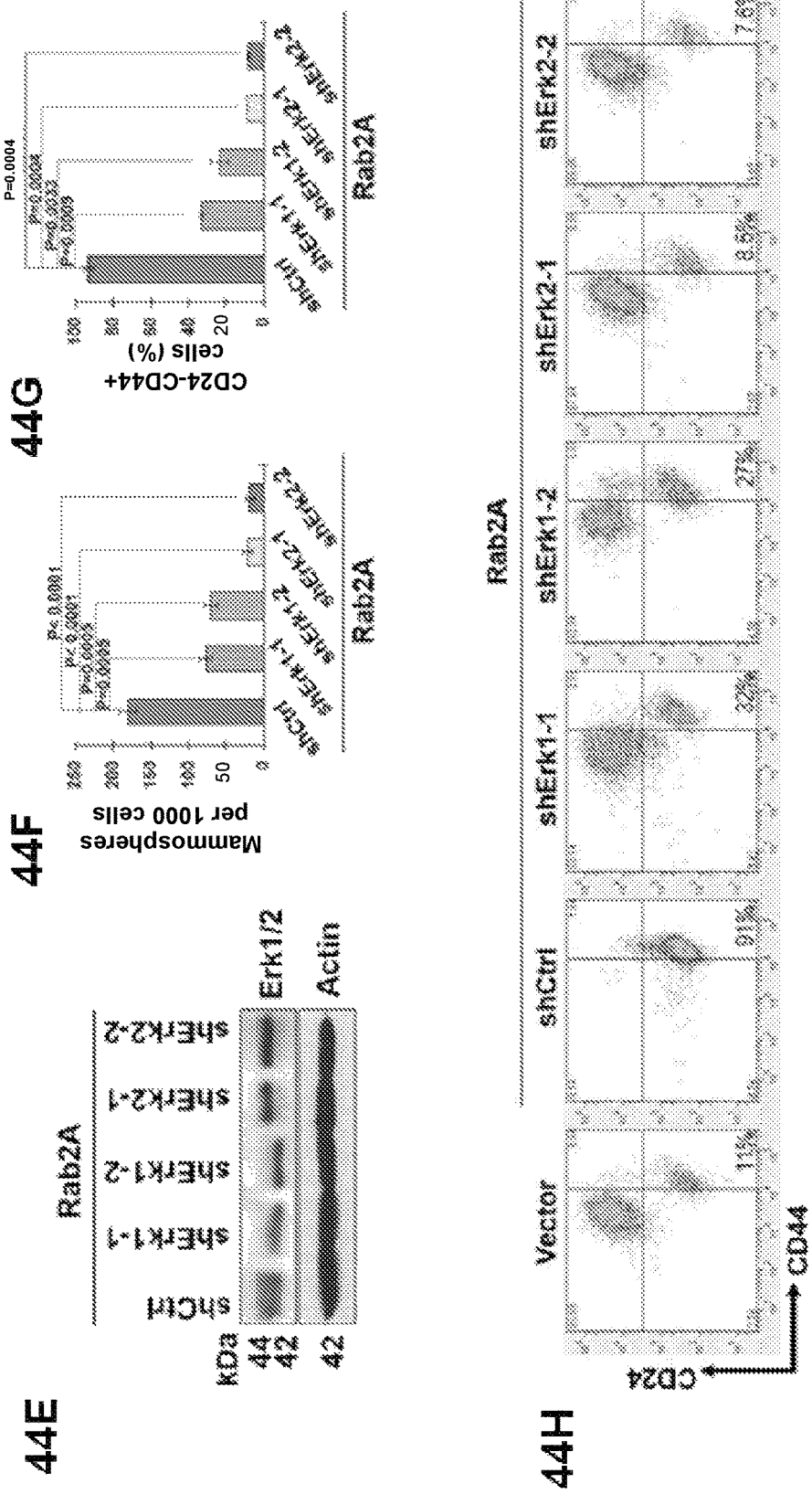

FIG. 44A is a series of immunoblots showing that Rab2A regulated Erk1/2 phosphorylation and downstream Zeb1 expression. HMLE cells stably expressing Rab2A or shRNA or control vectors were treated with EGF after serum starvation for the indicated time points to activate Erk1/2 and subsequently analyzed by immunoblot.

FIG. 44B is a plot showing P-Erk1/2 levels in FIG. 44A quantified with Actin, which was used as a loading control.

FIGS. 44C and 44D show immunoblots and a plot, respectively, demonstrating that Rab2A Q58H mutant activated Erk1/2 faster than WT Rab2A when overexpressed at the endogenous levels after EGF treatment for the indicated time points following serum starvation. The arrowhead indicates exogenous Flag-Rab2A, while the arrow indicates endogenous Rab2A. Relative p-Erk1/2 levels were quantified in 44D.

FIG. 44E is a Western blot showing that Erk1 or Erk2 was knocked down by two independent lentivirus-mediated shRNAs in Rab2A-overexpressing cells.

FIG. 44F shows that KD of Erk1/2, especially Erk2, prevented Rab2A from increasing the mammosphere forming capability.

FIGS. 44G and 44H show that KD of Erk1/2, especially Erk2, prevented Rab2A from increasing the CD24$^-$CD44$^+$ population.

Figure 45:
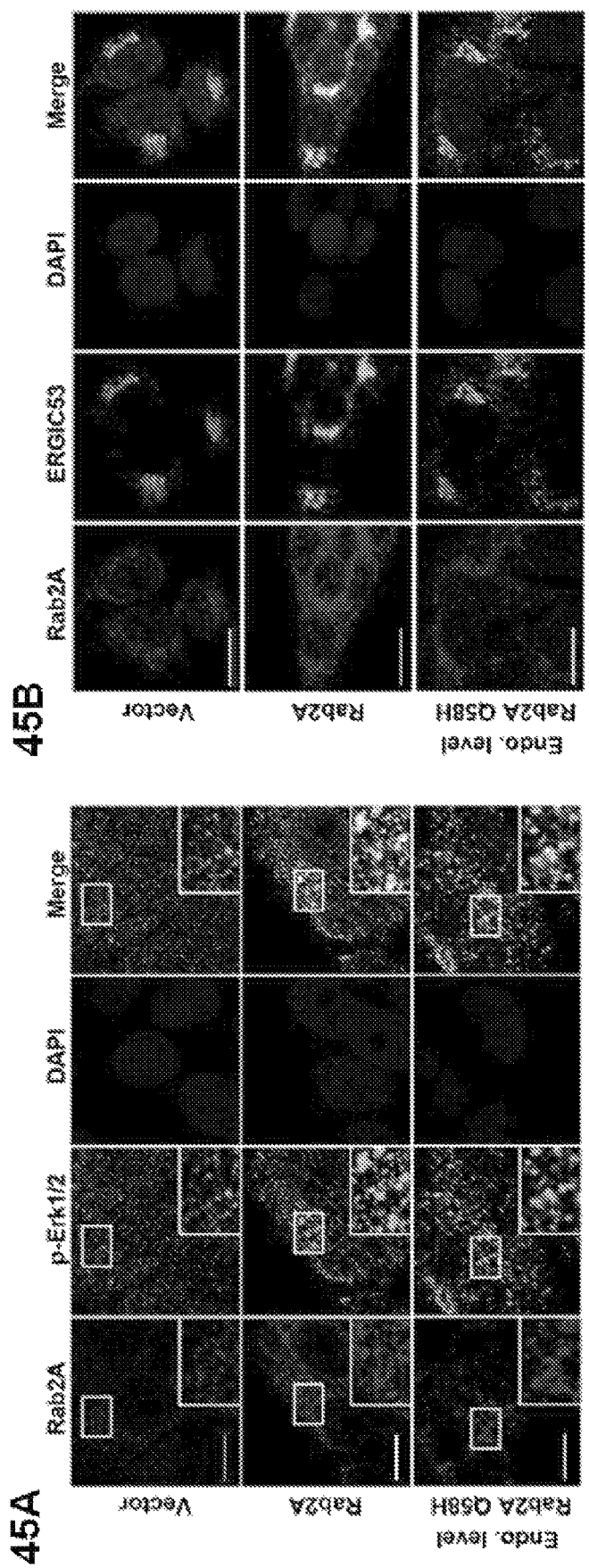

FIG. 45A includes images showing that overexpressed Rab2A and its Q58H mutant co-localized with p-Erk1/2. Stable HMLE cells were starved in serum-free medium for 16 h and then treated with 10 ng/ml EGF for 5 minutes, before staining for Rab2A and p-Erk1/2. (Scale bar, 10 µm)

FIG. 45B includes images showing that wild-type Rab2A and its Q58H mutant co-localized with ERGIC53, an ER-Golgi intermediate compartment (ERGIC) marker. (Scale bar, 20 µm) FIG. 45C is a Western blot showing reciprocal co-IP of endogenous Rab2A with Erk1/2. Lysates of HMLE cells were immunoprecipitated with Rab2A or Erk1/2 antibodies, followed by western blot for Rab2A and Erk1/2, respectively.

FIG. 45D is a blot showing Rab2A immunoprecipitated with total Erk1/2 and p-Erk1/2 in HEK293 cells co-transfected with Flag-Rab2A and constitutive activated MEK1 (AcMEK1).

FIG. 45E shows the consensus Erk docking motifs found in Rab2A and several other Erk binding partners. Conserved residues in Rab2A were mutated as indicated. + and φ represent basic and hydrophobic amino acids, respectively. X represents any amino acids.

FIG. 45F demonstrates that mutations in the Erk docking motif in Rab2A impaired its binding to Erk1/2. Endogenous Erk1/2 was pulled down by wild-type GST-Rab2A fusion protein. While Mut1 or mut2 reduced binding with Erk markedly, mutating both sequences completely abolished the binding.

FIG. 45G shows that Rab2A and MKP3 competed to bind Erk1/2. Lysates of 293T cells transfected with decreasing doses of myc-MKP3 and a constant dose of Flag-Rab2A were immunoprecipitated with M2 (Flag) antibody, followed by western blot for Erk1/2 and Flag-Rab2A.

FIG. 45H shows that Rab2A competed with MKP3 and kept Erk1/2 in the phosphorylated status. 293T cells were transfected to express epitope-tagged Rab2A, MKP3 as well as a constitutively active MEK1 mutant, which induced Erk1/2 phosphorylation in serum-starved cells, which was largely reversed by Myc-MKP3 expression, whereas Flag-Rab2A expression dose-dependently restored Erk1/2 phosphorylation.

Figure 46:
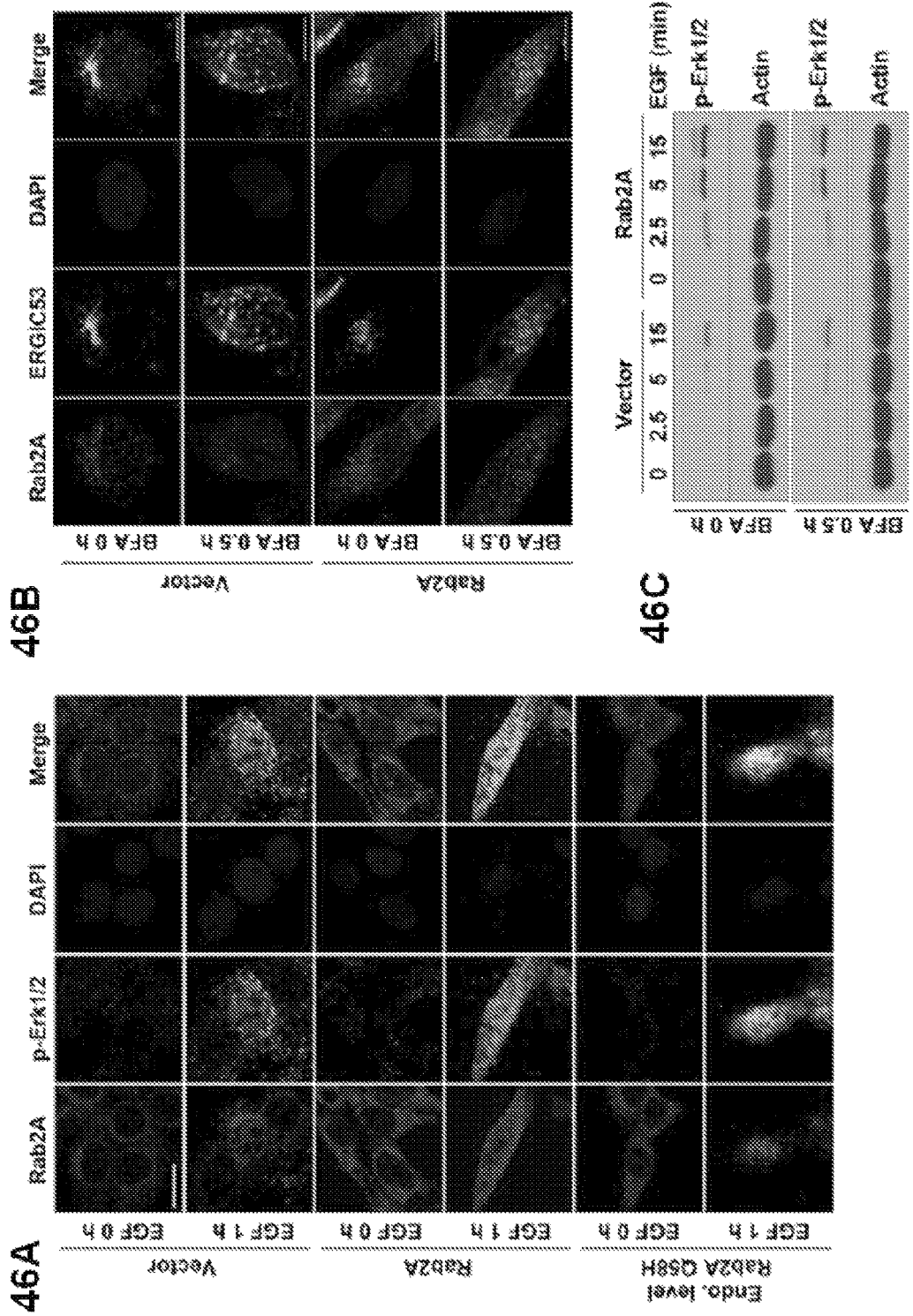

FIG. 46A is a series of images showing that P-Erk1/2 co-localized with Rab2A overexpressed at three times of the endogenous level and Q58H mutant overexpressed at the endogenous level after EGF stimulation.

FIG. 46B shows that treatment of 10 µg/ml BFA on vector control or Rab2A-overexpressing HMLEs for 0.5 hours destroyed the ERGIC structure, as measured by ERGIC53 staining.

FIG. 46C is a series of blots indicating that BFA treatment, which blocked retrograde transportation, did not affect Erk1/2 activation in either vector control or RAB2A-overexpressing HMLEs. (Scale bars, 10 µm)

Figure 47:
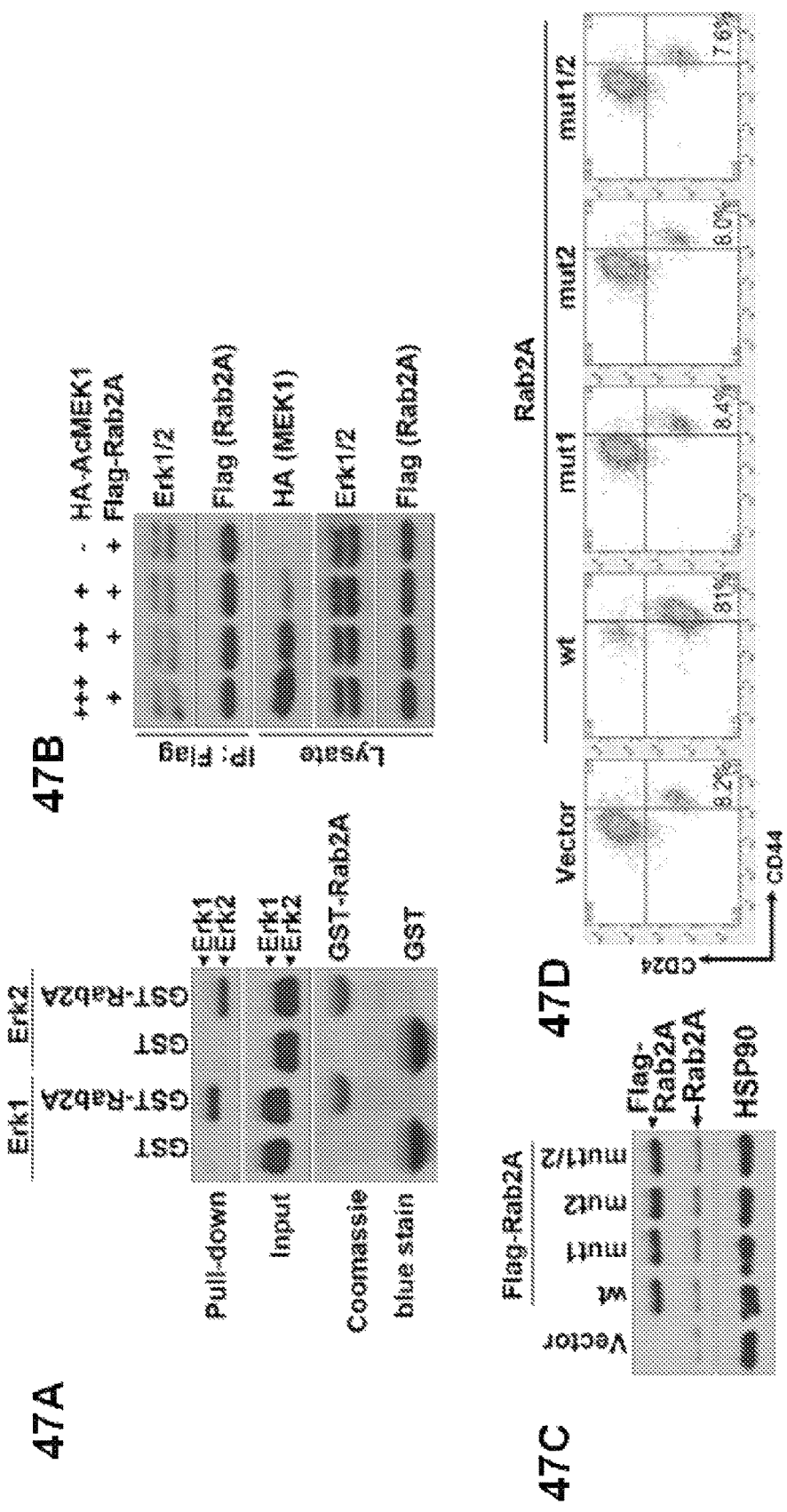

FIG. 47A shows that recombinant Erk1 or Erk2 interacted with GST-Rab2A directly.

FIG. 47B shows that Rab2A did not compete with MEK1 to bind Erk1/2. Lystates of 293T cells transfected with decreasing doses of HA-AcMKP3 and a constant dose of Flag-Rab2A were immunoprecipitated with M2 (Flag) antibody).

FIGS. 47C and 47D show that overexpression of Rab2A mutants with impaired binding to Erk failed to increase the abundance of CD24-CD44+ cells.

FIGS. 47E, 47F, and 47G show that ectopic expression of Flag-Rab1A in HMLE cells, as shown by immunoblot (47E) did not affect mammosphere formation (47F) and the abundance of CD24–CD44+ cells (47G).

FIGS. 47H and 47I show that overexpressed Flag-Rab1A, which co-localized with ERGIC53 (47H) did not promote Erk1/2 activation or co-localize with p-Erk1/2.

Figure 48:
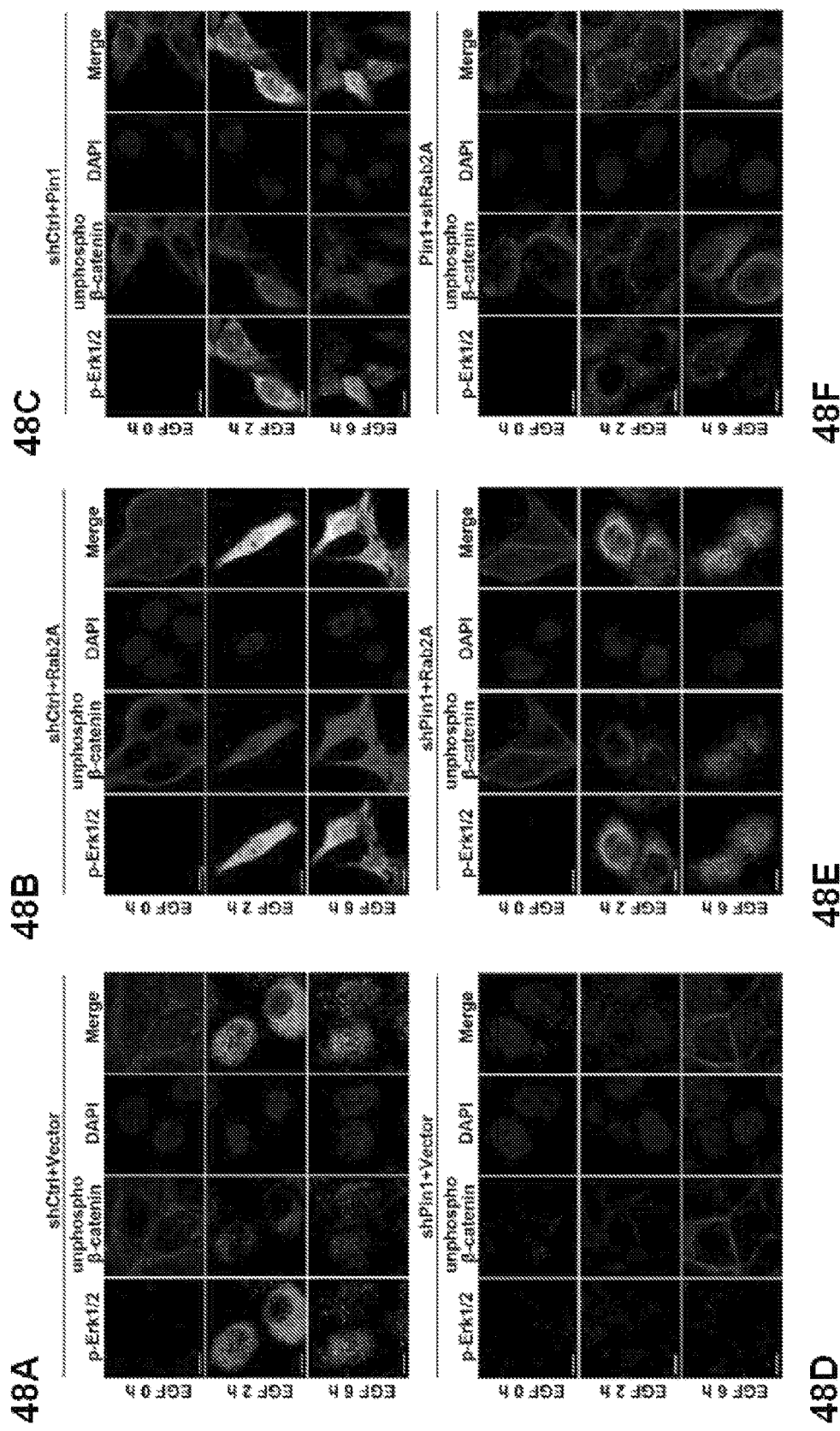
Figure 48:
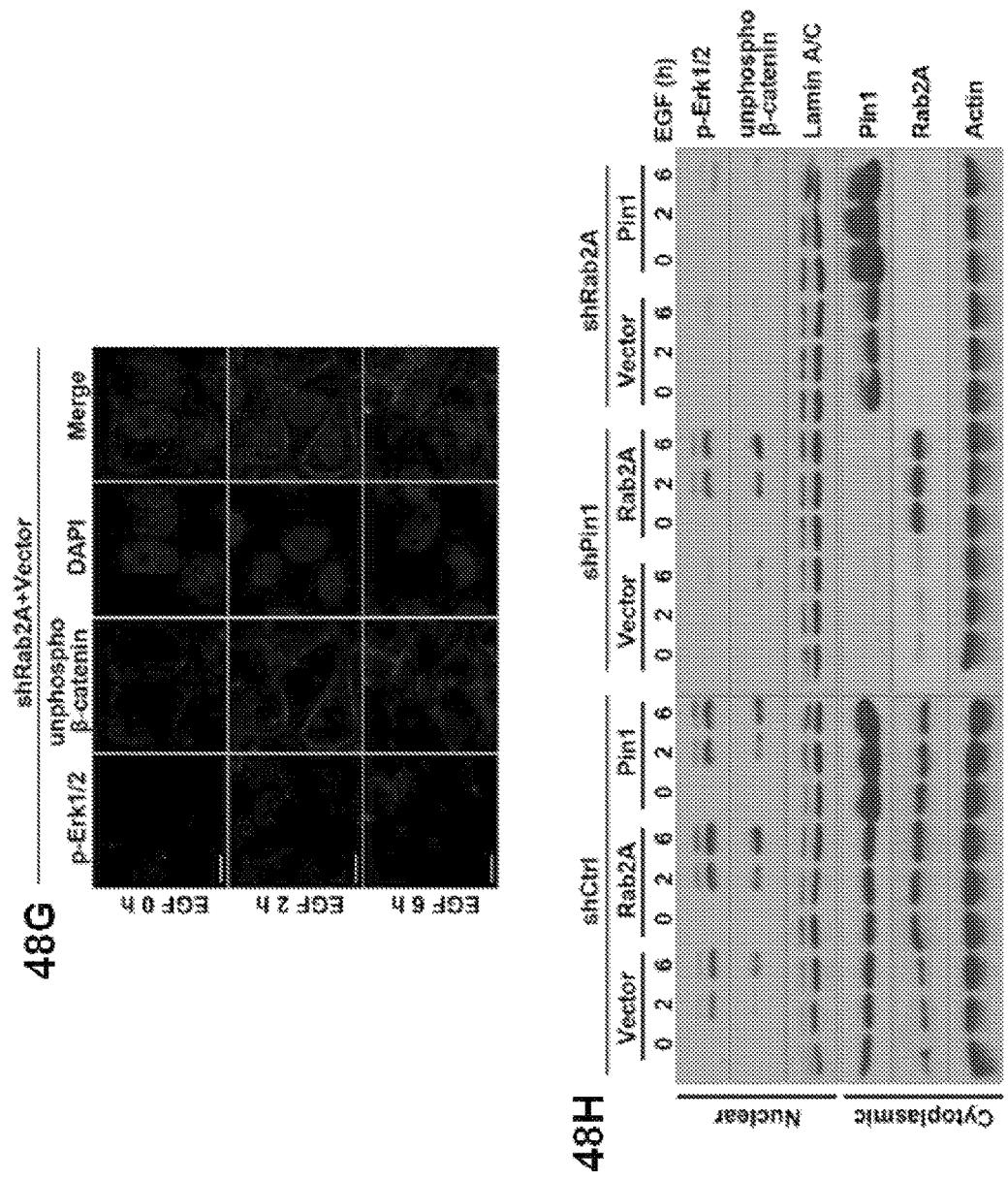

FIGS. 48A and 48B include images showing that Rab2A promoted the nuclear translocation of unphosphorylated β-catenin (active form). HMLE cells were serum starved and then stimulated by EGF for the indicated time points. In control cells, unphosphorylated β-catenin translocated from the cell membrane to the cytoplasm 2 hours after EGF stimulation, and to the nucleus 6 hours after stimulation (48A). In Rab2A overexpressing cells, β-catenin appeared in the nucleus as early as 2 hours after EGF stimulation (48B).

FIGS. 48C, 48D, and 48E show that Pin1 also promoted the nuclear translocation of unphosphorylated β-catenin and Rab2A overexpression in Pin1 KD cells rescued Erk1/2 activation and β-catenin translocation from the cell membrane to the nucleus.

FIGS. 48F, 48G include images showing that Rab2A KD in Pin1-overexpressing or vector control cells inhibited p-Erk1/2 activation and β-catenin nuclear translocation, while FIG. 48H shows that Rab2A promoted the nuclear accumulation of p-Erk1/2 and unphosphorylated β-catenin. Nuclear and total proteins were extracted after EGF stimulation following serum starvation at indicated time points, followed by immunoblotting analysis (48F). The graph showed quantified nuclear levels of unphosphorylated β-catenin relative to Lamin A/C (48G). (Scale bars, 10 µm)

Figure 49:
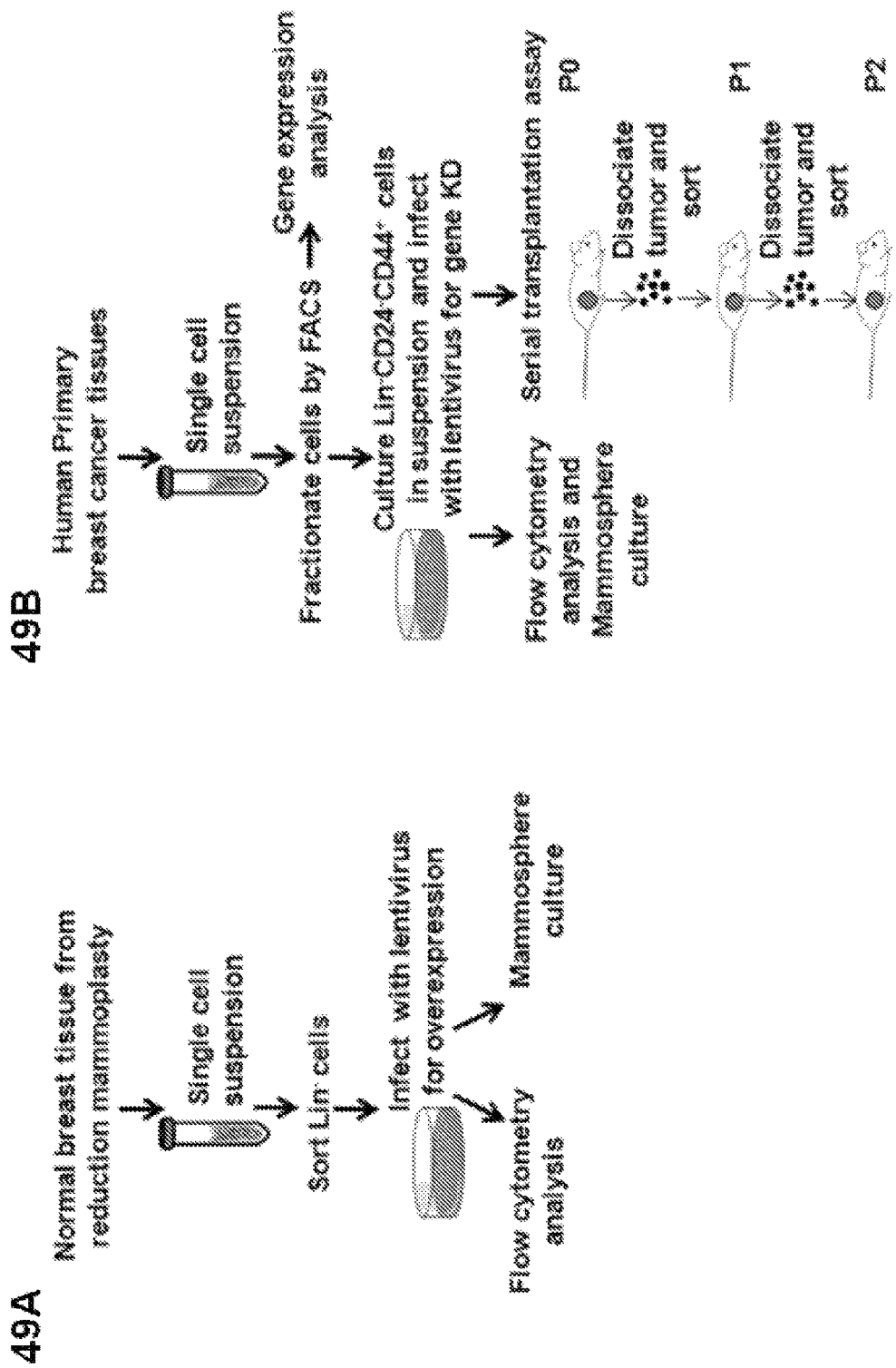

FIG. 49A is a schematic of the experiments on normal human MECs from reduction mammoplasty tissues.

FIG. 49B is a schematic of the experiments on freshly isolated primary human BCSCs.

Figure 50:
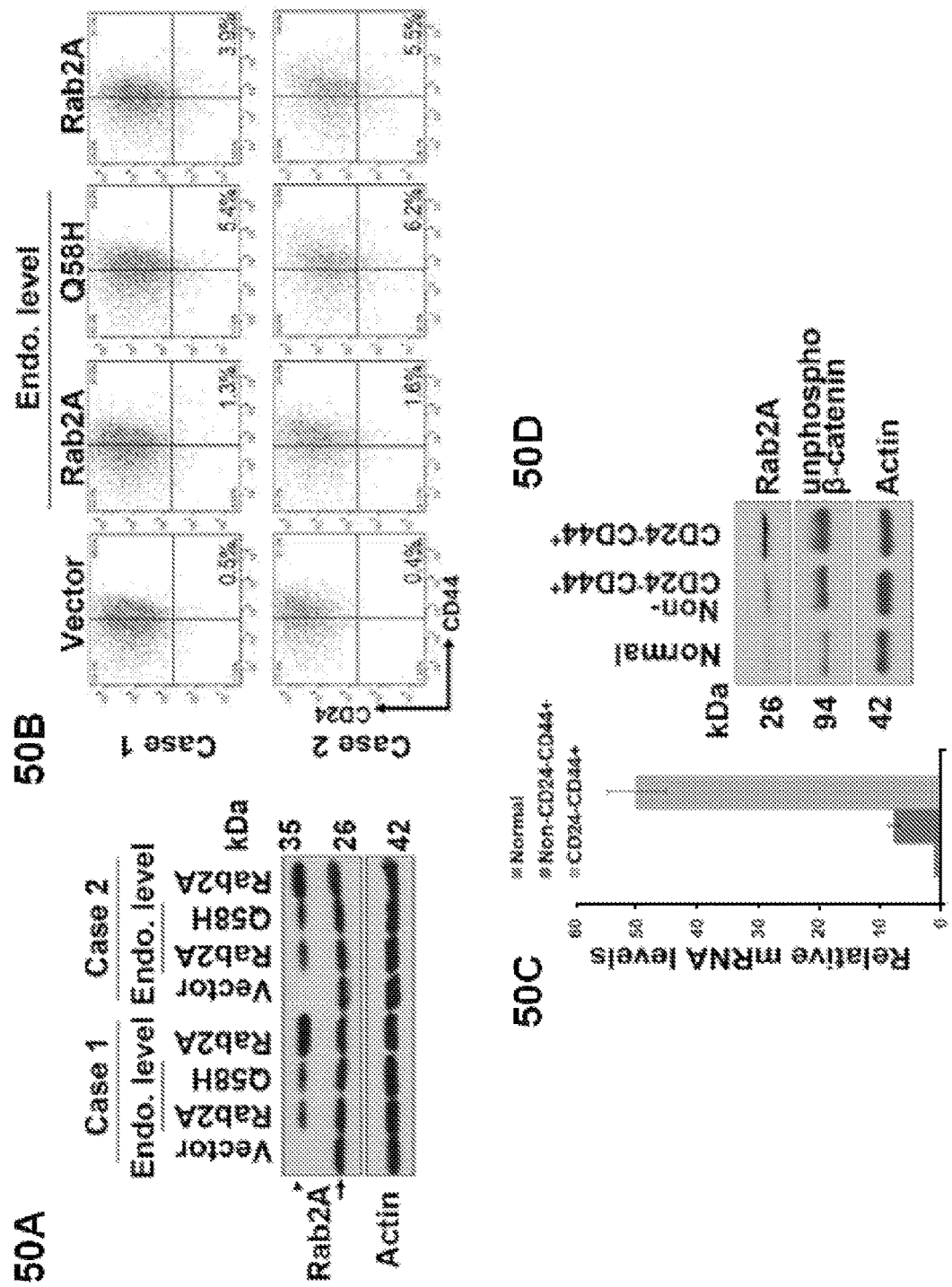
Figure 50:
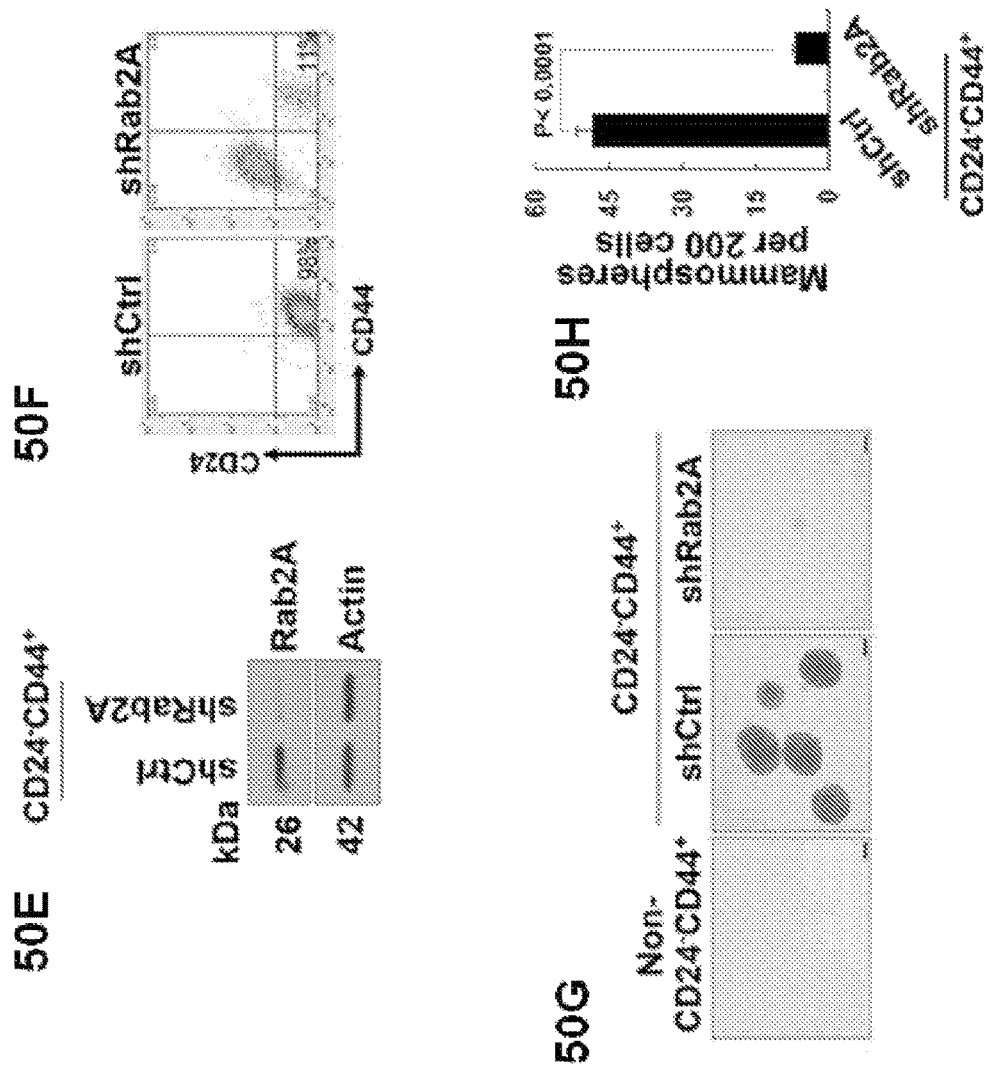
Figure 50:
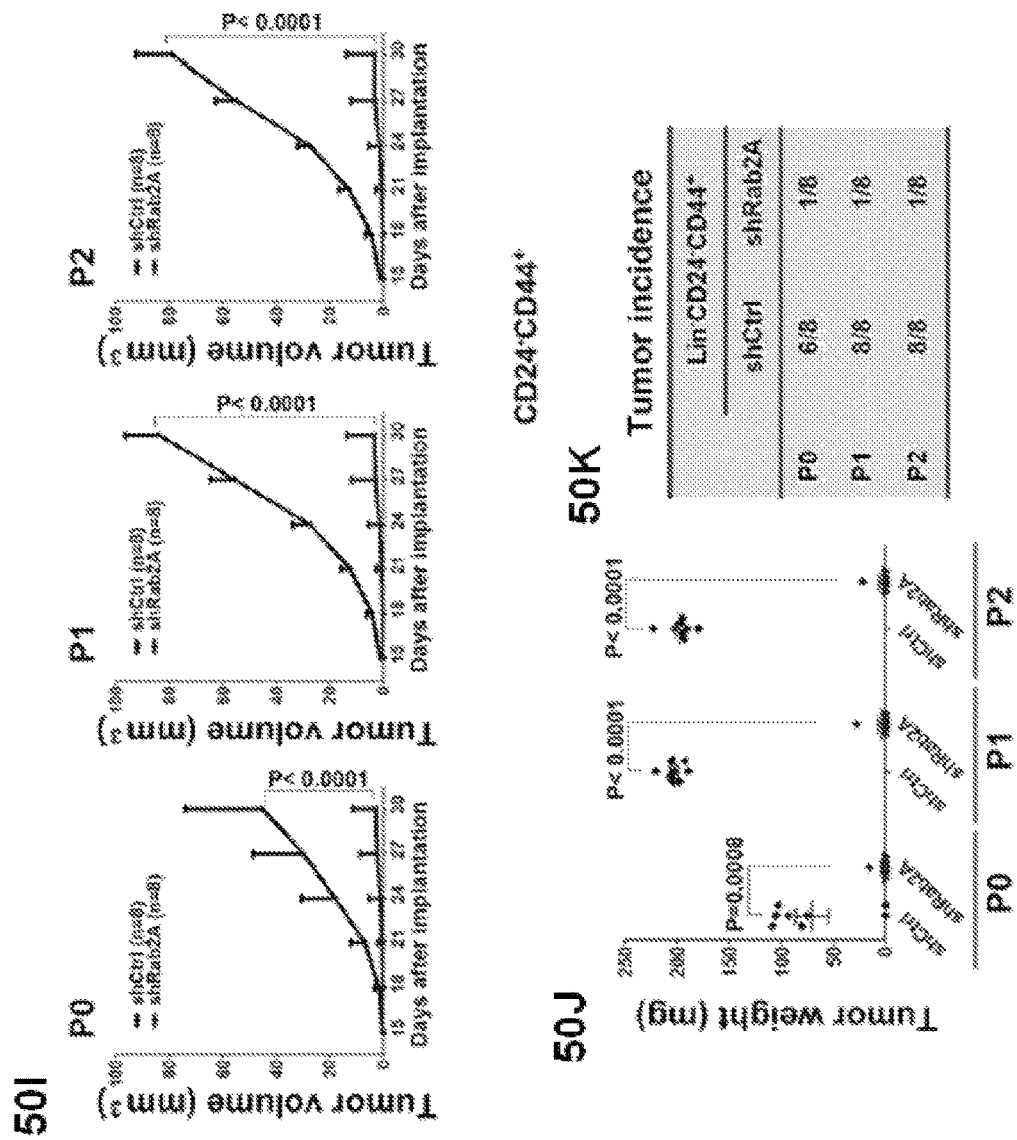

FIG. 50A is a Western blot showing lentivirus-mediated overexpression of Rab2A and Q58H mutant in two cases of human normal Lin MECs. Lin cells were isolated from normal human reduction mammoplasty tissues and sorted using lineage markers, and then infected with lentivirus expressing vector, Rab2A or its Q58H mutant. The arrowhead indicates exogenous Flag tagged protein, while the arrow indicates endogenous protein.

FIG. 50B includes plots showing that Rab2A or Rab2A Q58H mutant increased the CD24$^-$CD44$^+$ population in primary human MECs. Overexpressed Rab2A Q58H mutant at the endogenous level increased the CD24$^-$CD44$^+$ population even more potently than did Rab2A overexpressed at 3-time over the endogenous level.

FIG. 50C is a bar graph obtained from real-time PCR that shows that expression of Rab2A mRNA was markedly increased in the Lin$^-$CD24$^-$CD44$^+$ population, comparing to the Lin Non-CD24$^-$CD44$^+$ or normal epithelial cells.

FIG. 50D includes blots showing that expression of Rab2A and unphosphorylated β-catenin protein was markedly increased in the BCSC-enriched population in primary human breast cancer specimens. Lin$^-$CD24$^-$CD44$^+$ and Lin$^-$ non-CD24$^-$CD44$^+$ cells were sorted from human breast cancer tissues. Rab2A and unphosphorylated β-catenin levels were lower in the normal breast tissues from the same patient, compared to cancer tissues.

FIG. 50E shows that Rab2A was knocked down in Lin$^-$CD24$^-$CD44$^+$ cells sorted from human breast cancer tissues.

FIG. 50F shows that Rab2A KD in Lin$^-$ CD24$^-$CD44$^+$ breast cancer cells decreased the CD24$^-$ CD44$^+$ population.

FIGS. 50G and 50H show that Rab2A KD in Lin$^-$CD24$^-$CD44$^+$ breast cancer cells decreased the mammosphere formation. (Scale bar, 100 □m)

FIGS. 50I, 50J, and 50K show that Rab2A KD interfered with both tumor initiation and growth of primary BCSCs in vivo, as shown by tumor growth curve (50I), tumor weights (50J) and tumor incidence (50K). 2,000 lentivirus transduced Lin$^-$ CD24$^-$CD44$^+$ cells isolated from eight breast cancer patients were serially transplanted as xenografts into eight nude mice. P0 indicates freshly isolated primary cells, P1 indicates passage 1, and P2 indicates passage 2.

FIG. 51 is a table providing patient information for isolation of Lin$^-$ CD24$^-$CD44$^+$ cells from human breast cancer.

Figure 52:
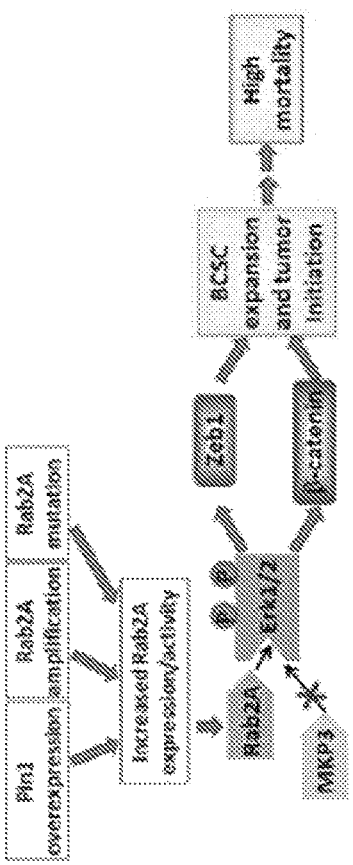

FIGS. 52A, 52B, and 52C show that Rab2A expression correlated with Pin1 and ALDH1 expression in the tissue array dataset. Serial sections of tissue arrays of normal and cancerous human breast tissues were subjected to immunohistochemistry using anti-Pin1, Rab2A, and ALDH1 antibodies. In each sample, Pin1, Rab2A, and ALDH1 were semi-quantified in a double-blind manner as high, medium or low. Correlation between Pin1 and Rab2A (52B), or Rab2A and ALDH1 (52C) were analyzed by Pearson correlation test.

FIG. 52D is a plot showing that Rab2A is a strong and independent biomarker to predict breast cancer specific survival in Curtis breast cancer dataset by Cox regression analyses. Expression of Rab2A, MKI67 and PCNA mRNAs was treated as continuous variables in the univariate and multivariate analyses. Rab2A expression was significantly prognostic for disease-specific survival, even by multivariate analysis adjusted for proliferation markers (MKI67, PCNA), or tumor grade, stage, size, or HER2, ER, PR status.

FIG. 52E is a box plot of Rab2A expression stratified by the PAM50 classifier in Curtis breast cancer dataset. Rab2A expresses significantly higher in LumB, Her2 and basal subtypes than in Normal and LumA subtypes.

FIG. 52F is a box plot of Rab2A expression stratified by the IntClust subtypes in Curtis breast cancer dataset. Rab2A expresses at low levels in IntClust subtype 3 and 4, which correlate with better clinical outcome, and expresses at high levels in IntClust subtype 5, 6, 9, and 10, which correlate with worse clinical outcome.

FIG. 52G is a table summarizing a univariate Cox regression analysis that shows that HER2 negative, non-triple negative, or PAM50 Normal subtypes of breast cancer patients with higher Rab2A mRNA level had a higher risk of breast cancer mortality.

FIG. 52H shows that Rab2A expression correlates with expression of β-catenin downstream target genes (FN1 and MYC), and Zeb-1 downstream target genes (KLF4 and INDAL), as shown by the Pearson correlation test.

FIG. 52I is a schematic model for how the Pin1/Rab2A/Erk signal pathway regulates tumor initiation via Zeb1 and β-catenin, contributing to high mortality in breast cancer. Inhibitors of this pathway might offer new therapies targeted at BCSCs.

Figure 53:
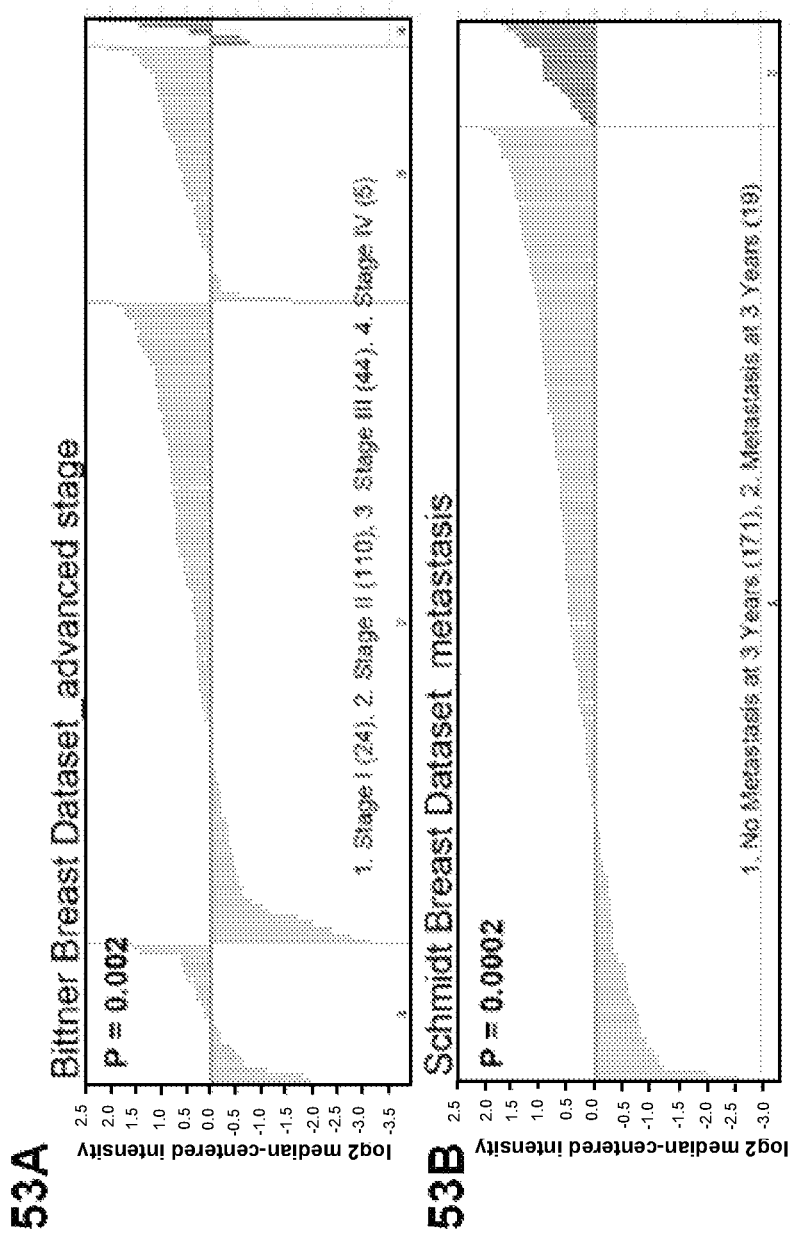
Figure 53:
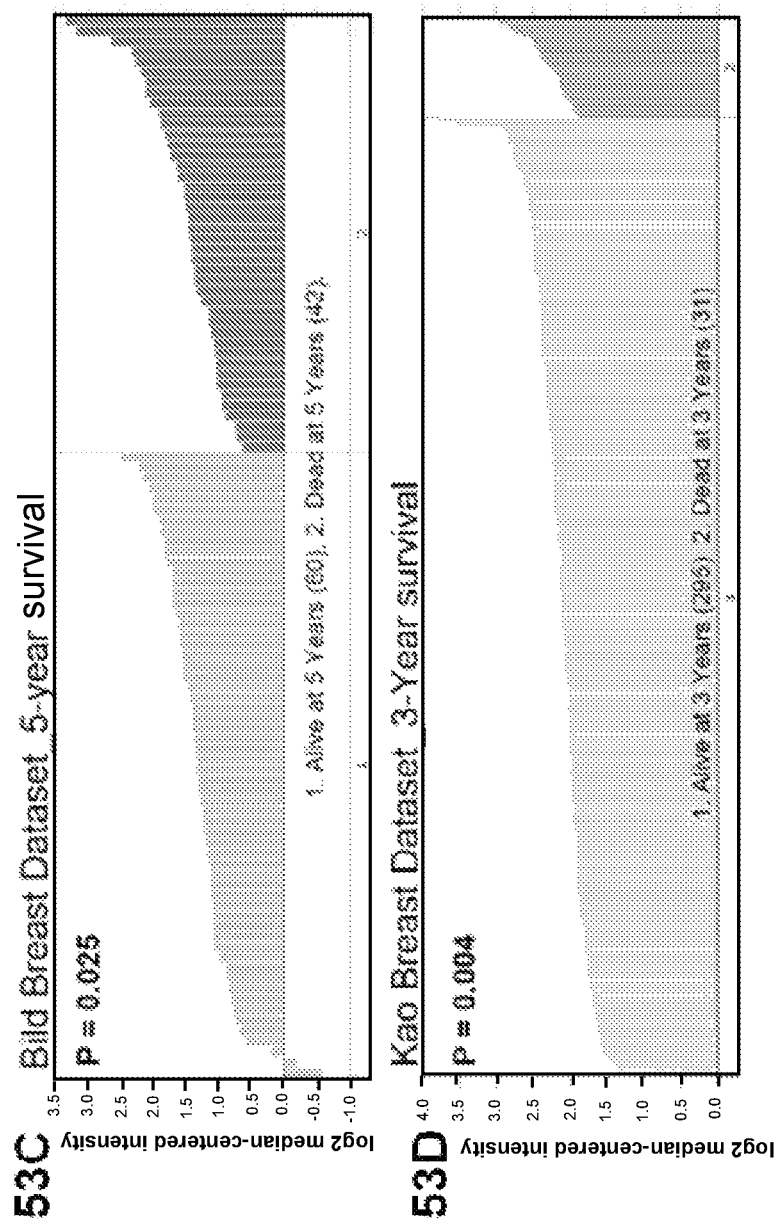

FIG. 53A shows that Rab2A expression correlates with advanced stage in Bittner Breast dataset (ductal breast carcinoma). Each bar in the graph represents the Rab2A level in one patient.

FIG. 53B shows that Rab2A expression correlates with metastatic event at three years in Schmidt Breast dataset (invasive breast carcinoma). Each bar in the graph represents the Rab2A level in one patient.

FIG. 53C shows that Rab2A expression correlates with death at five years in Bild Breast dataset (breast carcinoma). Each bar in the graph represents the Rab2A level in one patient.

FIG. 53D shows that Rab2A expression correlates with death at three years in Kao Breast dataset (breast carcinoma). Each bar in the graph represents the Rab2A level in one patient.

Figure 54:
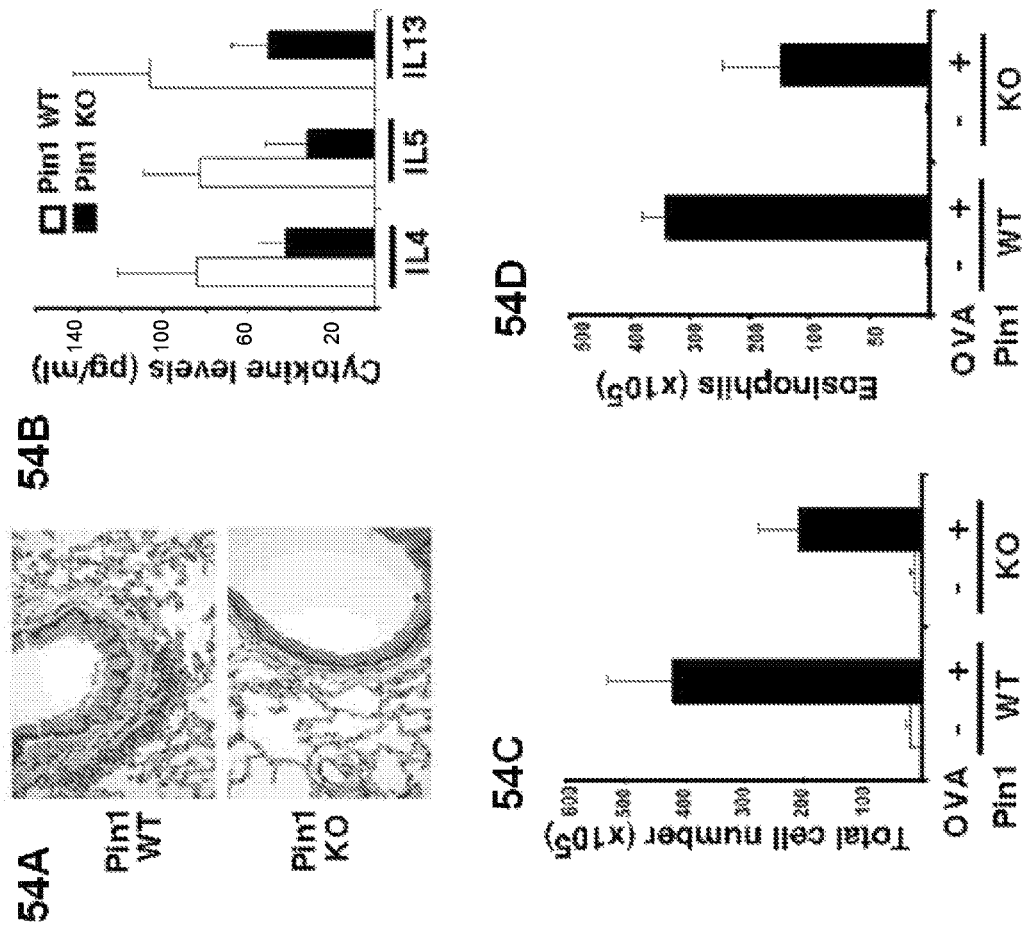

FIGS. 54A, 54B, 54C, and 54D show that Pin1 KO reduced Th2 response and asthma after an OVA allergen challenge in mice. FIG. 54A includes images showing that Pin1 KO reduced OVA-induced asthma relative to Pin1 WT, while FIG. 54B shows the reduction in cytokine levels by Pin1 KO. FIGS. 54C and 54D demonstrate the reduced total cells and eosinophils in BAL by Pin1 KO.

Figure 55:
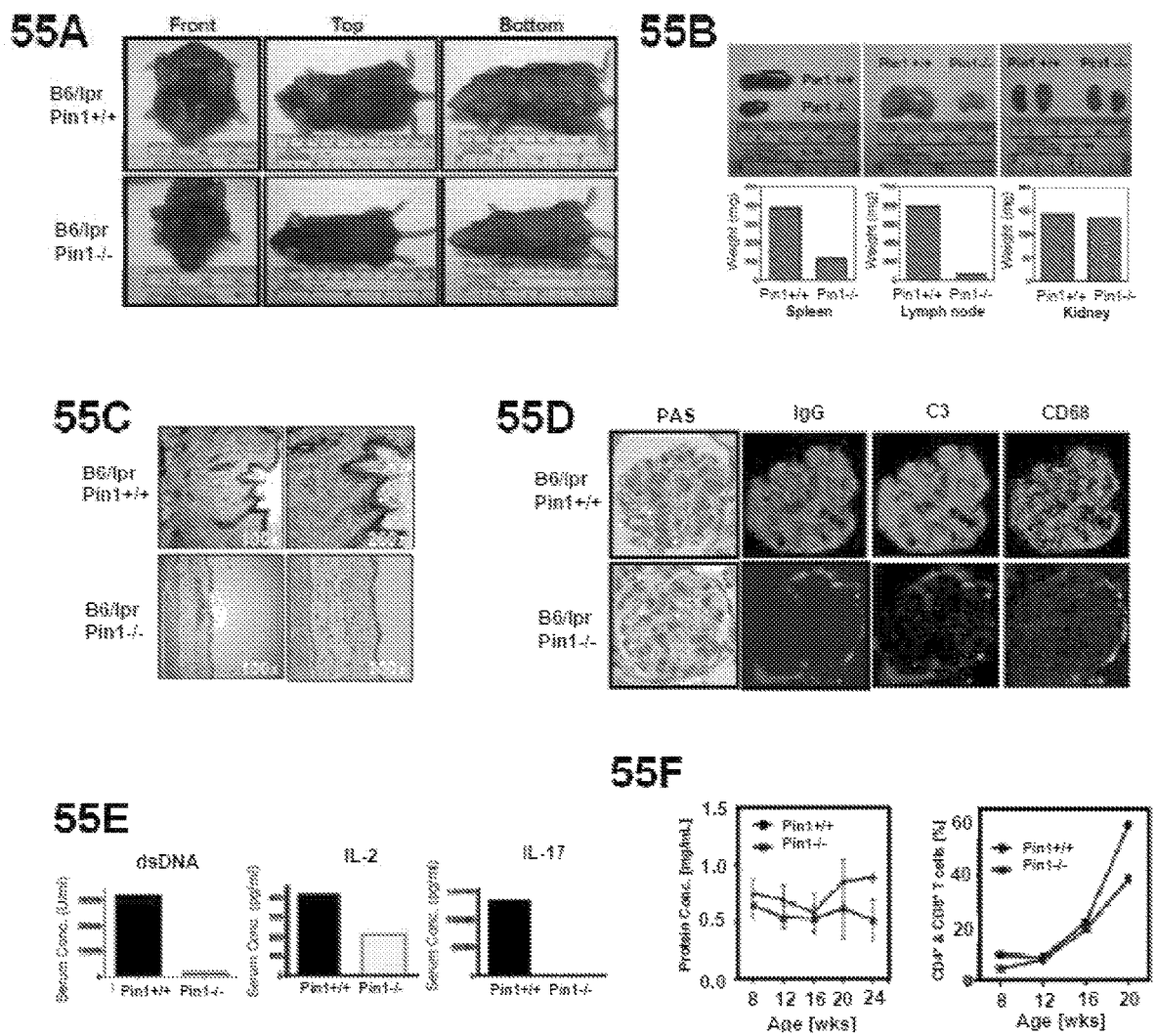

FIG. 55A shows that Pin1 KO potently reduced fur loss, skin papillomas, acanthosis, and lymphoid hyperplasia in B6.MRL/lpr lupus prone mice, while FIG. 55B displays the sizes of spleens, lympth nodes, and kidneys in Pin1 KO and Pin1 WT mice. FIGS. 55C, 55D, and 55E display the difference in skin hyperkeratosis; deposition of IgG, complement C3, and CD68 in the glomerulus; and the production of anti-double strand DNA antibodies, IL-2, and IL-17 in Pin1 KO and Pin1 WT mice.

FIG. 55F includes graphs showing the levels of proteinuria and CD4 and CD8 double-negative T cell populations in B6.MRL/lpr lupus prone mice.

Figure 56:
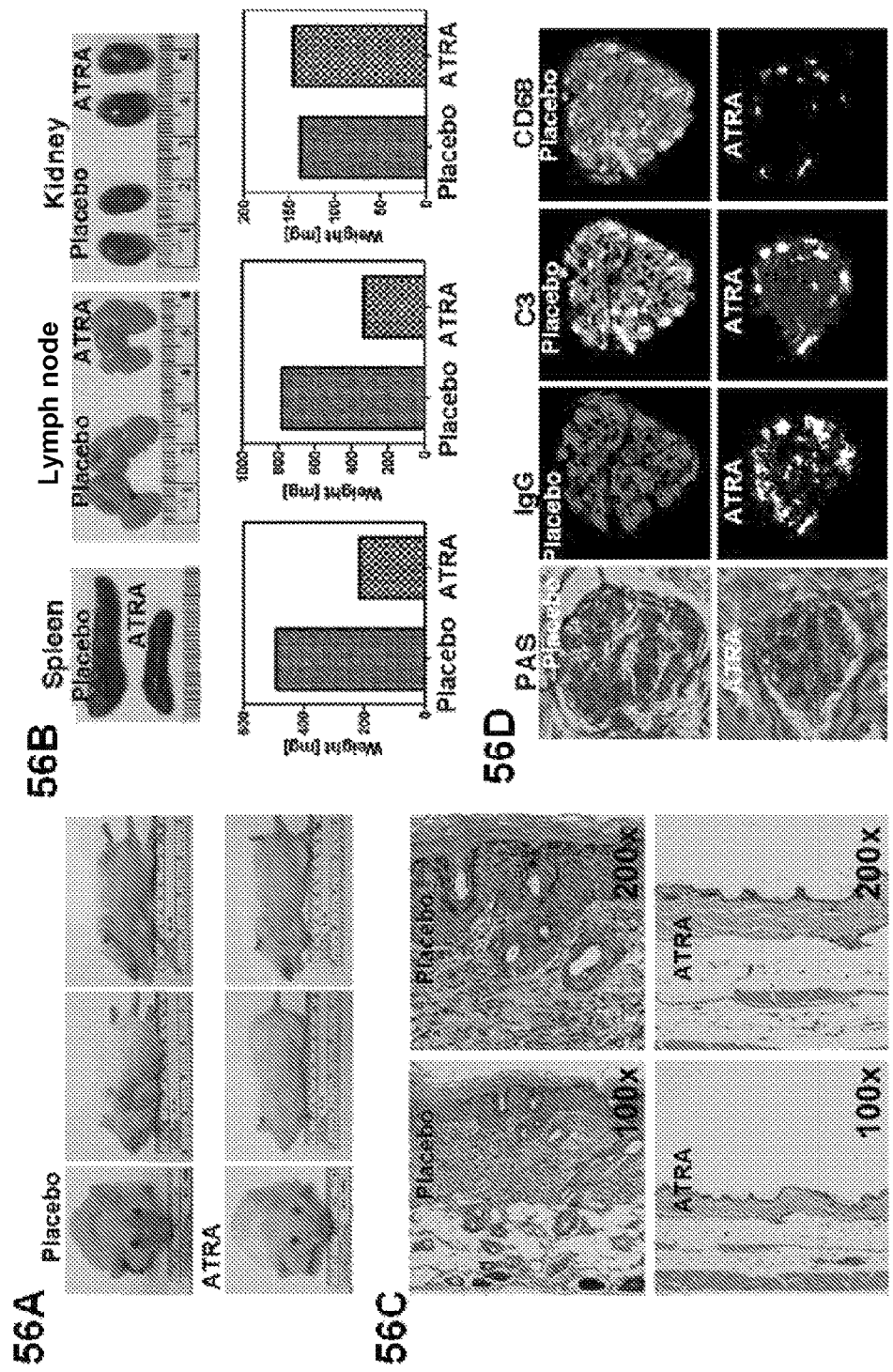

FIG. 56A shows that administration of ATRA potently reduced fur loss, skin papillomas and acanthosis, and lymphoid hyperplasia in MRL/lpr lupus prone mice. ATRA administration also reduced the size of the spleen and lymph node (56B) and skin hyperkeratosis (56C). In addition, FIG. 56D shows that ATRA reduced the deposition of IgG, complement C3, and CD68 into the glomerulus in MRL/lpr lupus prone mice.

DETAILED DESCRIPTION OF THE INVENTION

In general, the invention features all-trans retinoic acid (ATRA)-related compounds having high affinities for Pin1 and methods of treating a proliferative disorder, autoimmune disorder, or addiction condition characterized by an elevated Pin1 marker level or Pin1 degradation in a subject by administering an ATRA-related compound of the invention. The invention also features methods of treating proliferative disorders, autoimmune disorders, and addiction conditions (e.g., diseases, disorders, and conditions characterized by elevated Pin1 marker levels) by administering an ATRA-related compound of the invention in combination with one or more anti-proliferative, anti-microbial, anti-viral, or anti-inflammatory compounds or therapeutic species.

Inhibitors of Pin1 (e.g., retinoic acid compounds, such as ATRA-related compounds) are useful for treating proliferative disorders, autoimmune disorders, and addiction conditions (e.g., diseases, disorders, or conditions characterized by increased Pin1 activity or resulting from disregulation of Toll-like receptor signaling or type I interferon-mediated immunity). Because Pin1 acts in several different oncogenic pathways, Pin1 inhibition would be expected to behave synergistically with many anti-proliferative compounds. Furthermore, because Pin1 associated aberrant IRAK1 activation and type I IFN overproduction occurs in various immune diseases, Pin1 inhibition would be expected to behave synergistically with many anti-inflammatory compounds.

Identification of Pin1 PPIase Active Site Catalytic Inhibitors

The PPIase active site of Pin1 includes one or more binding pockets or portions that associate with Pin1 catalytic inhibitors. By identifying the one or more binding pockets of the active site, a substrate or catalytic inhibitor capable of associating with all or a portion of the Pin1 active site could be conceptualized, e.g., by using information about the geometric and electrostatic characteristics of the one or more binding sites to design a Pin1 catalytic inhibitor. A Pin1 catalytic inhibitor conceptualized in this manner could be subsequently synthesized and interacted with Pin1 in a binding or inhibition assay in order to determine the affinity and selectivity of the designed catalytic inhibitor for the active site or portion thereof (e.g., one or more binding pockets). The potency and half-life of the catalytic inhibitor and/or protein-inhibitor complex could subsequently be measured in other biological assays. Accordingly, the present invention provides for drug discovery based on structure-activity relationships, and for the design, screening, optimization, and evaluation of Pin1 catalytic inhibitors (e.g., retinoic acid compounds and ATRA-related compounds) for Pin1.

In order to identify one or more binding pockets of the active site, it is useful to examine the structure of the Pin1 active site, e.g., that determined by X-ray crystallographic methods. X-ray crystallographic interrogation of a crystal of a protein provides structural coordinates determined from X-ray diffraction patterns via iterative and widely available computer software such as COOT known to those of skill in the art. These structural coordinates can be evaluated and used to generate a three-dimensional model of a protein (e.g., Pin1) or an active site thereof, for example, using software such as PROCHECK and MolProbity and others described herein. The three-dimensional model may be presented in a variety of formats (e.g., ball and stick, wire frame, portions excluded, etc.) and optimized to provide a visual representation of the one or more binding pockets of an active site of a protein.

As described above, Pin1 includes at least two active sites including the WW domain and the PPIase active site. The amino acid residues involved in the PPIase domain are presented in SEQ ID NO:1. The PPIase active site includes at least one binding pocket where a Pin1 catalytic inhibitor can interact with one or more amino acid species.

Upon identifying one or more binding pockets of an active site, e.g., of Pin1, a molecule having appropriate characteristics for interaction with one or more of the binding pockets could be conceptualized and subsequently evaluated, as described above. For example, a molecular component capable of forming one or more hydrogen bonds (e.g., a carboxylic acid group) could be designed for a binding pocket consisting of amino acid residues having hydroxyl or amino groups (e.g., lysine, K; arginine, R; and serine, S). Similarly, a molecular component with high hydrophobicity (e.g., consisting primarily of hydrogen and carbon) could be designed for a binding pocket consisting primarily of hydrophobic residues (e.g., leucine, L, and phenylalanine, F). Molecular bridges linking components designed for interaction with different binding groups could be similarly conceptualized. For example, for an active site including two binding pockets spaced approximately 10 Å apart, an alkyl or alkenyl chain approximately 10 Å in length could be designed to link the two associative components. The rigidity of the chain or linker could also be optimized, e.g., by varying the number of unsaturations (e.g., double bonds) in the chain and/or designing an anchor or other component to add bulk at one or more locations between one or more binding pockets. Geometric parameters such as the distance between one or more residues of an active site of a protein could be used to infer the optimal size, geometry, and electrostatics of a molecular component to associate with one or more binding pockets. For example, the distance between hydrogen bonding residues could be used to design an associative molecular component: a carboxyl group may be appropriate for a binding pocket having two hydrogen bonding partners that are relatively close to one another, while a binding pocket having a single hydrogen bonding residue or one or more hydrogen bonding partners diametrically or otherwise distantly positioned may associate more strongly with one or more hydroxyl or other groups. Physico-biochemical interaction models may also be applied to the catalytic inhibitor design process. For example, phosphate groups are generally known to have poor cell permeability. Accordingly, groups such as carboxylic acids, which have electron densities similar to phosphate groups but are more likely to be cell permeable, could be used in place of phosphate groups in electropositive portions of an active site.

Alternatively, iterative drug design could be carried out using crystallographic methods. Analysis of a three-dimensional structure of a crystal or co-crystal structure can provide structural and chemical insight into the activity of a protein and its association with a catalytic inhibitor. Thus, by forming successive protein-compound complexes and then crystallizing each new complex (e.g., as described herein), potential catalytic inhibitors could be screened for their selectivity and affinity for Pin1. High throughput crystallization assays could be used to find new crystallization conditions or to optimize the original protein or complex crystallization condition for a new complex. Pre-formed protein crystals could also be soaked in the presence of a catalytic inhibitor (e.g., an ATRA-related compound), thereby forming a new protein-inhibitor complex and obviating the need to crystallize each individual protein-inhibitor complex. Such an approach could provide insight into the association between the protein and inhibitor of each complex by selecting substrates with inhibitory activity (e.g., as identified in a binding assay) and by comparing the associations (e.g., as measured with modeling, as described herein) and visualizations of the three-dimensional structures of different co-crystals and observing how changes in a substrate (e.g., catalytic inhibitor) affected associations between the protein and substrate. However, this type of optimization process requires extensive lab time as well as significant access to crystallography instrumentation and analytical tools.

Alternatively, one or more binding pockets of an active site of a protein can be identified by first identifying a molecule (e.g., catalytic inhibitor) capable of associating with the active site of the protein (e.g., with a binding assay)

and subsequently examining the active site or portion thereof. For example, a binding assay (e.g., a fluorescence probe high-throughput screen) could be performed to identify one or more molecules (e.g., catalytic inhibitors) capable of associating with all or a portion of an active site. A substrate with particularly high affinity (e.g., with a Z score significantly different than the average, such as a Z score with an absolute value of 2 or greater) for the active site could be selected as a starting point for analysis. Subsequently, the structure of the high affinity substrate (e.g., catalytic inhibitor) could be compared to a three-dimensional model of the active site generated from structural coordinates (e.g., on a computer from data collected by crystallographic methods). Comparison of the structure of the active site and the structure of the high affinity substrate could be performed to identify one or more binding pockets of the active site. In this context, comparison may involve visually inspecting the structure of the active site for grooves, pockets, indentations, folds, or other structural features, and making chemical inferences based on electrostatic, geometric, and steric considerations with regard to the residues occupying or in the vicinity of the active site or a portion thereof (e.g., a groove, pocket, indentation, or the like) to determine how the substrate may associate with the active site of the protein. For example, the Pin1 active site includes a region wherein a lysine residue (K63) and an arginine residue (R69) are in close proximity. Accordingly, if a substrate selected from a binding assay includes a carboxylic acid group, comparison between the structure of the active site and the structure of the substrate and application of chemical intuition would suggest that the carboxylic acid group should associate with the active site in a manner that permits the carboxylic acid group to hydrogen bond with the K63 and R69 residues. A high electron density binding pocket would have thus been identified.

Molecular Modeling

Comparison of the structure of an active site of a protein and the structure of a high affinity substrate may also involve performing a fitting operation between the high affinity substrate and all or a portion of the active site. For example, the structure of the high affinity substrate could be optimized (e.g., using force-field optimizations or computational methods such as density functional theory as is well known in the art) and structural coordinates for the substrate obtained. A computer could then be used to position the substrate structure in the vicinity the structure of the active site of the protein. The substrate structure could be initially manually or automatically positioned in the vicinity of the active site structure. Manual positioning may be followed by automated optimization, e.g., using a protein-substrate docking molecular modeling technique. Molecular modeling processes permit prediction of the position and orientation of a substrate relative to the active site of the protein. A modeling process may therefore be used to predict how one or more components of a substrate interact with one or more binding pockets of an active site.

Protein-substrate docking may involve molecular dynamics (MD) simulations (e.g., holding the protein structure rigid while permitting free movement of a substrate and subsequently annealing). While computationally expensive due to the many short energy minimization steps typically involved, MD simulations are often applied in protein-substrate docking. Alternatively, the molecular modeling process may involve shape-complementarity methods. These methods apply descriptors to the protein and substrate that reflect structural and binding complementarity (e.g., geometric parameters such as solvent-accessible surface area, overall shape, geometric constraints, hydrogen bonding interactions, hydrophobic contacts, and van der Waals interactions). Descriptors are provided in the form of structural templates and are interpreted to describe how well a substrate may bind to a protein (e.g., the binding affinity). Such methods may be computationally less expensive than molecular dynamics simulations. Genetic algorithms involving energy optimizations of substrate-protein complexes over large conformational spaces may also be performed. Genetic algorithms are generally temporally expensive due to the size of the conformational space. Commercially available computational docking programs such as AutoDock and Schrödinger's Glide may be used to perform one or more protein-substrate docking methods. Computational docking programs may also quantify the association between a protein and a substrate. For example, a program may generate a "docking score" associated with a given substrate. If multiple substrates are analyzed with molecular modeling, the docking scores of the substrates may be compared to determine which substrate may associate most strongly with a Pin1 active site, for example, in a screening method. Docking score rankings could also readily be compared to the results of binding assays to evaluate the effectiveness and predictiveness of a particular molecular modeling method. A binding energy or binding affinity cutoff could also be used to identify one or more substrates that may be particularly selective or potent Pin1 substrates (e.g., catalytic inhibitors). For example, Pin1 catalytic inhibitors having a deformation energy of binding with a binding pocket of less than −7 kcal/mol could be selected for further analysis (e.g., further computational analysis and/or in vitro assays). The ATRA-related compounds exemplified herein (see, e.g., Tables 1-5) have calculated binding energies (MMGBSA energies) of approximately −30 kcal/mol or less.

A screening method, in which a compound capable of associating with all or a portion of a Pin1 active site is designed or selected, may include the steps of i) utilizing a three-dimensional model of the Pin1 active site including one or more binding pockets (e.g., on a computer, where the model is generated using structural coordinates obtained from crystallographic methods), where one or more Pin1 binding pockets for a substrate (e.g., a retinoic acid compound or an ATRA-related compound) are specified, and where at least one binding pocket includes one or more of H59, K63, S67, R68, R69, S71, S72, W73, Q75, E76, Q77, D112, C113, S114, S115, A116, K117, A118, R119, G120, D121, L122, Q129, M130, Q131, K132, F134, D153, S154, and H157; ii) performing a fitting operation between a first substrate and all or a portion of the one or more Pin1 binding pockets; iii) quantifying the association between the first substrate and all or a portion of the one or more Pin1 binding pockets (e.g., generating docking scores from molecular modeling results or determining a binding affinity or deformation energy of binding); iv) repeating steps i) to iii) with one or more further substrates (e.g., ATRA-related compounds); v) selecting one or more substrates (e.g., ATRA-related compounds) of steps i) to iv) based on the quantified association (e.g., the docking scores), where the quantified association indicates that the one or more substrates are capable of associating with all or a portion of a Pin1 active site; and vi) measuring the catalytic activity of at least one of the substrates (e.g., catalytic inhibitors) selected in step v) using an in vitro assay to classify or determine the potency of the at least one substrate relative to Pin1. In some embodiments, the one or more Pin1 binding pockets are identified using a three-dimensional model of Pin1. In other embodiments, the one or more binding pockets are identified using a three-dimensional model generated from a co-crystal structure of Pin1 and ATRA. In certain embodiments, the first substrate (e.g., ATRA-related compound) is selected for evaluation based on the one or more binding pockets.

Using the method described above, two or more substrates may be screened for their ability to associate with an active site of Pin1 (e.g., their binding affinity). A graphical representation of the association between the substrate (e.g., ATRA-related compound) and one or more Pin1 binding pockets could also be optionally generated using the three-dimensional model of the Pin1 active site and a graphical representation of the substrate to facilitate the identification of the one or more Pin1 binding pockets and, accordingly, the optimization/selection of the substrate (e.g., catalytic inhibitor).

Catalytic Activity

Upon quantifying the association between a high affinity substrate and an active site of a protein, the catalytic activity of a complex of the substrate and protein can be measured. With regard to Pin1, inhibition of catalytic activity is desirable, as inhibition of Pin1 prevents Pin1 from activating oncogenes and inactivating tumor suppressors. The catalytic activity of the protein can be measured using, for example, fluorescence probe, photoaffinity, or PPIase assays, as detailed in the Materials and Methods and Examples sections. The catalytic activity can be classified by, for example, measuring the % decrease in catalytic activity of the protein (e.g., Pin1) at a given concentration (e.g., 5, 10, 15, 20, or 25 μM) of substrate. The degree of decrease in the catalytic activity of Pin1 upon interaction with a given substrate (e.g., catalytic inhibitor) is indicative of the potency of the substrate as an antagonist for Pin1. A substrate with a high affinity and high potency for Pin1 will inactivate Pin1 by inhibiting its ability to isomerize proline residues. Inactive Pin1 is unable to participate in the stimulation of oncogenes and the inactivation of tumor suppressors that characterize its role in cancer. Accordingly, a potent and selective Pin1 substrate (e.g., catalytic inhibitor) may be useful in the treatment of proliferative diseases including cancers (e.g., as described herein).

Co-crystal Structures

Co-crystal structures of Pin1 and a substrate can be used in methods of identifying Pin1 substrates capable of associating with all or a portion of a Pin1 active site.

Co-crystals are crystalline solid including two or more components. The two components may have distinct physiochemical properties (e.g., structure, melting point, etc.) but are typically solids at room temperature. Co-crystals of the invention include Pin1 and a Pin1 substrate (e.g., catalytic inhibitor) such as ATRA or an ATRA-related compound. In a particular embodiment, a co-crystal includes Pin1 and ATRA. Co-crystals of the invention may additionally include other components including one or more water or other solvent molecules (e.g., DMSO or glycerol) or one or more salts (e.g., ammonium sulfate or sodium citrate) or components thereof (e.g., ammonium, sulfate, sodium, or citrate ions). Without wishing to be bound by theory, the components of a co-crystal may have hydrogen bonding (including water-mediated hydrogen bonding), van der Waals, hydrophobic, and other intermolecular interactions. A substrate (e.g., ATRA) of a co-crystal may be positioned at the active site of a protein (e.g., Pin1) of a co-crystal. For example, a substrate (e.g., ATRA) of Pin1 may dock to an active site of Pin1 or a portion thereof based on hydrogen bonding interactions between a component of the substrate (e.g., catalytic inhibitor) and one or more binding pockets of Pin1. The PPIase domain of Pin1 may be phosphorylated or dephosphorylated in a crystal or co-crystal structure.

Methods of forming co-crystals are known to those of skill in the art. In one embodiment, ATRA or a retinoic acid compound (e.g., an ATRA-related compound) may be produced by a well-known method, including synthetic methods such as solid phase, liquid phase, and combinations of solid phase/liquid phase syntheses; recombinant DNA methods, including cDNA cloning, optionally combined with site-directed mutagenesis; and/or purification of a natural product. In one embodiment, co-crystals are prepared by purifying and concentrating Pin1, preparing a substrate solution, combining a solution including purified Pin1 and the substrate solution, and performing vapor diffusion. The mixture of Pin1 and substrate solutions may be incubated at 0° C. for several hours prior to performing vapor diffusion. Pin1 may be derived and purified according to known methods. For example, Pin1 may be overexpressed in *E. coli* and separated from cells by lysing. The lysate may be subsequently purified with nickel affinity chromatography, dialysed, and incubated with a protease. The protein mixture may be further purified by chromatographic separation with an additional nickel affinity column and subsequent separation by size-exclusion chromatography. The purified Pin1 solution can be combined and incubated with a substrate solution including, in one embodiment, the substrate dissolved in DMSO.

Protein crystallization by vapor diffusion and other methods are well known to those of skill in the art and include hanging-drop, sitting-drop, sandwich-drop, dialysis, and microbatch or microtube batch devices, among others. For example, in a vapor diffusion method, a droplet of the solution including the protein and substrate is permitted to equilibrate with a reservoir including a buffered solution (the "hanging drop" method). Crystallization may be optionally seeded with other crystals (e.g., with apo PPIase domain crystals). Subsequent to their formation, co-crystals may be cryoprotected by adding glycerol and vitrifying with liquid nitrogen.

Co-crystals or portions thereof may be interrogated and characterized using crystallographic methods such as X-ray, neutron, or electron diffraction. In some embodiments, synchrotron (e.g., X-ray) radiation may be used to analyze a co-crystal. Diffraction patterns measured using crystallographic interrogation can be processed using standard software packages (e.g., the CCP4 suite and COOT). Computer software can also be used to evaluate structural determinations (e.g., with programs such as PROCHECK and MolProbity) and to extract structural coordinates from data and to use the structural coordinates to generate a three-dimensional model or visual representation of a protein (e.g., Pin1) and substrate (e.g., ATRA). For example, software including but not limited to QUANTA, O, Sybyl, and RIBBONS can be used to generate three-dimensional structures (e.g., models) of a protein-substrate complex or portion thereof. Certain software programs may imbue a graphical representation with physio-chemical attributes which are known or can be derived from the chemical composition of the molecule including residue charge, hydrophobicity, and torsional or rotational degrees of freedom for a residue or segment, among others. In some embodiments, a three-dimensional graphical representation may include an electron density map or other representation of electron density distribution in the protein-substrate complex. Three-dimensional structural information may be generated by instructions such as a computer program or commands that can generate a three-dimensional structure or graphical representation and may involve measurement of distances between atoms, the calculation of chemical energies for a substrate associating with an active site or portion thereof (e.g., a binding energy of deformation or a binding affinity), the calculation or minimization of energies of association between the substrate (e.g., catalytic inhibitor) and the protein, and other processes. These types of programs and activities are known in the art. Data generated from any such program, activity, or process may be viewed, presented, shared, saved, stored, processed, or transferred in any manner or format known in the art.

Those of skill in the art may understand that a set of structural coordinates for a protein-substrate complex or a portion thereof (e.g., derived from a Pin1-ATRA co-crystal), is a relative set of points that define a shape in three dimensions. Thus, it is possible that an entirely different set of coordinates could define a similar or identical shape. Moreover, slight variations in the individual coordinates will have little effect on overall shape. In terms of binding pockets, these variations would not be expected to significantly alter the nature of substrates (e.g., catalytic inhibitors) that could associate with those pockets. Those of skill in the art will also understand that one or more water molecules may be included in a crystal, co-crystal, and/or a structural representation of a crystal or co-crystal. The number and distribution of water molecules in and/or around a protein-substrate complex is dynamic and may depend on factors including temperature, modeling parameters, and the quality of the crystal or co-crystal.

The variations in coordinates discussed above may be generated as a result of mathematical manipulations of the Pin1 structure coordinates. For example, the structure coordinates could be manipulated by crystallographic permutations of the structure coordinates, fractionalization of the structure coordinates, integer additions or subtractions to sets of the structure coordinates, inversion of the structure coordinates or any combination of the above.

Graphical representations of protein-substrate complexes can be used to identify binding pockets of an active site. For example, a co-crystal of Pin1 and ATRA can be used to generate a graphical representation of a Pin1-ATRA complex that can be visually and/or computationally inspected for one or more binding pockets of Pin1's active site. Using a co-crystal structure, distances between atoms and/or functional groups of Pin1 and a substrate can be measured and used to make chemical inferences regarding the natural of an intermolecular interaction between a portion of Pin1 and a substrate or component thereof. For instance, hydrogen bonding between the active site of Pin1 and a substrate can be readily inferred if hydrogen bonding groups (e.g., amines, alcohols, and carboxylic acids) are spaced approximately 2.5 Å apart or less. Hydrophobic interactions can be inferred by, for example, areas of interaction including primarily carbon and hydrogen atoms. These areas of interaction may be classified as binding pockets. Accordingly, visualization of the relative orientations of Pin1 and a Pin1 substrate (e.g., ATRA) can facilitate the identification of one or more binding pockets of the active site of Pin1.

Pin1's PPIase active site includes residues lysine 63 (K63), arginine 69 (R69), leucine 122 (L122), methionine 130 (M130), glutamine 131 (Q131), and phenylalanine 134 (F134), among others. Notably, K63 and R69 are positioned in proximity to one another, while L122, M130, Q131, and F134 are clustered several Angstroms away. The portion of the active site including K63 and R69 also includes serine 71 (S71), the phosphorylation of which inactivates Pin1. Due to the proximity of K63 and R69 to S71, it is likely that inactivation is caused by hydrogen bonding between K63 and R69 and phosphorylated S71. Accordingly, a potent Pin1 substrate should include a molecular component capable of associating with the high electron density binding pocket including the K63, R69, and S71 residues. As phosphate groups are known to be largely cell-impermeable, a carboxylic acid group may be desirable for inclusion in a substrate. Indeed, ATRA includes a carboxylic acid group, and the co-crystal structure of Pin1 and ATRA (FIGS. 2K, 2L, and 7A) demonstrate that the carboxyl group interacts the K63 and R69 substrates at a distance of 4 or fewer Angstroms.

The residues L122, M130, Q131, and F134 form a groove at the surface of Pin1 that readily lends itself to identification as a binding pocket. As these residues are generally hydrophobic, it is reasonable to expect that they would experience a hydrophobic interaction with a molecular component of a substrate. The co-crystal structure of ATRA and Pin1 reveals that the cyclohexene group of ATRA associates with the L122, M130, Q131, and F134 residues. Thus, the residues represent a hydrophobic binding pocket of the active site of Pin1. As shown in FIG. 5A, the residues H59, R68, 5154, and H157 may also be located within 4 Å of a compound (e.g., ATRA-related compound) or portion thereof occupying or associating with this groove.

As is evident from the co-crystal structure of Pin1 and ATRA, a narrow groove connects the high electron density and hydrophobic binding pockets of the active site of Pin1. This groove may also be considered a binding pocket of Pin1. In the co-crystal structure of Pin1 and ATRA, the conjugated alkene backbone of ATRA extends along the groove in proximity to (e.g., within 4 Å of) residues K63, R68, R69, S71, S72, D112, and S154 (FIG. 6A). This groove may therefore be thought of as a "backbone binding pocket."

Figure 4:
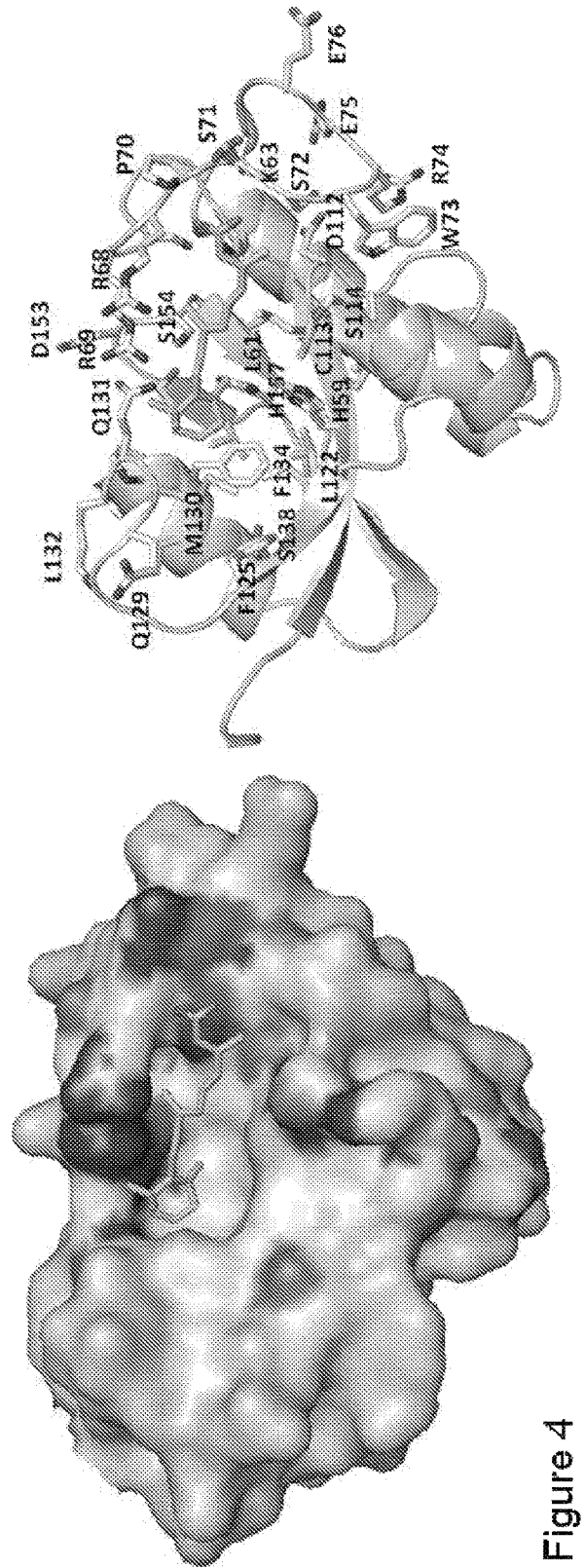

By examining the ATRA-Pin1 crystal structure, one or more binding pockets of the PPIase active site can be identified. A binding pocket may include one or more residues that are located within 10, 9, 8, 7, 6, 5, 4, 3, 2, or 1 Å of ATRA or another reference molecule (e.g., an ATRA-related compound; FIGS. 3 and 4). The distance between one or more residues and ATRA or another reference molecule may be determined when Pin1 is activated or inactivated or in any conformation. Distances referred to with regard to potential binding pockets may be defined from a particular reference residue, from a predetermined center (e.g., a center of a potential binding pocket), or between residues (e.g., each residue of a pocket is a given distance away from every other residue of the pocket). For example, Pin1 residues within 4 Å of the carboxylic acid group of ATRA (e.g., K63, R69, and S71) can be used to define a high electron density pocket. Alternatively, residues within 8 Å of the carboxylic acid group (e.g., H59, L60, L61, K63, S67, R68, R69, P70, S71, S72, W73, R74, Q75, E76, I78, S111, D112, C113, S114, S115, L122, F125, Q129, M130, Q131, K132, P133, F134, E135, S138, V150, T152, D153, S154, G155, I156, H157, and I159) may be considered part of the high electron density pocket (FIGS. 7A and 7B). Similarly, Pin1 residues within 4 Å (e.g., H59, R68, L122, M130, Q131, F134, S154, and H157) or 8 Å (.g., H59, L60, L61, K63, R68, R69, D112, C113, S115, L122, F125, Q129, M130, Q131, K132, P133, F134, E135, S138, V150, T152, D153, S154, G155, I156, H157, and I159) of the cyclohexenyl group of ATRA may define a hydrophobic binding pocket (FIGS. 5A and 5B). Finally, Pin1 residues within 4 Å (e.g., K63, R68, R69, S71, S72, D112, and S154) or 8 Å (e.g., H59, L61, K63, S67, R68, R69, P70, S71, S72, W73, R74, Q75, I78, S111, D112, C113, S114, S115, L122, F125, Q129, M130, Q131, F134, T152, D153, S154, G155, and H157) of the double bonds (e.g., backbone) of ATRA may define a backbone pocket.

Thus, by examining a graphical representation of a crystal structure of Pin1 or a co-crystal structure including Pin1 and a Pin1 substrate, multiple binding pockets can readily be identified. Additional Pin1 substrates, such as analogs of the reference substrate (e.g., ATRA-related compounds), can be designed based on the information obtained from the co-crystal structure. As the co-crystal structure of Pin1 and ATRA reveals the presence of at least three binding pockets, a substrate including components optimized for association with each binding pocket can be designed using the reference substrate as a starting point. For example, ATRA can be characterized as having three distinct molecular regions: a head group X including a trimethylcyclohexene ring, a backbone Y including a conjugated carbon chain, and an end group Z including a carboxylic acid. Each of these molecular regions or components associates with a different binding pocket of Pin1 (e.g., the hydrophobic pocket, the backbone pocket, or the high electron density pocket). Thus, one or more components of ATRA could be derivatized, substituted, reduced or increased in size, or otherwise changed or optimized to yield an ATRA-related compound.

Figure 8:
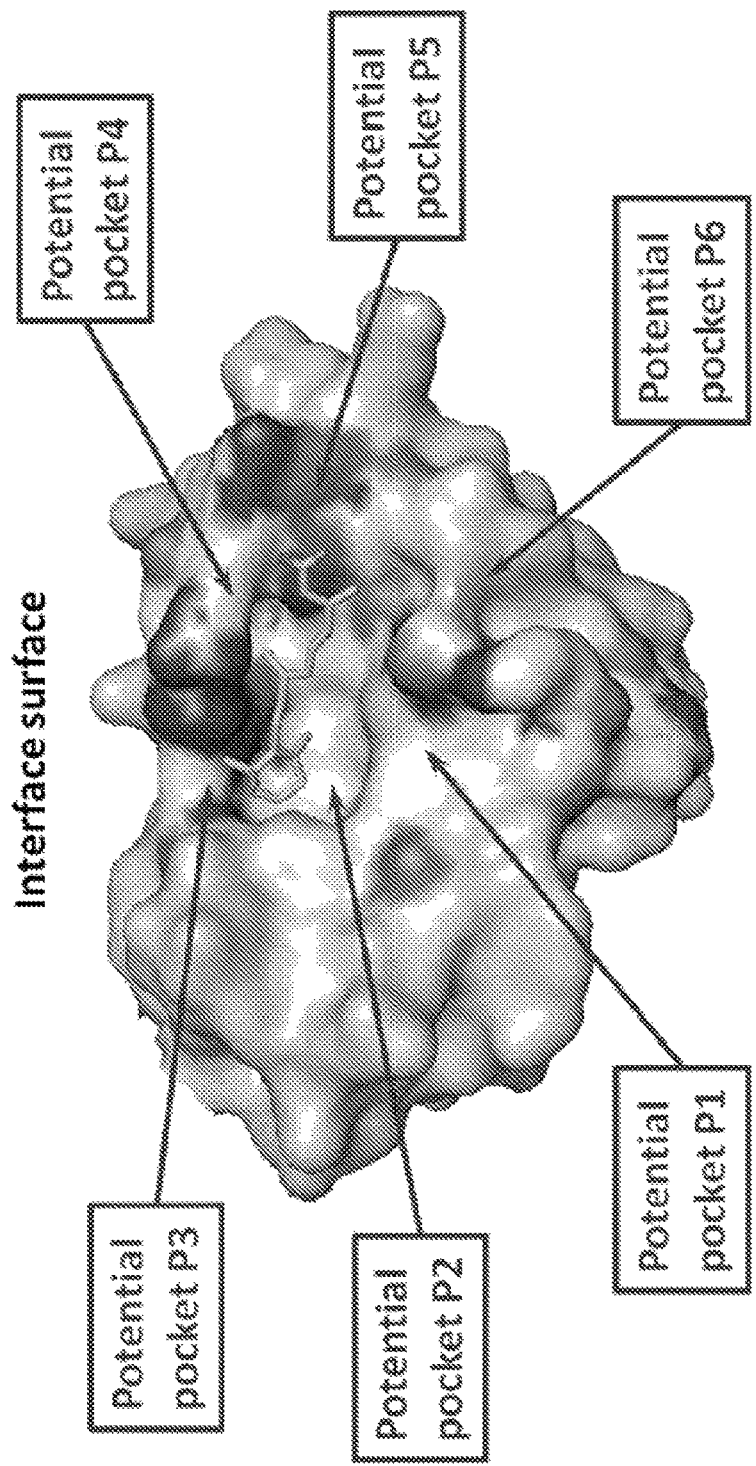
FIG. 8 depicts the location of potential binding pockets P1, P2, P3, P4, P5 and P6 for ATRA-related compounds.
Figure 9:
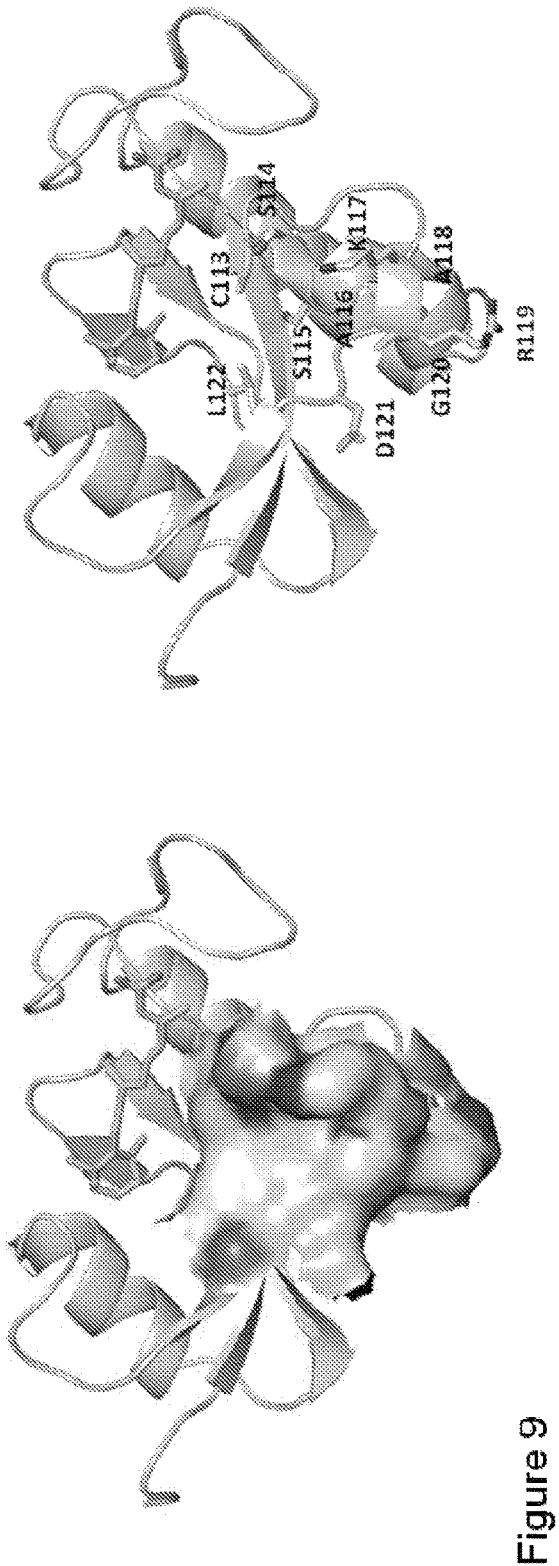

Though binding pockets of an active site can be defined with reference to one or more substrates, they may also be defined with reference to the active site itself, e.g., by examining the crystal structure of active site and identifying portions thereof where a substrate or portion thereof might conceivably associate or interact. For example, FIG. 8 shows six potential binding pockets apparent in the crystal structure of the Pin1 PPIase active site. Pocket P1 includes residues C113, S114, S115, A116, K117, A118, R119, G120, D121, and L122 within about 4 Å (FIGS. 9A, 9B, and 9C). Extending to consider residues within 8 Å, pocket P1 may include residues C57, H59, L61, D112, C113, S114, S115, A116, K117, A118, R119, G120, D121, L122, G123, A124, F125, Q129, M130, and F134 (FIGS. 10A, 10B, and 10C). Pocket P2 includes residues H59, R68, L122, M130, Q131, F134, S154, and H157 when considering only residues within about 4 Å and includes residues H59, L60, L61, V62, K63, R68, R69, D112, C113, S115, L122, F125, Q129, M130, Q131, K132, P133, F134, E135, S138, V150, T152, D153, S154, G155, I156, H157, and I159 when considering residues within 8 Å (FIGS. 11A, 11B, 11C, 12A, 12B, and 12C). Pocket P3 includes residues R68, Q129, M130, Q131, K132, and D153 when considering only residues within about 4 Å and includes R68, R69, G128, Q129, M130, Q131, K132, P133, F134, E135, F151, T152, D153, S154, G155, and H157 when considering residues within 8 Å (FIGS. 13A, 13B, 13C, 14A, 14B, and 14C). Pocket P4 includes K63, S67, R68, R69, and S154 within 4 Å and includes L61, V62, K63, H64, Q66, S67, R68, R69, P70, S71, S72, I78, D112, Q131, T152, D153, S154, G155, I156, and H157 when extended to within about 8 Å (FIGS. 15A, 15B, 15C, 16A, 16B, and 16C). Pocket P5 includes S71, S72, W73, Q75, E76, and Q77 within 4 Å and K63, R69, P70, S71, S72, W73, R74, Q75, E76, Q77, I78, T79, D112, and S114 within 8 Å (FIGS. 17A, 17B, 17C, 18A, 18B, and 18C). Finally, pocket P6 includes S71, S72, W73, D112, C113, and S114 within 4 Å and S71, S72, W73, R74, E104, S105, L106, A107, S108, Q109, F110, S111, D112, C113, S114, S115, A116, K117, A118, R119, and G120 within 8 Å (FIGS. 19A, 19B, 19C, 20A, 20B, and 20C). The residues included in each potential binding pocket are summarized in Table 7, in which a "Y" indicates that a residue is included in a given pocket.

TABLE 7

Summary of potential binding pockets P1-P6.

| Residue | P1 | P2 | P3 | P4 | P5 | P6 |
|---------|----|----|----|----|----|----|
| C57 | Y | | | | | |
| H59 | Y | Y | | | | |
| L60 | | Y | | | | |
| L61 | Y | Y | | Y | | |
| V62 | | Y | | Y | | |
| K63 | | Y | | Y | Y | |
| H64 | | | | Y | | |
| Q66 | | | | Y | | |
| S67 | | | | Y | | |
| R68 | | Y | Y | Y | | |
| R69 | | Y | Y | Y | Y | |
| P70 | | | Y | Y | | |
| S71 | | | Y | Y | Y | Y |
| S72 | | | Y | | Y | Y |
| W73 | | | | | Y | Y |
| R74 | | | | | Y | Y |
| Q75 | | | | | Y | |
| E76 | | | | | Y | |
| Q77 | | | | | Y | |
| I78 | | | | Y | Y | |
| T79 | | | | | Y | |
| E104 | | | | | | Y |
| S105 | | | | | | Y |
| L106 | | | | | | Y |
| A107 | | | | | | Y |
| S108 | | | | | | Y |
| Q109 | | | | | | Y |
| F110 | | | | | | Y |
| S111 | | | | | | Y |
| D112 | Y | Y | | Y | Y | Y |
| C113 | Y | Y | | | | Y |
| S114 | Y | | | | Y | Y |
| S115 | Y | Y | | | | Y |
| A116 | Y | | | | | Y |
| K117 | Y | | | | | Y |
| A118 | Y | | | | | Y |
| R119 | Y | | | | | Y |
| G120 | Y | | | | | Y |
| D121 | Y | | | | | |
| L122 | Y | Y | | | | |
| G123 | Y | | | | | |
| A124 | Y | | | | | |
| F125 | Y | Y | | | | |
| G128 | | | Y | | | |
| Q129 | Y | Y | Y | | | |
| M130 | Y | Y | Y | | | |
| Q131 | | Y | Y | Y | | |
| K132 | | Y | Y | | | |
| P133 | | Y | Y | | | |
| F134 | Y | Y | Y | | | |
| E135 | | Y | Y | | | |
| S138 | | Y | | | | |
| V150 | | Y | | | | |
| F151 | | | Y | | | |
| T152 | | Y | Y | Y | | |
| D153 | | Y | Y | Y | | |
| S154 | | Y | Y | Y | | |
| G155 | | Y | Y | Y | | |
| I156 | | Y | | Y | | |
| H157 | | Y | Y | Y | | |
| I159 | | Y | | | | |

As is evident from the definitions above, one or more pockets may have one or more residues in common. Potential binding pockets identified by examining the structure of an active site may or may not be identical to those identified by examining a co-crystal structure. A binding pocket identified by the latter method may include one or more potential pockets identified by examining the structure of an active site, or vice versa. For example, the high electron density pocket including residues K63, R69, and S71 shares residues with potential binding pockets P4, P5, and P6. In particular, P4 and P5 both include K63, R69, and S71. Similarly, the hydrophobic binding pocket including residues L122, M130, Q131, and F134 shares residues with P1, P2, P3, and P4. Like binding pockets identified by methods involving one or more reference molecules (e.g., from a co-crystal structure of Pin1 and a substrate such as ATRA), binding pockets identified by examining the structure of an active site (e.g., the PPIase active site of Pin1) can be used, alone or in combination, to identify, select, or design substrates (e.g., catalytic inhibitors) capable of associating with the active site or portion thereof. For instance, potential binding pockets P4 and P5 could be taken together to determine that a substrate should include a group capable of hydrogen bonding. Similar, potential binding pockets P2 and P3 could be taken together to determine that a substrate should include a hydrophobic group. Applying chemical intuition to this structural analysis may result in the design of one or more substrates (e.g., ATRA-related compound) capable of associating with the active site, as described herein.

In addition to being capable of physically and structurally associating (e.g., by means of intermolecular interactions including hydrogen bonding, van der Waals interactions, hydrophobic interactions, and other electrostatic interactions) with all or a portion of a Pin1 active site (e.g., one or more binding pockets of the PPIase active site), a Pin1 substrate must also be able to assume a conformation that allows it to associate with the active site or portion thereof directly. Although certain portions of a substrate may not directly participate in these associations, these portions of the substrate may still influence the overall conformation of the molecule, which may in turn have a significant impact on the potency of the substrate. Such conformational requirements may include the overall three-dimensional structure and orientation of the substrate in relation to all or a portion of the active site or portion thereof (e.g., a binding pocket), or the spacing between functional groups of a substrate including several chemical entities that directly interact with the Pin1 or Pin1-like binding pockets of an active site (e.g., a between a carboxyl group and a cycloalkyl head group that interact with a high electron density binding pocket and a hydrophobic binding pocket, respectively).

A Pin1 substrate may be an ATRA-related compound, which may be a retinoic acid compound. ATRA-related compounds need not be synthetically produced from ATRA. Indeed, many such species are readily commercially available. Instead, ATRA-related compounds could be designed manually, using a computer software package, or via comparison between ATRA and published molecular libraries. An ATRA-related compound according to the present invention may include one or more components of ATRA, such as the cyclohexenyl group or a modified version thereof, the "backbone" moiety or a modified version thereof, or the carboxylic acid group or a modified version thereof, or portions thereof. One or more of these groups or portions thereof may be modified, replaced, or eliminated, e.g., by adding, changing, or eliminating one or more substitutions, replacing one or more groups (e.g., replacing a carboxyl group with an ester group), and/or increasing or decreasing the size or length of a component of ATRA (e.g., replacing a six-membered ring with a seven-membered ring or increasing the length of a carbon chain), to yield an ATRA-related compound, as described herein. In some embodiments, an ATRA-related compound may include, in place of the cyclohexenyl group of ATRA, one or more rigid or sterically bulky groups such as one or more aryl, heteroaryl, cycloalkyl, cycloalkenyl, heterocycloakyl, or heterocycloalkenyl rings or a fusion thereof for interaction with the hydrophobic binding pocket (e.g., a pocket including residues such as L122, M130, Q131, and F134). A cycloalkyl group may optionally include one or more unsaturations (e.g., multiple bonds, such as double bonds, or rings) and alkyl substitutions and may optionally be fused to one or more aryl or heteroaryl groups. In some embodiments, an ATRA-related compound may include a "backbone" moiety that is an alkyl chain including one or more rings and/or one or more double bonds for association with the groove binding pocket. In certain embodiments, an ATRA-related compound includes the carboxylic acid group of ATRA or another group with a high electron density for interaction with the high electron density binding pocket (e.g., a pocket including residues K63 and R69). Additional modifications are described herein. In particular embodiments, an ATRA-related compound may include molecular components for association with each binding pocket of Pin1 (e.g., pockets P1, P2, P3, P4, P5, and P6 or a hydrophobic pocket, a high electron density pocket, and a backbone pocket). In other embodiments, an ATRA-related compound may include a non-optimized or non-optimal molecular component for association with one or more binding pockets, or may lack a molecular component for association with one or more binding pockets. For example, an ATRA-related compound may include a carboxyl group for association with the high electron density binding pocket and a carbon chain for association with the groove binding pocket and/or may not include a head group (e.g., a cyclohexenyl group or other sterically bulky group) for interaction with the hydrophobic binding pocket. In some embodiments, the absence of one or more components may not affect the ability of a substrate to associate with Pin1. For instance, a compound including a group too bulky to strongly associate with a hydrophobic binding pocket may still associate strongly with a high electron density pocket and potentially inactivate the PPIase active site by blocking the phosphorylation site.

The co-crystal structure of ATRA and Pin1 can be used to identify a Pin1 substrate capable of associating with all or a portion of a Pin1 active site including one or more binding pockets. A method of identifying a Pin1 substrate capable of associating with all of a portion of a Pin1 active site may include one or more of the following steps: i) generating, accessing, or otherwise obtaining (e.g., opening, modeling, or calculating) a three-dimensional model of the Pin1-ATRA complex based on the co-crystal structure; ii) identifying one or more Pin1 binding pockets for ATRA, as described herein; and iii) designing or selecting one or more substrates (e.g., ATRA-related compounds) based on the association between ATRA and the one or more Pin1 binding pockets. A method of identifying a Pin1 substrate capable of associating with all or a portion of a Pin1 active site may include the steps of: i) performing a fitting operation between a substrate (e.g., an ATRA-related compound) and all or a portion of the active site (e.g., one or more binding pockets) using a three-dimensional model (e.g., generated from structural coordinates obtained by crystallographic methods) of the Pin1 active site (e.g., using a molecular modeling program), ii) quantifying the association between the substrate (e.g., ATRA-related compound) and all or a portion of the active site (e.g., with a docking score produced by a molecular modeling program or by determining a binding energy, energy of deformation, or a binding affinity), and viii) measuring the catalytic activity of a complex of Pin1 and the substrate (e.g., using an in vitro assay, such as one of those described herein) to classify or determine the potency of a substrate relative to Pin1. The one or more binding pockets of Pin1 may be identified using a three-dimensional model of Pin1 or using a three-dimensional model generated from a co-crystal structure of Pin1 and ATRA. The substrate (e.g., ATRA-related compound) selected for evaluation may be selected based on the one or more Pin1 binding pockets (e.g., based on physiochemical intuition that a group or feature of a compound will interact with one or more binding pockets). The method may further involve, prior to performing the fitting operation, i) generating a three-dimensional model of Pin1 and ATRA on a computer using structural coordinates obtained from a co-crystal structure of Pin1 and ATRA; ii) utilizing the three-dimensional model to identify one or more Pin1 binding pockets for ATRA; and iii) selecting a substrate (e.g., an ATRA-related compound) for evaluation based on the one or more Pin1 binding pockets.

Measurement of Pin1 Marker Levels

In some aspects, the present invention pertains to the treatment of proliferative diseases, autoimmune diseases, and addiction conditions identified as coinciding with elevated Pin1 marker levels with retinoic acid compounds (e.g., ATRA-related compounds). In some aspects, the invention features the determination of Pin1 marker levels in a subject; where a retinoic acid compound (e.g., an ATRA-related compound) is administered in subjects where Pin1 marker levels are determined to be elevated. In other aspects, the invention can also feature the measurement of Pin1 marker levels (e.g., Ser71 phosphorylation or Pin1 degradation) subsequent to the administration of a retinoic acid compound in order to evaluate the progress of therapy in treating a proliferative disorder, autoimmune disease, or addiction condition or select a patient population for further treatment.

Accordingly, one aspect of the present invention relates to diagnostic assays for measuring levels of Pin1 marker, as well as Pin1 activity, in the context of a biological sample (e.g., tumor samples, blood, urine, biopsies, lymph, saliva, phlegm, and pus) to thereby determine whether an individual is a candidate for treatment with a retinoic acid compound. The invention features treatment of subjects exhibiting symptoms of a proliferative disorder, autoimmune disorder, or addiction condition; individuals at risk for developing a proliferative disorder, autoimmune disorder, or addiction condition; and subjects demonstrating a response to treatment of a proliferative disorder, autoimmune disorder, or addiction condition (e.g., subjects having Pin1 degradation after administration of a retinoic acid compound).

Diagnostic Assays

An exemplary method for detecting the presence or absence of Pin1 protein or nucleic acid in a biological sample involves obtaining a biological sample (e.g., tumor sample, blood, urine, biopsies, lymph, saliva, phlegm, and pus) from a test subject and contacting the biological sample with a compound or an agent capable of detecting Pin1 protein or a nucleic acid (e.g., mRNA, genomic DNA) that encodes Pin1 protein such that the presence of Pin1 protein or nucleic acid is detected in the biological sample. A preferred agent for detecting Pin1 mRNA or genomic DNA is a labeled nucleic acid probe capable of hybridizing to Pin1 mRNA or DNA. The nucleic acid probe can be, for example, a Pin1 nucleic acid or a corresponding nucleic acid such as an oligonucleotide of at least 15, 30, 50, 100, 250 or 500 nucleotides in length which is capable of specifically hybridizing under stringent conditions to Pin1 mRNA or genomic DNA. Other suitable probes for use in the diagnostic assays of the invention are described herein.

A preferred agent for detecting Pin1 marker is an antibody capable of binding to Pin1 protein, preferably an antibody with a detectable label. Antibodies can be polyclonal, or more preferably, monoclonal. An intact antibody, or a fragment thereof (e.g., Fab or F(ab')2) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

With respect to antibody-based detection techniques, one of skill in the art can raise anti-Pin1 antibodies against an appropriate antigen and/or immunogen, such as isolated and/or recombinant Pin1 or a portion or fragment thereof (including synthetic molecules, such as synthetic peptides) using no more than routine experimentation. Synthetic peptides can be designed and used to immunize animals, such as rabbits and mice, for antibody production. The nucleic and amino acid sequence of Pin1 is known (Hunter et al., WO 97/17986 (1997); Hunter et al., U.S. Pat. Nos. 5,952,467 and 5,972,697, the teachings of all of which are hereby incorporated by reference in their entirety) and can be used to design nucleic acid constructs for producing proteins for immunization or in nucleic acid detection methods or for the synthesis of peptides for immunization.

Conditions for incubating an antibody with a test sample can vary depending upon the tissue or cellular type. Incubation conditions can depend on the format employed in the assay, the detection methods employed, and the type and nature of the antibody used in the assay. One skilled in the art will recognize that any one of the commonly available immunological assay formats (such as radioimmunoassays, enzyme-linked immunoadsorbent assays, diffusion based Ouchterlony, or rocket immunofluorescent assays) can readily be adapted to employ the antibodies of the present invention. Examples of such assays can be found in Chard, "An Introduction to Radioimmunoassay and Related Techniques," Elsevier Science Publishers, Amsterdam, The Netherlands (1986); Bullock et al., "Techniques in Immunocytochemistry," Academic Press, Orlando, Fla. Vol. 1 (1982), Vol. 2 (1983), Vol. 3 (1985); Tijssen, "Practice and Theory of enzyme Immunoassays: Laboratory Techniques in Biochemistry and Molecular Biology," Elsevier Science Publishers, Amsterdam, The Netherlands (1985).

The detection method of the invention can be used to detect Pin1 mRNA, protein, or genomic DNA in a biological sample in vitro as well as in vivo. For example, in vitro techniques for detection of Pin1 mRNA include Northern hybridizations and in situ hybridizations. In vitro techniques for detection of Pin1 protein include enzyme linked immunoadsorbent assays (ELISAs), Western blots, immunoprecipitations, immunofluorescence, or quantitative sequencing reactions. In vitro techniques for detection of Pin1 genomic DNA include Southern hybridizations. The detection of genomic mutations in Pin1 (or other genes that effect Pin1 marker levels) can be used to identify inherited or somatic mutations. Furthermore, in vivo techniques for detection of Pin1 protein include introducing into a subject a labeled anti-Pin1 antibody. For example, the antibody can be labeled with a radioactive marker whose presence and location in a subject can be detected by standard imaging techniques.

In another embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods involve obtaining a control biological sample from a control subject, contacting the control sample with a compound or agent capable of detecting Pin1 marker such that the presence of Pin1 marker is detected in the biological sample, and comparing the presence of Pin1 marker in the control sample with the presence of Pin1 marker in the test sample.

The immunological assay test samples of the present invention may include cells, protein or membrane extracts of cells, blood or biological fluids such as ascites fluid or brain fluid (e.g., cerebrospinal fluid). The test sample used in the above-described method is based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized. The invention also encompasses kits for detecting the presence of Pin1 in a biological sample. For example, the kit can comprise a labeled compound or agent capable of detecting Pin1 protein or mRNA in a biological sample; means for determining the amount of Pin1 in the sample; and means for comparing the amount of Pin1 in the sample with a standard. The compound or agent can be packaged in a suitable container. The kit can further comprise instructions for using the kit to detect Pin1 protein or nucleic acid.

Pin1 marker levels can also be measured in an assay designed to evaluate a panel of target genes, e.g., a microarray or multiplex sequencing reaction. In the embodiments of the invention described herein, well known biomolecular methods such as northern blot analysis, RNase protection assays, southern blot analysis, western blot analysis, in situ hybridization, immunocytochemical procedures of tissue sections or cellular spreads, and nucleic acid amplification reactions (e.g., polymerase chain reactions) may be used interchangeably. One of skill in the art would be capable of performing these well-established protocols for the methods of the invention. (See, for example, Ausubel, et al., "Current Protocols in Molecular Biology," John Wiley & Sons, NY, N.Y. (1999)).

Diagnostic assays can be carried out in, e.g., subjects diagnosed with or at risk of a proliferative disorder, autoimmune disease, or addiction condition (e.g., any of those described herein).

Prognostic Assays

The diagnostic methods described herein can furthermore be utilized to identify subjects having or at risk of developing a disease or disorder associated with aberrant Pin1 expression or activity. For example, the assays described herein, such as the preceding diagnostic assays or the following assays, can be utilized to identify a subject having or at risk of developing a disease, disorder, or condition associated with Pin1 marker (e.g., a proliferative disorder, autoimmune disease, or addiction condition). Thus, the present invention provides a method for identifying a disease or disorder associated with aberrant Pin1 expression or activity in which a test sample is obtained from a subject and Pin1 protein or nucleic acid (e.g., mRNA, genomic DNA) is detected, wherein the presence of Pin1 protein or nucleic acid is diagnostic for a subject having or at risk of developing a Pin1-associated disease, disorder, or condition and is, therefore, susceptible to treatment with a retinoic acid compound (e.g., an ATRA-related compound).

Furthermore, the present invention provides methods for determining whether a subject can be effectively treated with a retinoic acid compound (e.g., an ATRA-related compound) for a disorder associated with aberrant Pin1 expression or activity in which a test sample is obtained and Pin1 protein or nucleic acid expression or activity is detected (e.g., wherein the abundance of Pin1 protein or nucleic acid expression or activity is diagnostic for a subject that can be administered the agent to treat a disorder Pin1-associated disorder). The invention also provides for a method of identifying a patient population previously treated with a retinoic acid compound (e.g., an ATRA-related compound) that is susceptible to such treatment (e.g., has Pin1 degradation) and selecting the patient population for additional treatment with the retinoic acid compound.

In one embodiment, the present invention provides methods for determining Pin1 post-translational modifications. For example, phosphorylation of Pin1 on Ser71 in the catalytic active site by the tumor suppressor DAPK1 completely inhibits Pin1 catalytic activity and cell function to promote oncogenesis. More importantly, phosphorylation of Pin1 on Ser71 in the catalytic active site also prevents retinoic acid compounds (e.g., ATRA-related compounds) from binding to Pin1 active site and inducing Pin1 degradation and inhibiting Pin1 function. Therefore, detecting reduced Ser71 phosphorylation using phospho-specific Pin1 antibodies that we have generated is a method of selecting patients for treatments with a retinoic acid compound (e.g., an ATRA-related compound) and explaining why some patients may not respond to treatments with a retinoic acid compound. Because aberrantly proliferating cells exhibit reduced Ser71 phosphorylation, these cells are more sensitive to treatments with a retinoic acid compound compared to normal cells.

The methods of the invention can also be used to detect genetic alterations in a Pin1 gene, thereby determining if a subject with the altered gene is at risk for a disorder associated with the Pin1 gene and, consequently, a candidate for retinoic acid therapy. In preferred embodiments, the methods include detecting, in a sample of cells from the subject, the presence or absence of a genetic alteration characterized by at least one of an alteration affecting the integrity of a gene encoding a Pin1-protein, or the misexpression of the Pin1 gene. For example, such genetic alterations can be detected by ascertaining the existence of at least one of 1) a deletion of one or more nucleotides from a Pin1 gene; 2) an addition of one or more nucleotides to a Pin1 gene; 3) a substitution of one or more nucleotides of a Pin1 gene, 4) a chromosomal rearrangement of a Pin1 gene; 5) an alteration in the level of a messenger RNA transcript of a Pin1 gene, 6) aberrant modification of a Pin1 gene, such as of the methylation pattern of the genomic DNA, 7) the presence of a non-wild type splicing pattern of a messenger RNA transcript of a Pin1 gene, 8) a non-wild type level of a Pin1-protein, 9) allelic loss of a Pin1 gene, and 10) inappropriate post-translational modification of a Pin1-protein. As described herein, there are a large number of assay techniques known in the art which can be used for detecting alterations in a Pin1 gene. A preferred biological sample is a tissue or serum sample isolated by conventional means from a subject, e.g., a cardiac tissue sample.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in the Pin1-gene (see Abravaya et al. (1995) Nucleic Acids Res 0.23:675-682). This method can include the steps of collecting a sample from a patient, isolating nucleic acid (e.g., genomic, mRNA or both) from the sample, contacting the nucleic acid sample with one or more primers which specifically hybridize to a Pin1 gene under conditions such that hybridization and amplification of the Pin1-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli, J. C. et al., (1990) Proc. Natl. Acad. Sci. USA 87:1874-1878), transcriptional amplification system (Kwoh, D. Y. et al, (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a Pin1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in Pin1 can be identified by hybridizing a sample and control nucleic acids, e.g., DNA or RNA, to high density arrays containing hundreds or thousands of oligonucleotide probes (Cronin, M. T. et al. (1996) Human Mutation 7: 244-255; Kozal, M. J. et al. (1996) Nature Medicine 2: 753-759). For example, genetic mutations in Pin1 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the Pin1 gene and detect mutations by comparing the sequence of the sample Pin1 with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Biotechniques 19:448), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in the Pin1 gene include methods in which protection from cleavage agents is used to detect mismatched bases in RNA/RNA or RNA/DNA heteroduplexes (Myers et al. (1985) Science 230: 1242). In general, the art technique of "mismatch cleavage" starts by providing heteroduplexes formed by hybridizing (labeled) RNA or DNA containing the wild-type Pin1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with 51 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Nat Acad Sci USA 85:4397; Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in Pin1 cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on a Pin1 sequence, e.g., a wild-type Pin1 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in Pin1 genes. For example, single strand conformation polymorphism (SSCP) may be used to detect differences in electrophoretic mobility between mutant and wild type nucleic acids (Orita et al. (1989) Proc Natl. Acad. Sci. USA: 86:2766, see also Cotton (1993) Mutat Res 285:125-144; and Hayashi (1992) Genet Anal Tech Appl 9:73-79). Single-stranded DNA fragments of sample and control Pin1 nucleic acids will be denatured and allowed to renature. The secondary structure of single-stranded nucleic acids varies according to sequence; the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl Acad. Sci USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner et al. (1993) Tibtech 11:238). In addition it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a Pin1 gene.

Furthermore, any cell type or tissue in which Pin1 is expressed may be utilized in the prognostic assays described herein.

As with the diagnostic assay described above, prognostic assays of Pin1 activity can be included as part of a panel of target genes.

Additional methods of detecting Pin1 activity and diagnosing Pin1 related disorders are disclosed in U.S. Patent Application Publication Nos.: 2009/0258352, 2008/0214470, 2006/0074222, 2005/0239095, US2002/0025521, U.S. Pat. No. 6,495,376, and PCT Application Publication No. WO02/065091, each of which is hereby incorporated by reference in its entirety.

The present invention also features methods and compositions to diagnose, treat and monitor the progression of a disorder, disease, or condition described herein (e.g., a cellular proliferation disorder, autoimmune disease, or addiction condition) by detection and measurement of, for example, Pin1 substrates (or any fragments or derivatives thereof) containing a phosphorylated Ser/Thr-Pro motif in a cis or trans conformation, as described in U.S. patent application Ser. No. 13/504,700, which is hereby incorporated by reference in its entirety. The methods can include measurement of absolute levels of the Pin1 substrate (examples of which are listed in Tables 2, 3A, 3B, 3C, and 4 of WO2012125724A1) in a cis or trans conformation as compared to a normal reference, using conformation specific antibodies. For example, a serum level or level in a biopsy of a Pin1 substrate in the cis or trans conformation that is less than 5 ng/ml, 4 ng/ml, 3 ng/ml, 2 ng/ml, or less than 1 ng/ml serum or a biopsy is considered to be predictive of a good outcome in a patient diagnosed with a disorder (e.g., a disorder associated with a deregulation of Pin1 activity). A serum level of the substrate in the cis or trans conformation that is greater than 5 ng/ml, 10 ng/ml, 20 ng/ml, 30 ng/ml, 40 ng/ml, or 50 ng/ml is considered diagnostic of a poor outcome in a subject already diagnosed with a disorder, e.g., associated with a deregulation of Pin1 activity.

For diagnoses based on relative levels of substrate in a particular conformation (e.g., a Pin1 substrate in the cis or trans conformation), a subject with a disorder (e.g., a disorder associated with a deregulation of PPIase activity) will show an alteration (e.g., an increase of 10%, 20%, 30%, 40%, 50%, 60%, 70%, 80%, 90%, or more) in the amount of the substrate in, for example, the cis conformation. A normal reference sample can be, for example, a prior sample taken from the same subject prior to the development of the disorder or of symptoms suggestive of the disorder, a sample from a subject not having the disorder, a sample from a subject not having symptoms of the disorder, or a sample of a purified reference polypeptide in a given conformation at a known normal concentration (i.e., not indicative of the disorder).

Standard methods may be used to measure levels of the substrate in any bodily fluid, including, but not limited to, urine, blood, serum, plasma, saliva, amniotic fluid, or cerebrospinal fluid. Such methods include immunoassay, ELISA, Western blotting, and quantitative enzyme immunoassay techniques.

For diagnostic purposes, conformation-specific antibodies may be labeled. Labeling of an antibody is intended to encompass direct labeling of the antibody by coupling (e.g., physically linking) a detectable substance to the antibody, as well as indirect labeling the antibody by reacting the antibody with another reagent that is directly labeled. For example, an antibody can be labeled with a radioactive or fluorescent marker whose presence and location in a subject can be detected by standard imaging techniques.

The diagnostic methods described herein can be used individually or in combination with any other diagnostic method described herein for a more accurate diagnosis of the presence or severity of a disorder (e.g., a cellular proliferation disorder, autoimmune disorder, addiction condition, or a neurological disorder). Examples of additional methods for diagnosing such disorders include, e.g., examining a subject's health history, immunohistochemical staining of tissues, computed tomography (CT) scans, or culture growths.

Monitoring the Effects of Retinoic Acid Treatment, and Disease Progression

In one embodiment, the present invention features a method for monitoring the effectiveness of treatment of a subject with a retinoic acid compound (e.g., an ATRA-related compound) comprising the steps of (i) obtaining a pre-administration sample from a subject prior to administration of the compound; (ii) detecting the level of expression or activity of a Pin1 protein, Pin1 phosphorylation on Ser71, mRNA, or genomic DNA in the pre-administration sample; (iii) obtaining one or more post-administration samples from the subject after administration of the compound; (iv) detecting the level of expression or activity of the Pin1 protein, mRNA, or genomic DNA in the post-administration samples; (v) comparing the level of expression or activity of the Pin1 protein, mRNA, or genomic DNA in the pre-administration sample with the Pin1 protein, mRNA, or genomic DNA in the post administration sample or samples; and (vi) altering the administration of the retinoic acid compound (e.g., ATRA-related compound) to the subject accordingly. According to such an embodiment, Pin1 expression, phosphorylation or activity may be used as an indicator of the effectiveness of the retinoic acid compound (e.g., ATRA-related compound), even in the absence of an observable phenotypic response.

In another embodiment, the present invention provides a method of selecting a patient population who may derive increased benefit from treatment with a retinoic acid compound (e.g., an ATRA-related compound) comprising the steps of (i) administering a retinoic acid compound to a subject having a proliferative disorder; (ii) detecting whether a subject has Pin1 degradation; and (iii) selecting a subject having Pin1 degradation for additional treatment with a retinoic acid compound. This method may include additional steps such as detecting the level of a Pin1 marker from a sample from a subject prior to the first administration of a retinoic acid compound to a subject; obtaining a sample from a subject after the first administration of a retinoic acid compound for detection of the level of a Pin1 marker; and comparing the levels of Pin1 marker in pre-administration and post-administration samples to determine whether the subject has Pin1 degradation. For example, a subject exhibiting a response to initial treatment with a retinoic acid compound (e.g., an ATRA-related compound) and also showing Pin1 degradation may be a candidate for additional treatment with the retinoic acid compound, whereas a subject not also showing Pin1 degradation may be a candidate for treatment with, e.g., a different retinoic acid compound.

In another embodiment, the diagnostic methods described herein can also be used to measure the levels of, for example, polypeptides (e.g., Pin1 substrates listed in Tables 2, 3A, 3B, 3C, and 4 of WO2012125724A1) with pSer/Thr-Pro motifs in the cis or trans conformation using conformation specific antibodies. The methods can include repeated measurements, using, e.g., conformation specific antibodies, for diagnosing the disorder and monitoring the treatment or management of the disorder. In order to monitor the progression of the disorder in a subject, subject samples can be obtained at several time points and conformation specific antibodies can be used to monitor the levels of cis and trans isomers of Pin1 substrates (e.g., those listed in Tables 2, 3A, 3B, 3C, and 4 of WO02012125724 A1). For example, the diagnostic methods can be used to monitor subjects during chemotherapy (e.g., therapy with a retinoic acid compound or other agent described herein). In this example, serum samples from a subject can be obtained before treatment with a chemotherapeutic agent, again during treatment with a chemotherapeutic agent, and again after treatment with a chemotherapeutic agent. In this example, the level of Pin1 substrate with a pSer/Thr-Pro motif in the cis conformation in a subject is closely monitored using the conformation-specific antibodies of the invention and, if the level of Pin1 substrate with a pSer/Thr-Pro motif in the cis conformation begins to increase during therapy, the therapeutic regimen for treatment of the disorder can be modified as determined by the clinician (e.g., the dosage of the therapy may be changed or a different therapeutic may be administered). The monitoring methods of the invention may also be used, for example, in assessing the efficacy of a particular drug or therapy in a subject, determining dosages, or in assessing progression, status, or stage of the disease, disorder, or condition.

Methods of Treatment

The present invention provides for both prophylactic and therapeutic methods of treating a subject at risk of (or susceptible to) or having a proliferative disorder, autoimmune disorder, or addiction condition (e.g., a disorder associated with increased Pin1 expression or activity) with a retinoic acid compound (e.g., an ATRA-related compound).

Certain embodiments of the invention feature formulation of a retinoic acid compound (e.g., an ATRA-related compound) for, e.g., controlled or extended release. Many strategies can be pursued to obtain controlled and/or extended release in which the rate of release outweighs the rate of metabolism of the therapeutic compound. For example, controlled release can be obtained by the appropriate selection of formulation parameters and ingredients (e.g., appropriate controlled release compositions, excipients, formulation types, and coatings). Examples include single or multiple unit tablet or capsule compositions, oil solutions, suspensions, emulsions, microcapsules, microspheres, nanoparticles, patches, films, and liposomes. The release mechanism can be controlled such that the retinoic acid compound and/or a second therapeutic compound used in combination with a retinoic acid compound is released at period intervals, near-simultaneously with administration, or with delay. In a delayed release formulation, one of the agents of the combination could be affected such that a particular agent is released earlier than another agent or both agents could be released at approximately the same time.

Certain embodiments of the invention feature an isotopically substituted (e.g., deuterated) or labeled retinoic acid compound (e.g., ATRA-related compound) that is made by replacing one or all atoms of a given element with an isotope of that element. For example, a fully or partially deuterated retinoic acid compound could be made by replacing some or all hydrogen atoms with deuterium atoms using state of the art techniques (e.g., as described herein and at www.concertpharma.com).

Prophylactic Methods

In one aspect, the invention provides a method for preventing a proliferative disorder, autoimmune disorder, or addiction condition in a subject by administering to the subject a retinoic acid compound (e.g., an ATRA-related compound). Subjects at risk for a disease, disorder, or condition which is caused, characterized, or contributed to by aberrant Pin1 expression or activity can be identified by, for example, any or a combination of diagnostic or prognostic assays as described herein. Administration of a retinoic acid compound can occur prior to the manifestation of symptoms characteristic of the Pin1 aberrancy, such that a disease or disorder is prevented or, alternatively, delayed in its progression.

Combination Therapies

Anti-proliferative and other anti-cancer compounds (e.g., those described herein, including anti-angiogenic compounds), anti-viral compounds, anti-microbial compounds, anti-inflammatory compounds, and other therapeutic species are useful for treating proliferative disorders, autoimmune diseases, and addiction conditions in combination with the retinoic acid compounds of the invention. With regard to anti-proliferative compounds, the ability of a compound to inhibit the growth of a neoplasm can be assessed using known animal models.

Compounds which are known to interact with other proteins implicated in Pin1 signaling pathways can also be useful in combination with a retinoic acid compound (see, e.g., the targets and compounds in Table 5 of WO2012125724A1). Such compounds can act synergistically with a retinoic acid compound (e.g., an ATRA-related compound). Additionally, co-administration with a retinoic acid compound may result in the efficacy of the therapeutic agent at lower (and thus safer) doses (e.g., at least 5%, 10%, 20%, 50%, 80%, 90%, or even 95%) less than when the therapeutic agent is administered alone.

Therapy according to the invention may be performed alone or in conjunction with another therapy and may be provided at home, a doctor's office, a clinic, a hospital's outpatient department, or a hospital. Treatment optionally begins at a hospital so that the doctor can observe the therapy's effects closely and make any adjustments that are needed, or it may begin on an outpatient basis. The duration of the therapy depends on the type of disease, disorder, or condition being treated; the age and condition of the patient; the stage and type of the patient's disease; and how the patient responds to the treatment. Additionally, a person having a greater risk of developing a proliferative or autoimmune disease may receive treatment to inhibit or delay the onset of symptoms.

Routes of administration for the various embodiments include, but are not limited to, topical, transdermal, transmucosal, transepithelial, nasal, and systemic administration (such as, intravenous, intramuscular, subcutaneous, cutaneous, injection, infusion, infiltration, irrigation, intra-articular, intra-tumoral, inhalation, rectal, buccal, vaginal, intraperitoneal, intraarticular, ophthalmic, otic, or oral administration). As used herein, "systemic administration" refers to all nondermal routes of administration, and specifically excludes topical and transdermal routes of administration. Depending on the intended use, a retinoic acid compound or salt thereof, optionally in combination with one or more additional therapeutic agents, may be prepared in any useful manner and with any useful components such as pharmaceutical excipients, coatings, fillers, bulking agents, viscosity enhancers/reducers, chelating agents, adjuvants, disintegrants, lubricants, glidants, binders, stabilizers, buffers, solubilizers, solvents, dispersion media, diluents, dispersion aids, suspension aids, granulating aids, liquid vehicles, buffers, propellants, tonicity modifiers, isotonic agents, thickening or emulsifying agents, surfactants, surface altering agents, flavoring or taste-masking agents, preservatives, coloring agents, perfuming agents, oils, waxes, carbohydrates, polymers, permeability enhancers, or other components. Such species are well known in the art (see for example Remington's *The Science and Practice of Pharmacy*, 21$^{st}$ Edition, A. R. Gennaro; Lippincott, Williams & Wilkins, Baltimore, Md., 2006). Conventional excipients and accessory ingredients, including those approved for use in humans and/or for veterinary use, may be used in any pharmaceutical composition of the invention, except insofar as any conventional excipient or accessory ingredient may be incompatible with a retinoic acid compound of the invention. An excipient or accessory ingredient may be incompatible with a component of a retinoic acid compound if its combination with the compound may result in any undesirable biological effect or otherwise deleterious effect.

Excipients and other useful components may make up any total mass or volume of a pharmaceutical composition including a retinoic acid compound, including greater than 40%, 50%, 60%, 70%, 80%, 90%, or 95% of a composition. Similarly, a pharmaceutical composition may include any useful amount of retinoic acid compound, e.g., between 0.1% and 100% (wt/wt) of a pharmaceutical composition. Pharmaceutical compositions including retinoic acid compounds of the invention and/or for use in the methods of the invention may be prepared, packaged, and/or sold in bulk, as single unit doses, and/or as a plurality of single unit doses, where a "unit dose" is a discrete amount of a pharmaceutical composition including a predetermined amount of a retinoic acid compound.

A retinoic acid compound may be preparing in any useful form of a pharmaceutical composition suitable for a variety of routes of administration. For example, pharmaceutical compositions of the invention may be prepared in liquid dosage forms (e.g., emulsions, microemulsions, nanoemulsions, solutions, suspensions, syrups, and elixirs), injectable forms, solid dosage forms (e.g., capsules, tablets, pills, powders, films, and granules), dosage forms for topical and/or transdermal administration (e.g., liniments, ointments, pastes, creams, lotions, gels, powders, solutions, sprays, inhalants, and patches), suspensions, powders, and other forms.

In combination therapy (e.g., administration of a retinoic acid compound with a second therapeutic agent), the dosage and frequency of administration of each component of the combination can be controlled independently. For example, one compound may be administered three times per day, while the second compound may be administered once per day. Alternatively, one compound may be administered earlier and the second compound may be administered later. Combination therapy may be given in on-and-off cycles that include rest periods so that the patient's body has a chance to recover from any as yet unforeseen side effects induced by one or more therapeutic agents. The compounds may also be formulated together, e.g., as described herein, such that one administration delivers both compounds.

Each compound of the combination may be formulated in a variety of ways that are known in the art. For example, the first and second anti-proliferative agents may be formulated together or separately. Desirably, the first and second anti-proliferative agents are formulated together for the simultaneous or near simultaneous administration of the agents. Such co-formulated compositions can include the two drugs together in the same pill, ointment, cream, foam, capsule, liquid, etc. It is to be understood that, when referring to the formulation of combinations of the invention, the formulation technology employed is also useful for the formulation of the individual agents of the combination, as well as other combinations of the invention. By using different formulation strategies for different agents, the pharmacokinetic profiles for each agent can be suitably matched.

The individually or separately formulated agents can be packaged together as a kit. Non-limiting examples include kits that contain, e.g., two pills, a pill and a powder, a suppository and a liquid in a vial, two topical creams, ointments, foams etc. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. The kit may be include one or more single-use unit doses or multiple-use doses for a particular patient (e.g., at a constant dose or in which the individual compounds may vary in potency as therapy progresses). Alternatively, the kit may contain multiple doses suitable for administration to multiple patients ("bulk packaging"). The kit components may be assembled in cartons, blister packs, bottles, tubes, and the like.

Materials and Methods

Cell Culture and Reagents

In the experiments described below, 293T, HeLa, AU565, BT474, HCC1937, MCF7, MDA-MB-231, MDA-MB-468, SKBR3 and T47D cells (originally obtained from ATCC and maintained in our laboratory) were cultured in Dulbecco's modified Eagle's medium (DMEM), while NB4 cells (obtained from the Pandolfi lab at BIDMC) was cultured in RPMI-1640 and immortalized human mammary epithelial cells (HMLE) and MCF10A cells were cultured in F12/DMEM medium. RARα, β, γ triple KO MEFs were from Dr. Hugues de Thé (Université Paris Diderot). HMLE cells and transformed HMLE cells (HMLE-Ras) were kindly provided by Dr. Robert A. Weinberg, and maintained as described (Elenbaas et al. (2001) Genes Dev. 15:50-65). HeLa and HEK293 cells were maintained in DMEM with 10% FBS. Freshly isolated primary normal human MEC or breast cancer cells were cultured in MEGM with supplements (Keller et al. (2012) Proc. Natl. Acad. Sci. USA 109:2772-2777).

All mediums were supplemented with 10% fetal bovine serum (FBS) and all of the cells were cultured at 37° C. in a humidified incubator containing 5% CO2. HA-Pin1 was previously described. 13cRA, ATRA, EGCG and Juglone were from purchased from Sigma. ATRA-releasing pellets were from Innovative Research of America. All mutations were generated by site-directed mutagenesis. Antibodies against various proteins were obtained from the following sources: mouse monoclonal antibodies: Pin1 as described by Liou et al. (2002) Proc. Natl. Acad. Sci. USA 99:1335-40; α-tubulin, β-actin, Flag from Sigma; cyclin D1 from Santa Cruz Biotechnology; rabbit antibodies: HER2, ERa, PML (immunostaining), RARα (immunoblotting) from Santa Cruz Biotechnology. Antibodies against pS71 Pin1 were described by Lee et al. (2011) Mol. Cell. 22:147-159. AC-93253, Ro-415253 and DAPK1 inhibitor were purchased from Sigma Aldrich.

PPIase Assays

The PPIase activity on GST-Pin1, GST-FKBP12, or GST-cyclophilin in response to 13cRA or ATRA were determined using the chymotrypsin coupled PPIase activity assay with the substrate Suc-Ala-pSer-Pro-Phe-pNA (SEQ ID NO: 2), Suc-Ala-Glu-Pro-Phe-pNA (SEQ ID NO: 3) or Suc-Ala-Ala-Pro-Phe-pNA (SEQ ID NO: 4) (50 mM) in a buffer containing 35 mM HEPES (pH 7.8), 0.2 mM DTT, and 0.1 mg/ml BSA, at 10° C. Compounds were preincubated with enzymes for 0.5 to 2 hours at 4° C. $K_i$ values obtained from PPIase assays are derived from the Cheng-Prusoff equation:

$$K_i = \frac{IC_{50}}{1 + \frac{S}{K_m}}$$

where $K_m$ is the Michaelis constant for the used substrate, S is the initial concentration of the substrate in the assay, and the $IC_{50}$ value is of the inhibitor.

Cell Growth Assays

For cell growth assays described below, cells were seeded in a density of 3000 cells per well in 96-well flat-bottomed plates, and incubated for 24 h in 10% FBS-supplemented DMEM culture medium. Cells were then treated with ATRA alone or in combination with other drugs. Control cells received DMSO at a concentration equal to that in drug-treated cells. After 72 hours, the number of cells was counted after trypsin digestion, or medium containing 0.5 mg/ml 3-(4,5-dimethylthiazol-2-yl)-2,5-diphenyl-2H-tetrazolium bromide was added to each well for 2 hours of incubation at 37° C., followed by removal of the media before the addition of 200 µl DMSO. Absorbance was determined at 570 nm.

Immunoprecipitation and Immunoblotting

For immunoprecipitation and immunoblotting in the examples below, cells were polyethylenimine (PEI)- or lipofemamine-transfected with 8 µg of various plasmids, incubated in 10 cm dishes for 24 hours, and subsequently treatment with drugs as needed. When harvesting, cells were lysed for 30 minutes at 4° C. in an IP lysis buffer (50 mM HEPES, pH7.4, 150 mM NaCl, 1% Tritin X-100, and 10% glycerol) with freshly added phosphatase and protease inhibitors consisting of 100 µM 4-(2-aminoethyl)-benzenesulfonyl fluoride, 80 nM aprotinin, 5 µM bestatin, 1.5 µM E-64 protease inhibitor, 2 µM leupeptin, 1 µM pepstatin A, 2 mM imidazole, 1 mM sodium fluoride, 1 mM sodium molybdate, 1 mM sodium orthovanadate, and 4 mM sodium tartrate dihydrate. After centrifugation at 13,000 g for 10 minutes, one tenth of the supernatant was stored as input, and the remainder was incubated 12 hours with M2 Flag agarose (Sigma). After brief centrifugation, immunoprecipitates were collected, extensively washed with the aforementioned lysis buffer twice, suspended in 2×SDS sample buffer (100 mM Tris-HCl, pH 6.8, 4% SDS, 5% β-mercaptoethanol, 20% glycerol, and 0.1% bromphenol blue), boiled for 10 minutes, and subjected to immunoblotting analysis. Equal amounts of protein were resolved in 15% SDS-polyacrylamide gels. After electrophoresis, gel was transferred to nitrocellulose membranes using a semidry transfer cell. The transblotted membrane was washed twice with Tris-buffered saline containing 0.1% Tween 20 (TBST). After blocking with TBST containing 5% bovine serum albumin (BSA) for 1 hour, the membrane was incubated with the appropriate primary antibody (diluted 1:1000) in 2% BSA-containing TBST at 4° C. overnight. After incubation with the primary antibody, the membrane was washed three times with TBST for a total of 30 minutes followed by incubation with horseradish peroxidase (HRP)-conjugated goat anti-rabbit or anti-mouse IgG (diluted 1:2500) for 1 hour at room temperature. After three extensive washes with TBST for a total of 30 minutes, the immunoblots were visualized by enhanced chemiluminescence.

Immunostaining and Fluorescent Microscopy

Human APL samples were kindly provided by Dr. Eduardo Rego from Brazil. Tissue samples were washed with PBS and fixed with 4% paraformaldehyde at room temperature for 20 minutes, followed by permeabilization and blocking with PBS containing 0.1% Triton X-100 and 5% FBS for 1 hour. After another wash with PBS, immunostaining was performed by incubating the cells with mouse anti-Pin1 (1:1000), or rabbit anti-PML (Santa Cruz; 1:100) primary antibodies at 4° C. overnight. Primary antibodies were diluted in PBS containing 0.1% Triton X-100, 0.2% BSA, 0.5 mM PMSF, and 1 mM dithiothreitol. After washing with PBS, secondary Alexa Fluor 488-conjugated goat anti-mouse antibodies or Alexa Fluor 564-conjugated goat anti-rabbit antibodies (Invitrogen; 1:200) were added at room temperature for 2 hours. Samples were nuclear counterstained with 4,6-diamidino-2-phenylindole (DAPI), mounted and visualized with a LSM510 confocal imaging system. For centrosome duplication assays, NIH3T3 cells were used. Cells were synchronized in G1/S phase by adding 10 µg/ml aphidicolin for 24 hours, then fixed with 4% paraformaldehyde at room temperature for 20 minutes. Cells were then stained for centrosomes with anti-γ-tubulin antibodies (Sigma; 1:100) and analyzed by confocal microscopy.

Animal Studies

For xenograft experiments, $2 \times 10^6$ of MDA-MB-231 parent cells or expressing Pin1 or control vectors were injected subcutaneously into flank of 8 weeks-old BALB/c nude mice (Jackson Laboratories). After one week, when tumor growth was just notable, mice were randomly selected to receive ATRA treatment. For intraperitoneal injection, vehicle or 12.5 mg/kg ATRA were administered three times a week for 8 weeks. For implantation, placebo, 5 or 10 mg 21 day ATRA-releasing pellets (Innovative Research of America) were implanted one week after injection in the back of nude mice. Tumor sizes were recorded weekly by a caliber for up to 8 weeks and tumor volumes were calculated using the formula $L \times W^2 \times 0.52$, where L and W represent length and width, respectively. For NB4 cells transplantation, 8 weeks-old NOD.Cg-prkdc$^{scid}$ ll2rg$^{tm1 Wjl}$/SzJ (termed NSG) were used as transplant recipients after sublethal irradiation at 350 Gy. Each mouse was transplanted with $5 \times 10^5$ NB4 cells stably expressing Tet-on shPin1 via retro-orbital injection. Five days later, mice were randomly selected to receive regular or doxycycline food and survival curve was recorded. For PML-RARα transgenic cells transplantation, each C57BL/6 mice were given 350 Gy irradiation followed by transplantation with $1 \times 10^6$ APL cells from hCG-PML-RARα transgenic mice. After 5 days, mice were randomly selected to receive placebo (21 days placebo-releasing pills), ATRA (5 mg of 21 days ATRA-releasing pills) or EGCG (12.5 mg/kg/day, intraperitoneal), Juglone (1mg/kg/day, intravenous). Mice were sacrificed 3 weeks after when APL blastic cells appeared in peripheral blood smear of placebo mice. Spleen weight was measured and bone marrow was collected for immunoblotting detection on PML-RARα and Pin1. Animal work was carried out in compliance with the ethical regulations approved by the Animal Care Committee, Beth Israel Deaconess Medical Center, Boston, Mass., USA.

Human APL Samples

Bone marrow aspirates were obtained with informed consent from the iliac crest of patients in whom the diagnosis of acute promyelocytic leukemia was suspected based on the morphological evaluation of peripheral blood smear. Immediately after the procedure, therapy with ATRA was started. Second bone marrow aspirate samples were obtained on day 3 or 10 of ATRA therapy in order to complement the laboratorial investigation of the cases. Samples tested positive for the PML/RARα rearrangement by RT-PCR. The human sample collection has been approved by the Institutional Review Board at University of Sao Paulo (HCRP #13496/2005) or at Tor Vergata University (IRB #12/07).

Generation of Stable Cell Lines

For overexpression, Pin1 and RAB2A CDS were subcloned into the pBabe retroviral vector or pBybe lentiviral vector. To overexpress Rab2A and the Q58H mutant using lentivirus-mediated gene expression at levels similar to or 3 times over the endogenous level, less optimal Kozak sequences were introduced into the vector, namely GCCTTT and GCCGCC, respectively. Specific point mutations were introduced using the Quickchange kit (Stratagene) and sequences were verified. All lentiviral shRNA constructs were provided by Dr. William C. Hahn. The target sequence of Pin1 shRNA is CCACCGTCACACAGTATTTAT (SEQ ID NO: 5). The target sequences of Rab2A shRNAs are GCTCGAATGATAACTATTGAT (SEQ ID NO: 6) and CCAGTGCATGACCTTACTATT (SEQ ID NO: 7). The production of retroviruses or lentiviruses as well as the infection of target cells was described previously (Stewart et al. (2003) RNA 9:493-501). Following infection, the cells were selected using puromycin, hygromycin or blasticidin. Cells were used immediately following selection and for up to one month after selection.

Microarray Analysis

RNA from Lin MECs and neuron cells of Pin1 KO and WT mice was extracted with the total RNA isolation mini kit (Agilent). Microarray expression profiles were collected using the Affymetrix GeneChip Mouse Expression Array 430A. Affymetrix.CEL files were analyzed with BRB-ArrayTools (Simon et al. (2007) Cancer Inform. 3:493-501) (http://linus.nci.nih.gov/BRB-ArrayTools.html). Microarray data have been deposited in NCBI Gene Expression Omnibus with series accession number GSE49971. Genes that expressed lower in KO cells than in WT cells with fold change <0.8 (P<0.05) were selected as "downregulated" ones. Two datasets obtained from NCBI's Gene Expression Omnibus (GEO; http://www.ncbi.nlm.nih.gov/geo/) with GEO Series accession numbers GSE3711 (Stingl et al. (2006) Nature 439:993-997) and GSE8863 (Zhang et al. (2008) Cancer Res. 68:4674-4682) were reanalyzed together with our raw data. In GSE3711, mammary stem cells (MaSC, defined as lineage-CD49f$^{++}$CD24$^+$) were compared to myoepithelial cells (MYO, defined as lineage-CD49f$^+$CD24$^+$) and colony-forming progenitor cells (CFC, defined as lineage-CD49PCD24"). Genes that expressed higher in MaSC than in both MYO and CFC with fold change >1.5 (P<0.05) were selected as "upregulated" ones. In GSE8863, the Lin-CD29$^{High}$CD24$^{High}$ subpopulation of CSCs was compared to the Lin-CD29$^{Low}$CD24$^{Low}$ subpopulation of non-CSCs. Genes that expressed higher in CSC than in non-CSC with fold change >1.5 (P<0.05) were selected as "upregulated" ones. When comparing the upregulated gene list in these two datasets (SC/non-SC>1.5, P<0.05) with the downregulated gene list in Pin1 KO cells (KO/WT<0.8, P<0.05), 14 genes were repeatedly found in the two gene lists and were identified as candidate genes.

Western Blotting

Primary monoclonal Pin1 antibody (1:5000), polyclonal RAB2A antibody (1:1000) (Proteintech Group), polyclonal Erk1/2 (1:4000) and pErk antibody (1:2000) (Cell Signaling Technology), monoclonal unphosphorylated β-catenin antibody (1:2000) (Millipore), monoclonal M2 antibody for Flag tag (1:2000) (Sigma), and monoclonal Actin antibody (1:5000) (Sigma) were used in Western blots.

Quantitative RT-PCR

RNA from cells was extracted with the Total RNA isolation mini kit (Agilent). cDNA was prepared with transcriptor first strand cDNA synthesis kit (Roche) and PCR was carried out with iQ SYBR Green Supermix (Bio-Rad). Samples were run on the QIAGEN Rotor-Gene Q real-time cycler. GAPDH was used as an internal control. Analysis was performed with the delta-delta ct method. The following primers were used:

```
                                          (SEQ ID NO: 8)
GAPDH forward CATGAGAAGTATGACAACAGCCT
```

GAPDH reverse AGTCCTTCCACGATACCAAAGT (SEQ ID NO: 9)

Pin1 forward GCCTCACAGTTCAGCGACT (SEQ ID NO: 10)

Pin1 reverse ACTCAGTGCGGAGGATGATGT (SEQ ID NO: 11)

Ecad forward TGCCCAGAAAATGAAAAAGG (SEQ ID NO: 12)

Ecad reverse GTGTATGTGGCAATGCGTTC (SEQ ID NO: 13)

Ncad forward ACAGTGGCCACCTACAAAGG (SEQ ID NO: 14)

Ncad reverse CCGAGATGGGGTTGATAATG (SEQ ID NO: 15)

FN1 forward CAGTGGGAGACCTCGAGAAG (SEQ ID NO: 16)

FN1 reverse TCCCTCGGAACATCAGAAAC (SEQ ID NO: 17)

Vim forward GAGAACTTTGCCGTTGAAGC (SEQ ID NO: 18)

Vim reverse GCTTCCTGTAGGTGGCAATC (SEQ ID NO: 19)

Cmpk1 forward TGGGAAGGCAGATGTATCTTTCG (SEQ ID NO: 20)

Cmpk 1 reverse TGTTGACTGAAGGTAGGTCTGA (SEQ ID NO: 21)

ELAVL1 forward AACCATTAAGGTGTCGTATGCTC (SEQ ID NO: 22)

ELAVL1 reverse CGCCCAAACCGAGAGAACA (SEQ ID NO: 23)

EMP2 forward CATCCAGCTAATGTCATGTCTGT (SEQ ID NO: 24)

EMP2 reverse CTCTGGTCACGGGATAGAATTTC (SEQ ID NO: 25)

GLE1 forward ACGCAAGCTCTGCCTTTTC (SEQ ID NO: 26)

GLE1 reverse CGTGAGGACTGAAGTACCATAGA (SEQ ID NO: 27)

HMGN1 forward GCGAAGCCGAAAAAGGCAG (SEQ ID NO: 28)

HMGN1 reverse TCCGCAGGTAAGTCTTCTTTAGT (SEQ ID NO: 29)

HTATSF1 forward ATGGTGACACCCAGACCGAT (SEQ ID NO: 30)

HTATSF1 reverse GAGAAGCCATAATTGGCCTGAT (SEQ ID NO: 31)

LAMP2 forward TCCCAAAGATCTGCCTTCAC (SEQ ID NO: 32)

LAMP2 reverse TTCTGCATTGTGCTGAGAGG (SEQ ID NO: 33)

Magi3 forward TCTTCTTTTGAGGCCAGGAA (SEQ ID NO: 34)

Magi3 reverse GGAAAGACCAAGAAAAGCCC (SEQ ID NO: 35)

RAB2A forward AGTTCGGTGCTCGAATGATAAC (SEQ ID NO: 36)

RAB2A reverse AATACGACCTTGTGATGGAACG (SEQ ID NO: 37)

SEH1L forward TGAATCTCAGCCAGTGGTCTT (SEQ ID NO: 38)

SEH1L reverse TCATCACTTCCTACGGCGAT (SEQ ID NO: 39)

TM7SF3 forward TTCCTTTTCTCCGACTCTCCTT (SEQ ID NO: 40)

TM7SF3 reverse CCCCAAGTACCAAGTGCATGT (SEQ ID NO: 41)

TM9SF3 forward TGCCAGCCACTTACTGTGAAA (SEQ ID NO: 42)

TM9SF3 reverse GCCTCACCAACAATACCCCATA (SEQ ID NO: 43)

ZDHHC3 forward AGATTGGACAACCTATGGACTGA (SEQ ID NO: 44)

Zdhhc3 reverse GCACTCTGTCGAACTGAAGTTA (SEQ ID NO: 45)

ZYG11B forward GAGGAGGCGTCTCCCTATTC (SEQ ID NO: 46)

ZYG11B reverse GCATCTGGTTGCCCCTAAAAA (SEQ ID NO: 47)

Luciferase Reporter Assays

For the reporter assay of RAB2A promoter, two deletion luciferase reporter constructs of RAB2A were generated. The promoter sequences from −1310 and −904, which contain the −1293 and −890 AP-1 binding sites, respectively, were subcloned into pGL3 vector. HEK293 cells were plated in 12-well plates for 24 hr and transfected with luciferase reporter constructs, pRL-tk renilla luciferase and Flag-Pin1 or control vector. Increasing dose of Flag-Pin1 or control vector plasmid were add as 0.15, 0.5 1.5 µg. Cells were harvested and luciferase activity was measured 48 hr later using the Dual-Luciferase Reporter Assay System (Promega).

Chromatin Immunoprecipitation (ChIP)

ChIP assay was performed according to the manufacturer's instruction (Upstate Biotechnology). Monoclonal Pin1 antibody (generated by our lab) or polyclonal c-Jun antibody (Abcam) were used to precipitate the chromatin-protein complexes. Re-ChIP assay was performed as described (Petruk et al. (2012) Cell 150:922-933). Real-time PCR primers for the −1293 locus were CCTGTGGTCTTTTT-GAACAGAG (SEQ ID NO: 48) and CAACTGGAGGC-CCTGTATGT (SEQ ID NO: 49), and for the −890 locus were ACACACACATAAACAGATCATCTCGG (SEQ ID NO: 50) and AGTCTCTGAACCTGTCCTGGTTCTG (SEQ ID NO: 51).

In Vitro Assays

Mammosphere culture was performed as described (Dontu et al. (2003) Genes Dev. 17:1253-1270). A single-cell suspension was plated on ultra-low attachment plates (Corning, Costar) in DMEM/F-12 HAM medium containing bFGF, EGF, heparin and B-27 supplement. The mammospheres were cultured for two weeks. Then the mammospheres with diameter >75 µm were counted.

Soft agar assays were done by seeding cells at a density of $10^3$ in 60 mm culture dishes containing 0.3% top low-melt agarose and 0.5% bottom low-melt agarose, as described (Ryo et al. (2001) Nat. Cell Biol. 3:793-801). Cells were fed every 4 days, and colonies were stained with 0.2% p-iodonitrotetrazolium violet and counted after 3 weeks.

For wound healing assays, cells were grown to confluence and then wounded using a yellow pipette tip, and migration was visualized by time-lapse imaging. The rate of wound closure was calculated by a ratio of the average distance between the two wound edges and the total duration of migration.

Transwell migration assay were performed as previously described (Luo et al. (2006) Cancer Res. 66:11690-11699). Assay media with EGF (5 ng/ml) was added to the bottom chamber. Cells ($5 \times 10^4/100$ μl) were added to the top chamber of cell culture inserts (8 mm pore size) (Corning, Costar). After 12 hours of incubation, cells that migrated to the bottom surface of the insert were fixed with methanol and stained with 0.4% crystal violet. The number of cells that had migrated was quantified by counting ten random distinct fields using a microscope.

GTP Hydrolysis Assay

Rab2A GTPase hydrolysis assay were performed as described (Davis et al. (2013) Proc. Natl. Acad. Sci. USA 110:912-917) with small modifications. GST-Rab2A or GST-Rab2A Q58H (100 nM) was incubated in 20 mM Tris-HCl (pH 7.5), 50 mM NaCl, 10 mM MgCl2, 0.5 uM GTP and 3 pmol of [$\alpha$-$^{32}$P] GTP at room temperature for the indicated time. The Rab2a-bound nucleotides were eluted with elution buffer (2 mM EDTA, 0.2% sodium dodecyl sulfate, 1 mM GDP, 1 mM GTP). 1 μL of the reaction mixture was spotted onto polyethyleneimine-cellulose sheets. Chromatograms were developed in 0.75M KH2PO4 (pH 3.4). GTP and GDP resolved by thin-layer chromatography were visualized by autoradiography film exposure.

Tumor Implantation

Aliquots of indicated numbers of cells were injected into 5-week-old BALB/c nude mice (Jackson Laboratories), as described (Mani et al. (2008) Cell 133:704-715). The tumor incidence was monitored by palpation and determined at two months after injection, with the same tumor incidence at 6 months postinjection. After tumors were detected, tumor size was measured every three days.

Preparation of Single-cell Suspensions

Human mammary reduction plasty tissues and breast cancer tissues were mechanically disaggregated and then digested with 200 U/ml collagenase (Sigma) and 100 U/ml hyaluronidase (Sigma), as described (Al-Hajj et al. (2003) Proc. Natl. Acad. Sci. USA 100:3983-3988). The resultant organoids were further digested in 0.25% trypsin-EDTA and Dispase/DNaseI, and then filtered through a 40 μm mesh.

Serial Transplantation Assay

Lin$^-$CD24$^-$CD44$^+$ cells were sorted from eight breast cancer specimens and cultured as single cell suspension in ultra-low attachment dishes, and then infected with lentivirus expressing control vector or Rab2A shRNA. After one week of puromycin selection, 2,000 transduced cells from each patient were injected into the mammary fat pads of 5-week-old nude mice. For serial passaging, cells from the primary tumors were sorted again for Lin$^-$CD24$^-$CD44$^+$ cells. Among the 6 primary tumors formed in the shCtrl group, four tumors were randomly selected and passaged into eight mice (two mice per tumor). For the one tumor formed from 2,000 shRab2A cells, this tumor cells were injected into eight mice for serial passaging. The same procedure was applied to the second passage of xenograft cells. The size of tumors was measured every 3 d by calipers, and tumor volumes were calculated as Volume (mm$^3$)=L× W$^2$×0.4, as described (Yu et al. (2007) Cell 131:1109-1123).

All studies involving human subjects were approved by the Institutional Review Board at Beth Israel Deaconess Medical Center or Sun Yat-Sen Memorial Hospital. All studies involving mice were approved by the Institutional Animal Care and Use Committee at Beth Israel Deaconess Medical Center and performed in accordance with the relevant protocols.

Immunohistochemistry Analyses on Tissue Microarrays

Formalin-fixed and paraffin-embedded tissue microarrays of human breast tissue were purchased from Imgenex (IMH-364 and 371). Rab2A (Proteintech Group) and ALDH1 (BD biosciences) staining was performed following the manufacturer's protocol Immunolabeling was visualized with a mixture of DAB solution (Vector Laboratories), followed by counterstaining with hematoxylin. Microscopic analysis was assessed in a blinded manner. Immunostaining results were scored using percentage (P)×intensity (I), as described (Ginestier et al. (2002) Am. J. Pathol. 161:1223-1233). In brief, percentage of positive cells ranged from 0 to 100, and intensity was categorized into three groups as 1 (negative or weak), 2 (moderate) and 3 (strong). Expression levels are scored as low (0<P×I≤100), medium (100<P×I≤200) and high (200<P×I≤300). For ALDH1, only the intensity was estimated, because the percentages of positive cells were low. Intensity in foci with maximum staining was scored as low, medium and high, as described (Kunju et al. (2011) Mod. Pathol. 24:786-793).

Statistical Analysis

The experiments described herein were routinely repeated at least three times, and the repeat number was increased according to effect size or sample variation. We estimated the sample size considering the variation and mean of the samples. No statistical method was used to predetermine sample size. No animals or samples were excluded from any analysis Animals were randomly assigned groups for in vivo studies; no formal randomization method was applied when assigning animals for treatment. Group allocation and outcome assessment was not done in a blinded manner, including for animal studies. All data are presented as the means±SD, followed by determining significant differences using the two-tailed student t test or ANOVA test, where *P<0.05, P<0.01, *P<0.001. Limiting dilution data were analyzed by the single-hit Poisson model using a complementary log-log generalized linear model with L-Calc Software (Stemcell Technologies). Correlations of Rab2A expression with other gene expression were analyzed with the Pearson correlation test. For survival analysis, Kaplan-Meier analysis, univariate and multivariate Cox regression analysis were used.

EXAMPLES

Example 1: Identification of Pin1 Inhibitors

Figure 2:
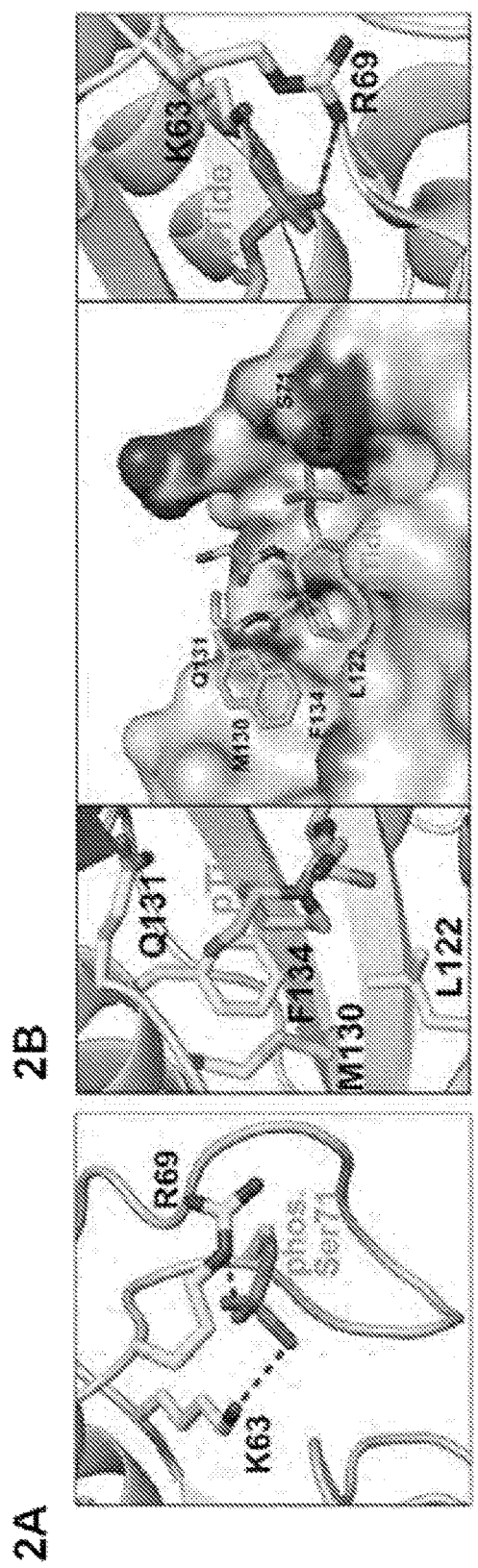
FIG. 2A depicts salt bridges between the pS71 phosphate group and K63 and R69 residues of the Pin1 active site.
FIG. 2B shows salt bridges between the phosphate group of Pin1-pTide and K63 and R69 of Pin1 (right panel) and the hydrophobic interaction between homoproline (Pip) of pTide and L122, M130, Q131 and F134 of Pin1 (left panel).
FIG. 2C is a plot showing fluorescence polarization (FP) of pTide-HiLyte™ Fluor 488 incubated with different Pin1 point mutants for 0.5 hours.
FIG. 2D is a graph showing Z scores obtained from FP-HTS for Pin1 inhibitors, with 13-cis-retinoic acid having the lowest Z score, as determined by folds of standard deviation below the mean of each screening plate.
FIGS. 2E and 2F show the structures of cis (13cRA) (2E) and trans (ATRA) (2F) of retinoic acid.
FIG. 2G presents a summary of $K_i$ or $K_d$ values of ATRA and 13cRA for Pin1 obtained from FP, photoaffinity labeling, or PPIase assays.
FIG. 2H is a plot showing the dose-dependence of [$^3$H] ATRA binding to Pin1. Pin1 was incubated with various concentrations of [$^3$H]ATRA, followed by UV exposure before SDS-gel and radiography (Inset).
FIG. 2I is a plot showing that change in inhibition of Pin1 catalytic activity by ATRA or 13cRA with concentration, as measured by PPIase assay.
FIG. 2J shows the structure of selected ATRA-related compounds and an FP readout of the result of adding pTide-HiLyte™ Fluor 488 to Pin1 and subsequently incubating different concentrations of compounds indicated for 0.5 hours.
FIGS. 2K and 2L show an electron density map measured after ATRA soaking (2K) and the ATRA-Pin1 co-crystal structure measured with synchrotron radiation (2L).
Figure 2:
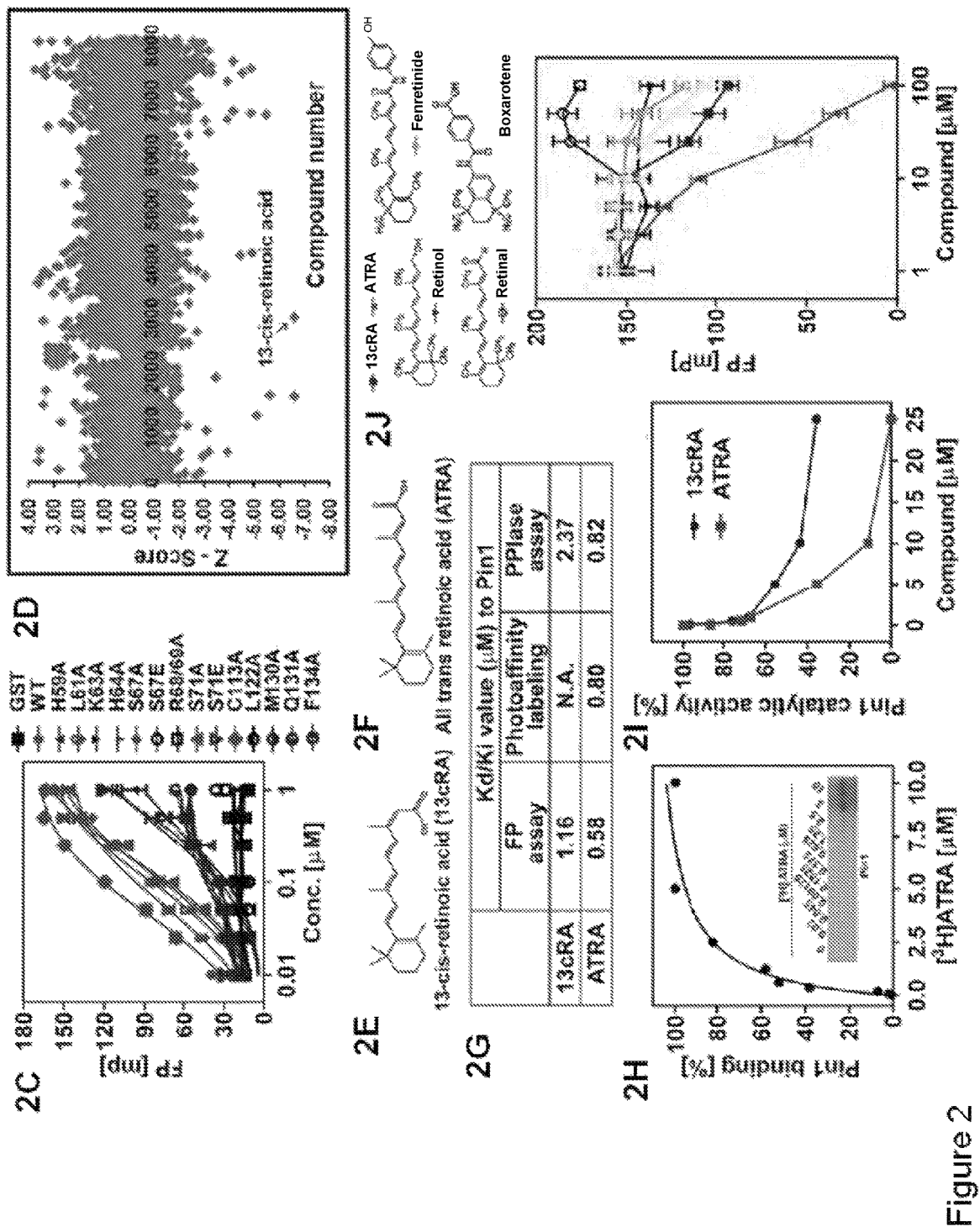

As described above, phosphorylation of Pin1 on S71 inhibits Pin1 catalytic activity and oncogenic function by blocking a phosphorylated substrate from entering the PPIase active site (see, for example, FIG. 2A). Accordingly, phosphorylated Pin1 can be referred to as inactive Pin1, while non-phosphorylated Pin1 can be referred to active Pin1.

We have previously shown that phosphorylation (e.g., inactivation) prevents Pin1 from binding to species with high affinity for Pin1. One such species is pTide (Bth-$_D$-phos.Thr-Pip-Nal), a substrate-mimicking inhibitor that selectively binds Pin1 at its PPIase domain and does not bind to the WW domain of Pin1 or to FKBP12 (FIG. 2B). pTide is also known to bind to the Pin1 S71A mutant but not to the S71E mutant, and its binding to the Pin1 PPIase active site is known to involve the residues K63, R69, L122, M130, Q131, and F134 (FIGS. 2C, 21A, 21B, 21C, and 21D). Further, pTide has low cell permeability due to its phosphate group. As it is desirable to develop Pin1 inhibitors with higher cell permeability, we developed a fluorescence polarization-based high-throughput screen (FP-HTS) to screen for chemical compounds that can compete with pTide for binding to the (non-phosphorylated) PPIase active site of Pin1.

The N-terminal HiLyte™ Fluor 488-, fluorescein- or TAMRA-labeled peptide had a 4 residue sequence core structure of pTide, which was synthesized by a commercial company (Anaspec). This sequence was optimized for solubility and binding to GST-PPI. For the screening assay, a solution containing 250 nM GST-Pin1, 5 nM labeled peptide, 10 µg/mL bovine serum albumin, 0.01% Tween-20 and 1 mM DTT in a buffer composed of 10 mM HEPES, 10 mM sodium chloride, and 1% glycerol at pH 7.4 was used. Measurements of fluorescence polarization and fluorescence absorbance were made in black 384-well plates (Corning) using a Synergy II plate reader. Compounds were transferred to plates using a custom-built Seiko pin-transfer robot at the Institute for Chemistry and Cell Biology at Harvard Medical School. The assay can tolerate up to 10% DMSO.

Molecules that compete with pTide for binding to the active site, e.g., Pin1 substrates, were detected under equilibrium conditions. A Z score was used to identify and rank those molecules that were most competitive with pTide (e.g., that have higher binding affinity). A Z score is defined as $Z=(x-\mu)/\sigma$, where x is a raw score, $\mu$ is the mean of the population, and $\sigma$ is the standard deviation of the population. Molecules with the most negative Z scores represent those with the highest Pin1 binding affinity. The Z' value for this assay was around 0.70 and was consistent for day-to-day performance, with a coefficient of variation in the range of 4-5%. FIG. 2D shows the result of the pTide competitive binding assay. Of the ~8200 compounds screened, 13-cis-retinoic acid (13cRA) had the lowest Z score and was thus the number 1 hit.

The structure of 13cRA and its isomer ATRA are shown in FIGS. 2E and 2F. In order to quantify the association between the substrates (e.g., 13cRA and ATRA) and Pin1, an equilibrium dissociation constant was calculated based on the FP assay results according to the Kenakin $K_i$ equation:

$$K_i = \frac{L_b \cdot EC_{50} \cdot K_d}{L_o \cdot R_o + L_b(R_o - L_o + L_b - K_d)}$$

in which $K_d$[M] is the equilibrium dissociation constant of the probe, $EC_{50}$ [M] is obtained from the FP assay, $L_o$[M] is the probe concentration in the FP assay, $L_b$ [M] is the concentration of the probe that binds to the target protein (85% of the total probe concentration), and $R_o$ [M] is the Pin1 concentration in the assay. Additional details are available in Auld et al., Assay Guidance Manual (Bethesda (Md.), 2004). A lower value of $K_i$ is indicative of higher association and, accordingly, higher affinity of the substrate to the protein.

As shown in FIG. 2G, the $K_i$ for ATRA was 0.58 µM while that for 13cRA was 1.16 µM, demonstrating that ATRA is more potent than 13cRA after a short period of incubation with Pin1. Notably, ATRA is a submicromolar Pin1 inhibitor. FIGS. 22A and 22B show that difference in binding between 13cRA and ATRA disappears after a longer incubation, likely because 13cRA isomerizes to the trans retinoic acid form. Additional results from an FP assay using a different fluorescence labeled pTide probe are presented in FIGS. 21A, 21B, 21C, 21D, and 21E. These results confirm the ATRA-Pin1 interaction.

Example 2: Photoaffinity Labeling with [³H]ATRA

Photoaffinity labeling of Pin1 with radiolabeled ATRA was performed to provide further confirmation of the direct binding between ATRA and Pin1. 10 pmol of Pin1 was incubated in microcentrifuge tubes with a series of concentrations of all-trans-[11,12-³H]-retinoic acid (PerkinElmer, 43.7 Ci/mmol) in 20 µl of the FP assay buffer at 23° C. with agitation for 2 hours in the dark. The caps of the microcentrifuge tubes were opened, and the samples were placed on ice and exposed to an Electrophoresis System 365/254 nm UV hand lamp (Fisher Scientific) suspended 6 cm above the surface of the liquid for 15 minutes. The samples were boiled in SDS sample buffer and subsequently separated on standard SDS/PAGE gels. The gels were dried and then used for fluorography at −80° C. for 5 days and quantified using Quantity One from BioRad.

Binding detected using SDS-containing gels confirms the direct binding of ATRA and Pin1 (FIG. 2H). The equilibrium dissociation constant $K_d$ for ATRA measured in the photoaffinity labeling study was 0.80 µM (FIG. 2G). Moreover, ATRA and 13cRA fully inhibited the PPIase activity of Pin1, with the $K_i$ values being 0.82 µM and 2.37 µM for ATRA and 13cRA, respectively, but did not inhibit cyclophilin or FKBP12 (FIGS. 2G, 22C, 22D, 22E, and 22F). Thus, ATRA is a selective, submicromolar Pin1 inhibitor.

Example 3: Pin1 Binding of Selected ATRA-related Compounds

Having determined ATRA to be a potent and selective Pin1 substrate, we compared the binding activity of ATRA to several ATRA-related compounds to investigate the structural features important to the association of the substrate with Pin1. These structures are presented in FIGS. 2J and 23A. As a major point of difference between the Pin1 inhibitors ATRA and pTide is the substitution in ATRA of a carboxylic acid group for a phosphate group, several ATRA-related compounds including carboxylic acid groups were selected for study. In the FP assay, ATRA dramatically outperformed the other species. Notably, species (e.g., retinol, retinyl acetate, and retinal) having other functional groups (e.g., hydroxyl, ester, or aldehyde) in place of a carboxylic acid group were totally inactive. The relative inhibition of Pin1 by other species was between 25-64% for fenretinide, bexarotene, acitretin, and tamibarotene, indicating marginal to moderate binding by these species. Bexarotene, acitretin, and tamibarotene each include carboxylic acid groups. However, while acitretin and tamibarotene demonstrated moderate binding relative to ATRA, bexarotene showed only marginal binding. Though the structure of acitretin differs from bexarotene and tamibarotene in its more flexible backbone and smaller head group, bexarotene and tamibarotene include similarly bulky head groups and each include a benzene ring in their backbone structure. The most obvious structural difference between bexarotene and tamibarotene is the substitution in tamibarotene of an amide group for a vinyl group. The resulting elongation and increased electron donating character of the backbone of tamibarotene may facilitate the binding of the compound to Pin1 relative to bexarotene. In contrast, fenretinide's structure differs from that of ATRA's only in its terminal group, demonstrating the importance the carboxylic acid group in ATRA-Pin1 binding. However, neither pravastatin nor indo-3-acetic acid demonstrated any binding despite including carboxylic acid groups, suggesting that the backbone and head group are also important features in Pin1 substrates.

Example 4: Determination of the ATRA-Pin1 Co-crystal Structure

To understand how ATRA inhibits Pin1 catalytic activity, we determined the co-crystal structure of ATRA and the Pin1 PPIase domain Pin1 PPIase domain (residue 51-163) was cloned into a pET28a derivative vector with an N-terminal hexahistidine tag followed by recognition sequences by thrombin and PreScission 3C proteases and then the recombinant gene. Mutations of K77Q, K82Q were created by QuikChange™ site directed mutagenesis.

The PPIase K77/82Q was purified by overexpression in *E. coli* BL21 (DE3) strain with isopropyl-β-D-thiogalactopyranoside (IPTG) and induction at 16° C. overnight. Cell lysate was first purified with nickel affinity chromatography. The elution was dialysed in a buffer of pH 8 including 20 mM HEPES, 100 mM NaCl, and 8 mM β-Mercaptoethanol while the protein was treated with PreScission Protease (GE) over night at 4° C. After His tag removal, Pin1 PPIase K77/82Q was separated from untruncated protein by a second round of nickel affinity chromatography, and subsequently purified by size exclusion chromatography columns Superdex 75 (GE Healthcare).

Purified PPIase K77/82Q was concentrated to 15 mg/mL. ATRA dissolved in DMSO at the concentration of 1 mM was mixed with the protein solution and the mixture incubated on ice for 3 hours before setting up trays. Incubated protein was co-crystallized by vapor diffusion using a hanging drop of 1 µL protein-ATRA plus 1 µL well solution. The complex formed crystals in 0.2 M ammonium sulfate, 0.1 M HEPES, and 0.9 M-1.4 M sodium citrate in pH 7-8.5 solutions after micro-seeding using apo PPIase domain crystals. The crystals were cryoprotected by adding 30% glycerol in mother liquor and vitrifying in liquid nitrogen before data collection.

X-ray diffraction was performed using synchrotron radiation at beamline 5.0.2 of the Advanced Light Source (Berkeley, Calif.) with 3×3 CCD array detectors (ADSC Q315R). Data were processed and scaled using the HKL2000 software suite. Data collection statistics are summarized in the tables below.

TABLE 8

Summary of data statistics for crystallography measurements.

| Data Statistics | PPIase K7782Q ATRA |
|---|---|
| Source | ALS 5.0.2 |
| Wavelength (Angstrom) | 1.00 |
| Resolution (Angstrom) | 50-1.33 (1.35-1.33) |
| Space Group | C2 |
| Unit Cell (Angstrom) a, b, c | 117.81, 36.29, 51.70 |
| Unit Cell Angles | 90, 101, 90 |
| Data Cutoff | F > 0 |
| Asymmetric Unit (asu) | 2 |
| Number of Unique Reflections | 49111 |
| Redundancy | 3.6 (3.4) |
| Completeness (%) | 98.3 (96.7) |
| I/σ (I) | 64.9 (2.9) |
| $R_{sym}$ (%) | 4.9 |

TABLE 9

Summary of refinement statistics for crystallography measurements.

| Refinement Statistics | PPIase K7782Q ATRA |
|---|---|
| Resolution limit (Å) | 57.84-1.33 |
| No. reflections (test) | 46613 (3177) |
| Data cutoff | None |
| $R_{work}/R_{free}$ (%)[b] | 17.8/19.8 |
| No. atoms: | 2024 |
| Protein | 1880 |
| ATRA | 22 |
| Water | 122 |
| B-factors (Å$^2$) | 15.1 |
| Protein | 14.4 |
| ATRA | 36.4 |
| Water | 22.2 |
| RMS Deviations: | |
| Bond Lengths (Å) | 0.02 |
| Bond Angles (Degrees) | 1.96 |
| Ramachandran plot (%) | |
| Most favored regions | 97 |
| Additional allowed regions | 3 |
| Generously allowed regions | 0 |
| Disallowed regions | 0 |
| MolProbilty score^ | 1.25 (94$^{th}$ percentile*) |
| Bad Rotamer | 0.97% |
| Clashscore | 4.83 (88$^{th}$ percentile*) |

*100$^{th}$ percentile is the best among structures of comparable resolution; 0$^{th}$ percentile is the worst. For Clashscore the comparative set of structures was selected in 2004; for MolProbity, in 2006.
^MolProbity score combines the clashscore, rotamer, and Ramachandran evaluations into a single score, normalized to be on the same scale as X-ray resolution.

The structure of PPIase K77/82Q bound with ATRA was determined by molecular replacement with PPIase K77/82Q (PDB: 3IKG) as the search model using program Phaser from the CCP4 package suite. The structure was refined with the Refmac5 program from CCP4 package and iterative model building in COOT. The final structure was evaluated by both PROCHECK and MolProbity. Refinement statistics are summarized in Table 9 above. The Pin1-ATRA structure was deposited into the Worldwide Protein Data Bank with the PDB code of 4TNS.

The co-crystal structure of ATRA and Pin1 is presented in FIGS. 2K, 2L, and 23B. As shown in FIG. 2K, strong electron density is observed at the Pin1 active site after ATRA soaking. The most well-defined region of ATRA was its carboxyl group, which formed salt bridges with the critical catalytic residues K63 and R69, both of which are essential for binding the phosphate group in the Pin1 substrate. At the high resolution of 1.3 Å, two alternative conformations of R69 were visible, both of which were within the distance range of salt bridge formation with the carboxyl group of ATRA. The trimethyl cyclohexene ring of ATRA was sandwiched in the hydrophobic Pro-binding pocket formed by L122, M130, Q131 and F134 of Pin1. Notably, the binding modes of ATRA and pTide significantly overlapped (FIGS. 2B and 2L). Thus, by mimicking the pSer/Thr-Pro motif in a substrate, the carboxylic and bulky cyclic moieties of ATRA take advantage of the substrate phosphate- and proline-binding pockets of the Pin1 active site, respectively (also described as the high electron density and hydrophobic binding pockets). These structural requirements are also consistent with our findings that the carboxyl group of ATRA is important to binding to Pin1 and that fenretinide and bexarotene are less potent than ATRA in binding Pin1.

Example 5: In Vivo Inhibition of Pin1

To determine whether ATRA inhibits Pin1 in vivo, we first compared its anti-proliferative effects on Pin1 KO (Pin1$^{-/-}$)

and wild-type (WT, Pin1+/+) mouse embryonic fibroblasts (MEFs). Although relatively high concentrations of ATRA were required to inhibit the growth of Pin1 WT MEFs, Pin1 knockout (KO) cells were much more resistant to ATRA (FIG. 24A), which were fully restored by re-expressing Pin1, but not its inactive W34/K63A mutant (FIG. 24B). Notably, ATRA also dose-dependently down-regulated Pin1, but not its mutant (FIGS. 24C and 24D).

In order to determine the mechanism of down-regulation of Pin1, ATRA's effect on Pin1 mRNA levels (FIG. 24E) was examined Pin1 mRNA levels showed no obvious effects as a result of ATRA treatment. Further, the ATRA effect can be rescued by a proteosome inhibitor (FIG. 24F). Finally, ATRA and 13cRA reduce the half-life of Pin1 (FIG. 24G), with ATRA being more potent in reducing Pin1 levels and stability than 13cRA (FIGS. 24C, 24D, and 24G). ATRA thus down-regulates Pin1 by promoting Pin1 degradation.

Example 6: In Vitro Inhibition of Pin1 Oncogenic Function

To determine whether ATRA inhibits Pin1 oncogenic function in vitro, we examined the effects of ATRA on the well-documented oncogenic phenotypes induced by Pin1 overexpression, such as inducing centrosome amplification, activating the cyclin D1 promoter, and enhancing foci formation. These phenotypes are all inhibited by DAPK1-mediated S71 phosphorylation in Pin1. Indeed, ATRA dose-dependently and fully inhibited the ability of Pin1 overexpression to induce centrosome amplification (FIGS. 24H and 24I) and activate the cyclin D1 promoter (FIG. 24J) in NIH 3T3 cells and to enhance foci formation in SKBR3 cells (FIGS. 24K and 24L). Thus, ATRA induces Pin1 degradation and inhibits its oncogenic function upon overexpression.

Example 7: The Role of RARs in ATRA-directed Degradation of PML-RARα

ATRA activates RARs to induce acute promyelocytic leukemia (APL) cell differentiation and also causes PML-RARα degradation to inhibit APL stem cells. Though ATRA has been approved for APL therapy, the mechanism of its activity is unknown. The ability of ATRA to activate RARα can be decoupled from its ability to induce PML-RARα degradation and to treat APL. Thus, the drug target(s) of ATRA for the latter effects remain elusive.

To examine the role of RARs in ATRA-directed degradation of PML-RARα, we used a pan-RARs agonist, AC-93253, and a pan-RARs inhibitor, Ro-415253, each structurally distinct from ATRA (FIG. 25A). As shown in FIG. 26A, both species exhibit the expected ability to activate or inhibit RAR transcriptional activity towards their downstream targets, respectively. While Ro-415253 showed minimal Pin1 binding, AC-93253 had no binding (FIG. 26B). Importantly, neither the inhibitor nor the activator affected ATRA to induce degradation of Pin1 or PML-RARα (FIGS. 25B and 25C), or to inhibit the growth of human APL NB4 cells (FIG. 25D). These RARs-independent ATRA effects were also confirmed using RARα, β, and γ triple KO MEFs, in which ATRA induced degradation of PML-RARα and Pin1 similar to that for WT controls (FIGS. 25E and 25F).

Example 8: Degradation of PML-RARα Induced by Pin1

Figure 1:
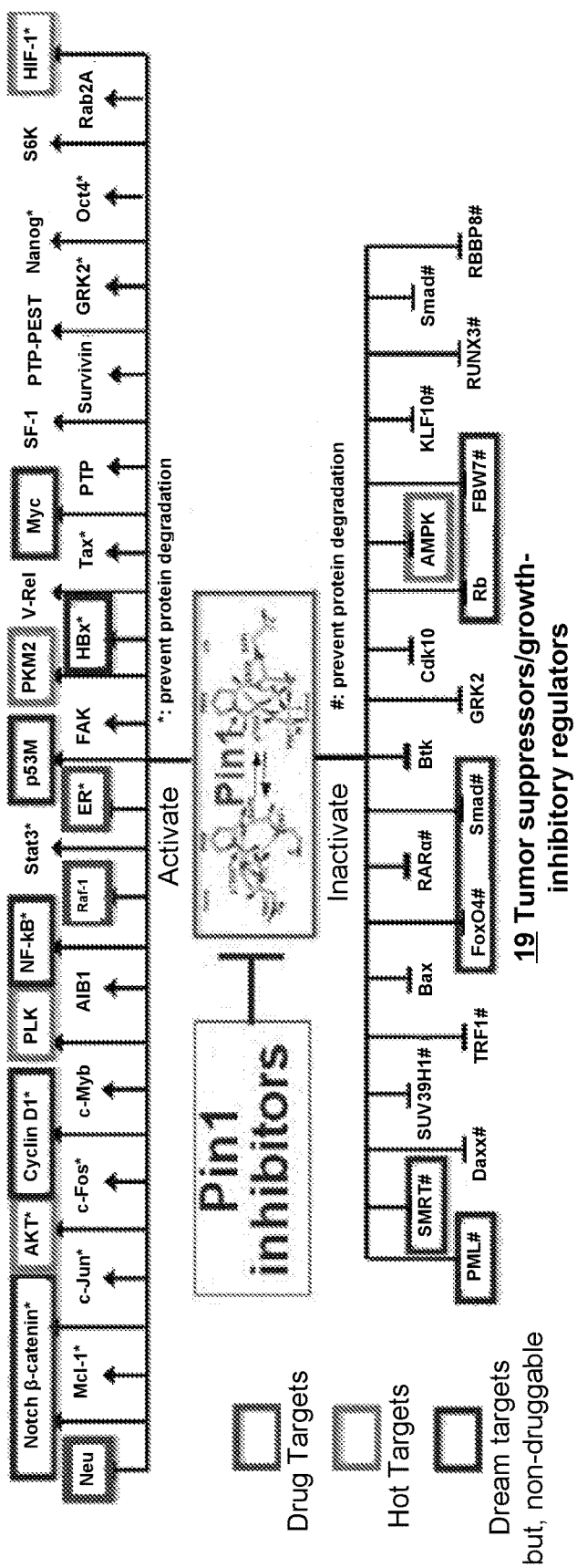
FIG. 1 is a schematic summary of selected Pin1 substrates including 32 oncogenes and 19 tumor suppressors and their druggable potentials.

ATRA-induced PML-RARα degradation is associated with phosphorylation on the Ser581-Pro motif, which corresponds to the Pin1 binding site pSer77-Pro in RARα. Since Pin1 binds to and increases protein stability of numerous oncogenes (FIG. 1), we hypothesized that Pin1 might bind to the pS581-Pro motif in PML-RARα and increase its protein stability, promoting APL cell growth. Indeed, Pin1 interacted with PML-RARα and, importantly, the point substitution of S581A, but not S578A. Pin1 not only abolished PML-RARα binding to Pin1 (FIG. 27A), but also reduced PML-RARα levels by reducing its protein stability (FIGS. 27B and 27C), as shown for many other Pin1 substrate oncogenes. Moreover, Pin1 knockdown (KD) using validated shRNA lentivirus reduced the protein stability of PML-RARα and inhibited APL cell growth, both of which were fully rescued by re-expression of shRNA-resistant Pin1, but not its inactive mutant. These results were also reflected in their protein stabilities (FIGS. 25G, 25H, 25I, 25J, and 25K). Relative to PML-RARα, Pin1 interacted much less with PLZF-RARα (FIG. 28A), and Pin1 KD only marginally reduced protein stability of PLZF-RARα (FIGS. 28B, 28C, 28D, and 28E). These results are consistent with the fact that APL induced by PLZF-RARα is usually resistant to ATRA. Thus, like ATRA, Pin1 KD induces PML-RARα degradation and inhibits APL cell growth.

Example 9: Genome-wide Gene Expression Profiling

Because Pin1 regulates many transcriptional factors (FIG. 1), we compared genome-wide gene expression profiles of ATRA-treated and stable Pin1 KD NB4 cells, along with their respective controls, using microarrays covering coding and non-coding transcripts in the human whole genome. Human NB4 cells were treated with 10 μM ATRA (Sigma Aldrich) or doxycycline-induced Pin1 knockdown for 3 days, and total RNA was extracted with Trizol reagent according to the manufacturer's instructions. The samples were then processed using an Affymetrix GeneChip WT PLUS Reagent Kit, followed by a Hybridization Wash and Stain kit. Microarray expression profiles were collected using Affymetrix Human Transcriptome Array 2.0. Original CEL files were analyzed by Affymetrix's Expression Console and Transcriptome Analysis Console software. Microarray data have been deposited in NCBI Gene Expression Omnibus with series accession number GSE63059. Genes that expressed lower in Pin1 KD or ATRA-treated cells than in VEC or DMSO-treated cells with fold change <0.5 ($P<0.05$) were selected as "downregulated" ones, and higher in Pin1 KD or ATRA-treated cells than in VEC or DMSO-treated cells with fold change >2 ($P<0.05$) were selected as "upregulated" ones. The array results have been deposited into GEO database (GSE63059).

Clustering analysis revealed that ATRA-treated cells and Pin1 KD cells have striking similarities. 528 genes were identified to be differentially expressed, with 304 upregulated and 224 downregulated including many growth-stimulators (e.g., CCL2, SPP1, IL1B, and IL8) and growth-suppressors (e.g., PDCD4 and SORL1) and no-coding RNAs both in Pin1 KD cells and ATRA-treated cells (FIG. 25L). Thus, both PML-RARα gene-specific and genome-wide analyses show that ATRA inhibits Pin1 in APL cells.

Example 10: Degradation of PML-RARα Induced by Pin1 in Animal Studies

Immunodeficient NOD-SCID-Gamma (NSG) mice transplanted with NB4 cells stably expressing an inducible Tet-on shPin1 after sublethal irradiation were used to corroborate the findings of in vitro studies that Pin1 KD can cause PML-RARα degradation. When doxycycline-containing food was given to the mice 5 days post-transplantation and throughout the course of the experiment, doxycycline-induced Pin1 KD also drastically reduced PML-RARα in the bone marrow (FIG. 25M). More importantly, these mice displayed normal spleen sizes, in contrast to obvious splenomegaly in control mice (FIGS. 25N and 29A). Assays of NB4 cells in the bone marrow using human CD45 antibody support this idea (FIGS. 29B, 29C, and 29D). The disease-free survival time of doxycycline-given mice was also significantly extended compared to that for mice not fed doxycycline (FIG. 25O). Notably, in a doxycycline-fed mouse that died early, Pin1 and PML-RARα levels were close to those in mice non-fed (non-induced) with doxycycline (FIG. 25P), supporting the role of Pin1 in APL survival. Thus, like ATRA, inducible Pin1 KD alone is sufficient to cause PML-RARα degradation and treat APL in vivo.

Example 11: Comparison of Pin1 Inhibitors in APL Cells

Based on the results presented herein, ATRA effectively binds, inhibits, and ablates Pin1 and thereby induces PML-RARα degradation to treat APL. This idea was further investigated by comparing ATRA to three less potent and specific and structurally distinct Pin1 inhibitors: PiB, EGCG, and Juglone. Like ATRA, these agents all dose-dependently reduced PML-RARα in APL cells. However, in contrast to ATRA, the non-ATRA species inhibited Pin1 without degrading it (FIG. 30A). Further, unlike ATRA or the pan-RARs activator, neither Pin1 inhibitors nor Pin1 KD induced APL cell differentiation (FIG. 30B). These results are further supported by the demonstration that ATRA potently induces RAR downstream targets, whereas Pin1 KD has only a minimal activity against these targets (FIG. 26C). The latter result could be attributed to the stabilization of RAR protein upon Pin1 KD.

To examine the effects of these Pin1 inhibitors on APL phenotypes in an in situ APL mouse model, sublethal irradiated B6 mice were engrafted for 5 days with APL cells isolated from hCG-PML-RARα transgenic mice and treated with EGCG or Juglone, or with ATRA-releasing pellets (5 mg 21 day). After 20 days, again, ATRA, but neither EGCG nor Juglone, induced APL cell differentiation in mice (FIG. 30C). Moreover, ATRA, but neither EGCG nor Juglone, reduced Pin1 levels in the bone marrow (FIG. 30D). The reduction of Pin1 levels in the bone marrow observed in the in situ model was not as profound as that seen in vitro (FIG. 30A), likely due to the presence of normal cells in the spleen, which are usually more resistant to ATRA (FIGS. 24A, 24B, 31A, 31B, and 31C). Nevertheless, all three Pin1 inhibitors effectively reduced PML-RARα in the bone marrow (FIG. 30D) and treated APL, with spleen weights nearly at basal levels (FIGS. 30E and 29E). Unlike ATRA-treated animals, EGCG or Juglone-treated mice were rather sick, likely due to the fact that EGCG and Juglone have other toxic effects. Thus, ATRA's ability to activate RARs and induce leukemia cell differentiation can be uncoupled from its activity to degrade PML-RARα and treat APL.

Example 12: ATRA Effects on Pin1 Levels in APL Patients

An ultimate question is whether ATRA treatment might lead to degradation of Pin1 and PML-RARα in APL patients. We used double immunostaining with antibodies against Pin1 and PML to detect Pin1 and PML-RARα levels and their localization in the bone marrow of normal controls or APL patients before or after the treatment with ATRA for 3 or 10 days or APL patients in complete remission (FIG. 32). In contrast to controls, Pin1 and PML-RARα were markedly overexpressed and distributed throughout the entire nucleus in all patients examined prior to treatment. After ATRA treatment, however, PML-RARα levels were significantly reduced, with the staining signal mainly in the PML nuclear bodies (FIG. 30F), which we have previously shown represents endogenous PML protein and reflects good ATRA response. Importantly, ATRA treatment caused a remarkable and time-dependent reduction of Pin1 and PML-RARα, both down to ~40% or <10% after only 3 or 10 days of treatment, respectively (FIGS. 30F, 30G, and 30H). Notably, PML-RARα/PML staining patterns were closely associated with Pin1 levels in APL cells. PML-RARα/PML was still diffusely distributed to the entire nucleus in APL cells containing more Pin1 (FIG. 30F, red arrows), but was almost exclusively localized to PML bodies (likely reflecting endogenous PML) in APL cells that contained much less Pin1 (FIG. 30F, yellow arrows). Similar results were also obtained by treating human APL NB4 cells with ATRA in vitro (FIG. 33). Notably, neither Pin1 nor PML-RARα was overexpressed in APL patients in complete remission (FIGS. 30F, 30G, and 30H). Thus, Pin1 inhibition by ATRA, three other inhibitors compounds, or inducible KD causes PML-RARα degradation and treats APL in cell and mouse models and even human patients. Accordingly, Pin1 is a key target for ATRA to treat APL.

Example 13: ATRA Activity Against Breast Cancer

Given that ATRA potently ablates Pin1, which regulates numerous cancer-driving molecules in solid tumors (FIG. 1), we hypothesized that ATRA might have anticancer activity against other cancer types. To test this possibility, we chose breast cancer as a model due to the substantial oncogenic role of Pin1 in vitro and in vivo. We first tested ATRA against 9 different human normal and breast cancer cell lines. Interestingly, non-transformed MCF10A and HMLE cells were highly resistant, but malignant cells showed differential susceptibility to ATRA (FIG. 31A).

To explore this range of ATRA sensitivity in breast cell lines, we first analyzed Pin1 levels. Compared with normal MCF10 and HMLE cells, Pin1 was overexpressed in all breast cancer cells (FIG. 31B). These cells expressed similar levels of cytochrome P450-dependent retinoic acid-4-hydroxylase (FIG. 31B) and its inhibitor liarazole only resulted in generally additive effects with ATRA (FIG. 34A), suggesting that ATRA metabolism likely does not account for the observed difference in ATRA sensitivity. Since the Pin1-ATRA co-crystal structure revealed that the carboxyl group of ATRA formed salt bridges with K63 and R69, which are responsible for binding the phosphate of pS71 Pin1 (FIGS. 2A, 2L, and 31C), we examined the possibility that S71 phosphorylation would affect ATRA sensitivity. Indeed the levels of S71 phosphorylation in different cell lines were tightly but inversely correlated with ATRA sensitivity. S71 was phosphorylated selectively in ATRA-resistant cells, whereas ATRA-responsive cells exhibited low or very little S71 phosphorylation (FIG. 31B). Given that S71 in Pin1 is phosphorylated by DAPK1, a tumor suppressor often lost in solid tumors, we examined expression of Pin1 and DAPK1 in human triple negative breast cancer tissues (FIG. 35). High Pin1 but low DAPK1 were detected in most breast cancer tissues with an inverse correlation (n=47) (FIGS. 31D and 31E). Thus, ATRA induces selective degradation of the S71 non-phosphorylated (thus active) Pin1 in cancer cells.

To examine whether the inhibitory effects of ATRA on breast cancer cell growth are related to RARs activation, we again used Ro-415253 and AC-93253 (FIG. 25A). Like APL cells (FIGS. 25A, 25B, and 25C), the pan-RARs inhibitor or the pan-RARs activator had no obvious effects on the ability of ATRA to induce Pin1 degradation or inhibit cell growth in breast cancer cells (FIGS. 34B, 34C, 34D, and 34E).

We next examined whether ATRA would affect protein levels of a select set of oncogenes and tumor suppressors whose protein stability has been shown to be regulated by Pin1 in breast cancer. Indeed, ATRA caused dose-dependent protein reduction in Pin1 and its substrate oncogenes, including cyclin D1, HER2, ERa, Akt, NFκB/p65, c-Jun, and PKM2, as well as protein induction in its substrate tumor suppressors such as Smad2/3 or SMRT, in all three sensitive cancer cell lines (FIG. 31F). Importantly, ATRA had no appreciable effects on normal MCF10A cells (FIG. 31F), further demonstrating the specificity of the ATRA effects. To further support the notion that these effects are due to Pin1 ablation, we stably introduced tetracycline-inducible Pin1 KD into these cells. Inducible Pin1 KO produced similar effects on the oncogenes and tumor suppressors (FIG. 31G). These effects were rescued by reconstitution of shRNA-resistant Pin1, but not its W34/K63A mutant (FIG. 31H). Thus, ATRA selectively ablates active Pin1 and thereby inhibits multiple cancer-driving pathways at once in a spectrum of breast cancer types as long as Pin1 is S71 dephosphorylated.

Example 14: In Vivo Inhibition of Breast Cancer by ATRA

The ability of ATRA to inhibit breast tumor growth in vivo was investigated using MDA-MB-231 and MDA-MB-468 cells in mouse xenograft models. Both cell types are associated with human triple negative breast cancer, which has the worst prognosis and fewest treatment options. In pilot experiments, MDA-MB-231 cells were subcutaneously injected into female nude mice in the flank. ATRA was subsequently administered in the flank or vehicle intraperitoneally 3 times a week for 8 weeks. ATRA had only modest antitumor activity (FIG. 36), which is consistent with the findings from clinical trials. This moderate efficacy may owe to ATRA's short half-life of ~45 min in humans.

In order to circumvent the short half-life, we implanted ATRA-releasing or placebo pills into mice to maintain a constant drug level for 8 weeks after cells were injected into nude mice for 1 week. ATRA potently and dose-dependently inhibited tumor growth, as well as reduced both Pin1 and its substrate cyclin D1 in tumors derived from MDA-MB-231 cells (FIGS. 37A, 37B, and 37C) or MDA-MB-468 cells (FIGS. 37D, 37E, and 37F). Moreover, similar dose-dependent potent inhibition of tumor growth was observed when ATRA was given to mice 3 weeks after inoculation when tumors had already formed (FIGS. 37G and 37H). To test whether the antitumor activity of ATRA against breast cancer is mediated by Pin1, we stably expressed Pin1 in MDA-MB-231 cells, before injection into mice. Pin1 overexpression markedly increased tumor growth (by ~8 fold), which again was effectively inhibited by ATRA in a dose-dependent manner (FIGS. 37I and 37J). Importantly, ATRA again dose-dependently reduced both endogenous and exogenous Pin1, and cyclin D1 (FIG. 37K). Thus, ATRA has potent antitumor activity against triple negative breast cancer through ablation of Pin1.

Schemes summarizing the activities of ATRA and Pin1 are presented in FIGS. 38A and 38B.

Example 15: Genomic Profiling Analysis of Pin1 Downstream Genes

We previously demonstrated a fundamental role of the unique prolyl isomerase Pin1 in driving the expansion, invasiveness and tumorigenicity of BCSCs, as well as the abundance and repopulating capability of mouse mammary stem cells (MaSCs) (Luo et al. (2014) Cancer Res. 71:3603-3616). To elucidate the underlying molecular mechanisms, we analyzed the effects of Pin1 KO on gene expression in mouse mammary epithelial cells (MECs). Global expression profiling of Lin$^-$ MECs isolated from two pairs of virgin Pin1 KO and WT littermates identified 1723 genes that were downregulated in both Pin1 KO mice (FIGS. 39A and 39B). To narrow down the list of Pin1-regulated genes, we compared MEC gene expression with that of neurons prepared from the same Pin1 KO and WT littermates. 671 genes were downregulated in both cell types in Pin1 KO mice (FIG. 39B). Although comparing expression profiles of stem cells from WT and Pin1 KO mice may be a better approach to identify Pin1 downstream genes in BCSCs, the MaSC-enriched Lin$^-$CD24$^+$CD29$^+$ or Lin$^-$CD24$^{med}$CD49f$^{hi}$ populations are very small in Pin1 KO mice, which made it difficult to get enough RNA from each mouse for the microarray analysis. As an alternative approach, we re-analyzed two published expression profiling datasets of mouse MaSCs and BCSCs (Stingl et al. (2006) Nature 439:993-997; Zhang et al. (2008) Cancer Res. 68:4674-4682), and compared them with our expression profiling of Lin$^-$ MECs and neurons from Pin1 KO and WT mice. There were 1932 genes upregulated in MaSCs or BCSCs, compared with non-MaSCs or non-BCSCs. 14 of these genes were in the 671 genes that were downregulated in both Pin1 KO MECs and neurons, namely, Cmpk1, Elavl1, Emp2, Gle1, Hmgn1, Htatsf1, Lamp2, Magi3, Rab2a, Sehl1, Tm7sf3, Tm9sf3, Zdhhc3, and Zyg11b (FIG. 39C).

To validate these candidate genes, we used qRT-PCR to determine the effects of Pin1 knockdown (KD) on their expression in six human breast cell lines. Rab2A was down-regulated after Pin1 KD in all 6 breast cancer cell lines examined, and Lamp2 and Magi3 were downregulated in 5 of 6 cell lines (FIGS. 39D and 40A). Pin1 KD also reduced Rab2A protein in all six cell lines (FIG. 40B). To test the effects of Rab2A, Lamp2 and Magi3 in BCSCs, we silenced their expression using two different shRNAs in MCF10A cells and examined the CD24$^-$CD44$^+$ subpopulation, which was identified to enrich human BCSCs. Only Rab2A KD consistently decreased the CD24$^-$CD44$^+$ subpopulation (FIG. 40C), suggesting a requirement of Rab2A for BCSC maintenance. Thus, we focused on Rab2A as a potential Pin1 target.

Example 16: Pin1 Regulation of Rab2A Transcription

Pin1 regulates its target function directly by isomerizing pSer/Thr-Pro motifs in the substrate or indirectly via regulating gene transcription. Rab2A does not have any Ser/Thr-Pro motif, but has two putative AP-1 binding sites (−1293 and −890) in its promoter region (FIG. 40D). Notably, Pin1 is known to activate transcription factors c-Jun and c-Fos to increase AP-1 activity. We therefore tested whether Pin1 might increase Rab2A transcription. The Rab2A promoter was cloned into the 5' UTR of a luciferase reporter and promoter activity was measured in cells co-transfected with increasing amounts of Pin1 expression plasmid or control vector. Pin1 expression enhanced transcription from the Rab2A promoter in a dose-dependent manner (FIG. 39E). Two luciferase reporter deletion constructs, −1293 and −890, that removed the putative AP-1 sites from the Rab2A promoter were generated and co-transfected with control vector or Pin1. Pin1 appeared to act on the distal AP-1 site, but not the proximal site (FIG. 39F).

To confirm that Pin1 regulates Rab2A transcription through AP-1, we first examined whether Pin1 binds to Rab2A promoter by the chromatin immunoprecipitation (ChIP) using cells transfected with Pin1 expression plasmid. Compared to control IgG, anti-Pin1 antibodies showed appreciable binding to the −1293 locus, as assayed by quantitative real-time PCR using primers flanking the −1293 and −890 loci (FIG. 39G). Next, we used c-Jun antibody to perform the ChIP assay in HMLE-Ras cells, because Pin1 binds to c-Jun that is phosphorylated by JNK and cooperates with Ras to increase the transcriptional activity of c-Jun towards its target genes. Indeed, c-Jun specifically associated with the −1293 locus in the Rab2A promoter (FIG. 39H). Moreover, to examine whether Pin1 and c-Jun formed a complex on the Rab2A promoter, we performed a sequential ChIP (re-ChIP). Re-ChIP analysis using c-Jun antibody followed by Pin1 antibody demonstrated that both proteins were present in the same complex on the −1293 locus (FIG. 39I). Given that Pin1 hasn't been reported to directly regulate transcription, Pin1 likely binds to the Rab2A promoter indirectly through AP-1. Thus, Pin1 activates Rab2A transcription and increases its protein levels in breast cancer cells.

Example 17: Rab2A Knockdown Suppresses BCSCs and Abrogates the BCSC-augmenting Effects of Pin1 Overexpression To investigate whether Rab2A is a functional downstream target of Pin1, we knocked down Rab2A in control or Pin1-overexpressing HMLE cells to examine whether Rab2A mediates the action of Pin1 in BCSCs (FIG. 39J). As shown previously, Pin1 overexpression drastically increased the population of BCSC-enriched CD24$^-$CD44$^+$ cells by 8-9 folds above that of the vector control-infected HMLE cells (FIGS. 39K and 39L). Rab2A KD greatly reduced the size of CD24$^-$CD44$^+$ population in vector control HMLE cells (FIGS. 39K and 39L), as did Pin1 KD. In Pin1-overexpressing cells, Rab2A KD partially decreased the abundance of CD24$^-$CD44$^+$ cells (FIGS. 39K and 39L). We then performed a mammosphere forming assay, which measures the frequency of early progenitor/stem cells and BCSCs in tumor tissues or cell lines. Rab2A KD decreased the mammosphere formation by both vector control and Pin1-overexpressing HMLE cells (FIG. 39M). Thus, Rab2A may be required to sustain the BCSC population both in control cells and Pin1-overexpressing cells.

We recently showed that Pin1 overexpression induces EMT in HMLE cells. Strikingly, Rab2A KD in Pin1-overexpressing cells reverted the EMT phenotype. After Rab2A KD, Pin1-overexpressing HMLE cells changed to epithelial morphology (FIG. 39N), with increased E-Cadherin and decreased N-Cadherin, vimentin, and fibronectin levels, as compared with those in Pin1-overexpressing cells expressing a control shRNA (FIG. 39O). Cell migration, a property associated with EMT, was also greatly attenuated by Rab2A KD in Pin1-overexpressing cells in wound healing (FIG. 41A) and transwell migration assays (FIG. 41B). These results suggest that Rab2A is a major mediator of Pin1 in BCSC function.

Example 18: Rab2A Gene is Amplified in Human Breast Cancers and its Overexpression Increases the BCSC Population Given that Rab2A KD suppresses BCSC expansion, we next sought to determine more directly the role of Rab2A in breast cancer. We first checked Rab2A gene alterations in cancers in the cBio Cancer Genomics Portal (Cerami et al. (2012) Cancer Discov. 2:401-404). Significantly, Rab2A gene amplification occurs in a wide range of human cancers, with the highest amplification frequency of ~9.5% (72 of 760) in invasive breast carcinoma patients (FIG. 42A). Importantly, Rab2A mRNA levels increase significantly with increasing copy number in these invasive breast carcinomas (P=1.56E-84) (FIG. 43A). Moreover, Rab2A is inside of the nearest peak of amplification at chr8:58922948-77138320, which is far away from MYC, an important oncogene on 8q that is inside of the nearest peak at chr8: 128573679-129017407, according to the Tumorscape software. Therefore, Rab2A is amplified and overexpressed in the breast cancer. We carried out gain-of-function experiments to test the role of Rab2A in regulating BCSCs.

We overexpressed Rab2A in control shRNA or Pin1 KD HMLE cells (FIG. 42B) to examine whether Rab2A would drive BCSC expansion and rescue Pin1 KD defects, respectively. Moderate Rab2A overexpression (2-3 times the endogenous level) not only strongly increased the CD24$^-$CD44+ population (FIGS. 42C and 43B) and mammosphere formation (FIG. 42D) in control HMLE cells, but also significantly rescued the BCSC defect in Pin1 KD cells (FIGS. 42C and 42D). Like Pin1 overexpression, ectopic Rab2A expression also induced EMT in HMLE cells, which developed an elongated fibroblast-like morphology with decreased cell-cell contact (FIG. 42E). Decreased E-Cadherin and increased N-Cadherin, vimentin, and fibronectin expression in Rab2A-overexpressing cells confirmed the EMT phenotype (FIG. 42F). Rab2A overexpression also enhanced cell migration in wound healing (FIGS. 43C and 43D) and transwell (FIGS. 43E and 43F) assays. These data indicate that Rab2A is a potential new oncogene that drives BCSC expansion and EMT.

To further investigate whether Rab2A is sufficient to induce HMLE cell transformation, we performed soft agar colony formation assay on Rab2A-overexpressing and control vector cells. Whereas control cells could hardly form colonies, Rab2A-overexpressing cells robustly formed colonies (FIGS. 43G and 43H), further supporting the oncogenic activity of Rab2A.

Example 19: Rab2A Impact on Tumorigenicity

To evaluate the impact of Rab2A on tumor initiation, we assessed the effects of Rab2A overexpression on tumor formation by limiting dilution transplantation assays in nude mice. We used HMLER cells, HMLE cells transformed with V12H-Ras, which is needed to enable Snail or Twist-overexpressing HMLE cells to form tumors in nude mice. When $1\times10^4$Rab2A-expressing HMLER cells were inoculated into nude mice, 3 of 6 mice generated tumors. All animals injected with 10- or 100-fold more cells developed tumors. By contrast, no mice inoculated with $1\times10^4$ control HMLER cells developed tumors, while tumors developed in only 2 of 8 mice inoculated with $10^5$ control cells and 3 of 6 mice injected with $10^6$ control cells (FIGS. 42G and 42H). To examine whether endogenous Rab2A is necessary for Pin1 to promote tumorigenicity of BCSCs, we knocked down Rab2A in Pin1-overexpressing HMLER cells. No tumors arose when $1\times10^4$Pin1-expressing cells infected with shRab2A were injected into mice (FIGS. 42G and 42H). Although 4 of 8 mice inoculated with $10^5$ Pin1-shRab2A HMLER cells formed tumors, 7 mice injected with an equal number of Pin1 cells developed tumors. Similarly, with Pin1 overexpression, $10^6$ Rab2A KD cells formed fewer tumors than control Pin1-overexpressing HMLER cells. Thus, Rab2A inhibition potently impairs the ability of Pin1 to promote the tumorigenicity of BCSCs. Taken together, these data support the notion that Rab2A overexpression via Rab2A gene amplification or Pin1 overexpression drives the expansion and tumorigenicity of BCSCs.

Example 20: Rab2A is Mutated in Human Cancers and the Q58H Mutation Activates Rab2A During our investigation into the clinical relevance of Rab2A genomic alterations in human cancer, we also noted that several Rab2A missense mutations have been identified in the cBio Cancer Genomics Portal (Cerami et al. (2012) Cancer Discov. 2:401-404) and the COSMIC database (Forbes et al. (2011) Nucleic Acids Res. 29:D945-950). Notably, the Rab2A Q58H mutation has been identified in a lung squamous cell carcinoma and a lung adenocarcinoma. Given that Q58 is highly conserved in Rab2A genes across species (FIG. 42I) and most of the oncogenic mutants in the Ras superfamily affect the enzyme's ability to hydrolyze GTP, we examined whether this mutation might affect the intrinsic ability of Rab2A to hydrolyze GTP using $[\alpha$-$^{32}$P]G-TP as a tracer to monitor the production of $[\alpha$-$^{32}$P]GDP by thin layer chromatography. Indeed, Rab2A Q58H hydrolyzed $[\alpha$-$^{32}$P]GTP to $[\alpha$-$^{32}$P]GDP more slowly than the WT protein (FIGS. 42J and 42K), resulting in more protein in the GTP-bound state, similar to many common gain-of-function mutations of Ras. Thus, the Q58H mutation reduces Rab2A GTP hydrolysis activity, leading to Rab2A activation likely by keeping it in the active GTP-bound form.

We then asked whether the Q58H mutation might increase the potency of Rab2A to expand the BCSC. We first stably expressed Flag-Rab2A and its mutant in HMLEs using lentiviruses with a less optimal or optimal Kozak sequence, resulting in proteins being expressed at levels similar to or 3 times of the endogenous level, respectively (FIG. 43I). When overexpressed close to the endogenous level, Rab2A increased the CD24$^-$CD44$^+$ percentage to 59%, but Rab2A Q58H increased this population to 79%, similar to a 3-fold higher level of Rab2A (FIG. 43J). To examine whether the Q58H mutation increased tumorigenicity, we examined tumor formation by injecting $1\times10^6$ HMLER cells infected with vector control or endogenous level of Flag-Rab2A and Q58H mutant into nude mice subcutaneously. Although cells expressing WT Rab2A or its Q58H mutant formed tumors in all mice, the Q58H mutant tumors grew significantly faster than WT controls (FIGS. 42L and 43K), suggesting that the Rab2A Q58H mutant is more active in expanding the BCSC population and more tumorigenic than WT Rab2A.

Example 21: Erk1/2 Activation is Essential for Rab2A to Regulate BCSC Expansion

To understand how Rab2A drives BCSC expansion, we examined whether Rab2A activates Erk1/2 (extracellular signal-regulated kinases 1/2)-MAP kinase pathway, which is crucial for Ras to induce EMT and increase the BCSC-enriched CD24$^-$CD44$^+$ population. First, we tested whether Rab2A activates Erk1/2 signaling. After serum starvation and EGF stimulation, Rab2A overexpression significantly increased Erk1/2 activation monitored by p-Erk1/2 in a time-dependent manner and also increased expression of Zeb1 (FIGS. 44A and 44B), a transcription factor critical for inducing EMT and the CD24$^-$CD44$^+$ population. In contrast, Rab2A KD substantially impaired Erk1/2 activation (FIGS. 44A and 44B). We then asked whether the Q58H mutation might increase Erk1/2 phosphorylation. When expressed at the endogenous level, the Q58H mutant induced Erk1/2 activation even faster than the WT Rab2A after EGF stimulation (FIGS. 44C and 44D). Thus, Rab2A and its Q58H mutant promote Erk1/2 activation.

Next, to examine whether Erk1/2 activation is required for mediating Rab2A's action in BCSCs, we silenced the expression of Erk1 or 2 in Rab2A-overexpressing HMLE cells. Since Erk2, but not Erk1, is required to induce EMT and CD24$^-$CD44$^+$ population, we knocked down Erk1 or Erk2 separately using lentiviral shRNA vector (FIG. 44E). While Erk1 KD only partially inhibited, but Erk2 KD completely abrogated BCSC expansion induced by Rab2A, as assayed by mammosphere formation (FIG. 44F) and CD24$^-$CD44$^+$ subpopulation (FIGS. 44G and 44H). Thus, Rab2A induces BCSCs by activating Erk1/2, especially Erk2.

Example 22: Rab2A Directly Interacts with Erk1/2

To elucidate how Rab2A overexpression or its Q58H mutation activates Erk1/2, we first examined whether Rab2A co-localized with Erk1/2. HMLE cells were starved and then stimulated by EGF to induce Erk1/2 phosphorylation. As compared with the vector control, overexpressing WT Rab2A not only activated Erk1/2, but also surprisingly colocalized with activated Erk1/2 at the perinuclear region at five minutes (FIG. 45A) and one hour (FIG. 46A) after EGF stimulation, as shown by co-immunostaining and confocal microscopy. Overexpressing Rab2A Q58H at levels similar to the endogenous level also activated and colocalized with Erk1/2 like overexpressing WT Rab2A at 3 times higher levels (FIGS. 45A and 46A). To determine where Rab2A or its Q58H mutant colocalized with Erk1/2 at the perinuclear region, we performed double immunostaining Rab2A and ERGIC53, an ER-Golgi intermediate compartment (ERGIC) marker. Both Rab2A and its Q58H mutant colocalized with Erk1/2 at the ERGIC (FIG. 45B). Thus, overexpressed Rab2A or its Q58H mutant co-localizes with Erk1/2 and promotes Erk1/2 activation at the ERGIC. To examine whether Rab2A's vesicular trafficking function is associated with Erk activation, we used brefeldin A (BFA) to block the trafficking from the ERGIC to ER because BFA dissociates ADP ribosylation factor (ARF) effectors from Golgi and ERGIC membranes, leading to block in both anterograde and retrograde transport. As expected, ERGIC structures were damaged after 30 min treatment of BFA, dispersing as cytoplasmic puncta, as shown by ERGIC53 staining (FIG. 46B). However, BFA treatment did not obviously affect Erk phosphorylation either in control vector or Rab2A-overexpressing cells (FIG. 46C). Although BFA treatment disturbs organelle integrity and is not specific for retrograde transport, this result suggests that the activation of ERK1/2 is likely to be independent of Rab2A's trafficking function.

The unexpected findings that Rab2A or its Q58H mutant colocalizes with activated Erk1/2 at the ERGIC suggested that Rab2A might directly interact with Erk1/2 to initiate Erk1/2 signaling. To test this possibility, we first examined whether Rab2A and Erk1/2 might form stable complexes given their colocalization. We detected co-immunoprecipitation of the endogenous Rab2A with Erk1/2 in HMLE cells by reciprocal co-immunoprecipitation (co-IP) experiments (FIG. 45C). Then, we investigated whether Rab2A interacted with p-Erk1/2, besides total Erk1/2. To obtain higher level of p-Erk1/2, we transfected constitutively active MEK1 (AcMEK1) into HEK293 cells. Indeed, Rab2A was found to bind p-Erk1/2 in the Co-IP assay (FIG. 45D). These data were further supported by our findings that Rab2A contains a conserved common docking motif for binding Erk (FIG. 45E). Moreover, GST-Rab2A fusion protein pulled down Erk1/2 in cells (FIG. 45F), and recombinant Erk1 or Erk2 bound to GST-Rab2A in vitro (FIG. 47A). To examine whether the integrity of this docking motif is required for Rab2A to bind Erk, we substituted the known critical residues KR (mut1), LXI (mut2), or both residues (mut1/2) with Ala residues. Comparing to wild-type Rab2A, while either mutt or mut2 reduced binding with Erk markedly, mutating both sequences completely abolished the ability of Rab2A to bind to Erk (FIG. 45F), as has been shown for other Erk-binding partners. Thus, Rab2A directly interacts with Erk through the specific Erk docking sequence in Rab2A.

Example 23: Rab2A Prevents Erk1/2 Inactivation by MKP3

Interestingly, the conserved docking motif described in Example 22 is also found in MKP3, a phosphatase that binds and dephosphorylates Erk, leading to Erk inactivation, and MEK1, a kinase that binds and phosphorylates Erk, leading to Erk activation. To examine whether Rab2A and MKP3 or MEK1 compete with each other to interact with Erk, HEK293 cells were co-transfected with decreasing doses of myc-MKP3 or the constitutively active HA-MEK1 and a constant dose of Flag-Rab2A. With decreasing amounts of MKP3 expressed, more Erk1/2 were immunoprecipitated by Rab2A using Flag antibody in a dose-dependent manner (FIG. 45G), suggesting that Rab2A competed with MKP3 to bind Erk1/2 in vivo. However, unlike the MKP3 competition results, similar amounts of Erk1/2 were immunoprecipitated by Flag-Rab2A even though decreasing amounts of MEK1 were expressed (FIG. 47B), suggesting that Rab2A may not compete with MEK1 to bind Erk1/2. These results may be expected because although the docking motif of MEK is important for the ERK-MEK interaction, there are other mechanisms to ensure the activation of Erk by MEK, such as scaffold proteins, which bring MEK and Erk into close proximity and efficiently facilitates the signal propagation, as well as the kinase-substrate interaction between the MEK catalytic site and the Erk activation loop.

The above results suggest that Rab2A might prevent the dephosphorylation of Erk1/2 by competing with MKP3 for Erk1/2 binding. To examine this possibility, we transfected HEK293 cells with MKP3 and the constitutively active MEK1 mutant as well as different amounts of epitope-tagged Rab2A, followed by assaying Erk phosphorylation. Expression of the active MEK1 induced Erk1/2 phosphorylation even in serum-starved cells and this was largely reversed by myc-MKP3 expression (FIG. 45H). However, Flag-Rab2A expression restored Erk1/2 phosphorylation in a dose-dependent manner (FIG. 45H). Thus, Rab2A directly binds to Erk1/2 and keeps it in an active form by competing with MKP3, a phosphatase that dephosphorylates and inactivates Erk1/2.

To further demonstrate whether this Rab2A-Erk interaction is functionally important for Rab2A to regulate BCSC, we infected HMLE cells with Flag-tagged wild-type Rab2A or its mutants defective in binding to Erk, followed by comparing their effects on BCSC by (FIG. 46C). Consistent with the above results (FIG. 45F), wild-type Rab2A markedly increased the BCSC-enriched population, but none of the Rab2A mutants altered the abundance of BCSCs (FIG. 47D), although mutt and mut2 retained some binding activity to Erk1/2. In addition, overexpression of RablA, the small GTPase that is highly related to Rab2A with over 70% similarity and also localized to the ERGIC, but has not a conserved docking motif for binding to Erk, had no effect either on Erk activation or the BCSC phenotype (FIGS. 47E, 47F, 47G, 47H, and 47I). Taken together, these results show that specific interaction between Rab2A and Erk1/2 is critical for Rab2A to activate Erk1/2 and to promote BCSC.

Example 24: Rab2A Promotes the Nuclear Translocation of Erk1/2 Downstream β-catenin As Erk1/2 signaling is known to increase the nuclear accumulation of unphosphorylated (active) β-catenin, a known regulator of CSCs, and Pin1 is known to have a similar effect on β-catenin in breast cancer cells, we examined whether Pin1/Rab2A/p-Erk signaling regulates nuclear β-catenin levels. Confocal analysis showed that most unphosphorylated β-catenin localized at the plasma membrane in starved HMLE cells, but translocated into the nucleus, along with increased p-Erk1/2 6 hr after EGF stimulation (FIG. 48A). However, in Rab2A-overexpressing and Pin1-overexpressing cells, not only was p-Erk1/2 obviously increased, but also unphosphorylated β-catenin was readily detected in the nucleus as early as 2 hours and accumulated further with time after EGF stimulation (FIGS. 48B and 48C). In contrast, in Rab2A or Pin1 KD cells, not only was p-Erk1/2 not increased, but also nuclear unphosphorylated β-catenin was hardly detectable even 6 hours after stimulation (FIGS. 48D and 48G). Notably, overexpression of Rab2A in Pin1 KD cells caused Erk1/2 activation and nuclear translocation and, importantly, unphosphorylated β-catenin localization to the nucleus (FIG. 48E). Conversely, Rab2A KD in Pin1-overexpressing cells prevented Erk1/2 activation and nuclear translocation of unphosphorylated β-catenin (FIG. 48F). Western blot analysis with nuclear fraction from cells further confirmed that after serum starvation followed by EGF stimulation, nuclear unphosphorylated β-catenin, along with nuclear p-Erk1/2, accumulated much faster in Rab2A-overexpressing cells, but more slowly in Rab2A or Pin1 KD cells, as compared with control cells (FIG. 48H). These results together support a model in which the Pin1/Rab2A/Erk1/2 pathway activates β-catenin and Zeb1, two important BCSC regulators.

Example 25: Rab2A Overexpression Endows BCSC Traits to Normal Primary Human MECs and is Required for Tumorigenesis of Freshly Isolated Human Primary BCSCs The above results demonstrate that Rab2A drives the expansion, invasiveness and tumorigenicity of BCSCs in human breast cell lines. To extend our findings to primary human cells, we first examined whether Rab2A or the Q58H mutant might confer BCSC properties to normal human primary MECs. As shown in FIG. 49A, we sorted Lin⁻ MECs isolated from reduction mammoplasty tissues from two human donors, and infected them with lentiviruses expressing Flag-Rab2A, Flag-Rab2A Q58H at levels similar to or 3 times of the endogenous level (FIG. 50A). Rab2A overexpression led to a dose-dependent increase in the CD24⁻CD44⁺ population (FIG. 50B). Overexpressing Rab2A Q58H similar to the endogenous level increased the CD24⁻CD44⁺ population more than overexpressing Rab2A at 3 times higher levels (FIG. 50B). Thus, increasing Rab2A activity by either overexpression or using naturally occurring cancer-derived mutation endows BCSC traits to normal human MECs.

We next assessed whether Rab2A is also important for tumorigenesis of BCSCs in primary breast cancers. To this end, we sorted Lin⁻CD24⁻CD44⁺ cells from freshly isolated human breast cancer cells of eight patients (FIG. 51), and analyzed Rab2A expression and its impact on BCSCs in vitro and in vivo, as shown in the flowchart (FIG. 49B). Comparing expression of Rab2A and β-catenin in Lin⁻CD24 CD44+, Lin⁻non-CD24⁻CD44⁺ cancer cells and normal MECs from patients showed that as compared with those in Lin⁻non-CD24⁻CD44⁺ cancer cells, Rab2A mRNA levels were ~7 times higher in BCSC-enriched Lin⁻CD24⁻CD44⁺ cells, and 5-7 times lower in normal breast epithelial cells (FIG. 50C). Consistent with these results, Rab2A protein and unphosphorylated β-catenin were more highly expressed in the Lin⁻CD24⁻CD44⁺ cells than in Lin⁻non-CD24⁻CD44⁺ cancer cells or normal MECs (FIG. 50D).

Given that Rab2A was highly expressed in the BCSC-enriched population, we tested whether endogenous Rab2A was required to maintain the BCSC population in the primary breast cancers by transducing Lin⁻CD24⁻CD44⁺ primary breast cancer cells with a lentivirus expressing Rab2A shRNA. Rab2A was efficiently silenced after three days of puromycin selection (FIG. 50E). As we cultured the sorted CD24⁻CD44⁺ cells in ultra-low attachment dishes, the cells infected with control shRNA still had a high percentage of CD24⁻CD44⁺ cells after selection (FIG. 50F). However, this population was significantly reduced in Rab2A KD cells, being only 1/9 of that in control cells (FIG. 50F). Rab2A KD also significantly decreased the mammosphere-forming activity of the CD24⁻CD44⁺ cells (FIGS. 50G and 50H). Thus, Rab2A is required for sustaining the BCSC properties of human primary breast cancer cells in vitro.

We finally investigated whether Rab2A was required for the tumorigenicity of the BCSC-enriched Lin⁻CD24⁻CD44⁺ population. We injected 2,000 control or Rab2A shRNA-transduced Lin⁻CD24⁻CD44⁺ cells, or Lin⁻non-CD24⁻CD44⁺ cells isolated from eight breast cancer patients into nude mice, using the same procedure as described previously (Yu et al. (2007) Cell 131:1109-1123). While no tumors developed in mice injected with the cells that were not CD24⁻CD44⁺, 2,000 control Lin⁻CD24⁻CD44+ cells generated six tumors in eight injected mice (FIGS. 50I, 50J, and 50K). Lentivirus-mediated KD of Rab2A not only drastically reduced tumor incidence (FIG. 50K), but also potently reduced tumor growth, as measured by tumor volumes and weights (FIGS. 50I and 50J). We then dissociated the tumors and sorted again for CD24⁻CD44⁺ cells for the serial transplantation. When control tumors were passaged in nude mice, they could be serially transplanted at least for two more passages without reduced tumorigenicity (FIG. 50K). However, Rab2A KD cells had substantially decreased frequency of tumor formation and reduced tumor growth (FIGS. 50I, 50J, and 50K). Thus, expression of Rab2A is highly enriched in primary human BCSCs and silencing Rab2A strongly interferes with the expansion and tumorigenesis of human primary BCSCs in vitro and in vivo.

Example 26: Rab2A Overexpression Correlates with Poor Clinical Outcomes and Upregulation of β-catenin or Zeb1 Downstream Targets in Human Breast Cancer Patients To assess whether the experimental findings of Rab2A expression and activity in BCSCs are relevant to human breast cancer patients in the clinic, we asked whether Rab2A might also be overexpressed in human breast cancer tissues and whether its expression might correlate with clinical outcome. We first analyzed expression of Rab2A, Pin1 and ALDH1, a marker for stem and progenitor cells as well as BCSCs, in normal and cancerous breast tissue arrays using immunohistochemistry. Pin1 and Rab2A were undetectable or low in all 24 human normal breast tissues, but their expression was dramatically increased in many of 65 human breast cancer tissues (FIGS. 52A and 52B). Remarkably, Rab2A expression was highly correlated with Pin1 expression in human normal and cancerous breast tissues (P<0.001) (FIGS. 52A and 52B). In breast cancer tissues, ALDH1 staining was detected in about 5-10% of tumor cells. Rab2A immunostaining significantly correlated with ALDH1 expression (P=0.029) (FIGS. 52A and 52C). The correlation of Rab2A with Pin1 and ALDH1 supports the role of Rab2A as a Pin1 target in regulating BCSC functions. We next analyzed the correlation of Rab2A expression and clinical outcome in the subset of 52 breast cancer patients, for which clinical data were available. Higher Rab2A expression was significantly associated with higher mortality in breast cancer patients, as shown by Kaplan-Meier survival curves (P=0.012) (FIG. 52D).

To expand our immunohistochemistry findings on limited samples, we studied multiple independent breast cancer datasets from Oncomine (Rhodes et al. (2007) Neoplasia 9:166-180), which collectively link clinical data with Rab2A mRNA expression in about 3,000 patients. Rab2A overexpression was closely associated with advanced stage in the Bittner dataset, with metastasis in the Schmidt dataset, and with death at 3 or 5 years in the Bild, Bittner, Kao and Schmidt breast datasets (Bild et al. (2006) Nature 439:353-357; Kao et al. (2011) BMC Cancer 11:143; Schmidt et al. (2008) Cancer Res. 68:5405-5413) (FIGS. 53A, 53B, 53C, and 53D). These data indicate that Rab2A overexpression is tightly linked to poor prognosis in breast cancer patients.

Giving that the microarray experiments and the methods to normalize data vary among different datasets making it difficult to pool the data from different datasets, we chose to further analyze the Curtis dataset, which has over 2,000 patients (Curtis et al. (2012) Nature 486:346-352). When treated as a continuous variable, Rab2A mRNA level was a strong prognostic factor for survival by univariate Cox regression analysis (FIG. 52E). Even using multivariate analysis adjusted for proliferation markers (MKI67 and PCNA), or tumor grade and stage, or the status of HER2, ER and PR, high Rab2A level was still independently associated with high mortality (FIG. 52E).

We next analyzed Rab2A expression in the PAM50 intrinsic subtypes (Parker et al. (2009) J. Clin. Oncol. 27:1160-1167) and integrative subgroups (Curtis et al., supra). Strikingly, high Rab2A mRNA levels were found in the poor prognosis subtypes, defined as PAM50 intrinsic subtypes, luminal B, HER2-enriched and basal-like, and in the IntClust5, IntClust6, IntClust9 and IntClust10 integrative subgroups (FIGS. 52F and 52G), whereas lower Rab2A levels were mostly observed in the better prognosis subtypes (normal-like PAM50 intrinsic subtype, integrative subgroups IntClust3 and IntClust4) (FIGS. 52F and 52G). Notably, high Rab2A level was tightly linked to high mortality in the most common subgroups of breast cancer patients, defined as HER2-negative or non-TNBC (triple negative) patients (FIG. 52H), which account for 87.5% and 87.3% of all cases, respectively. In these patients, it is difficult to predict clinical outcome without profiling expression of many genes. In parallel with the above four datasets, the data in the Curtis dataset provide further evidence that Rab2A plays a key oncogenic role in promoting BCSCs and aggravating breast cancer malignancy.

Example 27: ATRA Activity Against Asthma

It has been shown that Pin1 is activated in the airway of asthma patients, and promotes asthma by acting on multiple upstream and downstream targets in relevant signal pathways, thus suggesting that Pin1 inhibitors are promising new drug targets for asthma treatment.

In order to examine whether ATRA is useful in the treatment of asthma, the ovalbumin-induced (OVA) allergen challenge for asthma induction can be examined in mice. ATRA and other Pin1 inhibitors can be tested on well-established murine models of asthma including (i) a classical OVA sensitization and challenge protocol for asthma induction, (ii) a shorter OVA sensitization and challenge protocol of asthma, which might produce more obvious phenotypes, as shown for ST2 KO, and (iii) exposure to recombinant mIL-33 (Peprotech), HDM (Greer Laboratories) or its major allergen recombinant Der P2 (Indoor Biotechnologies), with PBS as a control. Pin1 KO or NF-kB inhibition suppresses airway remodeling in the OVA-induced chronic asthma mouse model. ATRA may be administered as liposomal ATRA (Sigma) through respiratory aerosol or if needed, continuous time-releasing ATRA pellets (Innovative Research of America) before and during IL-33 or HDM treatment, or OVA challenge. Dexamethasone and Pin1 KO are used as positive controls. The ability of ATRA or other Pin1 inhibitors to prevent asthma development or suppress active asthma may be examined by measuring AHR in response to acetylcholine, BAL eosinophilia, mucus production, mucoid cell hyperplasia, various cytokine levels in BAL, and serum IgE levels. As these reagents may inform whether Pin1 acts in the airway, an assay for Pin1 levels and IRAK1 activation in the airway of the treated mice can also be performed. Finally, ATRA has been shown to convert Th2 memory cells into Foxp3+ regulatory T cells suppressing Th2-mediated allergic asthma. A comparison of CD25+ Foxp3+ T-cells in Pin1 WT and KO mice, and in Pin1 WT mice treated with ATRA or vehicle following allergen exposure can be performed to determine if the phenotype involves ATRA mediated Pin1 inhibition.

It was found that Pin1 KO inhibited Th2 cytokine secretion, lung inflammation and eosinophilia after allergen challenge (FIGS. 54A, 54B, 54C, and 54D), consistent with the findings showing the requirement of Pin1 for pulmonary eosinophilia and bronchiolar remodeling after allergen challenge.

Other murine models such as BALB/c and house dust mite (HDM) may be employed to provide further insight into the effects of Pin1 inhibitors such as ATRA on asthma. Other sample models such as cell models and human samples may also be examined.

Example 28: ATRA Activity Against Systemic Lupus Erythematosus (SLE)

In order to demonstrate the cellular and serological role of Pin1 on systemic lupus erythematosus (SLE), phenotypes of lupus prone mouse models were identified. Deletion of Pin1 in the lupus-prone mice may result in suppression of lupus parameters, such as IFN-α, which is crucial for the development of disease in MRL/lpr mice as well as IRAK1 for Sle1 and Sle3 mice. Further procedures may include the examination of cell specific contribution of Pin1 deletion to lupus phenotype using a conditional Pin1 knock out (KO). This cell-type conditional Pin1 KO model may demonstrate the relative cell specific contribution of Pin1 to the lupus phenotype, for example in B cells, T cells or DCs.

Pin1 is an essential regulator of TLR signaling, a pathway known to play a major role in SLE. The prevention or suppression of autoimmunity with regard to Pin1 was examined in B6.MRL/lpr lupus prone mice in which Pin1 was removed. This lupus prone mouse model may be homozygous for lymphoproliferation spontaneous mutation ($Fas^{lpr}$) and may develop systemic autoimmunity, massive lymphadenopathy associated with proliferation of aberrant T cells, arthritis, and immune complex glomerulonephrosis, recapitulating many aspects of human SLE. Subsequently, B6.Pin1−/− mice were crossed with lupus-prone mice (B6.lpr, B6.Sle1 and B6.Sle3). B6.lpr::Pin1−/−, B6.Sle1::Pin1−/− and B6.Sle3::Pin1−/− mice, along with control mice, were followed between 9 and 20 months. The effects of Pin1 deficiency on the lupus-related phenotypes, including fur loss (butterfly rash area), skin inflammation, and lymphoid hyperplasia, in these mice were evaluated and compared with Pin1 WT controls (FIG. 55A). The spleen and lymph node in the B6.lpr::Pin1 KO mouse exhibited a normal size compared to those in B6.lpr::Pin1 WT mouse, which are 4 fold and 8 fold heavier in spleen and lymph node, respectively (FIG. 55B) Immunohistochemistry on the skin lesion area was performed and found that the Pin1 KO mouse was fully resistant to hyperkeratinosis that afflicted the Pin1 WT mouse (FIG. 55C). Although kidney sizes may be similar (FIG. 55B, right panel), renal pathological staining indicated significant deposition of antibodies and white blood cell antigens, such as IgG, complement C3, and CD68, in the glomeruli of the Pin1 WT mouse, but not in the Pin1 KO mouse (FIG. 55D). In addition, serum biomarkers dsDNA antibody, IL-2, and IL-17 were significantly higher in the Pin1 WT mouse (FIG. 55E). Thus, Pin1 KO could lead to a logarithmic elimination of dsDNA antibody and IL-17 production as well as a significant reduction on IL-2. By monitoring monthly levels of proteinuria and double negative T cell population, it was found that Pin1 KO significantly decreased both lupus markers (FIG. 55F).

In further studies, ATRA was shown to potently suppress the expression of autoimmunity in MRL/lpr lupus prone mice. To test the effects of inhibiting Pin1 on lupus-related phenotypes in a mouse models, ATRA was used to treat six pairs of MRL/lpr mice at 8 weeks with 5 mg ATRA or a placebo for 8 weeks to examine whether ATRA would prevent the development of lupus-related phenotypes in this mouse model, which usually occur at 12 weeks. It was strikingly observed that ATRA drastically suppressed visual lupus-related phenotypes in all six treated mice, including fur loss (butterfly rash area), skin inflammation, and lymphoid hyperplasia, as compared with placebo-treated controls (FIG. 56A). A pair of 14 week-old ATRA-treated and placebo-treated mice were sacrificed. The spleen and lymph node in the ATRA-treated mouse exhibited normal size, but the placebo-treated mouse spleen and lymph node was 2-4 fold heavier (FIG. 56B). ATRA treatment also potently inhibited hyperkeratinosis (FIG. 56C) and glomerular deposition of IgG, C3, and CD68 (FIG. 56D). These results strongly suggest that Pin1 inhibitors such as ATRA may have beneficial clinical efficacy in treating lupus.

Additional in vivo studies as well as other studies involving models including in vitro and human models may provide further insight into the efficacy of ATRA and ATRA-related compounds in the treatment of SLE.

Example 29: ATRA Activity Against Cocaine Addiction

Dopamine receptor and group I mGluR signaling may be cofunctional, and MAP Kinase phosphorylates mGluR5 (S1126) within the sequence that is bound by Homer (TPPSPF). D1 dopamine receptors activate MAP Kinase, and phosphorylation of mGluR5(S1126) increasing Homer binding avidity and influences mGluR signaling. In addition, phosphorylation of mGluR5(S1126) also creates a binding site for the prolyl isomerase Pin1, where Pin1 accelerates rotation of the phosphorylated S/T-P bond in target proteins, and acts as a molecular switch. It is believed that Pin1 may be co-functional with Homer in controlling mGluR1/5 signaling.

It has been demonstrated (Park et al., 2013) that Pin1 catalyzes isomerization of phosphorylated mGluR5 at the $pS^{1126}$-P site and consequently enhances mGluR5-dependent gating of NMDA receptor channels. The immediate early gene (IEG) Homer1a, induced in response to neuronal activity, plays an essential role by interrupting Homer cross-linking and therefore facilitating Pin1 catalysis. Mutant mice that constrain Pin1-dependent mGluR5 signaling fail to exhibit normal motor sensitization, implicating this mechanism in cocaine-induced behavioral adaptation. Subsequently, in vivo studies confirmed that Pin1 co-immunoprecipitates with mGluR5 from mouse brain. Consistent with the notion that cross-linking Homer proteins compete with Pin1 for mGluR5 binding, Pin1 co-immunoprecipitation with mGluR5 increased in brains of mice lacking Homer (Homer1−/− Homer2−/− Homer3−/−, Homer triple knockout, HTKO), and increased in parallel with mGluR5(S1126) phosphorylation induced by acute administration of cocaine. An increase of Pin1 binding in WT mice was not detected. This could challenge the notion that Pin1 is a natural signaling partner of mGluR5(S1126), but since Homer1a protein levels in vivo are many fold less than constitutively expressed Homer proteins, the possibility that effects of Homer1a may be restricted to a minority of mGluR5(S1126) that are not easily detected in biochemical assays was considered. Overall, the data indicate that the IEG isoform Homer1a facilitates the binding of Pin1 to mGluR5 that has been phosphorylated in response to cocaine and/or dopamine receptor stimulation (Park et al., 2013). Accordingly, administration to a subject affected by cocaine addition of a Pin1 inhibitor such as an ATRA-related compound may be efficacious in the treatment of the addiction condition.

Example 30: Identification of Pin1 Inhibitors Using a Screening Method

The screening method described herein was used to identify ATRA-related compounds with potential to be Pin1 catalytic inhibitors. The Schrödinger computational chemistry program was used to calculate binding energies for compounds having one or more structural or chemical differences from ATRA (e.g., those described herein). Calculated energies were provided in kcal/mol. ATRA-related compounds having the highest binding affinities (e.g., the most negative free energies) are provided in Tables 1-5.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method of treating a cancer in a subject with elevated levels of a Pin1 marker, said method comprising administering an all-trans retinoic acid (ATRA)-related compound to said subject in an amount sufficient to treat said subject, wherein said ATRA-related compound has the formula

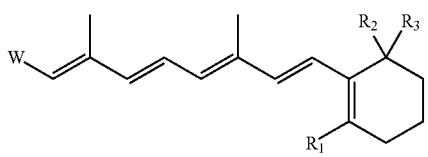

(Formula I)

wherein W is an optionally substituted triazole, and $R_1$, $R_2$, and $R_3$ are independently selected from the group consisting of a halogen atom, a carboxylic acid, an alcohol, an ester, an aldehyde, a carbonyl, an acyl halide, a carbonate, an acetal, a phosphate, a thiol, a sulfoxide, a sulfinic acid, a sulfonic acid, a thial, a sulfate, a sulfonyl, an amide, an azido, a nitro, a cyano, an isocyano, an acyloxy, an amino, a carbamoyl, a sulfonamide, an optionally substituted C1-C10 alkyl, an optionally substituted C2-C10 alkenyl, an optionally substituted C2-C10 alkynyl, an optionally substituted C1-C10 alkoxy, an optionally substituted C6-C10 aryloxy, an optionally substituted C3-C8 cycloalkyl, an optionally substituted C3-C8 cycloalkoxy, an optionally substituted C6-C10 aryl, an optionally substituted C6-10 aryl-C1-C10 alkoxy, an optionally substituted C3-C8 heterocyclyl, an optionally substituted C3-C8 heterocycloalkyl, an optionally substituted C4-C8 heterocycloalkenyl, or an optionally substituted C6-C10 heteroaryl group.

2. The method of claim 1, wherein, prior to said administering, the method comprises determining the level of said Pin1 marker in a sample from said subject.

3. The method of claim 1, wherein said subject has been previously treated with an ATRA-related compound and exhibits Pin1 degradation.

4. The method of claim 1, wherein, after said administering, said method further comprises determining whether said subject has Pin1 degradation.

5. The method of claim 1, wherein one or more of $R_1$, $R_2$, and $R_3$ are methyl groups.

6. The method of claim 1, wherein the ATRA-related compound has the formula of

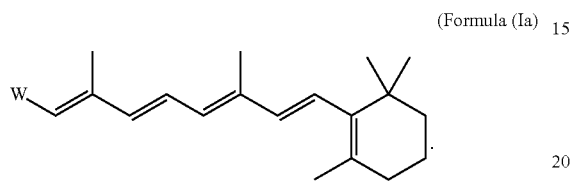

(Formula (Ia))

7. The method of claim 1, wherein the ATRA-related compound is selected from the group consisting of

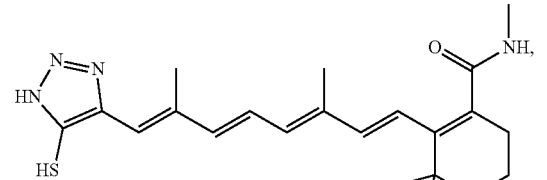

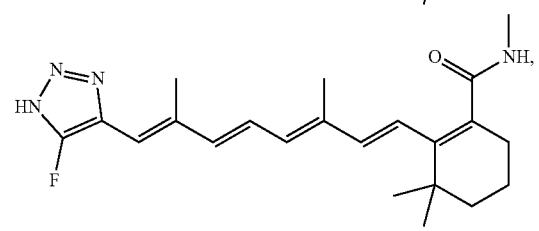

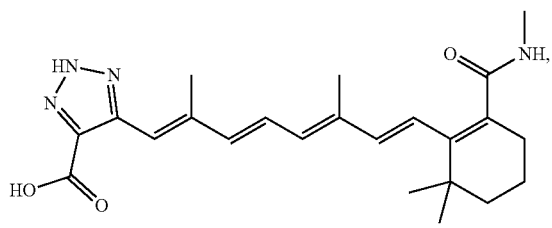

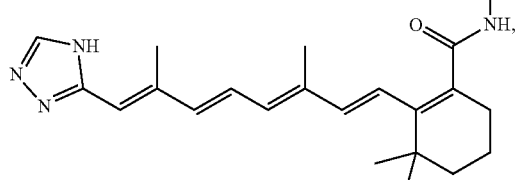

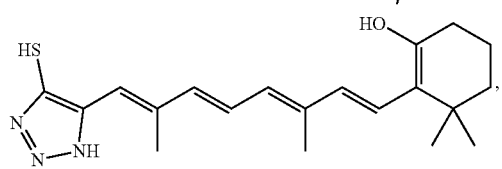

-continued

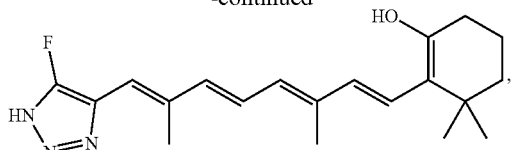

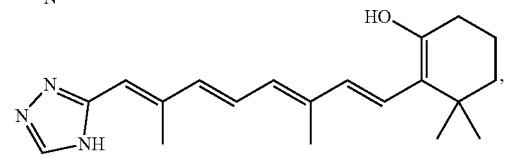

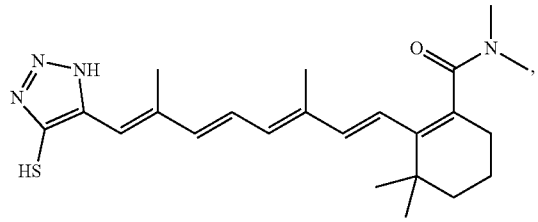

and

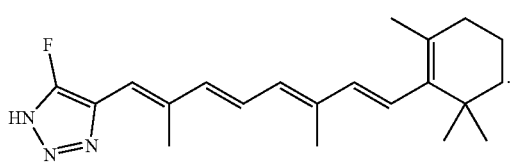

8. The method of claim 1, wherein said Pin1 marker is reduced Ser71 phosphorylation of Pin1 or overexpression of PML-RARα.

9. The method of claim 1, further comprising determining Pin1 marker levels in a sample from said subject after said administration of said compound.

10. The method of claim 9, wherein said sample is selected from the group consisting of tumor samples, blood, urine, biopsies, lymph, saliva, phlegm, and pus.

11. The method of claim 1, wherein said elevated Pin1 marker level is due to an inherited trait or a somatic mutation.

12. The method of claim 1, further comprising administering a second therapeutic compound to the subject.

13. The method of claim 12, wherein:
(a) said second therapeutic compound is an anti-proliferative compound, an anti-inflammatory compound, an anti-microbial compound, or an anti-viral compound;
(b) said second therapeutic compound is administered at a low dosage or at a different time;
(c) said second therapeutic compound is formulated as a liposomal formulation or a controlled release formulation; or
(d) said ATRA-related compound and said second therapeutic compound are formulated together.

14. The method of claim 13, wherein:
(a) said anti-proliferative compound is selected from the group consisting of MK-2206, ON013105, RTA402, BI 2536, Sorafenib, and ISIS-STAT3Rx;
(b) said anti-proliferative compound is selected from the group consisting of microtubule inhibitors, topoisomerase inhibitors, platins, alkylating agents, and antimetabolites;
(c) said anti-proliferative compound is selected from the group consisting of paclitaxel, gemcitabine, doxorubicin, vinblastine, etoposide, 5-fluorouracil, carboplatin, altretamine, aminoglutethimide, amsacrine, anastrozole, azacitidine, bleomycin, busulfan, carmustine, chlorambucil, 2-chlorodeoxyadenosine, cisplatin, colchicine, cyclophosphamide, cytarabine, cytoxan, dacarbazine, dactinomycin, daunorubicin, docetaxel, estramustine phosphate, floxuridine, fludarabine, gentuzumab, hexamethylmelamine, hydroxyurea, ifosfamide, imatinib, interferon, irinotecan, lomustine, mechlorethamine, melphalen, 6-mercaptopurine, methotrexate, mitomycin, mitotane, mitoxantrone, pentostatin, procarbazine, rituximab, streptozocin, tamoxifen, temozolomide, teniposide, 6-thioguanine, topotecan, trastuzumab, vincristine, vindesine, and vinorelbine;

(d) said anti-inflammatory compound is selected from the group consisting of corticosteroids, NSAIDs, COX-2 inhibitors, biologics, small molecule immunomodulators, non-steroidal immunophilin-dependent immunosuppressants, 5-amino salicylic acids, and DMARDs;

(e) said anti-inflammatory compound is selected from the group consisting of naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid (salsalate), fenoprofen, flurbiprofen, ketoprofen, meclofenamate sodium, meloxicam, oxaprozin, sulindac, tolmetin, rofecoxib, celecoxib, valdecoxib, lumiracoxib, inflixamab, adelimumab, etanercept, CDP-870, rituximab, atlizumab, VX 702, SCIO 469, doramapimod, RO 30201195, SCIO 323, DPC 333, pranalcasan, mycophenolate, merimepodib, cyclosporine, tacrolimus, pimecrolimus, ISAtx247, mesalamine, sulfasalazine, balsalazide disodium, olsalazine sodium, methotrexate, leflunomide, minocycline, auranofin, gold sodium thiomalate, aurothioglucose, azathioprine, hydroxychloroquine sulfate, and penicillamine;

(f) said anti-inflammatory compound is selected from the group consisting of algestone, 6-alpha-fluoroprednisolone, 6-alpha-methylprednisolone, 6-alpha-methylprednisolone 21-acetate, 6-alpha-methylprednisolone 21-hemisuccinate sodium salt, 6-alpha,9-alpha-difluoroprednisolone 21-acetate 17-butyrate, amcinafal, beclomethasone, beclomethasone dipropionate, beclomethasone dipropionate monohydrate, 6-beta-hydroxycortisol, betamethasone, betamethasone-17-valerate, budesonide, clobetasol, clobetasol propionate, clobetasone, clocortolone, clocortolone pivalate, cortisone, cortisone acetate, cortodoxone, deflazacort, 21-deoxycortisol, deprodone, descinolone, desonide, desoximethasone, dexamethasone, dexamethasone-21-acetate, dichlorisone, diflorasone, diflorasone diacetate, diflucortolone, doxibetasol, fludrocortisone, flumethasone, flumethasone pivalate, flumoxonide, flunisolide, fluocinonide, fluocinolone acetonide, 9-fluorocortisone, fluorohydroxyandrostenedione, fluorometholone, fluorometholone acetate, fluoxymesterone, flupredidene, fluprednisolone, flurandrenolide, formocortal, halcinonide, halometasone, halopredone, hyrcanoside, hydrocortisone, hydrocortisone acetate, hydrocortisone butyrate, hydrocortisone cypionate, hydrocortisone sodium phosphate, hydrocortisone sodium succinate, hydrocortisone probutate, hydrocortisone valerate, 6-hydroxydexamethasone, isoflupredone, isoflupredone acetate, isoprednidene, meclorisone, methylprednisolone, methylprednisolone acetate, methylprednisolone sodium succinate, paramethasone, paramethasone acetate, prednisolone, prednisolone acetate, prednisolone metasulphobenzoate, prednisolone sodium phosphate, prednisolone tebutate, prednisolone-21-hemisuccinate free acid, prednisolone-21-acetate, prednisolone-21(beta-D-glucuronide), prednisone, prednylidene, procinonide, tralonide, triamcinolone, triamcinolone acetonide, triamcinolone acetonide 21-palmitate, triamcinolone diacetate, triamcinolone hexacetonide, and wortmannin;

(g) said anti-microbial compound is selected from the group consisting of penicillins, cephalosporins, tetracyclines, aminoglycosides, macrolides, and fluoroquinolones;

(h) said anti-microbial compound is selected from the group consisting of penicillin G, ampicillin, methicillin, oxacillin, amoxicillin, cefadroxil, ceforanid, cefotaxime, ceftriaxone, doxycycline, minocycline, tetracycline, amikacin, gentamycin, kanamycin, neomycin, streptomycin, tobramycin, azithromycin, clarithromycin, erythromycin, ciprofloxacin, lomefloxacin, norfloxacin, chloramphenicol, clindamycin, cycloserine, isoniazid, rifampin, and vancomycin; or (i) said anti-viral compound is selected from the group consisting of 1-D-ribofuranosyl-1,2,4-triazole-3 carboxamide, 9->2-hydroxy-ethoxy methylguanine, adamantanamine, 5-iodo-2'-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir.

15. The method of claim 1, wherein:
(a) said cancer is selected from the group consisting of a leukemia, polycythemia vera, a lymphoma, Waldenstrom's macroglobulinemia, heavy chain disease, and a solid tumor; or
(b) said cancer is selected from the group consisting of acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia, Hodgkin's disease, non-Hodgkin's disease, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma.

16. The method of claim 1, wherein W is an optionally substituted 1,2,4-triazole.

17. The method of claim 1, wherein W is an optionally substituted 1,2,3-triazole.

* * * * *